US011220556B2

(12) United States Patent
Capon

(10) Patent No.: US 11,220,556 B2
(45) Date of Patent: Jan. 11, 2022

(54) HYBRID IMMUNOGLOBULIN CONTAINING NON-PEPTIDYL LINKAGE

(71) Applicant: Biomolecular Holdings LLC, Burlingame, CA (US)

(72) Inventor: Daniel Capon, Hillsborough, CA (US)

(73) Assignee: BIOMOLECULAR HOLDINGS LLC, Burlingame, CA (US)

(*) Notice: Subject to any disclaimer, the term of this patent is extended or adjusted under 35 U.S.C. 154(b) by 419 days.

(21) Appl. No.: 14/776,489

(22) PCT Filed: Mar. 14, 2014

(86) PCT No.: PCT/US2014/029511
§ 371 (c)(1),
(2) Date: Sep. 14, 2015

(87) PCT Pub. No.: WO2014/144911
PCT Pub. Date: Sep. 18, 2014

(65) Prior Publication Data
US 2016/0024226 A1    Jan. 28, 2016

Related U.S. Application Data

(60) Provisional application No. 61/799,784, filed on Mar. 15, 2013.

(51) Int. Cl.
| | | |
|---|---|---|
| C07K 19/00 | (2006.01) |
| C07K 1/107 | (2006.01) |
| C07K 16/28 | (2006.01) |
| A61K 47/68 | (2017.01) |
| A61K 38/17 | (2006.01) |
| A61K 39/395 | (2006.01) |
| C07K 14/715 | (2006.01) |

(52) U.S. Cl.
CPC .......... *C07K 19/00* (2013.01); *A61K 38/1793* (2013.01); *A61K 39/3955* (2013.01); *A61K 47/68* (2017.08); *A61K 47/6811* (2017.08); *A61K 47/6889* (2017.08); *C07K 1/1077* (2013.01); *C07K 14/7151* (2013.01); *C07K 16/2875* (2013.01); *C07K 2317/55* (2013.01); *C07K 2317/76* (2013.01)

(58) Field of Classification Search
CPC .. C07K 19/00; C07K 1/1077; A61K 47/6889; A61K 47/68
See application file for complete search history.

(56) References Cited

U.S. PATENT DOCUMENTS

| 9,725,503 | B2 | 8/2017 | Capon | |
| 2005/0027109 | A1* | 2/2005 | Mezo | ............ C07K 14/475 530/391.1 |
| 2008/0254512 | A1 | 10/2008 | Capon | |
| 2009/0042291 | A1 | 2/2009 | Chu | |
| 2010/0104589 | A1 | 4/2010 | Govindan et al. | |
| 2011/0178242 | A1 | 7/2011 | Harris | |
| 2011/0293632 | A1 | 12/2011 | Presta | |

(Continued)

FOREIGN PATENT DOCUMENTS

| WO | WO-9902711 A2 * | 1/1999 | ........... C07K 14/505 |
| WO | WO 2006/063042 A2 | 6/2006 | |

(Continued)

OTHER PUBLICATIONS

Debets et al. (Chem. Commun. 2010 46: 97-99) (Year: 2010).*
PCT International Search Report dated Oct. 10, 2014 in connection with PCT International Application No. PCT/US14/29511, filed Mar. 13, 2014.
Written Opinion of the International Searching Authority, dated Oct. 10, 2014 in connection with PCT International Application No. PCT/US14/29511, filed Mar. 13, 2014.
Jain, P. K., Karunakaran, D., & Friedman, S. H. (2013). Construction of a photoactivated insulin depot. *Angewandte Chemie*, 125(5), 1444-1449.

(Continued)

Primary Examiner — Peter J Reddig
(74) Attorney, Agent, or Firm — John P. White

(57) ABSTRACT

The present invention provides compounds producing compounds having the structure (I). Wherein A is a first polypeptide component of the compound; wherein C is a second polypeptide component of the compound, which polypeptide component comprises consecutive amino acids which (i) are identical to a stretch of consecutive amino acids present in a chain of an $F_c$ domain of an antibody; (ii) bind to an $F_c$ receptor; and (iii) have at their N-terminus a sequence selected from the group consisting of a cysteine, selenocysteine, CP, CPXCP (where X=P, R, or S) (SEQ ID NOs: 128-130), CDKTHTCPPCP (SEQ ID NO: 131), CVECPPCP (SEQ ID NO 132), CCVECPPCP (SEQ ID NO 133) and CDTPPPCPRCP (SEQ ID NO 134), wherein B is a chemical structure linking A and C; wherein the dashed line between B and C represents a peptidyl linkage; wherein the solid line between A and B represents a nonpeptidyl linkage comprising the structure (II).

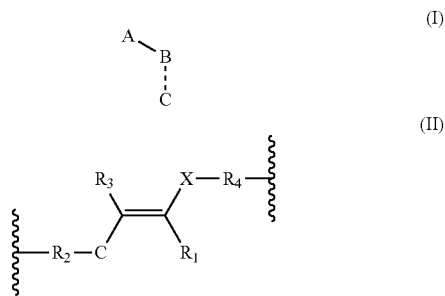

29 Claims, 23 Drawing Sheets
Specification includes a Sequence Listing.

(56) References Cited

U.S. PATENT DOCUMENTS

| | | |
|---|---|---|
| 2012/0308584 A1 | 12/2012 | Kim |
| 2013/0164286 A1 | 6/2013 | Chou et al. |
| 2015/0183858 A1 | 7/2015 | Capon |
| 2016/0024226 A1 | 1/2016 | Capon |
| 2016/0376601 A1 | 12/2016 | Capon |
| 2017/0008950 A1* | 1/2017 | Capon .................... C07K 16/00 |

FOREIGN PATENT DOCUMENTS

| | | | |
|---|---|---|---|
| WO | WO 2007/048127 A2 | 4/2007 | |
| WO | WO 2010/045193 A1 | 4/2010 | |
| WO | WO 2012/012612 A2 | 1/2012 | |
| WO | WO-2012125973 A2 * | 9/2012 | ....... C07K 14/43518 |
| WO | WO 2012/153193 A2 | 11/2012 | |
| WO | WO 2012/156918 A1 | 11/2012 | |
| WO | WO 2013/003555 A1 | 1/2013 | |
| WO | WO 2013/006706 A1 | 1/2013 | |
| WO | WO 2013/065343 | 5/2013 | |
| WO | WO 2014/014563 A1 | 1/2014 | |
| WO | WO 2015/138907 A2 | 9/2015 | |

OTHER PUBLICATIONS

Extended European Search Report dated Oct. 11, 2016 in connection with European Patent Application No. 14763801.9.
Debets, M. F., Van Berkel, S. S., Dommerholt, J., Dirks, A. T. J., Rutjes, F. P., & Van Delft, F. L. (2011). Bioconjugation with strained alkenes and alkynes. *Accounts of chemical research*, 44(9). 805-815.
Capon, D. J., Kaneko, N., Yoshimori, T., Shimada, T., Wurm, F. M., Hwang, P. K., . . . & Tanaka, K. (2011). Flexible antibodies with nonprotein hinges. *Proceedings of the Japan Academy, Series B*, 87(9), 603-616.
Elias, D. R., Cheng, Z., & Tsourkas, A. (2010). An Intein-Mediated Site-Specific Click Conjugation Strategy for Improved Tumor Targeting of Nanoparticle Systems. *Small*, 6(21), 2460-2468.
Communication pursuant to Rule 70(2) and 70a(2) EPC issued Oct. 28, 2016 in connection with European Patent Application No. 14763801.9.
Response to Communication pursuant to Rule 70(2) and 70a(2) EPC filed May 5, 2017 in connection with European Patent Application No. 14763801.9.
Communication pursuant to Rule 94(3) EPC dated Dec. 22, 2017 in connection with European Patent Application No. 14763801.9.
First Office Action dated Mar. 13, 2018 in connection with Japanese Patent Application 2016-503119 and its English translation.
Response to First Office Action filed Aug. 2, 2018 in connection with Japanese Patent Application 2016-503119 including English language version thereof.
Thomas et al. (2012) . Application of Strain-Promoted Azide-Alkyne Cycloaddition and Tetrazine Ligation to Targeted Fc-Drug Conjugates. Bioconjug Chem. 23(10):2007-2013.
Oct. 6, 2017 Extended European Search Report issued in connection with European Patent Application No. 15760986.8.
Response to Oct. 24, 2017 Communication pursuant to Rule 70(2) and 70a (2) EPC filed May 3, 2018 in connection with European Patent Application No. 15760986.8.
Oct. 24, 2017 Communication pursuant to Rules 70(2) and 70a (2) EPC issued in connection with European Patent Application No. 15760986.8.
Communication pursuant to Rule 94(3) EPC dated Aug. 2, 2018 in connection with European Patent Application No. 15760986.8.
PCT International Search Report dated Mar. 13, 2015 in connection with PCT International Application No. PCT/US2015/020458.
Van Geel, R. et al. (2012) . Preventing thiol-yne addition improves the specificity of strain-promoted azide-alkyne cycloaddition. Bioconjugate chemistry, 23 (3) , 392-398.
Second Office Action dated Dec. 11, 2019 in connection with Japanese Patent Application 2016-503119 and its English translation.
Uniprot database entry for IGHG1_Human, [online], Jan. 9, 2013, AC P01857, URL, https://www.uniprot.org/uniprot/P01857.txt?version=139.
Response to Second Office Action filed Jun. 10, 2019 in connection with Japanese Patent Application 2016-503119 including English language version.

* cited by examiner

TNR1B (SEQ ID NO: 106)
LPAQVAFTPY APEPGSTCRL REYYDQTAQM CCSKCSPGQH
AKVFCTKTSD TVCDSCEDST YTQLWNWVPE CLSCGSRCSS
DQVETQACTR EQNRICTCRP GWYCALSKQE GCRLCAPLRK
CRPGFGVARP GTETSDVVCK PCAPGTFSNT TSSTDICRPH
QICNVVAIPG NASMDAVCTS TSPTRSMAPG AVHLPQPVST
RSQHTQPTPE PSTAPSTSFL LPMGPSPPAE GSTGDGC

Fc6 (SEQ ID NO: 105)
CPPCPAPELL GGPSVFLFPP KPKDTLMISR TPEVTCVVVD
VSHEDPEVKF NWYVDGVEVH NAKTKPREEQ YNSTYRVVSV
LTVLHQDWLN GKEYKCKVSN KALPAPIEKT ISKAKGQPRE
PQVYTLPPSR DELTKNQVSL TCLVKGFYPS DIAVEWESNG
QPENNYKTTP PVLDSDGSFF LYSKLTVDKS RWQQGNVFSC
SVMHEALHNH YTQKSLSLSP GK

TNR1B-Alk-Az-DKTHT-Fc6

Figure 11

Exhibit A

HYBRID IMMUNOGLOBULIN CONTAINING NON-PEPTIDYL LINKAGE

The present application is a § 371 national stage of PCT International Application No. PCT/US2014/029511, filed Mar. 14, 2014, claiming the benefit of U.S. Provisional Patent Application No. 61/799,784, filed Mar. 15, 2013, the contents of each of which are hereby incorporated by reference in their entirety.

REFERENCE TO A SEQUENCE LISTING

This application incorporates-by-reference nucleotide and/or amino acid sequences which are present in the file named "181109_83134-PCT-US_SubstituteSequence-Listing_DH.txt," which is 272 kilobytes in size, and which was created Nov. 9, 2018 in the IBM-PC machine format, having an operating system compatibility with MS-Windows, which is contained in the text file filed Nov. 9, 2018 as part of this application.

Throughout this application, various publications are referenced. The disclosures of all referenced publications in their entireties are hereby incorporated by reference into this application in order to more fully describe the state of the art to which this invention pertains.

BACKGROUND OF THE INVENTION

Proteins prefer to form compact globular or fibrous structures, minimizing their exposure to solvent. This tendency is inherent both in the polypeptide backbone with its propensity for hydrogen-bonded secondary structure, and in side chain interactions that promote tertiary folding. Thus, previous efforts to introduce "flexibility" into antibodies using peptides have been largely inadequate. For example, it is common to employ combinations of an amino acid that favors solvent interactions (e.g., serine) with one that breaks up helical structure (e.g., glycine). While this approach is useful in making fusion proteins such as single-chain antibody fragments (scFv), the resulting structures are actually quite compact with no evidence of extendibility (for example, see Robert et al, (2009) Engineered antibody intervention strategies for Alzheimer's disease and related dementias by targeting amyloid and toxic oligomers. Protein Eng. Des. Sel. 22, 199-208). Furthermore, such sequences are likely to create additional problems due to their intrinsic immunogenicity and proteolytic susceptibility.

There is a need for new protein compounds, incorporating nonprotein chains, that are both flexible and extendible, as well as processes for producing such compounds.

SUMMARY OF THE INVENTION

The present invention provides a compound having the structure:

wherein A is a first polypeptide component of the compound;
wherein C is a second polypeptide component of the compound, which polypeptide component comprises consecutive amino acids which (i) are identical to a stretch of consecutive amino acids present in a chain of an $F_c$ domain of an antibody; (ii) bind to an $F_c$ receptor; and (iii) have at their N-terminus a sequence selected from the group consisting of a cysteine, selenocysteine, CP, CPXCP (where X=P, R, or S) (SEQ ID NOs: 128-130), CDKTHTCPPCP (SEQ ID NO: 131), CVECPPCP (SEQ ID NO: 132), CCVECPPCP (SEQ ID NO: 133) and CDTPPCPRCP (SEQ ID NO: 134), wherein B is a chemical structure linking A and C;
wherein the dashed line between B and C represents a peptidyl linkage;
wherein the solid line between A and B represents a non-peptidyl linkage comprising the structure:

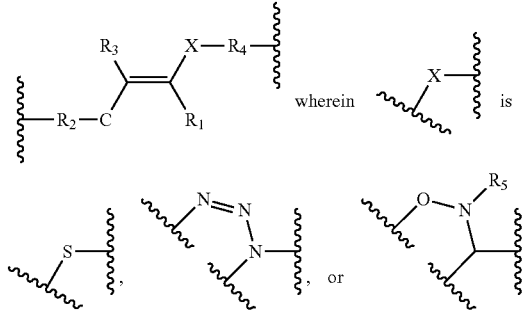

in which $R_5$ is an alkyl or aryl group
wherein $R_1$ is H or is part of an additional structure that is a cyclic structure, wherein the additional cyclic structure comprises $R_1$ or a portion of $R_1$, and may also comprise $R_2$ or a portion of $R_2$, and the carbon between $R_2$ and the alkene double bond;
with the proviso that if

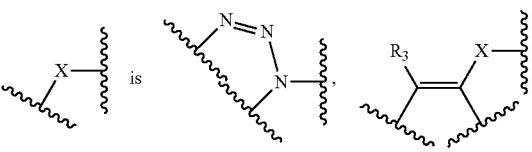

$R_3$ is a H; if

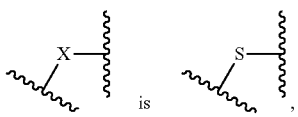

is a triazole ring that comprises

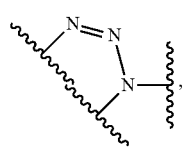 [SMILES: */N=N\N(*)*]

and if

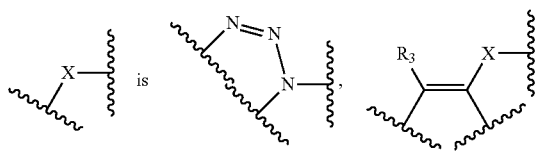

is a N-alkyl or aryl substituted isoxazoline ring that comprises

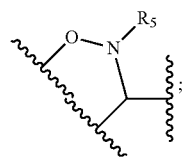

and
wherein $R_2$ represents an organic structure which connects to one of A or B and $R_4$ represents an organic structure which connects to the other of A or B.

The present invention provides a process for producing a compound having the structure:

wherein A is a first polypeptide component of the compound;
wherein C is a second polypeptide component of the compound, which polypeptide component comprises consecutive amino acids which (i) are identical to a stretch of consecutive amino acids present in a chain of an $F_c$ domain of an antibody; (ii) bind to an $F_c$ receptor; and (iii) have at their N-terminus a sequence selected from the group consisting of a cysteine, selenocysteine, CP, CPXCP (where X=P, R, or S) (SEQ ID NOs: 128-130), CDKTHTCPPCP (SEQ ID NO: 131), CVECPPCP (SEQ ID NO: 132), CCVECPPCP (SEQ ID NO: 133) and CDTPPPCPRCP (SEQ ID NO: 134),
wherein B is a chemical structure linking A and C;
wherein the dashed line between B and C represents a peptidyl linkage;
wherein the solid line between A and B represents a non-peptidyl linkage comprising the structure:

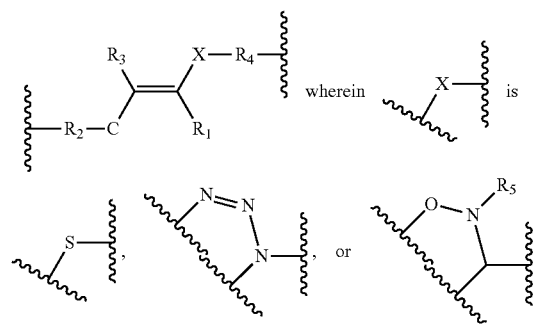

in which $R_5$ is an alkyl or aryl group
wherein $R_1$ is H or is part of an additional structure that is a cyclic structure, wherein the additional cyclic structure comprises $R_1$ or a portion of $R_1$, and may also comprise $R_2$ or a portion of $R_2$, and the carbon between $R_2$ and the alkene double bond;
with the proviso that if

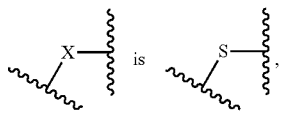

$R_3$ is a H;

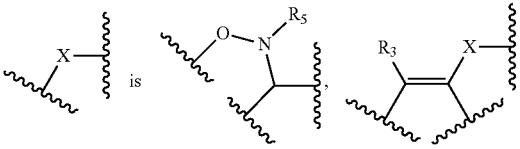

if is a triazole ring that comprises

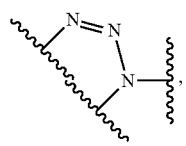 [SMILES: */N=N\N(*)*]

and if

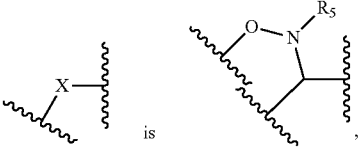

is a N-alkyl or aryl substituted isoxazoline ring that comprises

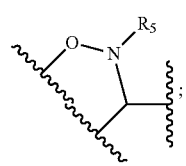

and
wherein $R_2$ represents an organic structure which connects to one of A or B and $R_4$ represents an organic structure which connects to the other of A or B;
which comprises the following steps:
a) obtaining an A' which comprises A or a derivative of A, and a first terminal reactive group;
b) obtaining a B' which comprises B or a derivative of B, a second terminal reactive group and a third terminal reactive group, wherein the second terminal reactive group is capable of reacting with the first terminal reactive group to form a non-peptidyl linkage;

c) obtaining a C' which comprises C or a derivative of C, and a fourth terminal reactive group, wherein the fourth terminal reactive group is capable of reacting with the third terminal reactive group to form a peptidyl linkage; and d) reacting A', B' and C' in any order to produce the compound.

BRIEF DESCRIPTION OF THE DRAWINGS

FIG. 11 shows tryptic peptided identified by LC/MS in the TNR1B-alkyne-azide-DKTHT-Fc6 product (Mr ~75,000) of FIG. 10. The underlined peptide sequences are those identified by LC/MS that are derived from the parent TNR1B (upper) and Fc6 (lower) sequences.

DETAILED DESCRIPTION OF THE INVENTION

Figure 1:
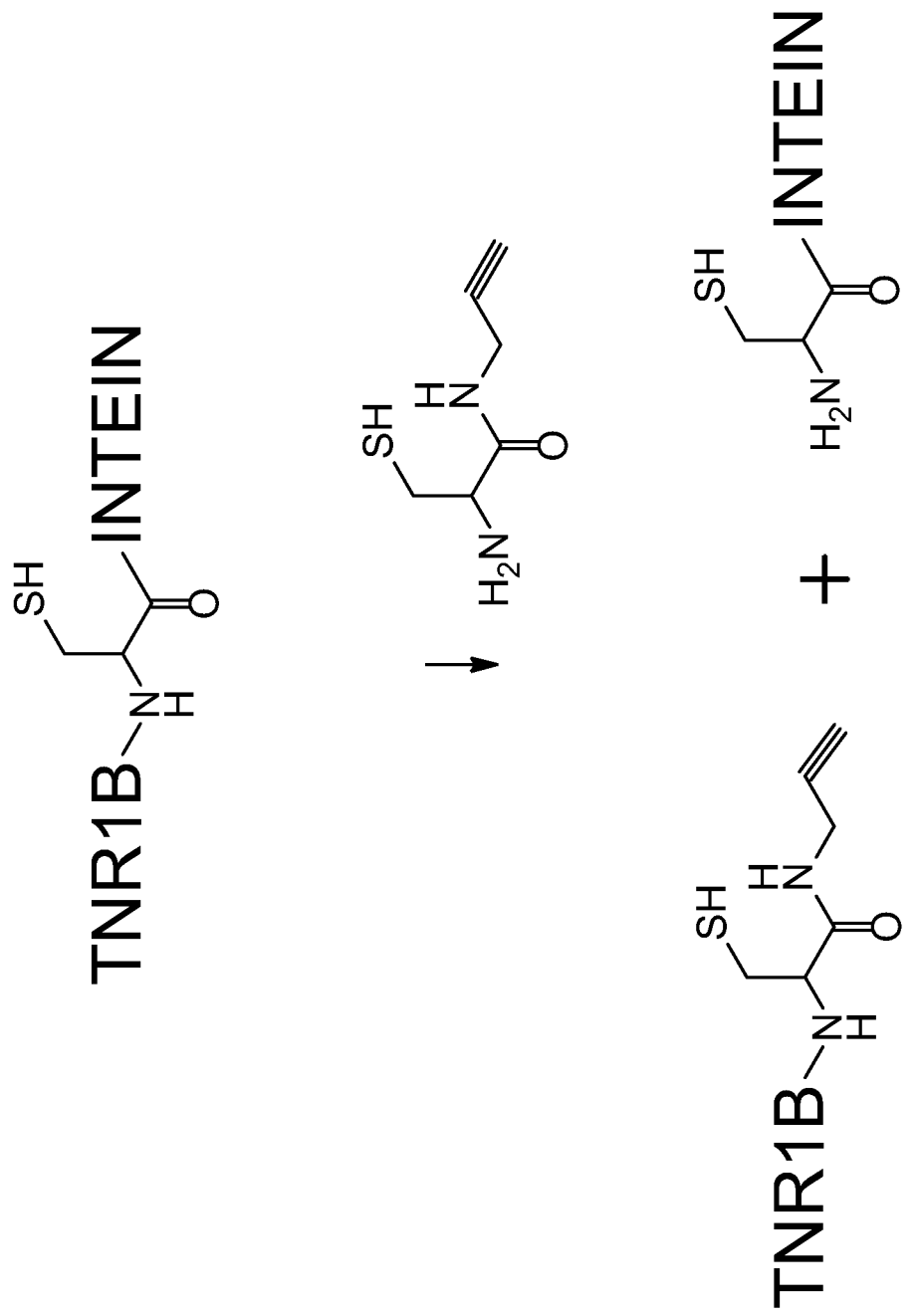
FIG. 1 shows the preparation of alkyne-modified TNR1B by cleavage of a TNR1B-intein fusion protein with cystyl-propargylamide. The intein by-product is removed by chitin chromatography. Azide-modified TNR1B and cycloalkyne-modified TNR1B are similarly prepared using cystyl-3-azidopropylamide, and various cyclooctyne (eg. DIBAC) derivatives of cysteine, respectively.

The present invention provides a compound having the structure:

wherein A is a first polypeptide component of the compound;
wherein C is a second polypeptide component of the compound, which polypeptide component comprises consecutive amino acids which (i) are identical to a stretch of consecutive amino acids present in a chain of an F$_c$ domain of an antibody; (ii) bind to an F$_c$ receptor; and (iii) have at their N-terminus a sequence selected from the group consisting of a cysteine, selenocysteine, CP, CPXCP (where X=P, R, or S) (SEQ ID NOs: 128-130), CDKTHTCPPCP (SEQ ID NO: 131), CVECPPCP (SEQ ID NO: 132), CCVECPPCP (SEQ ID NO: 133) and CDTPPCPRCP (SEQ ID NO: 134),
wherein B is a chemical structure linking A and C;
wherein the dashed line between B and C represents a peptidyl linkage;
wherein the solid line between A and B represents a nonpeptidyl linkage comprising the structure:

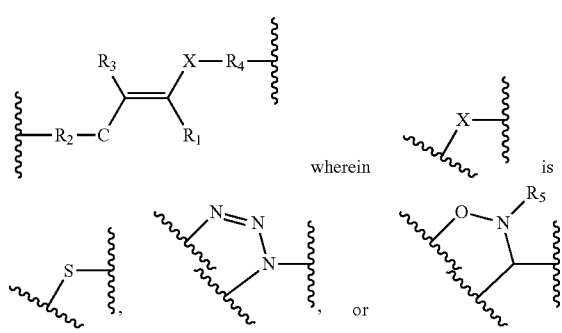

in which R$_5$ is an alkyl or aryl group
wherein R$_1$ is H or is part of an additional structure that is a cyclic structure, wherein the additional cyclic structure comprises R$_1$ or a portion of R$_1$, and may also comprise R$_2$ or a portion of R$_2$, and the carbon between R$_2$ and the alkene double bond;

with the proviso that if

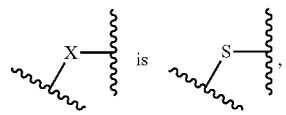

R$_3$ is a H; if

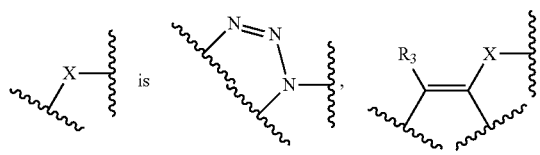

is a triazole ring that comprises

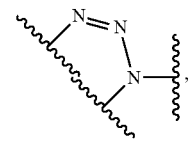 [SMILES: */N=N\N(*)*]

and if

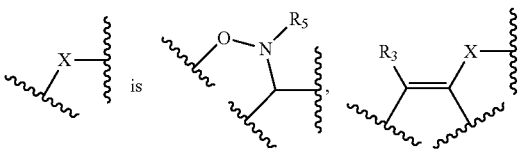

is a N-alkyl or aryl substituted isoxazoline ring that comprises

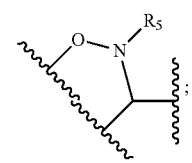

and
wherein R$_2$ represents an organic structure which connects to one of A or B and R$_4$ represents an organic structure which connects to the other of A or B.

In some embodiments, the solid line between A and B represents a nonpeptidyl linkage comprising the structure:

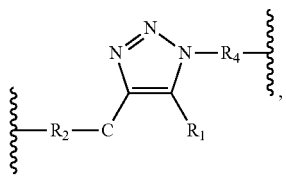

-continued

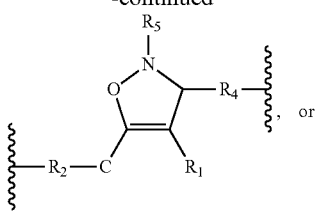, or

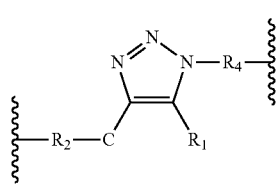, wherein $R_1$ is H or is part of an additional structure that is a cyclic structure, wherein the additional cyclic structure comprises $R_1$ or a portion of $R_1$, and may also comprise $R_2$ or a portion of $R_2$, and the carbon between $R_2$ and the alkene double bond.

In some embodiments, the solid line between A and B represents a nonpeptidyl linkage comprising the structure:

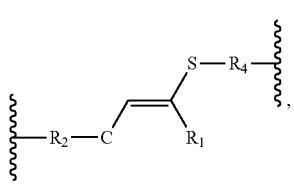

wherein $R_1$ is H or is part of an additional structure that is a cyclic structure, wherein the additional cyclic structure comprises $R_1$ or a portion of $R_1$, and may also comprise $R_2$ or a portion of $R_2$, and the carbon between $R_2$ and the alkene double bond.

In some embodiments, the solid line between A and B represents a nonpeptidyl linkage comprising the structure:

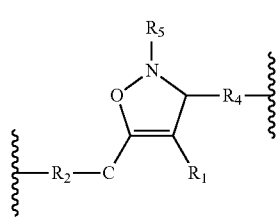

wherein $R_1$ is part of an additional structure that is a cyclic structure, wherein the additional cyclic structure comprises $R_1$ or a portion of $R_1$, and may also comprise $R_2$ or a portion of $R_2$, and the carbon between $R_2$ and the alkene double bond.

In some embodiments, the solid line between A and B represents a nonpeptidyl linkage comprising the structure:

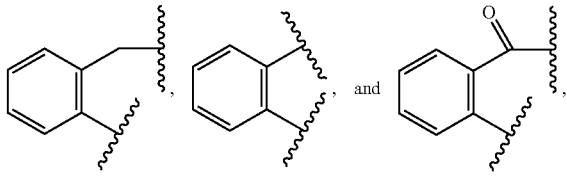

wherein $R_1$ is part of an additional structure that is a cyclic structure, wherein the additional cyclic structure comprises $R_1$ or a portion of $R_1$, and may also comprise $R_2$ or a portion of $R_2$, and the carbon between $R_2$ and the alkene double bond.

In some embodiments, $R_1$ and $R_2$ are linked via at least one direct bond so as to form a cyclic structure comprising
i) a portion of $R_1$,
ii) a portion of $R_2$,
iii) the carbon between $R_2$ and the alkene double bond, and
iv) the alkene double bond.

In some embodiments, $R_1$ is selected from the group consisting of:

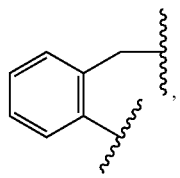 [SMILES: *Cc1ccccc1*]

which is optionally substituted at any position.

In some embodiments, $R_1$ is

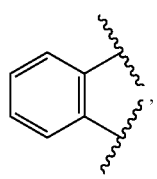

which is optionally substituted at any position.

In some embodiments, $R_1$ is

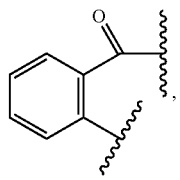 [SMILES: *C(=O)c1ccccc1*]

which is optionally substituted at any position.

In some embodiments, $R_1$ is which is optionally substituted at any position.

In some embodiments, the carbon between $R_2$ and the alkene double bond is:
(i) directly bonded to $R_2$ with a single bond and substituted with two substituents independently selected from the group consisting of hydrogen, halogen, optionally substituted benzyl, optionally substituted alkyl or optionally substituted alkoxy; or
(ii) directly bonded to $R_2$ via a double bond and a single bond.

In some embodiments, the carbon between $R_2$ and the alkene double bond is substituted with two hydrogens and directly bonded to $R_2$ with a single bond.

In some embodiments, the carbon between $R_2$ and the alkene double bond is directly bonded to $R_2$ via a double bond and a single bond.

In some embodiments, the carbon between $R_2$ and the alkene double bond is directly bonded to $R_2$ via a double bond and a single bond so as to form a phenyl ring which is optionally substituted at any position.

In some embodiments, $R_2$ is

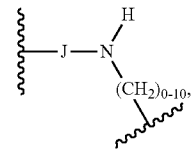

wherein $R_2$ is attached to A via J, and
wherein J is a bond or an organic structure comprising or consisting of a chain of 2, 3, 4, 5, 6, 7, 8, 9, 10 or more moieties selected from the group consisting of a [PEG(y)]z, polyalkylene glycol, polyoxyalkylated polyol, polyvinyl alcohol, polyvinyl alkyl ether, poly(lactic acid), poly(lactic-glycolic acid), polysaccharide, a branched residue, $C_1$-$C_4$ alkyl, amine, sulfur, oxygen, succinimide, maleimide, glycerol, triazole, isoxazolidine, $C_1$-$C_4$ acyl, succinyl, malonyl, glutaryl, phthalyl, adipoyl and an amino acid,
wherein [PEG(y)]z is:

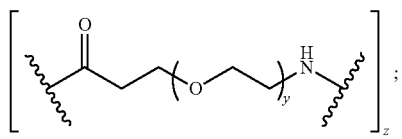

wherein y=1-100 and z=1-10.

In some embodiments, $R_2$ is

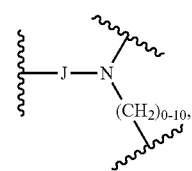

wherein $R_2$ is attached to A via J, and
wherein $R_2$ is attached to $R_1$ via the nitrogen atom of $R_2$, and
wherein J is a bond or an organic structure comprising or consisting of a chain of 2, 3, 4, 5, 6, 7, 8, 9, 10 or more moieties selected from the group consisting of [PEG(y)]z, polyalkylene glycol, polyoxyalkylated polyol, polyvinyl alcohol, polyvinyl alkyl ether, poly(lactic acid), poly(lactic-glycolic acid), polysaccharide, a branched residue, $C_1$-$C_4$ alkyl, amine, sulfur, oxygen, succinimide, maleimide, glycerol, triazole, isoxazolidine, $C_1$-$C_4$ acyl, succinyl, malonyl, glutaryl, phthalyl, adipoyl and an amino acid, wherein [PEG(y)]z is:

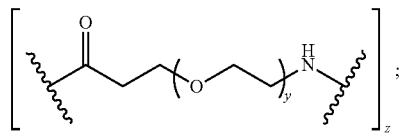

wherein y=1-100 and z=1-10.

In some embodiments, $R_2$ is

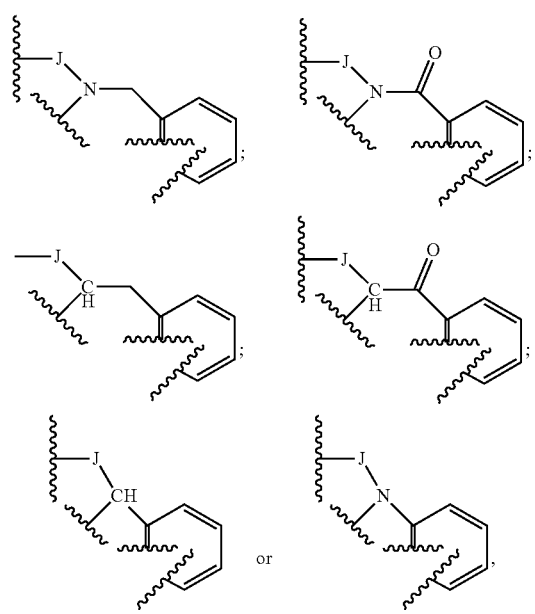

which is optionally substituted at any position,
wherein $R_2$ is attached to $R_1$ via the nitrogen atom of $R_2$, and
wherein J is a bond or an organic structure comprising or consisting of a chain of 2, 3, 4, 5, 6, 7, 8, 9, 10 or more moieties selected from the group consisting of [PEG(y)]z, polyalkylene glycol, polyoxyalkylated polyol, polyvinyl alcohol, polyvinyl alkyl ether, poly(lactic acid), poly(lactic-glycolic acid), polysaccharide, a branched residue, $C_1$-$C_4$ alkyl, amine, sulfur, oxygen, succinimide, maleimide, glycerol, triazole, isoxazolidine, $C_1$-$C_4$ acyl, succinyl, malonyl, glutaryl, phthalyl, adipoyl and an amino acid, wherein [PEG(y)]z is:

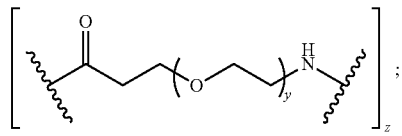

wherein y=1-100 and z=1-10.

In some embodiments, $R_2$ is

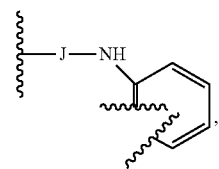

which is optionally substituted at any position.

In some embodiments, $R_2$ is

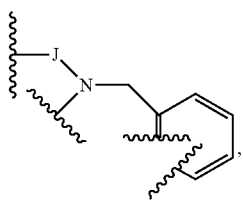

which is optionally substituted at any position.

In some embodiments, $R_2$ is

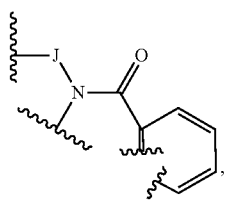

which is optionally substituted at any position.

In some embodiments, $R_2$ is

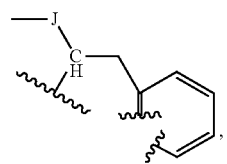

which is optionally substituted at any position.

In some embodiments, $R_2$ is

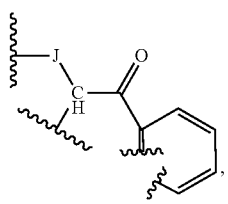

which is optionally substituted at any position.

In some embodiments, $R_2$ is

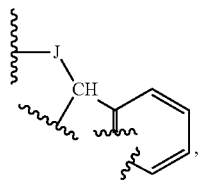

which is optionally substituted at any position.

In some embodiments, $R_1$ and $R_2$ taken together are:

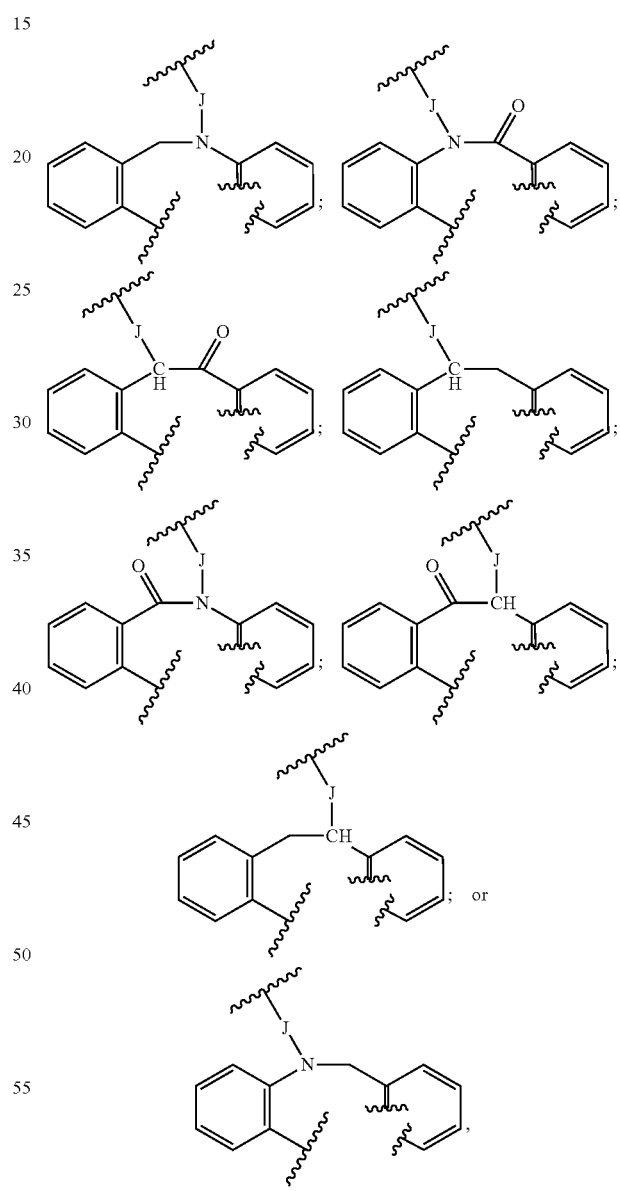

which is optionally substituted at any position, wherein J is a bond or an organic structure comprising or consisting of a chain of 2, 3, 4, 5, 6, 7, 8, 9, 10 or more moieties selected from the group consisting of [PEG(y)]z, polyalkylene glycol, polyoxyalkylated polyol, polyvinyl alcohol, polyvinyl alkyl ether, poly(lactic acid), poly(lactic-glycolic acid), polysaccharide, a branched residue, $C_1$-$C_4$ alkyl, amine, sulfur, oxygen, succinimide, maleimide, glycerol, triazole, isoxazolidine, $C_1$-$C_4$ acyl, succinyl, malonyl, glutaryl, phthalyl, adipoyl and an amino acid, wherein [PEG(y)]z is:

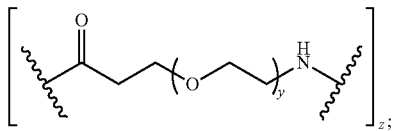

wherein y=1-100 and z=1-10.

In some embodiments, $R_1$ and $R_2$ taken together are

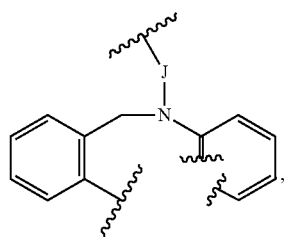

which is optionally substituted at any position.

In some embodiments, $R_1$ and $R_2$ taken together are

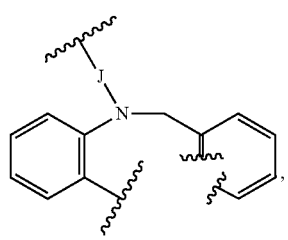

which is optionally substituted at any position.

In some embodiments, the solid line between A and B represents a nonpeptidyl linkage comprising the structure:

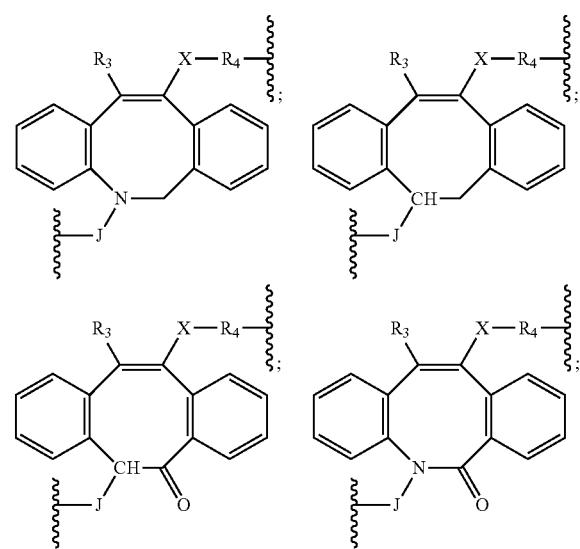

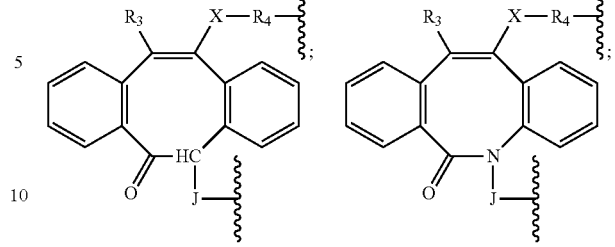

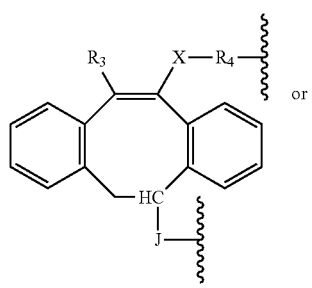

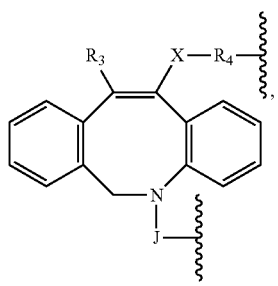

which is optionally substituted at any position, wherein J is a bond or an organic structure comprising or consisting of a chain of 2, 3, 4, 5, 6, 7, 8, 9, 10 or more moieties selected from the group consisting of [PEG(y)]z, polyalkylene glycol, polyoxyalkylated polyol, polyvinyl alcohol, polyvinyl alkyl ether, poly(lactic acid), poly(lactic-glycolic acid), polysaccharide, a branched residue, $C_1$-$C_4$ alkyl, amine, sulfur, oxygen, succinimide, maleimide, glycerol, triazole, isoxazolidine, $C_1$-$C_4$ acyl, succinyl, malonyl, glutaryl, phthalyl, adipoyl and an amino acid, wherein [PEG(y)]z is:

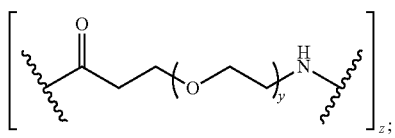

wherein y=1-100 and z=1-10.

In some embodiments, the solid line between A and B represents a nonpeptidyl linkage comprising the structure:

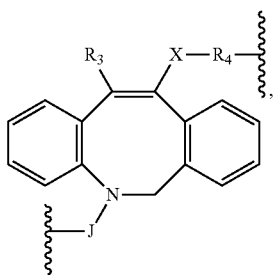

which is optionally substituted at any position.

In some embodiments, the solid line between A and B represents a nonpeptidyl linkage comprising the structure:

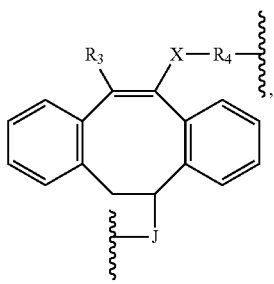

which is optionally substituted at any position.

In some embodiments, the solid line between A and B represents a nonpeptidyl linkage comprising the structure:

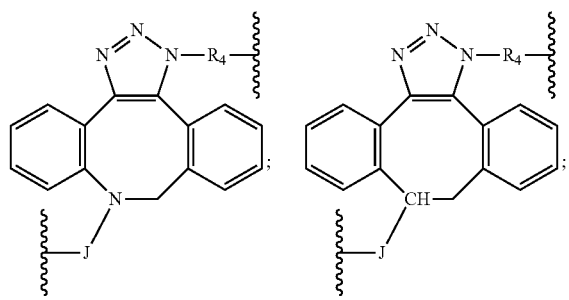

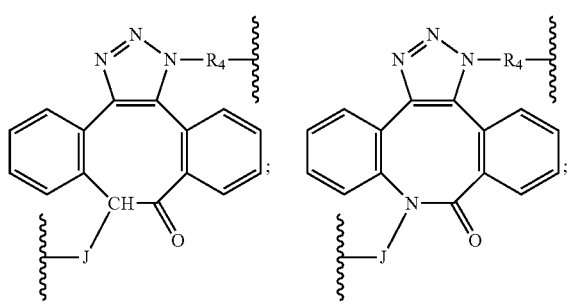

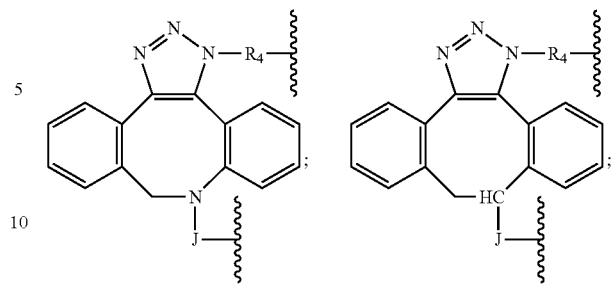

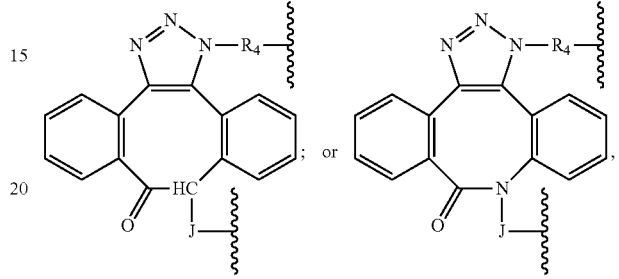

which is optionally substituted at any position, wherein J is a bond or an organic structure comprising or consisting of a chain of 2, 3, 4, 5, 6, 7, 8, 9, 10 or more moieties selected from the group consisting of [PEG(y)]z, polyalkylene glycol, polyoxyalkylated polyol, polyvinyl alcohol, polyvinyl alkyl ether, poly(lactic acid), poly(lactic-glycolic acid), polysaccharide, a branched residue, $C_1$-$C_4$ alkyl, amine, sulfur, oxygen, succinimide, maleimide, glycerol, triazole, isoxazolidine, $C_1$-$C_4$ acyl, succinyl, malonyl, glutaryl, phthalyl, adipoyl and an amino acid, wherein [PEG(y)]z is:

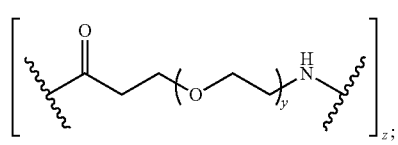

wherein y=1-100 and z=1-10.

In some embodiments, the solid line between A and B represents a nonpeptidyl linkage comprising the structure:

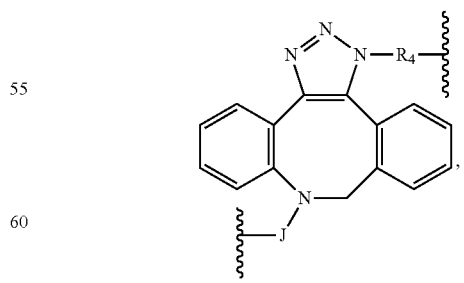

which is optionally substituted at any position.

In some embodiments, the solid line between A and B represents a nonpeptidyl linkage comprising the structure:

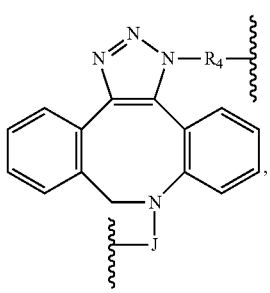

which is optionally substituted at any position,

In some embodiments, the solid line between A and B represents a nonpeptidyl linkage comprising the structure:

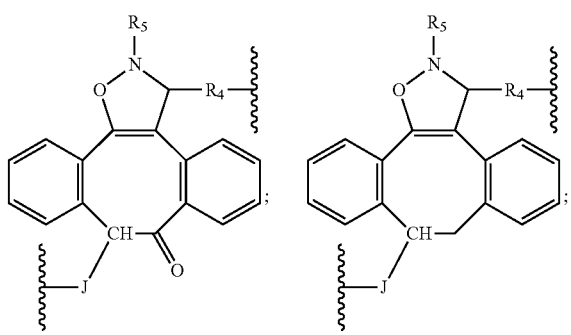

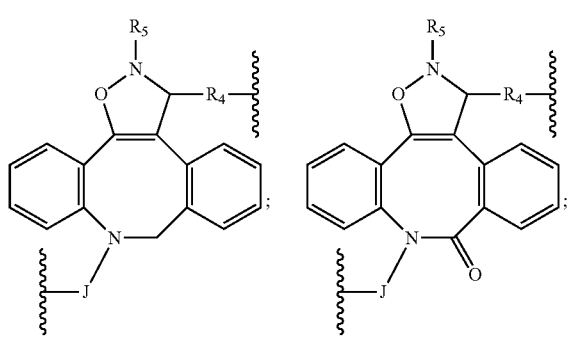

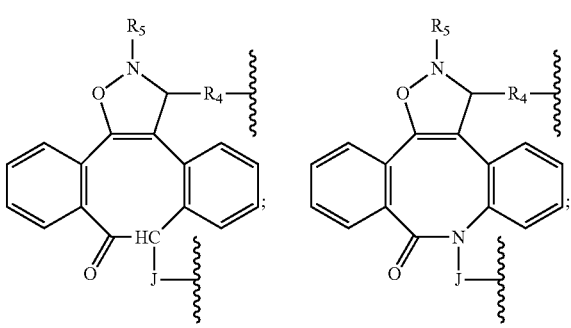

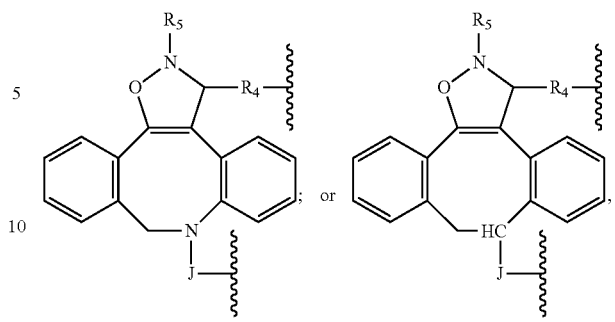

which is optionally substituted at any position, wherein J is a bond or an organic structure comprising or consisting of a chain of 2, 3, 4, 5, 6, 7, 8, 9, 10 or more moieties selected from the group consisting of [PEG(y)]z, polyalkylene glycol, polyoxyalkylated polyol, polyvinyl alcohol, polyvinyl alkyl ether, poly(lactic acid), poly(lactic-glycolic acid), polysaccharide, a branched residue, $C_1$-$C_4$ alkyl, amine, sulfur, oxygen, succinimide, maleimide, glycerol, triazole, isoxazolidine, $C_1$-$C_4$ acyl, succinyl, malonyl, glutaryl, phthalyl, adipoyl and an amino acid, wherein [PEG(y)]z is:

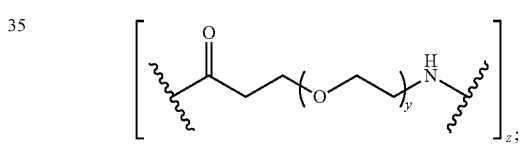

wherein y=1-100 and z=1-10.

In some embodiments, the solid line between A and B represents a nonpeptidyl linkage comprising the structure:

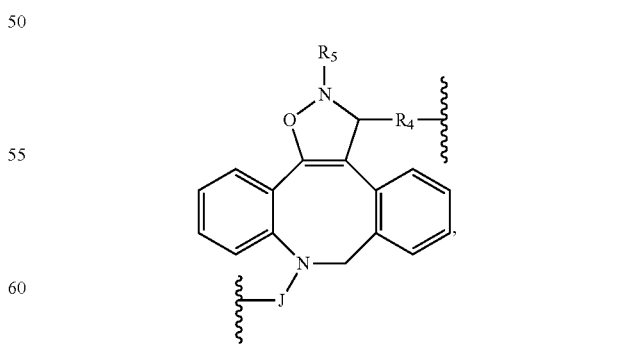

which is optionally substituted at any position.

In some embodiments, the solid line between A and B represents a nonpeptidyl linkage comprising the structure:

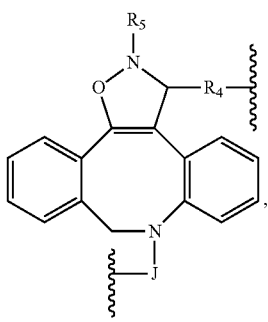

which is optionally substituted at any position.

In some embodiments, the solid line between A and B represents a nonpeptidyl linkage comprising the structure:

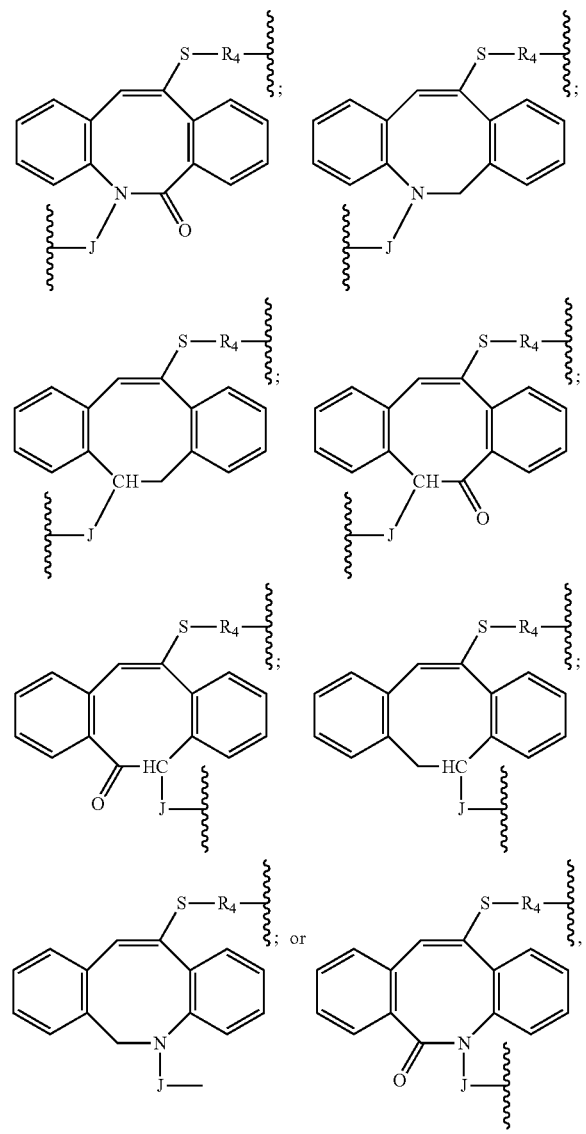

which is optionally substituted at any position,
wherein J is a bond or an organic structure comprising or consisting of a chain of 2, 3, 4, 5, 6, 7, 8, 9, 10 or more moieties selected from the group consisting of [PEG(y)]z, polyalkylene glycol, polyoxyalkylated polyol, polyvinyl alcohol, polyvinyl alkyl ether, poly(lactic acid), poly(lactic-glycolic acid), polysaccharide, a branched residue, $C_1$-$C_4$ alkyl, amine, sulfur, oxygen, succinimide, maleimide, glycerol, triazole, isoxazolidine, $C_1$-$C_4$ acyl, succinyl, malonyl, glutaryl, phthalyl, adipoyl and an amino acid, wherein [PEG(y)]z is:

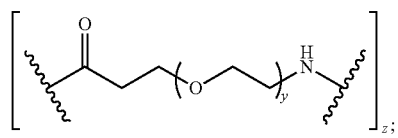

wherein y=1-100 and z=1-10.

In some embodiments, the solid line between A and B represents a nonpeptidyl linkage comprising the structure:

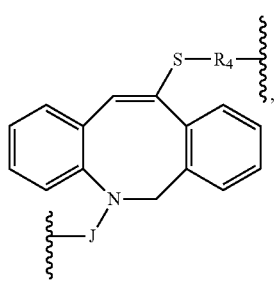

which is optionally substituted at any position.

In some embodiments, the solid line between A and B represents a nonpeptidyl linkage comprising the structure:

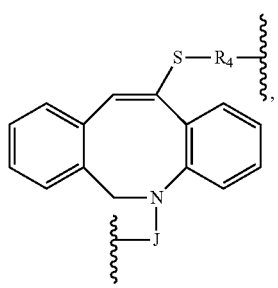

which is optionally substituted at any position.

In some embodiments, the solid line between A and B represents a nonpeptidyl linkage comprising the structure:

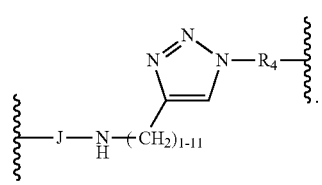

In some embodiments, $R_1$ is H.

In some embodiments, J is an organic structure comprising a [PEG(y)]z group.

In some embodiments, J is an organic structure comprising a polyalkylene glycol, polyoxyalkylated polyol, polyvinyl alcohol, polyvinyl alkyl ether, poly(lactic acid), poly(lactic-glycolic acid), or polysaccharide group.

In some embodiments, J is an organic structure comprising a $C_1$-$C_4$ alkyl group.

In some embodiments, J is an organic structure comprising a succinimide.

In some embodiments, J is an organic structure comprising an amine.

In some embodiments, J is an organic structure comprising a succinyl, malonyl, glutaryl, phthalyl or adipoyl.

In some embodiments, J is an organic structure comprising a malonyl.

In some embodiments, J is an organic structure comprising an amino acid.

In some embodiments, J is an organic structure comprising a cysteine.

In some embodiments, J is an organic structure comprising a lysine.

In some embodiments, J is an organic structure consisting of a chain of 3 moieties selected from the group consisting of [PEG(y)]z, polyalkylene glycol, polyoxyalkylated polyol, polyvinyl alcohol, polyvinyl alkyl ether, poly(lactic acid), poly(lactic-glycolic acid), polysaccharide, $C_1$-$C_4$ alkyl, amine, sulfur, oxygen, succinimide, maleimide, glycerol, triazole, isoxazolidine, $C_1$-$C_4$ acyl, succinyl, malonyl, glutaryl, phthalyl, adipoyl or an amino acid.

In some embodiments, J is an organic structure consisting of a chain of four moieties selected from the group consisting of [PEG(y)]z, polyalkylene glycol, polyoxyalkylated polyol, polyvinyl alcohol, polyvinyl alkyl ether, poly(lactic acid), poly(lactic-glycolic acid), polysaccharide, $C_1$-$C_4$ alkyl, amine, sulfur, oxygen, succinimide, maleimide, glycerol, triazole, isoxazolidine, $C_1$-$C_4$ acyl, succinyl, malonyl, glutaryl, phthalyl, adipoyl or an amino acid.

In some embodiments, J is an organic structure consisting of a chain of five moieties selected from the group consisting of [PEG(y)]z, polyalkylene glycol, polyoxyalkylated polyol, polyvinyl alcohol, polyvinyl alkyl ether, poly(lactic acid), poly(lactic-glycolic acid), polysaccharide, $C_1$-$C_4$ alkyl, amine, sulfur, oxygen, succinimide, maleimide, glycerol, triazole, isoxazolidine, $C_1$-$C_4$ acyl, succinyl, malonyl, glutaryl, phthalyl, adipoyl or an amino acid.

In some embodiments, J comprises a [PEG(y)]z group bonded to a lysine.

In some embodiments, J comprises a $C_1$-$C_4$ acyl group bonded to a succinimide group.

In some embodiments, J comprises a lysine bonded to a $C_1$-$C_4$ acyl.

In some embodiments, J comprises a [PEG(y)]z group, which is bonded to a glutaryl.

In some embodiments, J is an organic structure consisting of a chain of five moieties selected from the group consisting of [PEG(y)]z, succinimide, $C_1$-$C_4$ acyl, glutaryl or lysine.

In some embodiments, J is a bond.

In some embodiments, J is a cysteine.

In some embodiments, J has the structure:

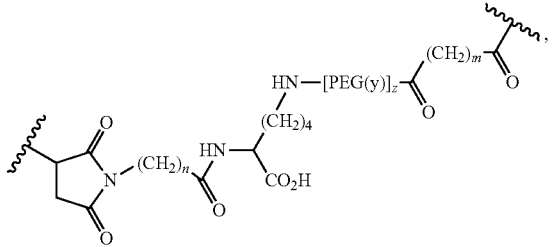

wherein n 1-3, m is 1-4, y is 1-100 and z is 1-10.

In some embodiments, J has a linear structure.

In some embodiments, J has a branched structure.

In some embodiments, $R_2$ is

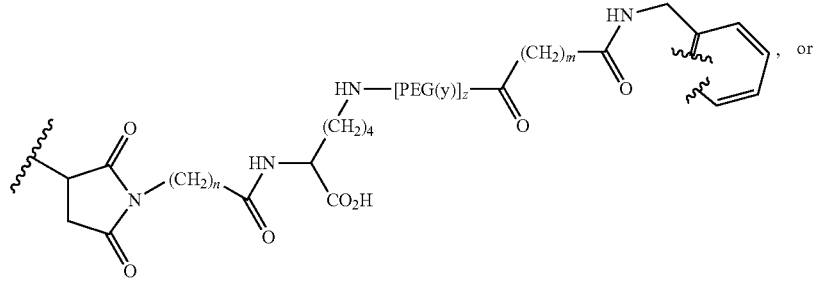

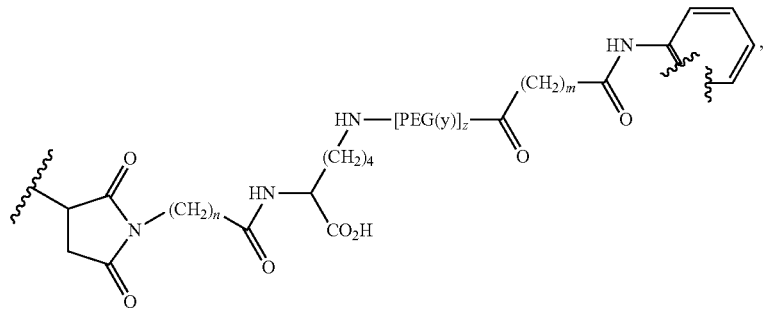

wherein n 1-3, m is 1-4, y is 1-100 and z is 1-10.

In some embodiments, $R_2$ is
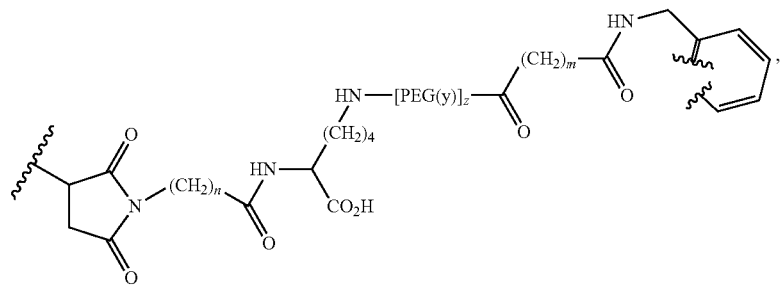
wherein n 1-3, m is 1-4, y is 1-100 and z is 1-10.
In some embodiments, $R_2$ is
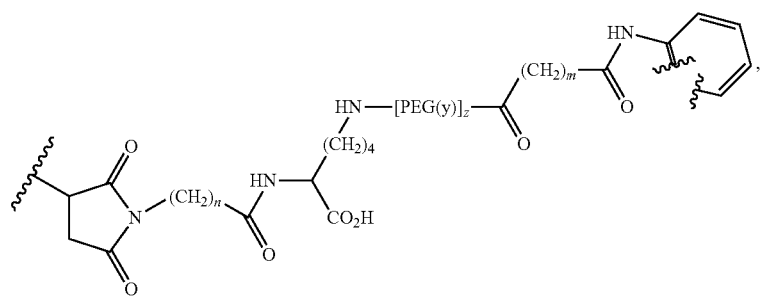
wherein n 1-3, m is 1-4, y is 1-100 and z is 1-10.
In some embodiments, $R_1$ and $R_2$ taken together are:
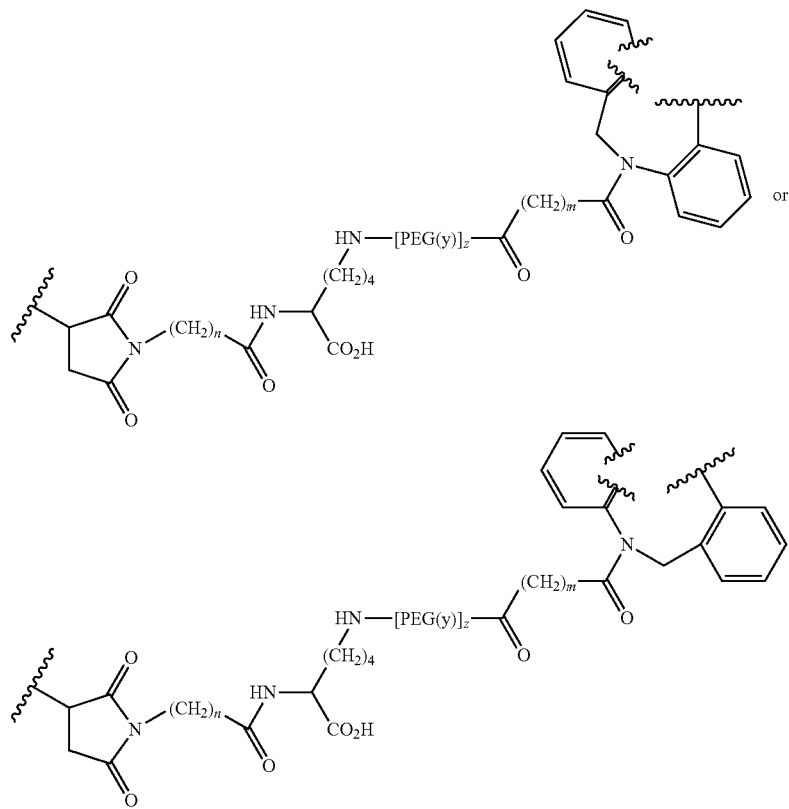
wherein n 1-3, m is 1-4, y is 1-100 and z is 1-10.

In some embodiments, $R_1$ and $R_2$ taken together are:
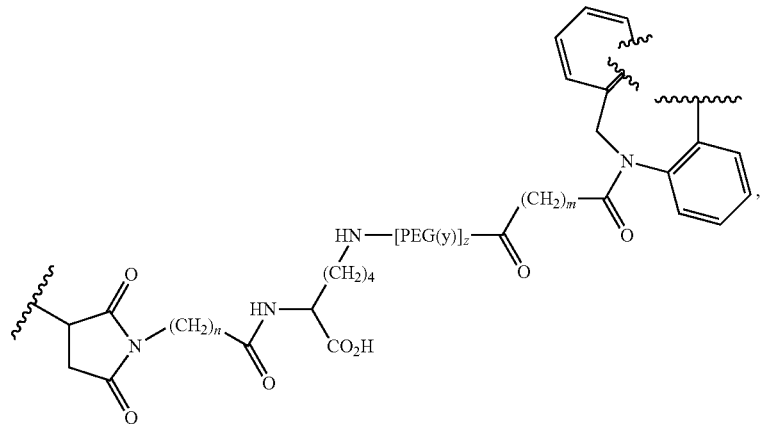
wherein n 1-3, m is 1-4, y is 1-100 and z is 1-10.
In some embodiments, $R_1$ and $R_2$ taken together are:
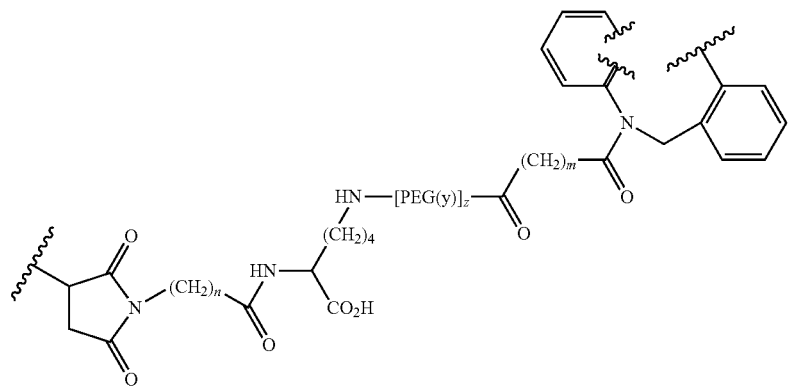
wherein n 1-3, m is 1-4, y is 1-100 and z is 1-10.
In some embodiments, the solid line between A and B represents a nonpeptidyl linkage comprising the structure:
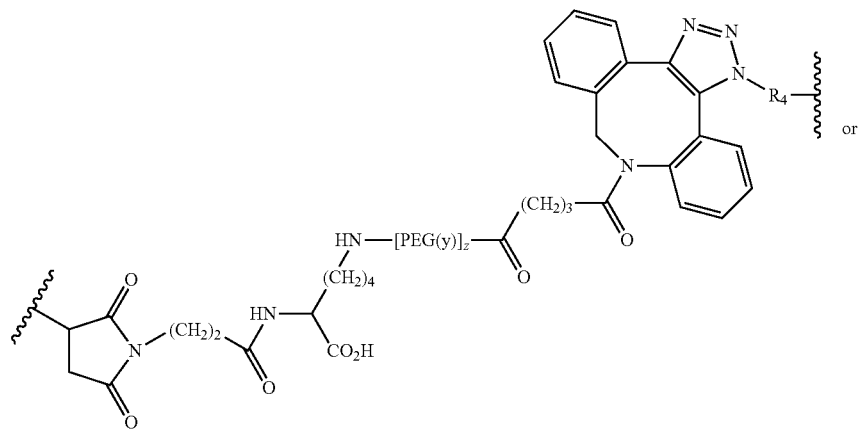

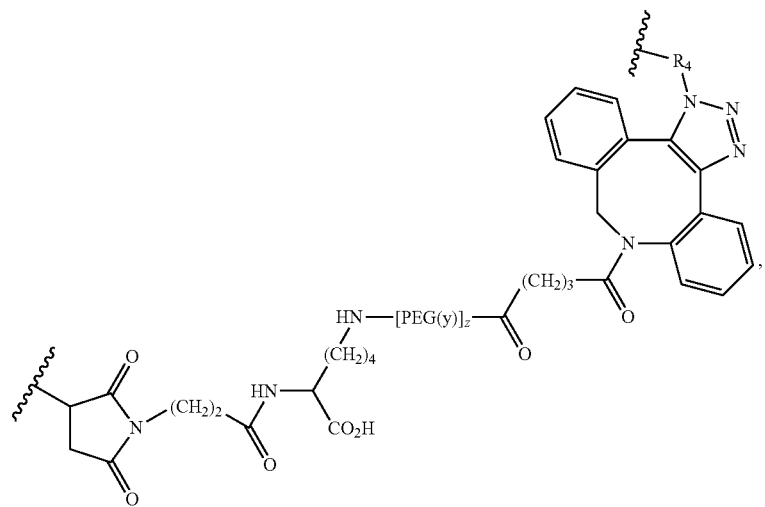
wherein [PEG(y)]z is:
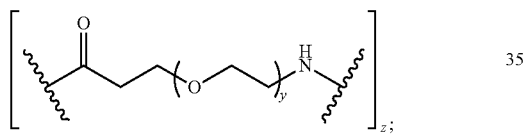
wherein y=1-100 and z=1-10.
In some embodiments, the solid line between A and B represents a nonpeptidyl linkage comprising the structure:
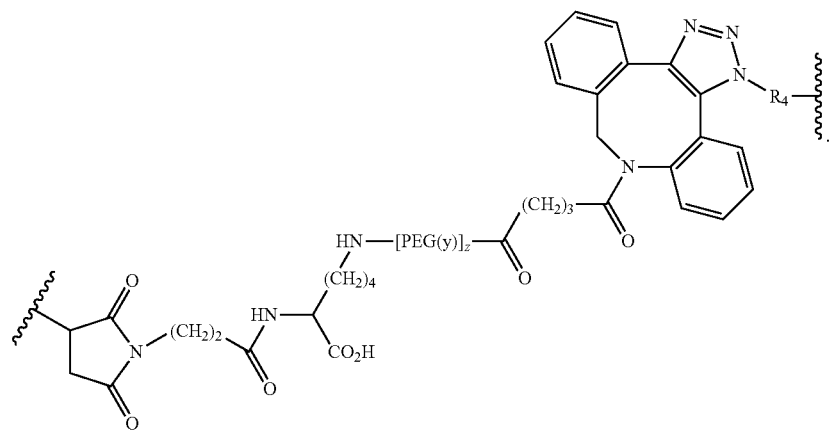

In some embodiments, the solid line between A and B represents a nonpeptidyl linkage comprising the structure:
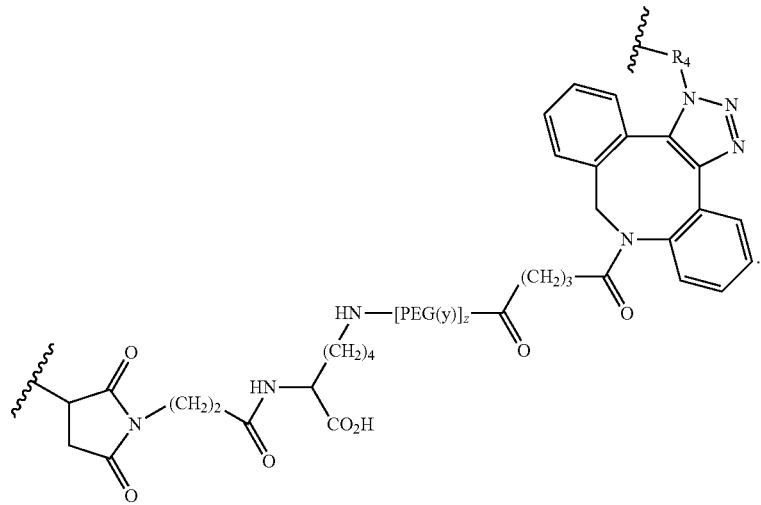
In some embodiments, the solid line between A and B represents a nonpeptidyl linkage comprising the structure:
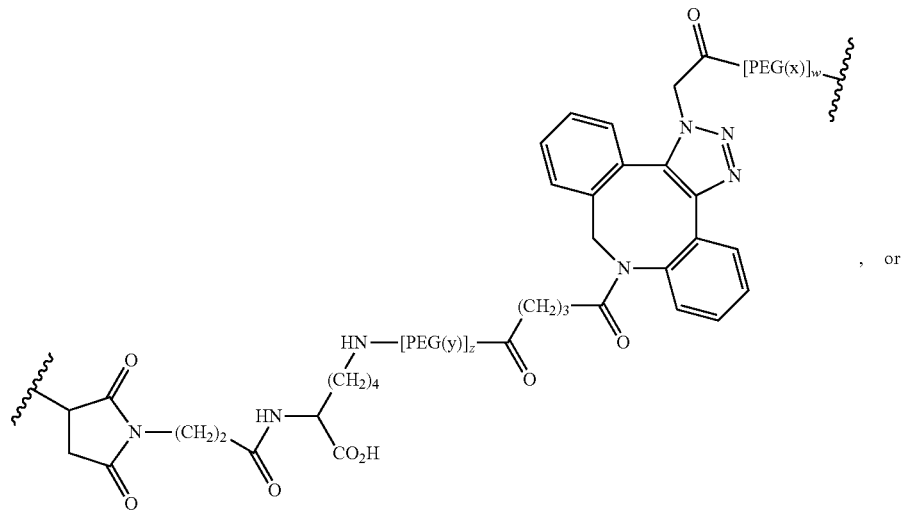
, or
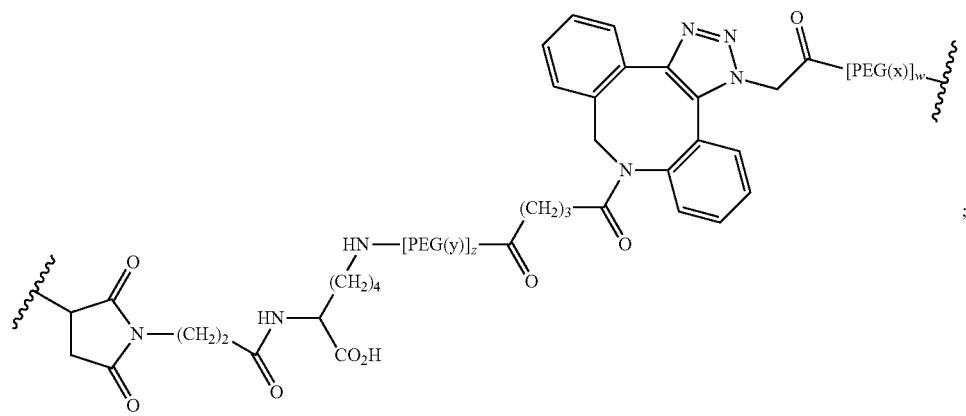
;

wherein [PEG(y)]z is:

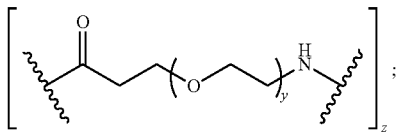

wherein y=1-100 and z=1-10;
wherein [PEG(x)]w is:

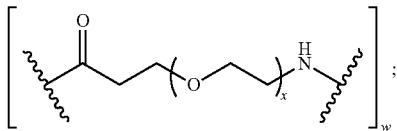

wherein x=1-100 and w=1-10.
In some embodiments, y is 1-20.
In some embodiments, y is 21-40.
In some embodiments, y is 41-60.
In some embodiments, y is 61-80.
In some embodiments, y is 30-50
In some embodiments, y is 12, 24, 36 or 48.
In some embodiments, z is 1.
In some embodiments, z is 0.
In some embodiments, the terminal carbonyl is of the [PEG(y)]z group is part of an amide bond.
In some embodiments, the terminal amine of the [PEG(y)]z group is part of an amide bond.
In some embodiments, $R_4$ is

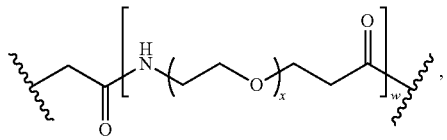

wherein x is 1-100, and w is 0-5.
In some embodiments, x is 1-20.
In some embodiments, x is 21-40.
In some embodiments, x is 41-60.
In some embodiments, x is 61-80.
In some embodiments, x is 30-50
In some embodiments, x is 12, 24, 36 or 48.
In some embodiments, w is 1.
In some embodiments, w is 0.
In some embodiments, $R_4$ has the structure:

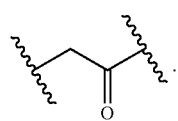

In some embodiments, $R_4$ is attached to B via the terminal carbonyl carbon.
In some embodiments, the solid line between A and B represents a nonpeptidyl linkage comprising the structure:

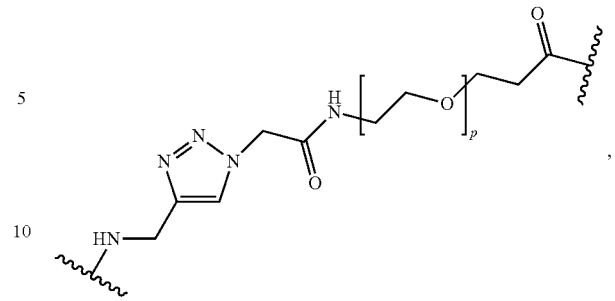

wherein p=0-5, 0-10, 0-50, or 0-100.
In some embodiments, $R_2$ is attached to A via a carbon-nitrogen bond or a carbon-sulfur bond.
In some embodiments, $R_2$ is attached to A via a carbon-nitrogen bond.
In some embodiments, the carbon-nitrogen bond is an amide bond.
In some embodiments, $R_2$ is attached to A via an amide bond between the C-terminal amino acid of A and an amino group in B.
In some embodiments, the terminal amino acid is cysteine.
In some embodiments, $R_2$ is attached to A via a carbon-sulfur bond.
In some embodiments, $R_2$ is attached to A via a carbon-sulfur bond formed between $R_2$ and a free thiol.
In some embodiments, $R_2$ is attached to A via a succinimide-sulfur bond.
In some embodiments, J comprises a branched residue.
In some embodiments, J is attached to more than one A via the branched residue.
In some embodiments, B comprises a branched residue.
In some embodiments, B is linked to more than one A, each via a nonpeptidyl linkage with the branched residue.
In some embodiments, B is an organic acid residue.
In some embodiments, B is a stretch of 1-50 amino acid residues, and optionally, an organic acid residue.
In some embodiments, B is a stretch of 1-10 consecutive amino acids.
In some embodiments, B comprises a stretch of consecutive amino acids in the sequence, or a portion thereof, EPKSCDKTHTCPPCP (SEQ ID NO: 135), ERKCCVECPPCP (SEQ ID NO: 136), ELKTPLGDTTH-TCPRCP(EPKSCDTPPPCPRCP)3 (SEQ ID NO: 137), ESKYGPPCPSCP (SEQ ID NO: 138).
In some embodiments, B has a threonine at its C-terminus.
In some embodiments, B is linked to C via a peptidyl linkage between the N-terminal cysteine or selenocysteine of C and an amino acid residue or an organic acid residue of B.
In some embodiments, C is a second polypeptide component of the compound, which polypeptide component comprises consecutive amino acids which (i) are identical to a stretch of consecutive amino acids present in a chain of an $F_c$ domain of an antibody; (ii) bind to an $F_c$ receptor; and (iii) have at their N-terminus a sequence comprising a naturally occurring cysteine selected from the group consisting of CP, CPXCP (where X=P, R, or S) (SEQ ID NOs: 128-130), CDKTHTCPPCP (SEQ ID NO: 131), CVECPPCP (SEQ ID NO: 132), CCVECPPCP (SEQ ID NO: 133) and CDTPPPCPRCP (SEQ ID NO: 134).

In some embodiments, C is a second polypeptide component of the compound, which polypeptide component comprises consecutive amino acids which (i) are identical to a stretch of consecutive amino acids present in a chain of an $F_c$ domain of an antibody; (ii) bind to an $F_c$ receptor; and (iii) have at their N-terminus a sequence comprising a non-naturally occurring cysteine or selenocysteine.

In some embodiments, C comprises consecutive amino acids which are identical to a stretch of consecutive amino acids present in the chain of an Fc domain of an antibody selected from the group consisting of IgG, IgM, IgA, IgD, and IgE.

In some embodiments, C comprises consecutive amino acids which are identical to a stretch of consecutive amino acids present in the chain of an Fcε domain of an antibody.

In some embodiments, A comprises a secreted protein.

In some embodiments, A comprises an extracellular domain of a protein.

In some embodiments, A has biological activity.

In some embodiments, the biological activity is target-binding activity.

In some embodiments, the A is an independently-folding protein or a portion thereof.

In some embodiments, A is a glycosylated protein.

In some embodiments, A comprises intra-chain disulfide bonds.

In some embodiments, A binds a cytokine.

In some embodiments, the cytokine is INFα.

In some embodiments, A comprises at least one stretch of consecutive amino acids which are identical to a stretch of consecutive amino acids present in the heavy chain of a Fab or a Fab' of an antibody.

In some embodiments, A comprises at least one at least one stretch of consecutive amino acids which are identical to a stretch of consecutive amino acids present in the light chain of a Fab or a Fab' of an antibody.

In some embodiments, A comprises at least one Fab or Fab' of an antibody, or a portion of the at least one Fab or Fab'.

In some embodiments, A comprises at least 2, 3, 4, 5, 6, 7, 8, 9, or 10 copies of the Fab or Fab' or portion thereof.

In some embodiments, A comprises Fab-1 or Fab'1, or a portion thereof of the antibody.

In some embodiments, A comprises Fab-2 or Fab'2, or a portion thereof of the antibody.

In some embodiments, A comprises two Fab or Fab' hands of the antibody.

In some embodiments, the Fab or Fab' is present in adalimumab

In some embodiments, A comprises at least one stretch of consecutive amino acids which are identical to a stretch of consecutive amino acids present in a single chain antibody.

In some embodiments, A comprises at least one stretch of consecutive amino acids which are identical to a stretch of consecutive amino acids present in a TNFα receptor.

In some embodiments, the TNFα receptor is TNR1B.

In some embodiments, the compound forms part of a homodimer.

In some embodiments, the compound forms part of a heterodimer.

The present invention provides a homodimer comprising a compound of the invention.

The present invention provides a heterodimer comprising a compound of the invention.

In some embodiments, each compound of the dimer is capable of binding to the other by at least one disulfide bond.

In some embodiments, each compound of the dimer is capable of binding to the other by at least one disulfide bond between the C of each compound.

In some embodiments, each compound of the dimer is bound to the other by at least one disulfide bond.

In some embodiments, each compound of the dimer is bound to the other by at least one disulfide bond between the C of each compound.

In some embodiments, each compound of the dimer is non-covalently bound to the other.

The present invention provides a process for producing a compound having the structure:

wherein A is a first polypeptide component of the compound;
wherein C is a second polypeptide component of the compound, which polypeptide component comprises consecutive amino acids which (i) are identical to a stretch of consecutive amino acids present in a chain of an $F_c$ domain of an antibody; (ii) bind to an $F_c$ receptor; and (iii) have at their N-terminus a sequence selected from the group consisting of a cysteine, selenocysteine, CP, CPXCP (where X=P, R, or S) (SEQ ID NOs: 128-130), CDKTHTCPPCP (SEQ ID NO: 131), CVECPPCP (SEQ ID NO: 132), CCVECPPCP (SEQ ID NO: 133) and CDTPPPCPRCP (SEQ ID NO: 134),
wherein B is a chemical structure linking A and C;
wherein the dashed line between B and C represents a peptidyl linkage;
wherein the solid line between A and B represents a non-peptidyl linkage comprising the structure:

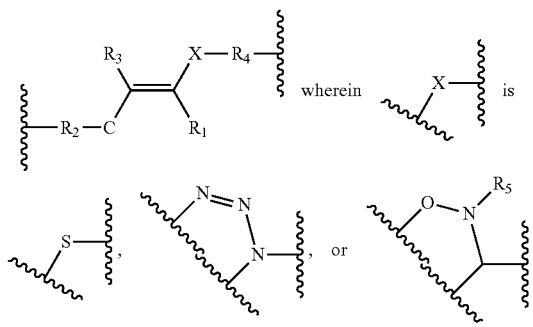

in which $R_5$ is an alkyl or aryl group
wherein $R_1$ is H or is part of an additional structure that is a cyclic structure, wherein the additional cyclic structure comprises $R_1$ or a portion of $R_1$, and may also comprise $R_2$ or a portion of $R_2$, and the carbon between $R_2$ and the alkene double bond;
with the proviso that if

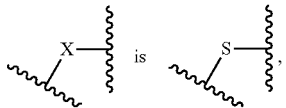

$R_3$ is a H;

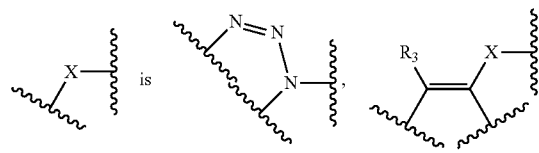

if is a triazole ring that comprises

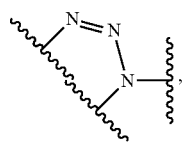

and if

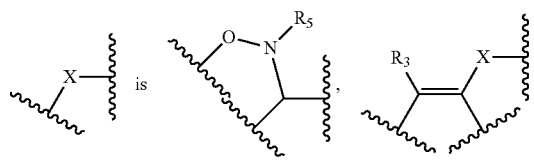

is a N-alkyl or aryl substituted isoxazoline ring that comprises

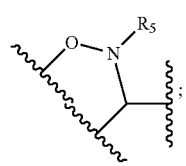

and
wherein $R_2$ represents an organic structure which connects to one of A or B and $R_4$ represents an organic structure which connects to the other of A or B;
which comprises the following steps:
a) obtaining an A' which comprises A or a derivative of A, and a first terminal reactive group;
b) obtaining a B' which comprises B or a derivative of B, a second terminal reactive group and a third terminal reactive group, wherein the second terminal reactive group is capable of reacting with the first terminal reactive group to form a non-peptidyl linkage;
c) obtaining a C' which comprises C or a derivative of C, and a fourth terminal reactive group, wherein the fourth terminal reactive group is capable of reacting with the third terminal reactive group to form a peptidyl linkage; and
d) reacting A', B' and C' in any order to produce the compound.

In some embodiments, step d) is performed by first reacting A' and B' to produce $$\begin{array}{c} A \\ | \\ B'', \end{array}$$

wherein B" comprises B and the third terminal reactive group, and the solid line between B" and A represents a non-peptidyl linkage; and then reacting $$\begin{array}{c} A \\ | \\ B'' \end{array}$$

with C' to produce the compound.

In some embodiments, step d) is performed by first reacting C' and B' to produce $$\begin{array}{c} B''; \\ \vdots \\ C \end{array}$$

wherein B" comprises B and the second terminal reactive group, and the dashed line between B" and C represents a peptidyl linkage; and then reacting $$\begin{array}{c} B'' \\ \vdots \\ C \end{array}$$

with A' to produce the compound.

In some embodiments, the first terminal reactive group is an azide, a thiol, a nitrone or an alkyne.
In some embodiments, the first terminal reactive group is an alkyne.
In some embodiments, the alkyne is a cycloalkyne
In some embodiments, the alkyne is an eight-membered ring.
In some embodiments, the alkyne is an azacyclooctyne.
In some embodiments, the cycloalkyne is a biarylazacyclooctyne.
In some embodiments, the cycloalkyne is a cyclooctyne.
In some embodiments, the alkyne is a terminal alkyne.
In some embodiments, the first terminal reactive group is an azide, thiol or nitrone.
In some embodiments, the first terminal reactive group is an azide.
In some embodiments, the first terminal reactive group is a thiol.
In some embodiments, the first terminal reactive group is a nitrone.
In some embodiments, the first terminal reactive group is an N-alkyl nitrone.
In some embodiments, the first terminal reactive group is an N-aryl nitrone.
In some embodiments, the second terminal reactive group is an azide, a thiol, a nitrone or an alkyne.
In some embodiments, the second terminal reactive group is an alkyne.
In some embodiments, the alkyne is a cycloalkyne
In some embodiments, the alkyne is an eight-membered ring.
In some embodiments, the alkyne is an azacyclooctyne.
In some embodiments, the cycloalkyne is a biarylazacyclooctyne.
In some embodiments, the cycloalkyne is a cyclooctyne.
In some embodiments, the alkyne is a terminal alkyne.
In some embodiments, the second terminal reactive group is an azide, thiol or nitrone.

In some embodiments, the second terminal reactive group is an azide.

In some embodiments, the second terminal reactive group is a thiol.

In some embodiments, the second terminal reactive group is a nitrone.

In some embodiments, the second terminal reactive group is an N-alkyl nitrone.

In some embodiments, the second terminal reactive group is an N-aryl nitrone.

In some embodiments, the first terminal reactive group is a terminal alkyne and the second terminal reactive group is an azide, thiol or nitrone.

In some embodiments, the second terminal reactive group is an azide.

In some embodiments, the second terminal reactive group is a thiol.

In some embodiments, the second terminal reactive group is a nitrone.

In some embodiments, the nitrone is an N-alkyl or N-aryl nitrone.

In some embodiments, the first terminal reactive group is an azide, thiol or nitrone, and the second terminal reactive group is a terminal alkyne.

In some embodiments, the first terminal reactive group is an azide.

In some embodiments, the first terminal reactive group is a thiol.

In some embodiments, the first terminal reactive group is a nitrone.

In some embodiments, the nitrone is an N-alkyl or N-aryl nitrone.

In some embodiments, the first terminal reactive group is a cycloalkyne and the second terminal reactive group is an azide, thiol or nitrone.

In some embodiments, the first terminal reactive group is an azide.

In some embodiments, the first terminal reactive group is a thiol.

In some embodiments, the first terminal reactive group is a nitrone.

In some embodiments, the nitrone is an N-alkyl or N-aryl nitrone.

In some embodiments, the first terminal reactive group is an azide, thiol or nitrone, and the second terminal reactive group is a cycloalkyne.

In some embodiments, the first terminal reactive group is an azide.

In some embodiments, the first terminal reactive group is a thiol.

In some embodiments, the first terminal reactive group is a nitrone.

In some embodiments, the nitrone is an N-alkyl or N-aryl nitrone.

In some embodiments, the cycloalkyne is an eight-membered ring.

In some embodiments, the alkyne is an azacyclooctyne.

In some embodiments, the cycloalkyne is a biarylazacyclooctyne.

In some embodiments, the cycloalkyne is a cyclooctyne.

In some embodiments, the first terminal reactive group is an azide and the second terminal reactive group is a terminal alkyne; or the second terminal reactive group is an azide and the first terminal reactive group is a cycloalkyne; or the first terminal reactive group is a thiol and the second terminal reactive group is a cycloalkyne; or the first terminal reactive group is a N-alkyl nitrone or N-aryl nitrone and the second terminal reactive group is a cyclooctyne.

In some embodiments, the second terminal reactive group is an azide and the first terminal reactive group is a terminal alkyne; or the second terminal reactive group is an azide and the first terminal reactive group is a cycloalkyne; or the second terminal reactive group is a thiol and the first terminal reactive group is a cycloalkyne; or the second terminal reactive group is a N-alkyl nitrone or N-aryl nitrone and the first terminal reactive group is a cyclooctyne.

In some embodiments, the first terminal reactive group and the second terminal reactive group react to produce a triazole, thiolene, N-alkyl isoxazoline or N-aryl isoxazoline.

In some embodiments, the first terminal reactive group and the second terminal reactive group react to produce a triazole.

In some embodiments, the first terminal reactive group and the second terminal reactive group react to produce a thiolene.

In some embodiments, the first terminal reactive group and the second terminal reactive group react to produce a N-alkyl isoxazoline or N-aryl isoxazoline.

In some embodiments, the the the third reactive group and the fourth terminal reactive group are each independently an amino acid or amino acid derivative.

In some embodiments, the third reactive group is a threonine or threonine derivative.

In some embodiments, the third reactive group is a thioester derivative of an amino acid.

In some embodiments, the fourth reactive group is cysteine, selenocysteine, homocysteine, or homoselenocysteine, or a derivative of cysteine, selenocysteine, homocysteine, or homoselenosysteine.

In some embodiments, the fourth reactive group is cysteine or a derivative of cysteine.

In some embodiments, the fourth reactive group is cysteine.

In some embodiments, A' is prepared by the following steps:
  i) obtaining an A" which comprises A or a derivative of A, and a stretch of consecutive amino acids comprising an intein;
  ii) obtaining a substituted cysteine, selenocysteine, homocysteine, or homoselenosysteine residue, or a substituted derivative of a cysteine, selenocysteine, homocysteine, or homoselenosysteine residue, wherein the cysteine residue is substituted at the C-terminus with an organic structure containing an alkyne, an azide, a thiol, or a nitrone; and
  iii) reacting A" with the substituted cysteine residue to produce A'.

In some embodiments, the organic structure containing an alkyne is N-propargyl amine.

In some embodiments, A' is prepared by the following steps:
  i) obtaining an A" which comprises A or a derivative of A, and which comprises at least one free thiol group;
  ii) obtaining a compound which comprises a first terminal reactive group and a terminal maleimide; and
  iii) reacting A" with the compound of step ii) to produce A'.

In some embodiments, A" is prepared by the following steps:
  a) obtaining an A'", wherein A'" is a polypeptide which comprises A or a derivative of A, and which comprises at least one disulfide bond; and b) treating A''' with mercaptoethylamine (MEA) to produce A''''.

In some embodiments, the A''' is prepared by the following steps:
  a) obtaining a monoclonal antibody which comprises A or derivative of A, and which comprises at least one disulfide bond; and
  b) treating the polypeptide of step a) with IdeS to produce A'''.

In some embodiments, the monoclonal antibody binds INFα.

In some embodiments, the monoclonal antibody is adalimumab.

In some embodiments, any one of the compounds of the invention is produced.

In some embodiments, if $R_1$ is hydrogen and the first terminal reactive group is alkyne, then in step d) B' is reacted in the presence of a metal catalyst.

In some embodiments, if $R_1$ is hydrogen and the second terminal reactive group is alkyne, then in step d) B' is reacted in the presence of a metal catalyst.

In some embodiments, the metal catalyst is Ag(I) or Cu(I).

In some embodiments, A' comprises one or more branched residue, wherein each branched residue comprises an additional first terminal reactive group.

In some embodiments, B' comprises one or more branched residue, wherein each branched residue comprises an additional second terminal reactive group.

In some embodiments, B' comprises one or more branched residue, wherein each branched residue comprises an additional third terminal reactive group.

In some embodiments, the branched residue is an amino acid residue.

In some embodiments, the amino acid residue is a lysine or a lysine derivative, arginine or an arginine derivative, aspartic acid or an aspartic acid derivative, glutamic acid or a glutamic acid derivative, asparagines or a asparagines derivative, glutamine or glutamine derivative, tyrosine or tyrosine derivative, cysteine or cysteine derivative or ornithine or ornithine derivative.

In some embodiments, the amino acid residue is substituted at the N-position with a residue containing a terminal amino or carbony reactive group.

In some embodiments, the branched residue is an organic residue containing two or more terminal amino groups or two or more terminal carbonyl groups.

In some embodiments, the organic residue is iminodipropionic acid, iminodiacetic acid, 4-amino-pimelic acid, 4-amino-heptanedioic acid, 3-aminohexanedioic acid, 3-aminoadipic acid, 2-aminooctanedioic acid, or 2-amino-6-carbonyl-heptanedioic acid.

In some embodiments, the branched residue is a lysine or a lysine derivative, arginine or an arginine derivative, aspartic acid or an aspartic acid derivative, glutamic acid or a glutamic acid derivative, asparagines or a asparagines derivative, glutamine or glutamine derivative, tyrosine or tyrosine derivative, cysteine or cysteine derivative or ornithine or ornithine derivative.

In some embodiments, the branched residue is an amino acid substituted at the N-position with a residue containing a terminal amino or carbonyl reactive group.

In some embodiments, the branched residue is an organic residue containing two or more terminal amino groups or two or more terminal carbonyl groups.

In some embodiments, the branched residue is an organic residue containing two or more terminal amino groups. In some embodiments, the branched residue is an organic residue containing two or more terminal carbonyl groups. In some embodiments, the branched residue is a diaminopropionic acid. In some embodiments, the branched residue is a diaminopropionic carbonyl compound.

In some embodiments, the branched residue is 4-(carbonylmethoxy)phenylalanine, 2-amino-6-(carbonylmethylamino)hexanoic acid, S-(carbonylpropyl)cysteine, S-(carbonylethyl)cysteine, S-(carbonylmethyl)cysteine, N-(carbonylethyl)glycine, N-(carbonylmethyl)glycine, iminodipropionic acid, iminodiacetic acid, 4-amino-pimelic acid, 4-amino-heptanedioic acid, 3-aminohexanedioic acid, 3-aminoadipic acid, 2-aminooctanedioic acid, or 2-amino-6-carbonyl-heptanedioic acid.

In some embodiments, the branched residue is prepared from Fmoc-L-Asp-AMC, Fmoc-L-Asp-pNA, Fmoc-L-Glu-AMC, Fmoc-L-Glu-pNA, Fmoc-L-Glu(Edans)-OH, Fmoc-L-Glu(PEG-biotinyl)-OH, (S)-Fmoc-2-amino-hexanedioic acid-6-tert-butyl ester, (S)-Fmoc-2-amino-adipic acid-6-tert-butyl ester, (S)-Fmoc-Aad(OtBu)-OH, (S)-Fmoc-2-amino-5-tert-butoxycarbonyl-hexanedioic acid-6-tert-butyl ester, (S)-Fmoc-2-amino-heptanedioic acid-7-tert-butyl ester, (S)-Fmoc-2-amino-pimelic acid-7-tert-butyl ester, (S)-Fmoc-2-amino-6-tert-butoxycarbonyl-heptanedioic acid-7-tert-butyl ester, (S)-Fmoc-2-amino-octanedioic acid-8-tert-butyl ester, (S)-Fmoc-2-amino-suberic acid-8-tert-butyl ester, (S)-Fmoc-Asu(OtBu)-OH, (R)-Fmoc-3-amino-hexanedioic acid-1-tert-butyl ester, (R)-Fmoc-3-amino-adipic acid-1-tert-butyl ester, (R)-Fmoc-4-amino-heptanedioic acid-1-tert-butyl ester, (R)-iminodiacetic acid, Fmoc-iminodiacetic acid, Boc-iminodipropionic acid, Fmoc-iminodipropionic acid, Fmoc-N-(tert-butoxycarbonylmethyl)-glycine, Fmoc-N-(tert-butoxycarbonylethyl)-glycine, Fmoc-L-Cys(tert-butoxycarbonylmethyl)-OH (R)-Fmoc-2-amino-3-(tert-butoxycarbonylmethylsulfanyl)-propionic acid, Fmoc-L-Cys(tert-butoxycarbonylpropyl)-OH (R)-Fmoc-2-amino-3-(3-tert-butoxycarbonylpropylsulfanyl)-propionic acid, Fmoc-L-Cys(tert-butoxycarbonylethyl)-OH (R)-Fmoc-2-amino-3-(2-tert-butoxycarbonylethylsulfanyl)-propionic acid, Fmoc-4-(tert-butoxycarbonylmethoxy)-L-phenylalanine, or (S)-Fmoc-2-amino-6-(Boc-tert-butoxycarbonylmethylamino)-hexanoic acid.

In some embodiments, the branched residue is prepared from N-α-Boc-DL-diaminopropionic acid, N-α-Boc-D-diaminopropionic acid, N-α-Boc-L-diaminopropionic acid, N-α-Fmoc-L-diaminopropionic acid, N-α-Boc-N-β-Alloc-D-diaminopropionic acid, N-α-Boc-N-β-Alloc-L-diaminopropionic acid, N-α-Fmoc-N-β-alloc-L-diaminopropionic acid, N-α-N-β-Bis-Boc-L-diaminopropionic acid, N-α-Fmoc-N-β-Boc-D-diaminopropionic acid, N-α-Fmoc-N-β-Boc-L-diaminopropionic acid, N-α-Z—N-β-Boc-L-diaminopropionic acid, N-α-Boc-N-β-Fmoc-D-diaminopropionic acid, N-α-Boc-N-β-Fmoc-L-diaminopropionic acid, N-α-N-β-Bis-Fmoc-L-diaminopropionic acid, N-α-Z—N-β-Fmoc-L-diaminopropionic acid, N-α-Boc-N-β-Z-L-diaminopropionic acid, N-α-Fmoc-N-β-Z-L-diaminopropionic acid, N-α-Fmoc-N-β-(Boc-aminooxyacetyl)-L-diaminopropionic acid, N-α-Boc-N-gamma-Fmoc-D-diaminobutyric acid, N-α-Boc-N-gamma-Fmoc-L-diaminobutyric acid, N-α-Boc-N-gamma-Fmoc-L-diaminobutyric acid, N-α-Fmoc-N-gamma-Boc-D-diaminobutyric acid, N-α-Fmoc-N-gamma-Boc-L-diaminobutyric acid, N-α-Fmoc-N-gamma-Alloc-L-diaminobutyric acid, (S)—N-b-Fmoc-N-gamma-Boc-3,4-diaminobutyric acid, H-L-ornithine, N-a-Boc-N-delta-Alloc-L-ornithine, N-a-Fmoc-N-delta-Alloc-L-ornithine, N-a-Fmoc-N-delta-Boc-L-ornithine, (S)-Boc-2-amino-5- azido-pentanoic acid.DCHA, (S)-Fmoc-2-amino-5-azido-pentanoic acid, N-a-N-delta-bis-Boc-N-a-N-delta-bis(3-Boc-aminopropyl)-L-ornithine, N-α-Boc-N-β-N-delta-N-delta-tris(3-Boc-aminopropyl)-L-ornithine, Fmoc-L-Lys (Biotin)-OH, Fmoc-L-Lys(Dabcyl)-OH, Fmoc-L-Lys(Boc) (Me)-OH, Fmoc-L-Lys(Boc)(iPr)-OH, (2S,5R)-Fmoc-2-amino-4-(3-Boc-2,2-dimethyl-oxazolidin-5-yl)-butyric acid, (S)-Fmoc-2-amino-6-(Boc-tert-butoxycarbonylmethyl-amino)-hexanoic acid, (S)-Fmoc-2-amino-7-(Boc-amino)-heptanoic acid, Fmoc-L-Arg(Me)(Pbf)-OH, Fmoc-L-Arg(Me)2(Pbf)-OH, Fmoc-L-Arg(Me)2-OH, (S)-Fmoc-3-amino-5-[(N'-Pbf-pyrrolidine-1-carboximidoyl)-amino]-pentanoic acid, Fmoc-L-Homoarg(Et)2-OH, Boc-3-amino-5-(Fmoc-amino)-benzoic acid, 3,5-bis[2-(Boc-amino)ethoxy]-benzoic acid, Fmoc-4-[2-(Boc-amino)ethoxy]-L-phenylalanine, N,N-bis(N'-Fmoc-3-aminopropyl)-glycine potassium hemisulfate, N,N-bis(N'-Fmoc-3-aminopropyl)-glycine potassium hemisulfate, Fmoc-N-(2-Boc-aminoethyl)-glycine, Fmoc-N-(3-Boc-aminopropyl)-glycine, Fmoc-N-(4-Boc-aminobutyl)-glycine, (R,S)—N-α-Fmoc-N-α'-Boc-diaminoacetic acid, N,N'-bis-Fmoc-diaminoacetic acid, (S)—N-4-Fmoc-N-8-Boc-diaminooctanoic acid, (R,S)—N-Fmoc-N'-Boc-imidazolidine-2-carboxylic acid, Fmoc-p(NH-Boc)-L-Phe-OH, Boc-p(NH-Fmoc)-L-Phe-OH, or Boc-p(NH—Z)-L-Phe-OH.

Each embodiment disclosed herein is contemplated as being applicable to each of the other disclosed embodiments. Thus, all combinations of the various elements described herein are within the scope of the invention.

It is understood that where a parameter range is provided, all integers within that range, and tenths thereof, are also provided by the invention. For example, "0.2-5 mg/kg/day" is a disclosure of 0.2 mg/kg/day, 0.3 mg/kg/day, 0.4 mg/kg/day, 0.5 mg/kg/day, 0.6 mg/kg/day etc. up to 5.0 mg/kg/day.

Terms

As used herein, and unless stated otherwise, each of the following terms shall have the definition set forth below.

Peptidyl linkage: the structure

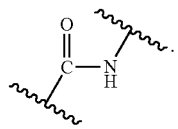 [SMILES: *NC(*)=O]

A peptidyl linkage may be a peptide bond.

Stretch of consecutive amino acids: a plurality of amino acids arranged in a chain, each of which is joined to a preceding amino acid by a peptide bond, excepting that the first amino acid in the chain may optionally not be joined to a preceding amino acid. The amino acids of the chain may be naturally or non-naturally occurring, or may comprise a mixture thereof. The amino acids, unless otherwise indicated, may be genetically encoded, naturally-occurring but not genetically encoded, or non-naturally occurring, and any selection thereof.

N-terminal amino acid residue: the terminal residue of a stretch of two or more consecutive amono acids having a free α-amino (NH$_2$) functional group, or a derivative of an α-amino (NH$_2$) functional group.

N-terminus: the free α-amino (NH$_2$) group (or derivative thereof) of a N-terminal amino acid residue.

C-terminal amino acid residue: the terminal residue of a stretch of two or more consecutive amono acids having a free α-carboxyl (COOH) functional group, or a derivative of a α-carboxyl (COOH) functional group.

C-terminus: the free a-carboxyl (COOH) group (or derivative thereof) of a C-terminal amino acid residue.

A "bond", unless otherwise specified, or contrary to context, is understood to include a covalent bond, a dipole-dipole interaction such as a hydrogen bond, and intermolecular interactions such as van der Waals forces.

A "Signal Sequence" is a short (3-60 amino acids long) peptide chain that directs the post-translational transport of a polypeptide.

"Amino acid" as used herein, in one embodiment, means a L or D isomer of the genetically encoded amino acids, i.e. isoleucine, alanine, leucine, asparagine, lysine, aspartate, methionine, cysteine, phenylalanine, glutamate, threonine, glutamine, tryptophan, glycine, valine, proline, arginine, serine, histidine, tyrosine, selenocysteine, pyrrolysine and also includes homocysteine and homoselenocysteine.

Other examples of amino acids include an L or D isomer of taurine, gaba, dopamine, lanthionine, 2-aminoisobutyric acid, dehydroalanine, ornithine and citrulline, as well as non-natural homologues and synthetically modified forms thereof including amino acids having alkylene chains shortened or lengthened by up to two carbon atoms, amino acids comprising optionally substituted aryl groups, and amino acids comprising halogenated groups, including halogenated alkyl and aryl groups as well as beta or gamma amino acids, and cyclic analogs.

Due to the presence of ionizable amino and carboxyl groups, the amino acids in these embodiments may be in the form of acidic or basic salts, or may be in neutral forms. Individual amino acid residues may also be modified by oxidation or reduction. Other contemplated modifications include hydroxylation of proline and lysine, phosphorylation of hydroxyl groups of seryl or threonyl residues, and methylation of the alpha-amino groups of lysine, arginine, and histidine side chains.

Covalent derivatives may be prepared by linking particular functional groups to the amino acid side chains or at the N- or C-termini.

Compounds comprising amino acids with R-group substitutions are within the scope of the invention. It is understood that substituents and substitution patterns on the compounds of the instant invention can be selected by one of ordinary skill in the art to provide compounds that are chemically stable from readily available starting materials.

"Natural amino acid" as used herein means a L or D isomer of the genetically encoded amino acids, i.e. isoleucine, alanine, leucine, asparagine, lysine, aspartate, methionine, cysteine, phenylalanine, glutamate, threonine, glutamine, tryptophan, glycine, valine, proline, arginine, serine, histidine, tyrosine, selenocysteine, pyrrolysine and homocysteine and homoselenocysteine.

"Non-natural amino acid" as used herein means a chemically modified L or D isomer of isoleucine, alanine, leucine, asparagine, lysine, aspartate, methionine, cysteine, phenylalanine, glutamate, threonine, glutamine, tryptophan, glycine, valine, proline, arginine, serine, histidine, tyrosine, selenocysteine, pyrrolysine, homocysteine, homoselenocysteine, taurine, gaba, dopamine, lanthionine, 2-aminoisobutyric acid, dehydroalanine, ornithine or citrulline, including cysteine and selenocysteine derivatives having $C_3$-$C_{10}$ aliphatic side chains between the alpha carbon and the S or Se. In one embodiment the aliphatic side chain is an alkylene. In another embodiment, the aliphatic side chain is an alkenylene or alkynylene.

In addition to the stretches of consecutive amino acid sequences described herein, it is contemplated that variants thereof can be prepared by introducing appropriate nucleotide changes into the encoding DNA, and/or by synthesis of the desired consecutive amino acid sequences. Those skilled in the art will appreciate that amino acid changes may alter post-translational processes of the stretches of consecutive amino acids described herein when expression is the chosen method of synthesis (rather than chemical synthesis for example), such as changing the number or position of glycosylation sites or altering the membrane anchoring characteristics.

Variations in the sequences described herein, can be made, for example, using any of the techniques and guidelines for conservative and non-conservative mutations set forth, for instance, in U.S. Pat. No. 5,364,934. Variations may be a substitution, deletion or insertion of one or more codons encoding the consecutive amino acid sequence of interest that results in a change in the amino acid sequence as compared with the native sequence. Optionally the variation is by substitution of at least one amino acid with any other amino acid in one or more of the domains. Guidance in determining which amino acid residue may be inserted, substituted or deleted without adversely affecting the desired activity may be found by comparing the sequence with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence. It is understood that any terminal variations are made within the context of the invention disclosed herein.

Amino acid sequence variants of the binding partner are prepared with various objectives in mind, including increasing the affinity of the binding partner for its ligand, facilitating the stability, purification and preparation of the binding partner, modifying its plasma half life, improving therapeutic efficacy, and lessening the severity or occurrence of side effects during therapeutic use of the binding partner.

Amino acid sequence variants of these sequences are also contemplated herein including insertional, substitutional, or deletional variants. Such variants ordinarily can prepared by site-specific mutagenesis of nucleotides in the DNA encoding the target-binding monomer, by which DNA encoding the variant is obtained, and thereafter expressing the DNA in recombinant cell culture. Fragments having up to about 100-150 amino acid residues can also be prepared conveniently by in vitro synthesis. Such amino acid sequence variants are predetermined variants and are not found in nature. The variants exhibit the qualitative biological activity (including target-binding) of the nonvariant form, though not necessarily of the same quantative value. While the site for introducing an amino acid sequence variation is predetermined, the mutation per se need not be predetermined. For example, in order to optimize the performance of a mutation at a given site, random or saturation mutagenesis (where all 20 possible residues are inserted) is conducted at the target codon and the expressed variant is screened for the optimal combination of desired activities. Such screening is within the ordinary skill in the art.

Amino acid insertions usually will be on the order of about from 1 to 10 amino acid residues; substitutions are typically introduced for single residues; and deletions will range about from 1 to 30 residues. Deletions or insertions preferably are made in adjacent pairs, i.e. a deletion of 2 residues or insertion of 2 residues. It will be amply apparent from the following discussion that substitutions, deletions, insertions or any combination thereof are introduced or combined to arrive at a final construct.

In an aspect, the invention concerns a compound comprising a stretch of consecutive amino acids having at least about 80% sequence identity, preferably at least about 81% sequence identity, more preferably at least about 82% sequence identity, yet more preferably at least about 83% sequence identity, yet more preferably at least about 84% sequence identity, yet more preferably at least about 85% sequence identity, yet more preferably at least about 86% sequence identity, yet more preferably at least about 87% sequence identity, yet more preferably at least about 88% sequence identity, yet more preferably at least about 89% sequence identity, yet more preferably at least about 90% sequence identity, yet more preferably at least about 91% sequence identity, yet more preferably at least about 92% sequence identity, yet more preferably at least about 93% sequence identity, yet more preferably at least about 94% sequence identity, yet more preferably at least about 95% sequence identity, yet more preferably at least about 96% sequence identity, yet more preferably at least about 97% sequence identity, yet more preferably at least about 98% sequence identity and yet more preferably at least about 99% sequence identity to an amino acid sequence disclosed in the specification, a figure, a SEQ ID NO. or a sequence listing of the present application.

The % amino acid sequence identity values can be readily obtained using, for example, the WU-BLAST-2 computer program (Altschul et al., Methods in Enzymology 266:460-480 (1996)).

Fragments of native sequences are provided herein. Such fragments may be truncated at the N-terminus or C-terminus, or may lack internal residues, for example, when compared with a full length native protein. Again, it is understood that any terminal variations are made within the context of the invention disclosed herein. Certain fragments lack amino acid residues that are not essential for a desired biological activity of the sequence of interest.

Any of a number of conventional techniques may be used. Desired peptide fragments or fragments of stretches of consecutive amino acids may be chemically synthesized. An alternative approach involves generating fragments by enzymatic digestion, e.g. by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired polypeptide/sequence fragment, by polymerase chain reaction (PCR). Oligonucleotides that define the desired termini of the DNA fragment are employed at the 5' and 3' primers in the PCR.

In particular embodiments, conservative substitutions of interest are shown in Table 1 under the heading of preferred substitutions. If such substitutions result in a change in biological activity, then more substantial changes, denominated exemplary substitutions in Table 1, or as further described below in reference to amino acid classes, are introduced and the products screened.

TABLE 1

| Original | Exemplary | Preferred |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in function or immunological identity of the sequence are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro;
(6) aromatic: trp, tyr, phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis (Carter et al., Nucl. Acids Res., 13:4331 (1986); Zoller et al., Nucl. Acids Res., 10:6487 (1987)), cassette mutagenesis (Wells et al., Gene, 34:315 (1985)), restriction selection mutagenesis (Wells et al., Philos. Trans. R. Soc. London SerA, 317:415 (1986)) or other known techniques can be performed on the cloned DNA to produce the variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant (Cunningham and Wells, Science, 244:1081-1085 (1989)). Alanine is also typically preferred because it is the most common amino acid. Further, it is frequently found in both buried and exposed positions (Creighton, The Proteins, (W.H. Freeman & Co., N.Y.); Chothia, J. Mol. Biol., 150:1 (1976)). If alanine substitution does not yield adequate amounts of variant, an isoteric amino acid can be used.

Covalent modifications: The stretch of consecutive amino acids may be covalently modified. One type of covalent modification includes reacting targeted amino acid residues with an organic derivatizing agent that is capable of reacting with selected side chains or the N- or C-terminal residues that are not involved in an -x-x- bond. Derivatization with bifunctional agents is useful, for instance, for crosslinking to a water-insoluble support matrix or surface for use in the method for purifying anti-sequence of interest antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-((p-azidophenyl)dithio)propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the .alpha.-amino groups of lysine, arginine, and histidine side chains (T. E. Creighton, Proteins: Structure and Molecular Properties, W.H. Freeman & Co., San Francisco, pp. 79-86 (1983)), acetylation of the N-terminal amine, and amidation of any C-terminal carboxyl group.

Another type of covalent modification comprises altering the native glycosylation pattern of the stretch of consecutive amino acids. "Altering the native glycosylation pattern" is intended for purposes herein to mean deleting one or more carbohydrate moieties found in amino acid sequences (either by removing the underlying glycosylation site or by deleting the glycosylation by chemical and/or enzymatic means), and/or adding one or more glycosylation sites that are not present in the native sequence. In addition, the phrase includes qualitative changes in the glycosylation of the native proteins, involving a change in the nature and proportions of the various carbohydrate moieties present.

Addition of glycosylation sites to the amino acid sequence may be accomplished by altering the amino acid sequence. The alteration may be made, for example, by the addition of, or substitution by, one or more serine or threonine residues to the native sequence (for O-linked glycosylation sites). The amino acid sequence may optionally be altered through changes at the DNA level, particularly by mutating the DNA encoding the amino acid sequence at preselected bases such that codons are generated that will translate into the desired amino acids.

Another means of increasing the number of carbohydrate moieties on the amino acid sequence is by chemical or enzymatic coupling of glycosides to the polypeptide. Such methods are described in the art, e.g., in WO 87/05330 published Sep. 11, 1987, and in Aplin and Wriston, CRC Crit. Rev. Biochem., pp. 259-306 (1981).

Removal of carbohydrate moieties present on the amino acid sequence may be accomplished chemically or enzymatically or by mutational substitution of codons encoding for amino acid residues that serve as targets for glycosylation. Chemical deglycosylation techniques are known in the art and described, for instance, by Hakimuddin, et al., Arch. Biochem. Biophys., 259:52 (1987) and by Edge et al., Anal. Biochem., 118:131 (1981). Enzymatic cleavage of carbohydrate moieties on polypeptides can be achieved by the use of a variety of endo- and exo-glycosidases as described by Thotakura et al., Meth. Enzymol., 138:350 (1987).

Another type of covalent modification comprises linking the amino acid sequence to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

The term "substitution", "substituted" and "substituent" refers to a functional group as described above in which one or more bonds to a hydrogen atom contained therein are replaced by a bond to non-hydrogen or non-carbon atoms, provided that normal valencies are maintained and that the substitution results in a stable compound. Substituted groups also include groups in which one or more bonds to a carbon(s) or hydrogen(s) atom are replaced by one or more bonds, including double or triple bonds, to a heteroatom. Examples of substituent groups include the functional groups described above, and halogens (i.e., F, Cl, Br, and I); alkyl groups, such as methyl, ethyl, n-propyl, isopropryl, n-butyl, tert-butyl, and trifluoromethyl; hydroxyl; alkoxy groups, such as methoxy, ethoxy, n-propoxy, and iso-propoxy; aryloxy groups, such as phenoxy; arylalkyloxy, such as benzyloxy (phenylmethoxy) and p-trifluoromethylbenzyloxy (4-trifluoromethylphenylmethoxy); heteroaryloxy groups; sulfonyl groups, such as trifluoromethanesulfonyl, methanesulfonyl, and p-toluenesulfonyl; nitro, nitrosyl; mercapto; sulfanyl groups, such as methylsulfanyl, ethylsulfanyl and propylsulfanyl; cyano; amino groups, such as amino, methylamino, dimethylamino, ethylamino, and diethylamino; and carboxyl. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

In the compounds used in the method of the present invention, alkyl, heteroalkyl, monocycle, bicycle, aryl, heteroaryl and heterocycle groups can be further substituted by replacing one or more hydrogen atoms with alternative non-hydrogen groups. These include, but are not limited to, halo, hydroxy, mercapto, amino, carboxy, cyano and carbamoyl.

It is understood that substituents and substitution patterns on the compounds used in the method of the present invention can be selected by one of ordinary skill in the art to provide compounds that are chemically stable and that can be readily synthesized by techniques known in the art from readily available starting materials. If a substituent is itself substituted with more than one group, it is understood that these multiple groups may be on the same carbon or on different carbons, so long as a stable structure results.

In choosing the compounds used in the method of the present invention, one of ordinary skill in the art will recognize that the various substituents, i.e. $R_1$, $R_2$, etc. are to be chosen in conformity with well-known principles of chemical structure connectivity.

As used herein, "alkyl" includes both branched and straight-chain saturated aliphatic hydrocarbon groups having the specified number of carbon atoms and may be unsubstituted or substituted. Thus, $C_1$-$C_n$ as in "$C_1$-$C_n$ alkyl" is defined to include groups having 1, 2, . . . , n–1 or n carbons in a linear or branched arrangement. For example, $C_1$-$C_6$, as in "$C_1$-$C_6$ alkyl" is defined to include groups having 1, 2, 3, 4, 5, or 6 carbons in a linear or branched arrangement, and specifically includes methyl, ethyl, n-propyl, isopropyl, n-butyl, t-butyl, pentyl, and hexyl. Unless otherwise specified contains one to ten carbons. Alkyl groups can be unsubstituted or substituted with one or more substituents, including but not limited to halogen, alkoxy, alkylthio, trifluoromethyl, difluoromethyl, methoxy, and hydroxyl.

As used herein, "$C_1$-$C_4$ alkyl" includes both branched and straight-chain $C_1$-$C_4$ alkyl.

As used herein, "aryl" is intended to mean any stable monocyclic, bicyclic or polycyclic carbon ring of up to 10 atoms in each ring, wherein at least one ring is aromatic, and may be unsubstituted or substituted. Examples of such aryl elements include but are not limited to: phenyl, p-toluenyl (4-methylphenyl), naphthyl, tetrahydro-naphthyl, indanyl, phenanthryl, anthryl or acenaphthyl. In cases where the aryl substituent is bicyclic and one ring is non-aromatic, it is understood that attachment is via the aromatic ring.

The term "phenyl" is intended to mean an aromatic six membered ring containing six carbons, and any substituted derivative thereof.

The term "benzyl" is intended to mean a methylene attached directly to a benzene ring. A benzyl group is a methyl group wherein a hydrogen is replaced with a phenyl group, and any substituted derivative thereof.

The compounds used in the method of the present invention may be prepared by techniques well know in organic synthesis and familiar to a practitioner ordinarily skilled in the art. However, these may not be the only means by which to synthesize or obtain the desired compounds.

The compounds of present invention may be prepared by techniques described in Vogel's Textbook of Practical Organic Chemistry, A. I. Vogel, A. R. Tatchell, B. S. Furnis, A. J. Hannaford, P. W. G. Smith, (Prentice Hall) 5$^{th}$ Edition (1996), March's Advanced Organic Chemistry: Reactions, Mechanisms, and Structure, Michael B. Smith, Jerry March, (Wiley-Interscience) 5$^{th}$ Edition (2007), and references therein, which are incorporated by reference herein. However, these may not be the only means by which to synthesize or obtain the desired compounds.

In some embodiments of the present invention, a compound comprises a nonproteinaceous polymer. In some embodiments, the nonproteinaceous polymer may be is a hydrophilic synthetic polymer, i.e., a polymer not otherwise found in nature. However, polymers which exist in nature and are produced by recombinant or in vitro methods are useful, as are polymers which are isolated from nature. Hydrophilic polyvinyl polymers fall within the scope of this invention, e.g. polyvinylalcohol and polyvinylpyrrolidone. Particularly useful are polyalkylene ethers such as polyethylene glycol, polypropylene glycol, polyoxyethylene esters or methoxy polyethylene glycol; polyoxyalkylenes such as polyoxyethylene, polyoxypropylene, and block copolymers of polyoxyethylene and polyoxypropylene (Pluronics); polymethacrylates; carbomers; branched or unbranched polysaccharides which comprise the saccharide monomers D-mannose, D- and L-galactose, fucose, fructose, D-xylose, L-arabinose, D-glucuronic acid, sialic acid, D-galacturontc acid, D-mannuronic acid (e.g. polymannuronic acid, or alginic acid), D-glucosamine, D-galactosamine, D-glucose and neuraminic acid including homopolysaccharides and heteropolysaccharides such as lactose, amylopectin, starch, hydroxyethyl starch, amylose, dextran sulfate, dextran, dextrins, glycogen, or the polysaccharide subunit of acid mucopolysaccharides,
e.g. hyaluronic acid; polymers of sugar alcohols such as polysorbitol and polymannitol; and heparin or heparon.

Salts

Salts of the compounds disclosed herein are within the scope of the invention. As used herein, a "salt" is salt of the instant compounds which has been modified by making acid or base salts of the compounds.

Fc Domains

The term "Fc domain", as used herein, generally refers to a monomer or dimer complex, comprising the C-terminal polypeptide sequences of an immunoglobulin heavy chain. The Fc domain may comprise native or variant Fc sequences. Although the boundaries of the Fc domain of an immunoglobulin heavy chain might vary, the human IgG heavy chain Fc domain is usually defined to stretch from an amino acid residue in the hinge region to the carboxyl terminus of the Fc sequence. The Fc sequence of an immunoglobulin generally comprises two constant regions, a CH2 region and a CH3 region, and optionally comprises a CH4 region. A human Fc domain may be obtained from any suitable immunoglobulin, such as the IgG1, IgG2, IgG3, or IgG4 subtypes, IgA, IgE, IgD or IgM.

Suitable Fc domains are prepared by recombinant DNA expression of pre-Fc chimeric polypeptides comprising 1) a signal peptide, obtained from a secreted or transmembrane protein, that is cleaved in front of a mature polypeptide having an N-terminal cysteine residue, contiguous with 2) an Fc domain polypeptide having an N-terminal cysteine residue.

Suitable examples of signal peptides are sonic hedgehog (SHH) (GenBank Acc. No. NM000193), IFNalpha-2 (IFN) (GenBank Acc. No. NP000596), and cholesterol ester transferase (CETP) (GenBank Accession No. NM000078). Other suitable examples include Indian hedgehog (Genbank Acc. No. NM002181), desert hedgehog (Genbank Acc. No. NM021044), IFNalpha-1 (Genbank Acc. No. NP076918), IFNalpha-4 (Genbank Acc. No. NM021068), IFNalpha-5 (Genbank Acc. No. NM002169), IFNalpha-6 (Genbank Acc. No. NM021002), IFNalpha-7 (Genbank Acc. No. NM021057), IFNalpha-8 (Genbank Acc. No. NM002170), IFNalpha-10 (Genbank Acc. No. NM002171), IFNalpha-13 (Genbank Acc. No. NM006900), IFNalpha-14 (Genbank Acc. No. NM002172), IFNalpha-16 (Genbank Acc. No. NM002173), IFNalpha-17 (Genbank Acc. No. NM021268) and IFNalpha-21 (Genbank Acc. No. NM002175).

Suitable examples of Fc domains and their pre-Fc chimeric polypeptides are shown in SEQ ID NO: 1 through SEQ ID NO: 96. The Fc domains are obtained by expressing the pre-Fc chimeric polypeptides in cells under conditions leading to their secretion and cleavage of the signal peptide. The pre-Fc polypeptides may be expressed in either prokaryotic or eukaryotic host cells. Preferably, mammalian host cells are transfected with expression vectors encoding the pre-Fc polypeptides.

Human IgG1 Fc domains having the N-terminal sequence CDKTHTCPPCPAPE, CPPCPAPE, and CPAPE are shown in SEQ ID NO: 1, SEQ ID NO: 9, and SEQ ID NO: 17, respectively, and the DNA sequences encoding them are shown in SEQ ID NO: 2, SEQ ID NO: 10, and SEQ ID NO: 18, respectively. The IgG1 domain of SEQ ID NO: 1 is obtained by expressing the pre-Fc chimeric polypeptides shown in SEQ ID NO: 3 (SHH signal peptide), SEQ ID NO: 5 (IFN signal peptide), and SEQ ID NO: 7 (CETP signal peptide), using the DNA sequences shown in SEQ ID NO: 4, SEQ ID NO: 6, and SEQ ID NO: 8, respectively. The IgG1 domain of SEQ ID NO: 9 is obtained by expressing the pre-Fc chimeric polypeptides shown in SEQ ID NO: 11 (SHH signal peptide), SEQ ID NO: 13 (IFN signal peptide), and SEQ ID NO: 15 (CETP signal peptide), using the DNA sequences shown in SEQ ID NO: 12, SEQ ID NO: 14, and SEQ ID NO: 16, respectively. The IgG1 domain of SEQ ID NO: 17 is obtained by expressing the pre-Fc chimeric polypeptides shown in SEQ ID NO: 19 (SHH signal peptide), SEQ ID NO: 21 (IFN signal peptide), and SEQ ID NO: 23 (CETP signal peptide), using the DNA sequences shown in SEQ ID NO: 20, SEQ ID NO: 22, and SEQ ID NO: 24, respectively.

Human IgG2 Fc domains having the N-terminal sequence CCVECPPCPAPE, CVECPPCPAPE, CPPCPAPE, and CPAPE are shown in SEQ ID NO: 25, SEQ ID NO: 33, SEQ ID NO: 41, and SEQ ID NO: 49, respectively, and the DNA sequences encoding them are shown in SEQ ID NO: 26, SEQ ID NO: 34, SEQ ID NO: 42, and SEQ ID NO: 50, respectively. The IgG2 domain of SEQ ID NO: 25 is obtained by expressing the pre-Fc chimeric polypeptides shown in SEQ ID NO: 27 (SHH signal peptide), SEQ ID NO: 29 (IFN signal peptide), and SEQ ID NO: 31 (CETP signal peptide), using the DNA sequences shown in SEQ ID NO: 28, SEQ ID NO: 30, and SEQ ID NO: 32, respectively. The IgG2 domain of SEQ ID NO: 33 is obtained by expressing the pre-Fc chimeric polypeptides shown in SEQ ID NO: 35 (SHH signal peptide), SEQ ID NO: 37 (IFN signal peptide), and SEQ ID NO: 39 (CETP signal peptide) using the DNA sequences shown in SEQ ID NO: 36, SEQ ID NO: 38, and SEQ ID NO: 40, respectively. The IgG2 domain of SEQ ID NO: 41 is obtained from the pre-Fc chimeric polypeptides shown in SEQ ID NO: 43 (SHH signal peptide), SEQ ID NO: 45 (IFN signal peptide), and SEQ ID NO: 47 (CETP signal peptide), using the DNA sequences shown in SEQ ID NO: 44, SEQ ID NO: 46, and SEQ ID NO: 48, respectively. The IgG2 domain of SEQ ID NO: 49 is obtained from the pre-Fc chimeric polypeptides shown in SEQ ID NO: 51 (SHH signal peptide), SEQ ID NO: 53 (IFN signal peptide), and SEQ ID NO: 55 (CETP signal peptide), using the DNA sequences shown in SEQ ID NO: 52, SEQ ID NO: 54, and SEQ ID NO: 56, respectively.

Human IgG3 Fc domains having the N-terminal sequence (CPRCPEPKSDTPPP)$_3$-CPRCPAPE, CPRCPAPE, and CPAPE are shown in SEQ ID NO: 57, SEQ ID NO: 65, and SEQ ID NO: 73, respectively, and the DNA sequences encoding them are shown in SEQ ID NO: 58, SEQ ID NO: 66, SEQ ID NO: 42, and SEQ ID NO: 74, respectively. The IgG3 domain of SEQ ID NO: 57 is obtained by expressing the pre-Fc chimeric polypeptides shown in SEQ ID NO: 59 (SHH signal peptide), SEQ ID NO: 61 (IFN signal peptide), and SEQ ID NO: 63 (CETP signal peptide), using the DNA sequences shown in SEQ ID NO: 60, SEQ ID NO: 62, and SEQ ID NO: 64, respectively. The IgG3 domain of SEQ ID NO: 65 is obtained by expressing the pre-Fc chimeric polypeptides shown in SEQ ID NO: 67 (SHH signal peptide), SEQ ID NO: 69 (IFN signal peptide), and SEQ ID NO: 71 (CETP signal peptide), using the DNA sequences shown in SEQ ID NO: 68, SEQ ID NO: 70, and SEQ ID NO: 72, respectively. The IgG3 domain of SEQ ID NO: 73 is obtained by expressing the pre-Fc chimeric polypeptides shown in SEQ ID NO: 75 (SHH signal peptide), SEQ ID NO: 77 (IFN signal peptide), and SEQ ID NO: 79 (CETP signal peptide), using the DNA sequences shown in SEQ ID NO: 76, SEQ ID NO: 78, and SEQ ID NO: 80, respectively.

The sequences of human IgG4 Fc domains having the N-terminal sequence CPSCPAPE and CPAPE are shown in SEQ ID NO: 81 and SEQ ID NO: 89, respectively, and the DNA sequences encoding them are shown in SEQ ID NO: 82 and SEQ ID NO: 90, respectively. The IgG4 domain of SEQ ID NO: 81 is obtained by expressing the pre-Fc chimeric polypeptides shown in SEQ ID NO: 83 (SHH signal peptide), SEQ ID NO: 85 (IFN signal peptide), and SEQ ID NO: 87 (CETP signal peptide), using the DNA sequences shown in SEQ ID NO: 84, SEQ ID NO: 86, and SEQ ID NO: 88, respectively. The IgG4 domain of SEQ ID NO: 89 is obtained by expressing the pre-Fc chimeric polypeptides shown in SEQ ID NO: 91 (SHH signal peptide), SEQ ID NO: 93 (IFN signal peptide), and SEQ ID NO: 95 (CETP signal peptide), using the DNA sequences shown in SEQ ID NO: 92, SEQ ID NO: 94, and SEQ ID NO: 96, respectively.

Suitable host cells include 293 human embryonic cells (ATCC CRL-1573) and CHO-K1 hamster ovary cells (ATCC CCL-61) obtained from the American Type Culture Collection (Rockville, Md.). Cells are grown at 37.degree. C. in an atmosphere of air, 95%; carbon dioxide, 5%. 293 cells are maintained in Minimal essential medium (Eagle) with 2 mM L-glutamine and Earle's BSS adjusted to contain 1.5 g/L sodium bicarbonate, 0.1 mM non-essential amino acids, and 1.0 mM sodium pyruvate, 90%; fetal bovine serum, 10%. CHO-K1 cells are maintained in Ham's F12K medium with 2 mM L-glutamine adjusted to contain 1.5 g/L sodium bicarbonate, 90%; fetal bovine serum, 10%. Other suitable host cells include CV1 monkey kidney cells (ATCC CCL-70), COS-7 monkey kidney cells (ATCC CRL-1651), VERO-76 monkey kidney cells (ATCC CRL-1587), HELA human cervical cells (ATCC CCL-2), W138 human lung cells (ATCC CCL-75), MDCK canine kidney cells (ATCC CCL-34), BRL3A rat liver cells (ATCC CRL-1442), BHK hamster kidney cells (ATCC CCL-10), MMT060562 mouse mammary cells (ATCC CCL-51), and human CD8.sup.+T lymphocytes (described in U.S. Ser. No. 08/258,152 incorporated herein in its entirety by reference).

Examples of a suitable expression vectors are pCDNA3.1 (+) shown in SEQ ID NO: 97 and pSA shown in SEQ ID NO: 98. Plasmid pSA contains the following DNA sequence elements: 1) pBluescriptIIKS(+) (nucleotides 912-2941/1-619, GenBank Accession No. X52327), 2) a human cytomegalovirus promoter, enhancer, and first exon splice donor (nucleotides 63-912, GenBank Accession No. K03104), 3) a human alpha1-globin second exon splice acceptor (nucleotides 6808-6919, GenBank Accession No. J00153), 4) an SV40 T antigen polyadenylation site (nucleotides 2770-2533, Reddy et al. (1978) Science 200, 494-502), and 5) an SV40 origin of replication (nucleotides 5725-5578, Reddy et al., ibid). Other suitable expression vectors include plasmids pSVeCD4DHFR and pRKCD4 (U.S. Pat. No. 5,336,603), plasmid pIK.1.1 (U.S. Pat. No. 5,359,046), plasmid pVL-2 (U.S. Pat. No. 5,838,464), plasmid pRT43.2F3 (described in U.S. Ser. No. 08/258,152 incorporated herein in its entirety by reference).

Suitable expression vectors for human IgG pre-Fc polypeptides may be constructed by the ligation of a HindIII-PspOM1 vector fragment prepared from SEQ ID NO: 98, with a HindIII-EagI insert fragment prepared from SEQ ID NOS: 4, 6, 8, 12, 14, 16, 20, 22, 24, 28, 30, 32, 36, 38, 40, 44, 46, 48, 52, 54, 56, 60, 62, 64, 68, 70, 72, 76, 78, 80, 84, 86, 88, 92, 94, and 96. Suitable selectable markers include the Tn5 transposon neomycin phosphotransferase (NEO) gene (Southern and Berg (1982) J. Mol. Appl. Gen. 1, 327-341), and the dihydrofolate reductase (DHFR) cDNA (Lucas et al. (1996) Nucl. Acids Res. 24, 1774-1779). One example of a suitable expression vector that incorporates a NEO gene is plasmid pSA-NEO, which is constructed by ligating a first DNA fragment, prepared by digesting SEQ ID NO: 99 with EcoRI and BglII, with a second DNA fragment, prepared by digesting SEQ ID NO:98 with EcoRI and BglII. SEQ ID NO:99 incorporates a NEO gene (nucleotides 1551 to 2345, Genbank Accession No. U00004) preceded by a sequence for translational initiation (Kozak (1991) J. Biol. Chem. 266, 19867-19870). Another example of a suitable expression vector that incorporates a NEO gene and a DHFR cDNA is plasmid pSVe-NEO-DHFR, which is constructed by ligating a first DNA fragment, prepared by digesting SEQ ID NO:99 with EcoRI and BglII, with a second DNA fragment, prepared by digesting pSVeCD4DHFR with EcoRI and BglII. Plasmid pSVe-NEO-DHFR uses SV40 early promoter/enhancers to drive expression of the NEO gene and the DHFR cDNA. Other suitable selectable markers include the XPGT gene (Mulligan and Berg (1980) Science 209, 1422-1427) and the hygromycin resistance gene (Sugden et al. (1985) Mol. Cell. Biol. 5, 410-413).

In one embodiment, cells are transfected by the calcium phosphate method of Graham et al. (1977) J. Gen. Virol. 36, 59-74. A DNA mixture (10 ug) is dissolved in 0.5 ml of 1 mM Tris-HCl, 0.1 mM EDTA, and 227 mM $CaCl_2$. The DNA mixture contains (in a ratio of 10:1:1) the expression vector DNA, the selectable marker DNA, and a DNA encoding the VA RNA gene (Thimmappaya et al. (1982) Cell 31, 543-551). To this mixture is added, dropwise, 0.5 mL of 50 mM Hepes (pH 7.35), 280 mM NaCl, and 1.5 mM $NaPO_4$. The DNA precipitate is allowed to form for 10 minutes at 25° C., then suspended and added to cells grown to confluence on 100 mm plastic tissue culture dishes. After 4 hours at 37° C., the culture medium is aspirated and 2 ml of 20% glycerol in PBS is added for 0.5 minutes. The cells are then washed with serum-free medium, fresh culture medium is added, and the cells are incubated for 5 days.

In another embodiment, cells are transiently transfected by the dextran sulfate method of Somparyrac et al. (1981) Proc. Nat. Acad. Sci. 12, 7575-7579. Cells are grown to maximal density in spinner flasks, concentrated by centrifugation, and washed with PBS. The DNA-dextran precipitate is incubated on the cell pellet. After 4 hours at 37° C., the DEAE-dextran is aspirated and 20% glycerol in PBS is added for 1.5 minutes. The cells are then washed with serum-free medium, re-introduced into spinner flasks containing fresh culture medium with 5 micrograms/ml bovine insulin and 0.1 micrograms/ml bovine transferring, and incubated for 4 days.

Following transfection by either method, the conditioned media is centrifuged and filtered to remove the host cells and debris. The sample contained the Fc domain is then concentrated and purified by any selected method, such as dialysis and/or column chromatography (see below). To identify the Fc domain in the cell culture supernatant, the culture medium is removed 24 to 96 hours after transfection, concentrated, and analyzed by SDS-polyacrylamide gel electrophoresis (SDS-PAGE) in the presence or absence of a reducing agent such as dithiothreitol.

For unamplified expression, plasmids are transfected into human 293 cells (Graham et al., J. Gen. Virol. 36:59 74 (1977)), using a high efficiency procedure (Gorman et al., DNA Prot. Eng. Tech. 2:3 10 (1990)). Media is changed to serum-free and harvested daily for up to five days. For unamplified expression, plasmids are transfected into human 293 cells (Graham et al., J. Gen. Virol. 36:59 74 (1977)), using a high efficiency procedure (Gorman et al., DNA Prot. Eng. Tech. 2:3 10 (1990)). Media is changed to serum-free and harvested daily for up to five days. The Fc domains are purified from the cell culture supernatant using HiTrap Protein A HP (Pharmacia). The eluted Fc domains are buffer-exchanged into PBS using a Centricon-30 (Amicon), concentrated to 0.5 ml, sterile filtered using a Millex-GV (Millipore) at 4° C.

Stretches of Consecutive Amino Acids

Examples of stretches of consecutive amino acids as referred to herein include, but are not limited to, consecutive amino acids including binding domains such as secreted or transmembrane proteins, intracellular binding domains and antibodies (whole or portions thereof) and modified versions thereof. The following are some non-limiting examples:

1) Immunoglobulins

The term "antibody" is used in the broadest sense and specifically covers monoclonal antibodies (including full length monoclonal antibodies), polyclonal antibodies, multispecific antibodies (e.g., bispecific antibodies), monovalent antibodies, multivalent antibodies, and antibody fragments so long as they exhibit the desired biological activity (e.g., Fab and/or single-armed antibodies).

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and μ, respectively.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g., scFv); and multispecific antibodies formed from antibody fragments.

The terms "full length antibody," "intact antibody," and "whole antibody" are used herein interchangeably to refer to an antibody having a structure substantially similar to a native antibody structure or having heavy chains that contain an Fc region as defined herein.

A "blocking" antibody or an "antagonist" antibody is one which significantly inhibits (either partially or completely) a biological activity of the antigen it binds.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. Kuby Immunology, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., J. Immunol. 150:880-887 (1993); Clarkson et al., Nature 352:624-628 (1991).

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, J. Mol. Biol. 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., Sequences of Proteins of Immunological Interest, 5th Ed. Public Health Service, National Institutes of Health, Bethesda, Md. (1991).) With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, Front. Biosci. 13:1619-1633 (2008).) Unless otherwise indicated, HVR residues and other residues in the variable domain (e.g., FR residues) are numbered herein according to Kabat et al., supra.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The phrase "N-terminally truncated heavy chain", as used herein, refers to a polypeptide comprising parts but not all of a full length immunoglobulin heavy chain, wherein the missing parts are those normally located on the N terminal region of the heavy chain. Missing parts may include, but are not limited to, the variable domain, CH1, and part or all of a hinge sequence. Generally, if the wild type hinge sequence is not present, the remaining constant domain(s) in the N-terminally truncated heavy chain would comprise a component that is capable of linkage to another Fc sequence (i.e., the "first" Fc polypeptide as described herein). For example, said component can be a modified residue or an added cysteine residue capable of forming a disulfide linkage.

"Fc receptor" or "FcR" describes a receptor that binds to the Fc region of an antibody. In some embodiments, an FcR is a native human FcR. In some embodiments, an FcR is one which binds an IgG antibody (a gamma receptor) and includes receptors of the FcγRI, FcγRII, and FcγRIII subclasses, including allelic variants and alternatively spliced forms of those receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain Inhibiting receptor FcγRIIB contains an immunoreceptor tyrosine-based inhibition motif (ITIM) in its cytoplasmic domain. (see, e.g., Daeron, Annu. Rev. Immunol. 15:203-234 (1997)). FcRs are reviewed, for example, in Ravetch and Kinet, Annu. Rev. Immunol 9:457-92 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein.

The term "Fc receptor" or "FcR" also includes the neonatal receptor, FcRn, which is responsible for the transfer of maternal IgGs to the fetus (Guyer et al., J. Immunol. 117:587

(1976) and Kim et al., J. Immunol. 24:249 (1994)) and regulation of homeostasis of immunoglobulins. Methods of measuring binding to FcRn are known (see, e.g., Ghetie and Ward., Immunol. Today 18(12):592-598 (1997); Ghetie et al., Nature Biotechnology, 15(7):637-640 (1997); Hinton et al., J. Biol. Chem. 279(8):6213-6216 (2004); WO 2004/92219 (Hinton et al.).

Binding to human FcRn in vivo and serum half life of human FcRn high affinity binding polypeptides can be assayed, e.g., in transgenic mice or transfected human cell lines expressing human FcRn, or in primates to which the polypeptides with a variant Fc region are administered. WO 2000/42072 (Presta) describes antibody variants with improved or diminished binding to FcRs. See also, e.g., Shields et al. J. Biol. Chem. 9(2):6591-6604 (2001).

The "hinge region," "hinge sequence", and variations thereof, as used herein, includes the meaning known in the art, which is illustrated in, for example, Janeway et al., Immuno Biology: the immune system in health and disease, (Elsevier Science Ltd., NY) (4th ed., 1999); Bloom et al., Protein Science (1997), 6:407-415; Humphreys et al., J. Immunol. Methods (1997), 209:193-202.

Unless indicated otherwise, the expression "multivalent antibody" is used throughout this specification to denote an antibody comprising three or more antigen binding sites. The multivalent antibody is preferably engineered to have the three or more antigen binding sites and is generally not a native sequence IgM or IgA antibody.

An "Fv" fragment is an antibody fragment which contains a complete antigen recognition and binding site. This region consists of a dimer of one heavy and one light chain variable domain in tight association, which can be covalent in nature, for example in scFv. It is in this configuration that the three HVRs of each variable domain interact to define an antigen binding site on the surface of the $V_H$-$V_L$ dimer. Collectively, the six HVRs or a subset thereof confer antigen binding specificity to the antibody. However, even a single variable domain (or half of an Fv comprising only three HVRs specific for an antigen) has the ability to recognize and bind antigen, although usually at a lower affinity than the entire binding site.

The "Fab" fragment contains a variable and constant domain of the light chain and a variable domain and the first constant domain (CH1) of the heavy chain. F(ab') 2 antibody fragments comprise a pair of Fab fragments which are generally covalently linked near their carboxy termini by hinge cysteines between them. Other chemical couplings of antibody fragments are also known in the art.

The phrase "antigen binding arm", as used herein, refers to a component part of an antibody fragment that has an ability to specifically bind a target molecule of interest. Generally and preferably, the antigen binding arm is a complex of immunoglobulin polypeptide sequences, e.g., HVR and/or variable domain sequences of an immunoglobulin light and heavy chain.

"Single-chain Fv" or "scFv" antibody fragments comprise the $V_H$ and $V_L$ domains of antibody, wherein these domains are present in a single polypeptide chain. Generally the Fv polypeptide further comprises a polypeptide linker between the $V_H$ and $V_L$ domains, which enables the scFv to form the desired structure for antigen binding. For a review of scFv, see Pluckthun in The Pharmacology of Monoclonal Antibodies, Vol 113, Rosenburg and Moore eds. Springer-Verlag, New York, pp. 269-315 (1994).

The term "diabodies" refers to small antibody fragments with two antigen-binding sites, which fragments comprise a heavy chain variable domain ($V_H$) connected to a light chain variable domain ($V_L$) in the same polypeptide chain ($V_H$ and $V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90:6444-6448 (1993).

The expression "linear antibodies" refers to the antibodies described in Zapata et al., Protein Eng., 8(10):1057-1062 (1995). Briefly, these antibodies comprise a pair of tandem Fd segments (V.sub.H-C.sub.H1-V.sub.H-C.sub.H1) which, together with complementary light chain polypeptides, form a pair of antigen binding regions. Linear antibodies can be bispecific or monospecific.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "chimeric" antibody refers to an antibody in which a portion of the heavy and/or light chain is derived from a particular source or species, while the remainder of the heavy and/or light chain is derived from a different source or species.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 Daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more HVRs, compared to a parent antibody which does not possess such alterations, such alterations resulting in an improvement in the affinity of the antibody for antigen.

An antibody having a "biological characteristic" of a designated antibody is one which possesses one or more of the biological characteristics of that antibody which distinguish it from other antibodies that bind to the same antigen.

A "functional antigen binding site" of an antibody is one which is capable of binding a target antigen. The antigen binding affinity of the antigen binding site is not necessarily as strong as the parent antibody from which the antigen binding site is derived, but the ability to bind antigen must be measurable using any one of a variety of methods known for evaluating antibody binding to an antigen. Moreover, the antigen binding affinity of each of the antigen binding sites of a multivalent antibody herein need not be quantitatively the same. For the multimeric antibodies herein, the number of functional antigen binding sites can be evaluated using ultracentrifugation analysis as described in Example 2 of U.S. Patent Application Publication No. 20050186208. According to this method of analysis, different ratios of target antigen to multimeric antibody are combined and the average molecular weight of the complexes is calculated assuming differing numbers of functional binding sites. These theoretical values are compared to the actual experimental values obtained in order to evaluate the number of functional binding sites.

A "species-dependent antibody" is one which has a stronger binding affinity for an antigen from a first mammalian species than it has for a homologue of that antigen from a second mammalian species. Normally, the species-dependent antibody "binds specifically" to a human antigen (i.e. has a binding affinity ($K_d$) value of no more than about $1 \times 10^{-7}$ M, preferably no more than about $1 \times 10^{-8}$ M and most preferably no more than about $1 \times 10^{-9}$ M) but has a binding affinity for a homologue of the antigen from a second nonhuman mammalian species which is at least about 50 fold, or at least about 500 fold, or at least about 1000 fold, weaker than its binding affinity for the human antigen. The species-dependent antibody can be any of the various types of antibodies as defined above. In some embodiments, the species-dependent antibody is a humanized or human antibody.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., J. Chromatogr. B 848:79-87 (2007).

2) Extracellular Proteins

Extracellular proteins play important roles in, among other things, the formation, differentiation and maintenance of multicellular organisms. A discussion of various intracellular proteins of interest is set forth in U.S. Pat. No. 6,723,535, Ashkenazi et al., issued Apr. 20, 2004, hereby incorporated by reference.

The fate of many individual cells, e.g., proliferation, migration, differentiation, or interaction with other cells, is typically governed by information received from other cells and/or the immediate environment. This information is often transmitted by secreted polypeptides (for instance, mitogenic factors, survival factors, cytotoxic factors, differentiation factors, neuropeptides, and hormones) which are, in turn, received and interpreted by diverse cell receptors or membrane-bound proteins. These secreted polypeptides or signaling molecules normally pass through the cellular secretory pathway to reach their site of action in the extracellular environment.

Secreted proteins have various industrial applications, including as pharmaceuticals, diagnostics, biosensors and bioreactors. Most protein drugs available at present, such as thrombolytic agents, interferons, interleukins, erythropoietins, colony stimulating factors, and various other cytokines, are secretory proteins. Their receptors, which are membrane proteins, also have potential as therapeutic or diagnostic agents. Efforts are being undertaken by both industry and academia to identify new, native secreted proteins. Many efforts are focused on the screening of mammalian recombinant DNA libraries to identify the coding sequences for novel secreted proteins. Examples of screening methods and techniques are described in the literature (see, for example, Klein et al., Proc. Natl. Acad. Sci. 93:7108-7113 (1996); U.S. Pat. No. 5,536,637)).

Membrane-bound proteins and receptors can play important roles in, among other things, the formation, differentiation and maintenance of multicellular organisms. The fate of many individual cells, e.g., proliferation, migration, differentiation, or interaction with other cells, is typically governed by information received from other cells and/or the immediate environment. This information is often transmitted by secreted polypeptides (for instance, mitogenic factors, survival factors, cytotoxic factors, differentiation factors, neuropeptides, and hormones) which are, in turn, received and interpreted by diverse cell receptors or membrane-bound proteins. Such membrane-bound proteins and cell receptors include, but are not limited to, cytokine receptors, receptor kinases, receptor phosphatases, receptors involved in cell-cell interactions, and cellular adhesin molecules like selectins and integrins. For instance, transduction of signals that regulate cell growth and differentiation is regulated in part by phosphorylation of various cellular proteins. Protein tyrosine kinases, enzymes that catalyze that process, can also act as growth factor receptors. Examples include fibroblast growth factor receptor and nerve growth factor receptor.

Membrane-bound proteins and receptor molecules have various industrial applications, including as pharmaceutical and diagnostic agents. Receptor immunoadhesins, for instance, can be employed as therapeutic agents to block receptor-ligand interactions. The membrane-bound proteins can also be employed for screening of potential peptide or small molecule inhibitors of the relevant receptor/ligand interaction.

3) Intein-Based C-Terminal Syntheses

As described, for example, in U.S. Pat. No. 6,849,428, issued Feb. 1, 2005, inteins are the protein equivalent of the self-splicing RNA introns (see Perler et al., Nucleic Acids Res. 22:1125-1127 (1994)), which catalyze their own excision from a precursor protein with the concomitant fusion of the flanking protein sequences, known as exteins (reviewed in Perler et al., Curr. Opin. Chem. Biol. 1:292-299 (1997); Perler, F. B. Cell 92(1):1-4 (1998); Xu et al., EMBO J. 15(19):5146-5153 (1996)).

Studies into the mechanism of intein splicing led to the development of a protein purification system that utilized thiol-induced cleavage of the peptide bond at the N-terminus of the Sce VMA intein (Chong et al., Gene 192(2):271-281 (1997)). Purification with this intein-mediated system generates a bacterially-expressed protein with a C-terminal thioester (Chong et al., (1997)). In one application, where it is described to isolate a cytotoxic protein, the bacterially expressed protein with the C-terminal thioester is then fused to a chemically-synthesized peptide with an N-terminal cysteine using the chemistry described for "native chemical ligation" (Evans et al., Protein Sci. 7:2256-2264 (1998); Muir et al., Proc. Natl. Acad. Sci. USA 95:6705-6710 (1998)).

This technique, referred to as "intein-mediated protein ligation" (IPL), represents an important advance in protein semi-synthetic techniques. However, because chemically-synthesized peptides of larger than about 100 residues are difficult to obtain, the general application of IPL was limited by the requirement of a chemically-synthesized peptide as a ligation partner.

IPL technology was significantly expanded when an expressed protein with a predetermined N-terminus, such as cysteine, was generated, as described for example in U.S. Pat. No. 6,849,428. This allows the fusion of one or more expressed proteins from a host cell, such as bacterial, yeast or mammalian cells. In one non-limiting example the intein a modified RIR1 *Methanobacterium thermoautotrophicum* is that cleaves at either the C-terminus or N-terminus is used which allows for the release of a bacterially expressed protein during a one-column purification, thus eliminating the need proteases entirely.

Intein technology is one example of one route to obtain components. In one embodiment, the subunits of the compounds of the invention are obtained by transfecting suitable cells, capable of expressing and secreting mature chimeric polypeptides, wherein such polypeptides comprise, for example, an adhesin domain contiguous with an isolatable c-terminal intein domain (see U.S. Pat. No. 6,849,428, Evans et al., issued Feb. 1, 2005, hereby incorporated by reference). The cells, such as mammalian cells or bacterial cells, are transfected using known recombinant DNA techniques. The secreted chimeric polypeptide can then be isolated, e.g. using a chitin-derivatized resin in the case of an intein-chitin binding domain (see U.S. Pat. No. 6,897,285, Xu et al., issued May 24, 2005, hereby incorporated by reference), and is then treated under conditions permitting thiol-mediated cleavage and release of the now C-terminal thioester-terminated subunit. The thioester-terminated adhesion subunit is readily converted to a C-terminal cysteine terminated subunit.

For example, following an intein autocleavage reaction, a thioester intermediate is generated that permits the facile addition of cysteine, selenocysteine, homocysteine, or homoselenocysteine, or a derivative of cysteine, selenocysteine, homocysteine, homoselenocysteine, to the C-terminus by native chemical ligation. Methods of adding a cysteine, selenocysteine, homocysteine, or homoselenocysteine, or a derivative of cysteine, selenocysteine, homocysteine, homoselenocysteine, to the C-terminus by native chemical ligation which are useful in aspects of the present invention are described in U.S. Patent Application No. 2008/0254512, Capon, published Oct. 16, 2008, the entire contents of which are hereby incorporated herein by reference.

Kits

Another aspect of the present invention provides kits comprising the compounds disclosed herein and the pharmaceutical compositions comprising these compounds. A kit may include, in addition to the compound or pharmaceutical composition, diagnostic or therapeutic agents. A kit may also include instructions for use in a diagnostic or therapeutic method. In a diagnostic embodiment, the kit includes the compound or a pharmaceutical composition thereof and a diagnostic agent. In a therapeutic embodiment, the kit includes the antibody or a pharmaceutical composition thereof and one or more therapeutic agents, such as an additional antineoplastic agent, anti-tumor agent or chemotherapeutic agent.

General Techniques

The description below relates primarily to production of stretches of consecutive amino acids or polypeptides of interest by culturing cells transformed or transfected with a vector containing an encoding nucleic acid. It is, of course, contemplated that alternative methods, which are well known in the art, may be employed. For instance, the amino acid sequence, or portions thereof, may be produced by direct peptide synthesis using solid-phase techniques (see, e.g., Stewart et al., Solid-Phase Peptide Synthesis, W.H. Freeman Co., San Francisco, Calif. (1969); Merrifield, J. Am. Chem. Soc., 85:2149-2154 (1963)). In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the stretches of consecutive amino acids or polypeptides of interest may be chemically synthesized separately and combined using chemical or enzymatic methods to produce the full-length stretches of consecutive amino acids or polypeptides of interest.

1. Selection and Transformation of Host Cells

Host cells are transfected or transformed with expression or cloning vectors described herein for production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in Mammalian Cell Biotechnology: a Practical Approach, M. Butler, ed. (IRL Press, 1991) and Sambrook et al., supra.

Methods of eukaryotic cell transfection and prokaryotic cell transformation are known to the ordinarily skilled artisan, for example, $CaCl_2$, $CaPO_4$, liposome-mediated and electroporation. Depending on the host cell used, transformation is performed using standard techniques appropriate to such cells. The calcium treatment employing calcium chloride, as described in Sambrook et al., supra, or electroporation is generally used for prokaryotes. Infection with *Agrobacterium tumefaciens* is used for transformation of certain plant cells, as described by Shaw et al., Gene, 23:315 (1983) and WO 89/05859 published Jun. 29, 1989. For mammalian cells without such cell walls, the calcium phosphate precipitation method of Graham and van der Eb, Virology, 52:456-457 (1978) can be employed. General aspects of mammalian cell host system transfections have been described in U.S. Pat. No. 4,399,216. Transformations into yeast are typically carried out according to the method of Van Solingen et al., J. Bact., 130:946(1977) and Hsiao et al., Proc. Natl. Acad. Sci. (USA), 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., Methods in Enzymology, 185:527-537 (1990) and Mansour et al., Nature, 336:348-352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5772 (ATCC 53,635). Other suitable prokaryotic host cells include Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis* (e.g., *B. licheniformis* 41P disclosed in DD 266,710 published Apr. 12, 1989), *Pseudomonas* such as *P. aeruginosa*, and *Streptomyces*. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (ATCC 55,244), which has the complete genotype tonAptr3phoA E15 (argF-lac)169 degP ompT kan.sup.r; *E. coli* W3110 strain 37D6, which has the complete genotype tonA ptr3 phoA E15 (argF-lac)169 degP ompT rbs7 ilvG kan.sup.r, *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued Aug. 7, 1990. Alternatively, in vitro methods of cloning, e.g., PCR or other nucleic acid polymerase reactions, are suitable.

In addition to prokaryotes, eukaryotic microbes such as filamentous fungi or yeast are suitable cloning or expression hosts for encoding vectors. *Saccharomyces cerevisiae* is a commonly used lower eukaryotic host microorganism. Others include *Schizosaccharomyces pombe* (Beach and Nurse, Nature, 290:140 (1981); EP 139,383 published May 2, 1985); *Kluyveromyces* hosts (U.S. Pat. No. 4,943,529; Fleer et al., Bio/Technology, 9:968-975 (1991)) such as, e.g., *K. lactis* (MW98-8C, CBS683, CBS4574; Louvencourt et al., J. Bacteriol., 737 (1983)), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., Bio/Technology, 8:135 (1990)), *K. thermotolerans*, and *K. marxianus; yarrowia* (EP 402,226); *Pichia pastoris* (EP 183,070; Sreekrishna et al., J. Basic Microbiol., 28:265-278 (1988)); *Candida; Trichoderma reesia* (EP 244,234); *Neurospora crassa* (Case et al., Proc. Natl. Acad. Sci. USA, 76:5259-5263 (1979)); *Schwanniomyces* such as *Schwanniomyces occidentalis* (EP 394,538 published Oct. 31, 1990); and filamentous fungi such as, e.g., *Neurospora, Penicillium, Tolypocladium* (WO 91/00357 published Jan. 10, 1991), and *Aspergillus* hosts such as *A. nidulans* (Ballance et al., Biochem. Biophys. Res. Commun., 112:284-289 (1983); Tilburn et al., Gene, 26:205-221 (1983); Yelton et al., Proc. Natl. Acad. Sci. USA, 81:1470-1474 (1984)) and *A. niger* (Kelly and Hynes, EMBO J., 4:475479 (1985)). Methylotropic yeasts are suitable herein and include, but are not limited to, yeast capable of growth on methanol selected from the genera consisting of *Hansenula, Candida, Kloeckera, Pichia, Saccharomyces, Torulopsis*, and *Rhodotorula*. A list of specific species that are exemplary of this class of yeasts may be found in C. Anthony, The Biochemistry of Methylotrophs, 269 (1982).

Suitable host cells for the expression of glycosylated stretches of consecutive amino acids or polypeptides of interest are derived from multicellular organisms. Examples of invertebrate cells include insect cells such as *Drosophila* S2 and *Spodoptera* Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., J. Gen Virol., 36:59 (1977)); Chinese hamster ovary cells/-DHFR (CHO, Urlaub and Chasin, Proc. Natl. Acad. Sci. USA, 77:4216 (1980)); mouse sertoli cells (TM4, Mather, Biol. Reprod., 23:243-251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

2. Selection and Use of a Replicable Vector

The nucleic acid (e.g., cDNA or genomic DNA) encoding the stretch of consecutive amino acids or polypeptides of interest may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The stretches of consecutive amino acids or polypeptides of interest may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the encoding DNA that is inserted into the vector. The signal sequence may be a prokaryotic signal sequence selected, for example, from the group of the alkaline phosphatase, penicillinase, 1pp, or heat-stable enterotoxin II leaders. For yeast secretion the signal sequence may be, e.g., the yeast invertase leader, alpha factor leader (including Saccharomyces and Kluyveromyces alpha-factor leaders, the latter described in U.S. Pat. No. 5,010,182), or acid phosphatase leader, the C. albicans glucoamylase leader (EP 362,179 published Apr. 4, 1990), or the signal described in WO 90/13646 published Nov. 15, 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2mu plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells are those that enable the identification of cells competent to take up the encoding nucleic acid, such as DHFR or thymidine kinase. An appropriate host cell when wild-type DHFR is employed is the CHO cell line deficient in DHFR activity, prepared and propagated as described by Urlaub et al., Proc. Natl. Acad. Sci. USA, 77:4216 (1980). A suitable selection gene for use in yeast is the trp1 gene present in the yeast plasmid YRp7 (Stinchcomb et al., Nature, 282:39 (1979); Kingsman et al., Gene, 7:141 (1979); Tschemper et al., Gene, 10:157 (1980)). The trp1 gene provides a selection marker for a mutant strain of yeast lacking the ability to grow in tryptophan, for example, ATCC No. 44076 or PEP4-1 (Jones, Genetics, 85:12 (1977)).

Expression and cloning vectors usually contain a promoter operably linked to the encoding nucleic acid sequence to direct mRNA synthesis. Promoters recognized by a variety of potential host cells are well known. Promoters suitable for use with prokaryotic hosts include the beta-lactamase and lactose promoter systems (Chang et al., Nature, 275:615 (1978); Goeddel et al., Nature, 281:544 (1979)), alkaline phosphatase, a tryptophan (trp) promoter system (Goeddel, Nucleic Acids Res., 8:4057 (1980); EP 36,776), and hybrid promoters such as the tac promoter (deBoer et al., Proc. Natl. Acad. Sci. USA, 80:21-25 (1983)). Promoters for use in bacterial systems also will contain a Shine-Dalgarno (S.D.) sequence operably linked to the encoding DNA.

Examples of suitable promoting sequences for use with yeast hosts include the promoters for 3-phosphoglycerate kinase (Hitzeman et al., J. Biol. Chem., 255:2073 (1980)) or other glycolytic enzymes (Hess et al., J. Adv. Enzyme Reg., 7:149 (1968); Holland, Biochemistry, 17:4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

Transcription from vectors in mammalian host cells is controlled, for example, by promoters obtained from the genomes of viruses such as polyoma virus, fowlpox virus (UK 2,211,504 published Jul. 5, 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the stretches of consecutive amino acids or polypeptides of interest by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, alpha-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding stretches of consecutive amino acids or polypeptides of interest.

Still other methods, vectors, and host cells suitable for adaptation to the synthesis of stretches of consecutive amino acids or polypeptides in recombinant vertebrate cell culture are described in Gething et al., Nature 293:620-625 (1981); Mantei et al., Nature, 281:4046 (1979); EP 117,060; and EP 117,058.

3. Detecting Gene Amplification/Expression

Gene amplification and/or expression may be measured in a sample directly, for example, by conventional Southern blotting, Northern blotting to quantitate the transcription of mRNA (Thomas, Proc. Natl. Acad. Sci. USA, 77:5201-5205

(1980)), dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence stretches of consecutive amino acids or polypeptides of interest or against a synthetic peptide based on the DNA sequences provided herein or against exogenous sequence fused to DNA encoding a stretch of consecutive amino acids or polypeptide of interest and encoding a specific antibody epitope.

4. Purification of Polypeptide

Forms of the stretches of consecutive amino acids or polypeptides of interest may be recovered from culture medium or from host cell lysates. If membrane-bound, it can be released from the membrane using a suitable detergent solution (e.g. Triton-X 100) or by enzymatic cleavage. Cells employed in expression of the stretches of consecutive amino acids or polypeptides of interest can be disrupted by various physical or chemical means, such as freeze-thaw cycling, sonication, mechanical disruption, or cell lysing agents.

It may be desired to purify the stretches of consecutive amino acids or polypeptides of interest from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms. Various methods of protein purification may be employed and such methods are known in the art and described for example in Deutscher, Methods in Enzymology, 182 (1990); Scopes, Protein Purification: Principles and Practice, Springer-Verlag, New York (1982). The purification step(s) selected will depend, for example, on the nature of the production process used and the particular stretches of consecutive amino acids or polypeptides of interest produced.

Example of Expression of Stretch of Consecutive Amino Acids or Polypeptide Component of Interest in *E. coli*

The DNA sequence encoding the desired amino acid sequence of interest or polypeptide is initially amplified using selected PCR primers. The primers should contain restriction enzyme sites which correspond to the restriction enzyme sites on the selected expression vector. A variety of expression vectors may be employed. An example of a suitable vector is pBR322 (derived from *E. coli*; see Bolivar et al., Gene, 2:95 (1977)) which contains genes for ampicillin and tetracycline resistance. The vector is digested with restriction enzyme and dephosphorylated. The PCR amplified sequences are then ligated into the vector. The vector will preferably include sequences which encode for an antibiotic resistance gene, a trp promoter, a polyhis leader (including the first six STII codons, polyhis sequence, and enterokinase cleavage site), the specific amino acid sequence of interest/polypeptide coding region, lambda transcriptional terminator, and an argU gene.

The ligation mixture is then used to transform a selected *E. coli* strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized amino acid sequence of interest or polypeptide can then be purified using a metal chelating column under conditions that allow tight binding of the protein.

The primers can contain restriction enzyme sites which correspond to the restriction enzyme sites on the selected expression vector, and other useful sequences providing for efficient and reliable translation initiation, rapid purification on a metal chelation column, and proteolytic removal with enterokinase. The PCR-amplified, poly-His tagged sequences can be ligated into an expression vector used to transform an *E. coli* host based on, for example, strain 52 (W3110 fuhA(tonA) lon galE rpoHts(htpRts) clpP(lacIq). Transformants can first be grown in LB containing 50 mg/ml carbenicillin at 30° C. with shaking until an O.D.600 of 3-5 is reached. Cultures are then diluted 50-100 fold into C RAP media (prepared by mixing 3.57 g $(NH_4)_2$ $SO_4$, 0.71 g sodium citrate-$2H_2O$, 1.07 g KCl, 5.36 g Difco yeast extract, 5.36 g Sheffield hycase SF in 500 mL water, as well as 110 mM MPOS, pH 7.3, 0.55% (w/v) glucose and 7 mM $MgSO_4$) and grown for approximately 20-30 hours at 30° C. with shaking. Samples were removed to verify expression by SDS-PAGE analysis, and the bulk culture is centrifuged to pellet the cells. Cell pellets were frozen until purification and refolding.

*E. coli* paste from 0.5 to 1 L fermentations (6-10 g pellets) was resuspended in 10 volumes (w/v) in 7 M guanidine, 20 mM Tris, pH 8 buffer. Solid sodium sulfite and sodium tetrathionate is added to make final concentrations of 0.1M and 0.02 M, respectively, and the solution was stirred overnight at 4° C. This step results in a denatured protein with all cysteine residues blocked by sulfitolization. The solution was centrifuged at 40,000 rpm in a Beckman Ultracentrifuge for 30 min. The supernatant was diluted with 3-5 volumes of metal chelate column buffer (6 M guanidine, 20 mM Tris, pH 7.4) and filtered through 0.22 micron filters to clarify. Depending the clarified extract was loaded onto a 5 mil Qiagen Ni-NTA metal chelate column equilibrated in the metal chelate column buffer. The column was washed with additional buffer containing 50 mM imidazole (Calbiochem, Utrol grade), pH 7.4. The protein was eluted with buffer containing 250 mM imidazole. Fractions containing the desired protein were pooled and stored at 4.degree. C. Protein concentration was estimated by its absorbance at 280 nm using the calculated extinction coefficient based on its amino acid sequence.

Expression of Stretch of Consecutive Amino Acids or Polypeptides in Mammalian Cells This general example illustrates a preparation of a glycosylated form of a desired amino acid sequence of interest or polypeptide component by recombinant expression in mammalian cells.

The vector pRK5 (see EP 307,247, published Mar. 15, 1989) can be employed as the expression vector. Optionally, the encoding DNA is ligated into pRK5 with selected restriction enzymes to allow insertion of the DNA using ligation methods such as described in Sambrook et al., supra.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 μg of the ligated vector DNA is mixed with about 1 μg DNA encoding the VA RNA gene [Thimmappaya et al., Cell 31:543 (1982)] and dissolved in 500 μl of I mM Tris-HCl, 0.1 mM EDTA, 0.227 M $CaCl_2$ To this mixture is added, dropwise, 500 μl of 50 mM HEPES (pH 7.35), 280 mM NaCl, 1.5 mM $NaPO_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 μCi/ml $^{35}$S-cysteine and 200 μCi/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of amino acid sequence of interest or polypeptide component. The cultures containing transfected cells may undergo further incubation (in serum free medium) and the medium is tested in selected bioassays.

In an alternative technique, the nucleic acid amino acid sequence of interest or polypeptide component may be introduced into 293 cells transiently using the dextran sulfate method described by Somparyrac et al., Proc. Natl. Acad. Sci., 12:7575 (1981). 293 cells are grown to maximal density in a spinner flask and 700 μg of the ligated vector is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 μg/ml bovine insulin and 0.1 μg/ml bovine transferrin. After about four days, the conditioned media is centrifuged and filtered to remove cells and debris. The sample containing expressed amino acid sequence of interest or polypeptide component can then be concentrated and purified by any selected method, such as dialysis and/or column chromatography.

In another embodiment, the amino acid sequence of interest or polypeptide component can be expressed in CHO cells. The amino acid sequence of interest or polypeptide component can be transfected into CHO cells using known reagents such as $CaPO_4$ or DEAE-dextran. As described above, the cell cultures can be incubated, and the medium replaced with culture medium (alone) or medium containing a radiolabel such as $^{35}$S-methionine. After determining the presence of amino acid sequence of interest or polypeptide component, the culture medium may be replaced with serum free medium. Preferably, the cultures are incubated for about 6 days, and then the conditioned medium is harvested. The medium containing the expressed amino acid sequence of interest or polypeptide component can then be concentrated and purified by any selected method.

Epitope-tagged amino acid sequence of interest or polypeptide component may also be expressed in host CHO cells. The amino acid sequence of interest or polypeptide component may be subcloned out of a pRK5 vector. The subclone insert can undergo PCR to fuse in frame with a selected epitope tag such as a poly-his tag into a Baculovirus expression vector. The poly-his tagged amino acid sequence of interest or polypeptide component insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged amino acid sequence of interest or polypeptide component can then be concentrated and purified by any selected method, such as by $Ni^{2+}$-chelate affinity chromatography.

In an embodiment the amino acid sequence of interest or polypeptide component are expressed as an IgG construct (immunoadhesin), in which the coding sequences for the soluble forms (e.g. extracellular domains) of the respective proteins are fused to an IgG1 constant region sequence containing the hinge, CH2 and CH2 domains and/or is a poly-His tagged form.

Following PCR amplification, the respective DNAs are subcloned in a CHO expression vector using standard techniques as described in Ausubel et al., Current Protocols of Molecular Biology, Unit 3.16, John Wiley and Sons (1997). CHO expression vectors are constructed to have compatible restriction sites 5' and 3' of the DNA of interest to allow the convenient shuttling of cDNA's. The vector used in expression in CHO cells is as described in Lucas et al., Nucl. Acids Res. 24:9 (1774-1779 (1996), and uses the SV40 early promoter/enhancer to drive expression of the cDNA of interest and dihydrofolate reductase (DHFR). DHFR expression permits selection for stable maintenance of the plasmid following transfection.

Expression of Stretch of Consecutive Amino Acids or Polypeptides in Yeast

The following method describes recombinant expression of a desired amino acid sequence of interest or polypeptide component in yeast.

First, yeast expression vectors are constructed for intracellular production or secretion of a stretch of consecutive amino acids from the ADH2/GAPDH promoter. DNA encoding a desired amino acid sequence of interest or polypeptide component, a selected signal peptide and the promoter is inserted into suitable restriction enzyme sites in the selected plasmid to direct intracellular expression of the amino acid sequence of interest or polypeptide component. For secretion, DNA encoding the stretch of consecutive amino acids can be cloned into the selected plasmid, together with DNA encoding the ADH2/GAPDH promoter, the yeast alpha-factor secretory signal/leader sequence, and linker sequences (if needed) for expression of the stretch of consecutive amino acids.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant amino acid sequence of interest or polypeptide component can subsequently be isolated and purified by removing the yeast cells from the fermentation medium by centrifugation and then concentrating the medium using selected cartridge filters. The concentrate containing the amino acid sequence of interest or polypeptide component may further be purified using selected column chromatography resins.

Expression of Stretches of Stretch of Consecutive Amino Acids or Polypeptides in Baculovirus-Infected Insect Cells The following method describes recombinant expression of stretches of consecutive amino acids in Baculovirus-infected insect cells.

The desired nucleic acid encoding the stretch of consecutive amino acids is fused upstream of an epitope tag contained with a baculovirus expression vector. Such epitope tags include poly-his tags and immunoglobulin tags (like Fc regions of IgG). A variety of plasmids may be employed, including plasmids derived from commercially available plasmids such as pVL1393 (Novagen). Briefly, the amino acid sequence of interest or polypeptide component or the desired portion of the amino acid sequence of interest or polypeptide component (such as the sequence encoding the extracellular domain of a transmembrane protein) is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BaculoGold™ virus DNA (Pharmingen) into *Spodoptera frugiperda* ("Sf9") cells (ATCC CRL 1711) using lipofectin (commercially available from GIBCO-BRL). After 4-5 days of incubation at 28° C., the released viruses are harvested and used for further amplifications. Viral infection and protein expression is performed as described by O'Reilley et al., Baculovirus expression vectors: A laboratory Manual, Oxford: Oxford University Press (1994).

Expressed poly-his tagged amino acid sequence of interest or polypeptide component can then be purified, for example, by $Ni^{2+}$-chelate affinity chromatography as follows. Extracts are prepared from recombinant virus-infected Sf9 cells as described by Rupert et al., Nature, 362:175-179 (1993). Briefly, Sf9 cells are washed, resuspended in sonication buffer (25 mL Hepes, pH 7.9; 12.5 mM $MgCl_2$; 0.1 mM EDTA; 10% Glycerol; 0.1% NP40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% Glycerol, pH 7.8) and filtered through a 0.45 μm filter. A $Ni^{2+}$-NTA agarose column (commercially available from Qiagen) is prepared with a bed volume of 5 mL, washed with 25 mL of water and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% Glycerol, pH 6.0), which elutes nonspecifically bound protein. After reaching $A_{280}$ baseline again, the column is developed with a 0 to 500 mM Imidazole gradient in the secondary wash buffer. One mL fractions are collected and analyzed by SDS-PAGE and silver staining or western blot with $Ni^{2+}$-NTA-conjugated to alkaline phosphatase (Qiagen). Fractions containing the eluted $His_{10}$-tagged sequence are pooled and dialyzed against loading buffer.

Alternatively, purification of the IgG tagged (or Fc tagged) amino acid sequence can be performed using known chromatography techniques, including for instance, Protein A or Protein G column chromatography.

Fc containing constructs of proteins can be purified from conditioned media as follows. The conditioned media is pumped onto a 5 ml Protein A column (Pharmacia) which is equilibrated in 20 mM Na phosphate buffer, pH 6.8. After loading, the column is washed extensively with equilibration buffer before elution with 100 mM citric acid, pH 3.5. The eluted protein is immediately neutralized by collecting 1 ml fractions into tubes containing 275 mL of 1 M Tris buffer, pH 9. The highly purified protein is subsequently desalted into storage buffer as described above for the poly-His tagged proteins. The homogeneity of the proteins is verified by SDS polyacrylamide gel (PEG) electrophoresis and N-terminal amino acid sequencing by Edman degradation.

Examples of Pharmaceutical Compositions

Non-limiting examples of such compositions and dosages are set forth as follows:

Compositions comprising a compound comprising a stretch of consecutive amino acids which comprises consecutive amino acids having the sequence of etanercept (e.g. Enbrel) may comprise mannitol, sucrose, and tromethamine. In an embodiment, the composition is in the form of a lyophilizate. In an embodiment, the composition is reconstituted with, for example, Sterile Bacteriostatic Water for Injection (BWFI), USP (containing 0.9% benzyl alcohol). In an embodiment the compound is administered to a subject for reducing signs and symptoms, inducing major clinical response, inhibiting the progression of structural damage, and improving physical function in subjects with moderately to severely active rheumatoid arthritis. The compound may be initiated in combination with methotrexate (MTX) or used alone. In an embodiment the compound is administered to a subject for reducing signs and symptoms of moderately to severely active polyarticular-course juvenile rheumatoid arthritis in subjects who have had an inadequate response to one or more DMARDs. In an embodiment the compound is administered to a subject for reducing signs and symptoms, inhibiting the progression of structural damage of active arthritis, and improving physical function in subjects with psoriatic arthritis. In an embodiment the compound is administered to a subject for reducing signs and symptoms in subjects with active ankylosing spondylitis. In an embodiment the compound is administered to a subject for the treatment of chronic moderate to severe plaque psoriasis. In an embodiment wherein the subject has rheumatoid arthritis, psoriatic arthritis, or ankylosing spondylitis the compound is administered at 25-75 mg per week given as one or more subcutaneous (SC) injections. In a further embodiment the compound is administered at 50 mg per week in a single SC injection. In an embodiment wherein the subject has plaque psoriasis the compound is administered at 25-75 mg twice weekly or 4 days apart for 3 months followed by a reduction to a maintenance dose of 25-75 mg per week. In a further embodiment the compound is administered at a dose of at 50 mg twice weekly or 4 days apart for 3 months followed by a reduction to a maintenance dose of 50 mg per week. In an embodiment the dose is between 2× and 100× less than the doses set forth herein. In an embodiment wherein the subject has active polyarticular-course JRA the compound may be administered at a dose of 0.2-1.2 mg/kg per week (up to a maximum of 75 mg per week). In a further embodiment the compound is administered at a dose of 0.8 mg/kg per week (up to a maximum of 50 mg per week). In some embodiments the dose is between 2× and 100× less than the doses set forth hereinabove.

Compositions comprising a compound comprising a stretch of consecutive amino acids which comprises consecutive amino acids having the sequence of infliximab (e.g. Remicade) may comprise sucrose, polysorbate 80, monobasic sodium phosphate, monohydrate, and dibasic sodium phosphate, dihydrate. Preservatives are not present in one embodiment. In an embodiment, the composition is in the form of a lyophilizate. In an embodiment, the composition is reconstituted with, for example, Water for Injection (BWFI), USP. In an embodiment the pH of the composition is 7.2 or is about 7.2. In one embodiment the compound is administered is administered to a subject with rheumatoid arthritis in a dose of 2-4 mg/kg given as an intravenous infusion followed with additional similar doses at 2 and 6 weeks after the first infusion then every 8 weeks thereafter. In a further embodiment the compound is administered in a dose of 3 mg/kg given as an intravenous infusion followed with additional similar doses at 2 and 6 weeks after the first infusion then every 8 weeks thereafter. In an embodiment the dose is adjusted up to 10 mg/kg or treating as often as every 4 weeks. In an embodiment the compound is administered in combination with methotrexate. In one embodiment the compound is administered is administered to a subject with Crohn's disease or fistulizing Crohn's disease at dose of 2-7 mg/kg given as an induction regimen at 0, 2 and 6 weeks followed by a maintenance regimen of 4-6 mg/kg every 8 weeks thereafter for the treatment of moderately to severely active Crohn's disease or fistulizing disease. In a further embodiment the compound is administered at a dose of 5 mg/kg given as an induction regimen at 0, 2 and 6 weeks followed by a maintenance regimen of 5 mg/kg every 8 weeks thereafter for the treatment of moderately to severely active Crohn's disease or fistulizing disease. In an embodiment the dose is adjusted up to 10 mg/kg. In one embodiment the compound is administered to a subject with ankylosing spondylitis at a dose of 2-7 mg/kg given as an intravenous infusion followed with additional similar doses at 2 and 6 weeks after the first infusion, then every 6 weeks thereafter. In a further embodiment the compound is administered at a dose of 5 mg/kg given as an intravenous infusion followed with additional similar doses at 2 and 6 weeks after the first infusion, then every 6 weeks thereafter. In one embodiment the compound is administered to a subject with psoriatic arthritis at a dose of 2-7 mg/kg given as an intravenous infusion followed with additional similar doses at 2 and 6 weeks after the first infusion then every 8 weeks thereafter. In a further embodiment the compound is administered at a dose of 5 mg/kg given as an intravenous infusion followed with additional similar doses at 2 and 6 weeks after the first infusion then every 8 weeks thereafter. In an embodiment the compound is administered with methotrexate. In one embodiment the compound is administered to a subject with ulcerative colitis at a dose of 2-7 mg/kg given as an induction regimen at 0, 2 and 6 weeks followed by a maintenance regimen of 2-7 mg/kg every 8 weeks thereafter for the treatment of moderately to severely active ulcerative colitis. In a further embodiment the compound is administered to a subject with ulcerative colitis at a dose of 5 mg/kg given as an induction regimen at 0, 2 and 6 weeks followed by a maintenance regimen of 5 mg/kg every 8 weeks thereafter. In some embodiments the dose is between 2× and 100× less than the doses set forth hereinabove for treating the individual diseases.

In each of the embodiments of the compositions described herein, the compositions, when in the form of a lyophilizate, may be reconstituted with, for example, sterile aqueous solutions, sterile water, Sterile Water for Injections (USP), Sterile Bacteriostatic Water for Injections (USP), and equivalents thereof known to those skilled in the art.

It is understood that in administration of any of the instant compounds, the compound may be administered in isolation, in a carrier, as part of a pharmaceutical composition, or in any appropriate vehicle.

Dosage

It is understood that where a dosage range is stated herein, e.g. 1-10 mg/kg per week, the invention disclosed herein also contemplates each integer dose, and tenth thereof, between the upper and lower limits. In the case of the example given, therefore, the invention contemplates 1.0, 1.1, 1.2, 1.3, 1.4, 1.5, 1.6, 1.7, 1.8, 1.9, 2.0, 2.1, 2.2, 2.3, 2.4 etc. mg/kg up to 10 mg/kg.

In embodiments, the compounds of the present invention can be administered as a single dose or may be administered as multiple doses.

In general, the daily dosage for treating a disorder or condition according to the methods described above will generally range from about 0.01 to about 10.0 mg/kg body weight of the subject to be treated.

Variations based on the aforementioned dosage ranges may be made by a physician of ordinary skill taking into account known considerations such as the weight, age, and condition of the person being treated, the severity of the affliction, and the particular route of administration chosen.

It is also expected that the compounds disclosed will effect cooperative binding with attendant consequences on effective dosages required.

Pharmaceuticals

The term "pharmaceutically acceptable carrier" is understood to include excipients, carriers or diluents. The particular carrier, diluent or excipient used will depend upon the means and purpose for which the active ingredient is being applied.

For parenteral administration, solutions containing a compound of this invention or a pharmaceutically acceptable salt thereof in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. The sterile aqueous media employed are all readily available by standard techniques known to those skilled in the art.

The compositions of this invention may be in a variety of forms. These include, for example, liquid, semi-solid and solid dosage forms, such as liquid solutions (e.g., injectable and infusible solutions), dispersions or suspensions. The preferred form depends on the intended mode of administration and therapeutic application. Some compositions are in the form of injectable or infusible solutions. A mode of administration is parenteral (e.g., intravenous, subcutaneous, intraperitoneal, intramuscular). In an embodiment, the compound is administered by intravenous infusion or injection. In another embodiment, the compound is administered by intramuscular or subcutaneous injection.

For therapeutic use, the compositions disclosed here can be administered in various manners, including soluble form by bolus injection, continuous infusion, sustained release from implants, oral ingestion, local injection (e.g. intracrdiac, intramuscular), systemic injection, or other suitable techniques well known in the pharmaceutical arts. Other methods of pharmaceutical administration include, but are not limited to oral, subcutaneously, transdermal, intravenous, intramuscular and parenteral methods of administration. Typically, a soluble composition will comprise a purified compound in conjunction with physiologically acceptable carriers, excipients or diluents. Such carriers will be nontoxic to recipients at the dosages and concentrations employed. The preparation of such compositions can entail combining a compound with buffers, antioxidants, carbohydrates including glucose, sucrose or dextrins, chelating agents such as EDTA, glutathione and other stabilizers and excipients. Neutral buffered saline or saline mixed with conspecific serum albumin are exemplary appropriate diluents. The product can be formulated as a lyophilizate using appropriate excipient solutions (e.g., sucrose) as diluents.

Other derivatives comprise the compounds/compositions of this invention covalently bonded to a nonproteinaceous polymer. The bonding to the polymer is generally conducted so as not to interfere with the preferred biological activity of the compound, e.g. the binding activity of the compound to a target. The nonproteinaceous polymer ordinarily is a hydrophilic synthetic polymer, i.e., a polymer not otherwise found in nature. However, polymers which exist in nature and are produced by recombinant or in vitro methods are useful, as are polymers which are isolated from nature. Hydrophilic polyvinyl polymers fall within the scope of this invention, e.g. polyvinylalcohol and polyvinylpyrrolidone. Particularly useful are polyalkylene ethers such as polyethylene glycol, polypropylene glycol, polyoxyethylene esters or methoxy polyethylene glycol; polyoxyalkylenes such as polyoxyethylene, polyoxypropylene, and block copolymers of polyoxyethylene and polyoxypropylene (Pluronics); polymethacrylates; carbomers; branched or unbranched polysaccharides which comprise the saccharide monomers D-mannose, D- and L-galactose, fucose, fructose, D-xylose, L-arabinose, D-glucuronic acid, sialic acid, D-galacturontc acid, D-mannuronic acid (e.g. polymannuronic acid, or alginic acid), D-glucosamine, D-galactosamine, D-glucose and neuraminic acid including homopolysaccharides and heteropolysaccharides such as lactose, amylopectin, starch, hydroxyethyl starch, amylose, dextran sulfate, dextran, dextrins, glycogen, or the polysaccharide subunit of acid mucopolysaccharides, e.g. hyaluronic acid; polymers of sugar alcohols such as polysorbitol and polymannitol; as well as heparin or heparon.

The pharmaceutical compositions of the invention may include a "therapeutically effective amount" or a "prophylactically effective amount" of a compound of the invention. A "therapeutically effective amount" refers to an amount effective, at dosages and for periods of time necessary, to achieve the desired therapeutic result. A therapeutically effective amount of the compound may vary according to factors such as the disease state, age, sex, and weight of the individual. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

All combinations of the various elements disclosed herein are within the scope of the invention.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Example 1: TNR1B-alkyne-azide-Fc6

TNR1B-alkyne-azide-Fc6 was prepared via the reaction of alkyne-modified TNR1B (TNF receptor 1B) with azide-modified Fc6 as follows. TNR1B-azide-alkyne-Fc6 is prepared using the same principles via the reaction of azide-modified TNR1B with alkyne-modified Fc6.

Alkyne-modified TNFR1B (TNR1B-Alk) was prepared by cleavage of TNR1B-intein (TNR1B-Mth fusion protein) with cystyl-propargylamide, $HSCH_2CH[NH_2]CONHCH_2C\equiv CH_3$ (FIG. 1) and azide-modified TNR1B (TNR1B-Az) was prepared by cleavage of TNR1B-intein with cystyl-3-azidopropylamide, $HSCH_2CH[NH_2]CONH(CH_2)_3NH_2$.

TNR1B-intein and Fc6 are described in U.S. Ser. No. 11/982,085, published Oct. 16, 2008, the whole of which is incorporated herein by reference.

TNR1B-intein fusion protein was produced using vector pCDNA3-TNR1B-Mth, the sequence of which is shown in SEQ ID NO: 100. The pre-TNR1B-intein chimeric polypeptide that is initially expressed, containing the TNR1B extracellular domain joined at its C-terminus by a peptide bond to the N-terminus of an Mth RIR1 self-splicing intein at the autocleavage site, is shown in SEQ ID NO: 101. Cleavage of the homologous TNR signal sequences by the cellular signal peptidase provides the mature TNR1B-intein fusion protein that is secreted into the cell culture fluid, the sequence of which is shown in SEQ ID NO: 102.

Fc6 protein was expressed using vector pCDNA3-SHH-IgG1-Fc11, the sequence of which is shown in SEQ ID NO: 103. The pre-Fc6 polypeptide that is initially expressed is shown in SEQ ID NO: 104. Cleavage of the heterologous sonic hedgehog (SHH) signal sequences by the cellular signal peptidase provides the mature Fc6 protein that is secreted into the cell culture fluid, the sequence of which is shown in SEQ ID NO: 105.

Protein production was executed by transient expression in CHO-DG44 cells, adapted to serum-free suspension culture. Transient transfections were done with polyethylenimine as transfection agent, complexed with DNA, under high density conditions as described by Rajendra et al., J. Biotechnol. 153, 22-26 (2011). Seed train cultures were maintained in TubeSpin® bioreactor 50 tubes obtained from TPP (Trasadingen, CH) and scaled up in volume to generate sufficient biomass for transfection. Transfections were carried out in cultures of 0.5-1.0 L. Cultures at this scale were maintained in 2 L or 5 L Schott-bottles with a ventilated cap. The bottles were shaken at 180 rpm in a Kühner incubator shaker with humidification and $CO_2$ control at 5%. The cell culture fluid was harvested after 10 days, centrifuged and sterile-filtered, prior to purification.

Cystyl-propargylamide and cystyl-3-azidopropylamide were prepared as follows. Boc-Cys(Trt)-OH, $(C_6H_5)_3CSCH_2CH[NHCO_2C(CH_3)_3]CO_2H$; propargylamine, $HC\equiv CCH_2NH$; 3-azidopropylamine, $NH_2CH_2CH_2CH_2N_3$; EDC, N-(3-Dimethylaminopropyl)-N'-ethylcarbodiimide hydrochloride; and HOBt, 1-Hydroxybenzotriazole, and were obtained from AnaSpec (Freemont, Calif.) or CPC Scientific (San Jose, Calif.). All other chemicals were obtained from Sigma-Aldrich (St. Louis, Mo.). For the synthesis of cystyl-propargylamide, a solution of Boc-Cys (Trt)-OH (100 mM) and propargylamine (100 mM) in CH2Cl2 was made 100 mM each in EDC, HOBt, and triethylamine. For the synthesis of cystyl-3-azidopropylamide, 3-azidopropylamine (100 mM) was substituted for propargylamine. Both reactions were worked up by the following procedure. After stirring overnight at room temperature, the reaction was stopped with an excess of saturated NaHCO₃ in water, extracted with CH2Cl2, dried over MgSO4, filtered, evaporated, and purified by column chromatography. To remove the Boc/Trt protecting groups, the intermediate product was dissolved at a concentration of 0.05M in TFA/triisopropylsilane/H2O (90:5:5) and stirred for 30 minutes at room temperature. The reaction was then dried by evaporation and extracted with CH2Cl2. The organic layer was then extracted with water, yielding the final cystyl-propargylamide product as a yellowish oil, and the final cystyl-3-azidopropylamide product as a yellowish solid.

To prepare the alkyne-modified TNR1B (FIG. 1) or the azide-modified TNR1B, the TNR1B-intein protein in the cell culture fluid was applied to a column packed with chitin beads obtained from New England BioLabs (Beverley, Mass.) that was pre-equilibrated with buffer A (20 mM Tris-HCl, 500 mM NaCl, pH 7.5). Unbound protein was washed from the column with buffer A. Cleavage was initiated by rapidly equilibrating the chitin resin in buffer B (20 mM Tris-HCl, 500 mM NaCl, pH 8.0) containing either 50 mM cystyl-propargylamide (for alkyne-modified TNR1B) or 50 mM cystyl-3-azidopropylamide (for azide-modified TNR1B) and incubation was carried out for 24 to 96 hours at room temperature. The cleaved alkyne-modified TNR1B (SEQ ID NO: 106) or azide-modified TNR1B proteins (SEQ ID NO: 107) were eluted from the column with buffer A, concentrated using an Amicon Ultracel-3 Centrifugal Filter Unit from Millipore (Billerica, Mass.), dialyzed against Dulbecco's phosphate buffered saline without Ca or Mg salts (PBS) obtained from the UCSF Cell Culture Facility (San Francisco, Calif.), and stored at 4° C. prior to use.

Figure 2:
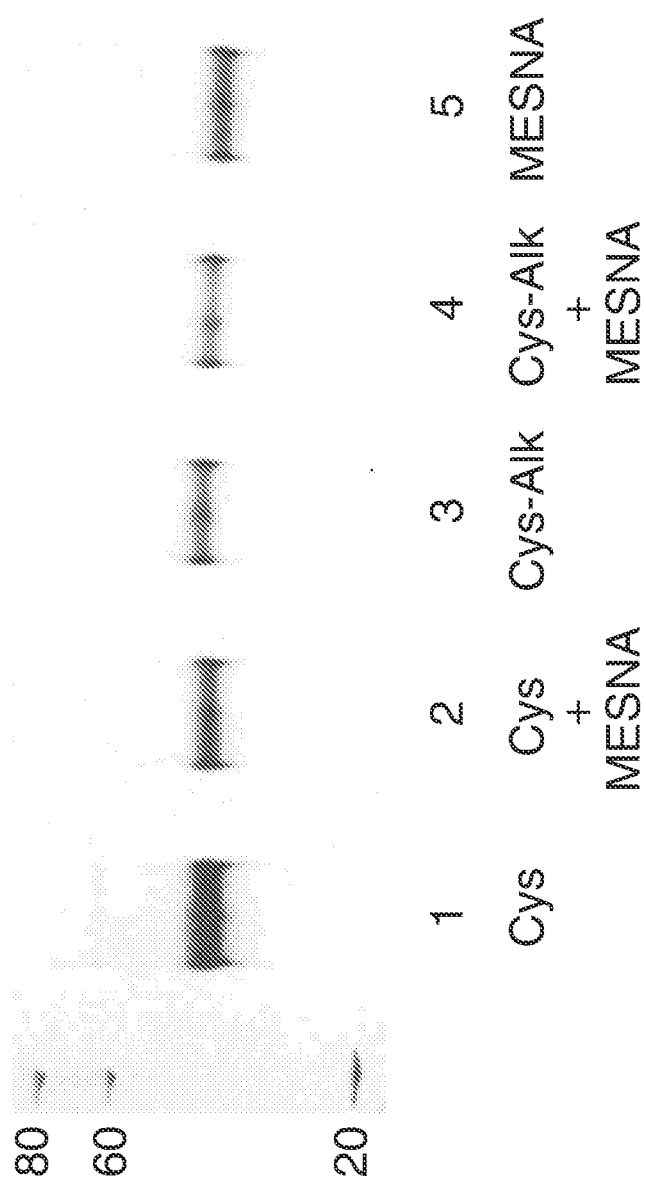
FIG. 2 shows the cleavage of TNR1B by (1) cysteine, (2) cysteine+mercaptoethane sulfonate (MESNA), (3) cystyl-propargylamide, (4) cystyl-propargylamide+MESNA, and (5) MESNA. All compounds were used at 50 mM concentration.

FIG. 2 shows SDS-polyacrylamide gel electrophoresis (SDS-PAGE) analysis of the alkyne-modified TNR1B, compared with cysteine-modified TNR1B (SEQ ID NO: 108) prepared using 50 mM cysteine instead of cystyl-propargylamide. SDS-PAGE was carried out using NuPAGE® Novex Bis-Tris Midi Gels (10%) obtained from Invitrogen (Carlsbad, Calif.). Proteins were visualized using Silver Stain Plus or Bio-Safe Coomassie Stain obtained from Bio-Rad (Hercules, Calif.). The alkyne-modified TNR1B (lane 3) and the cysteine-modified TNR1B (lane 1) had the same Mr ~43,000. In addition, the alkyne-modified TNR1B had comparable biological activity to cysteine-modified TNR1B as measured using a Human sTNFRII/TNFRSF1B Quantikine ELISA obtained from R&D Systems (Minneapolis, Minn.). Preparations of the cysteine-modified TNR1B (lane 2), alkyne-modified TNR1B (lane 4), or thioester-modified TNR1B (SEQ ID NO: 109) (lane 5) made in the presence of 50 mM MESNA had a similar Mr, but had less than 5% of the biological activity observed for preparations made in the absence of MESNA. Thus, alkyne-modified TNR1B prepared in the absence of MESNA was employed in further studies.

Figure 3:
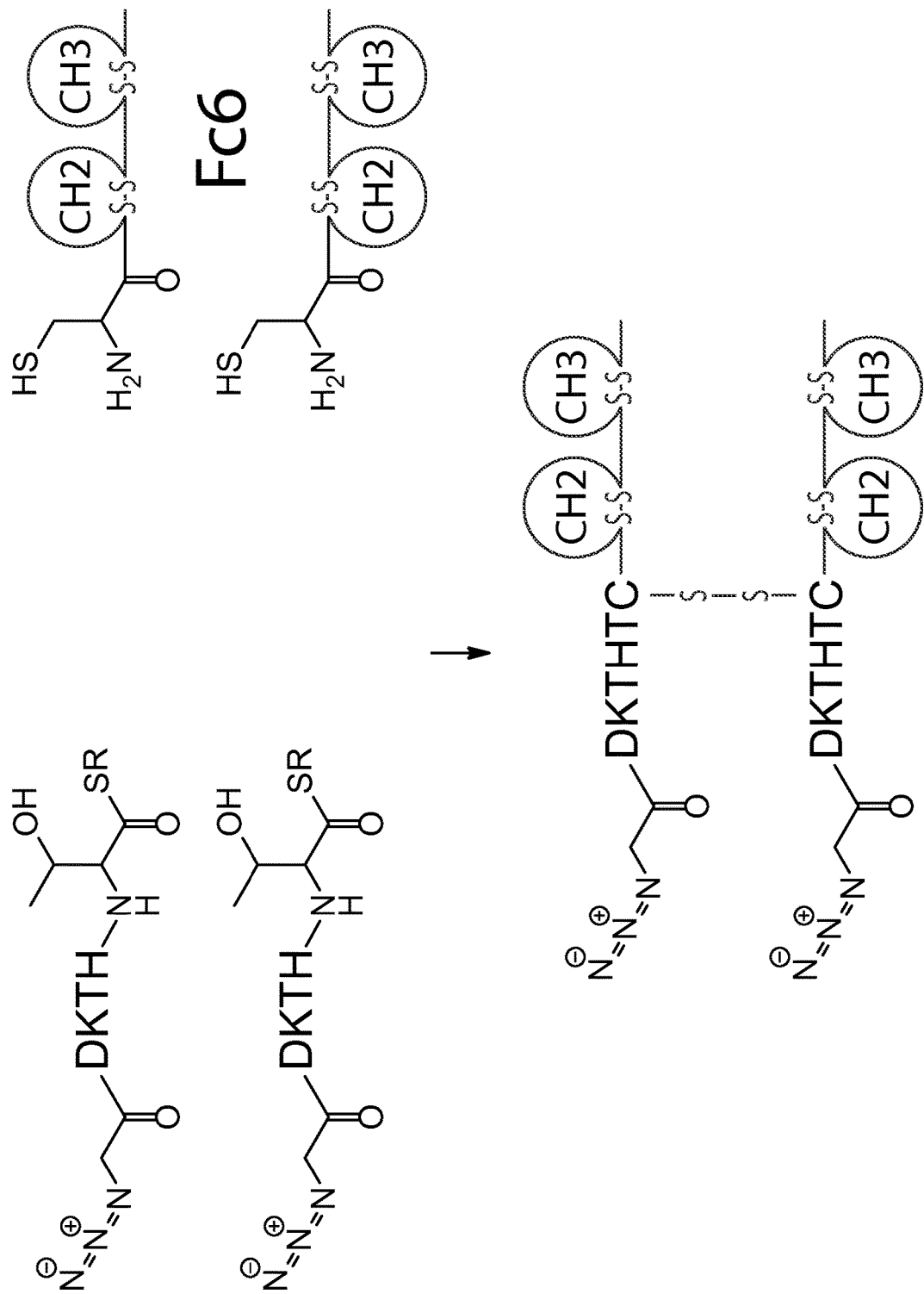
FIG. 3 shows the preparation of azide-modified Fc6 by ligation (peptidyl) of the Fc6 dimer and azide-DKTHT-thioester (Table 1).
Figure 4:
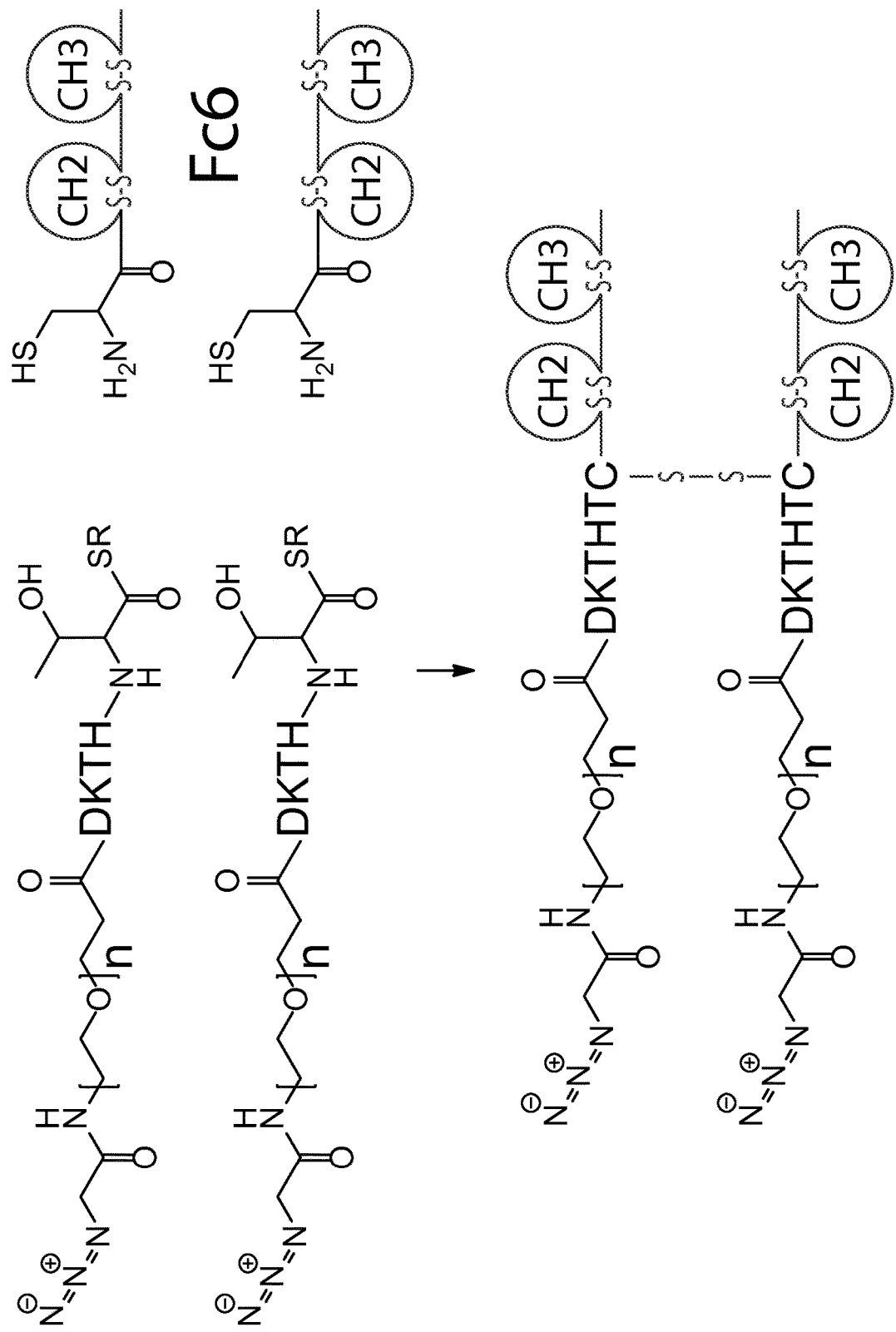
FIG. 4 shows the preparation of azide-modified Fc6 by ligation (peptidyl) of the Fc6 dimer and azide-$PEG_n$-DKTHT-thioester (Table 1). Cycloalkyne-modified Fc is similarly prepared by using DIBAC-$PEG_{12}$-thioester.

Azide-modified Fc6 (Az-Fc6) was prepared by the reaction of Fc6 protein with various azide-containing peptide thioesters (FIG. 3) and azide-containing PEG thioesters (FIG. 4). Alkyne-modified Fc6 (Alk-Fc6) was prepared by the reaction of alkyne-containing thioesters with Fc6 protein.

Recombinant Fc6 protein was expressed in Chinese hamster ovary (CHO) cells as described for TNR1B-intein (see above) and purified by Protein A affinity chromatography. The culture supernatant was applied to a column packed with rProtein A Fast Flow from Pharmacia (Uppsala, Sweden) pre-equilibrated with PBS. The column was washed extensively with PBS and the Fc6 protein then eluted with 0.1 M glycine buffer pH 2.7. Fractions were collected into tubes containing 0.05 vol/vol of 1.0 M Tris-HCl pH 9.0 (giving a final pH of 7.5), pooled, dialyzed against PBS, and stored at 4° C. prior to use.

Table 1 shows representative azide-containing and alkyne-containing peptide/PEG thioesters. Thioesters were synthesized by an Fmoc/t-Butyl solid-phase strategy on a 2-chlorotrityl chloride resin preloaded with the Fmoc-Thr (tBu)-OH. Amino acid derivatives were obtained from CPC Scientific (Sunnyvale, Calif.), Fmoc-PEG$_n$-OH derivatives were obtained from Quanta BioDesign (Powell, Ohio), and 2-(1H-benzotriazole-1-yl)-1,1,3,3-tetramethylaminium hexafluorophosphate (HBTU), dichloromethane (DCM), trichloroacetic acid (TFA), N,N'-diisopropylcarbodiimide (DIC), 1-hydroxybenzotriazole (HOBt), N,N'-diisopropylethylamine (DIEA) and triisopropylsilane (TIS) were obtained from Sigma (St. Louis, Mo.). The standard HBTU activation was employed for peptide elongation. Peptides containing PEG required the insertion of a Fmoc-PEG$_n$-OH. As a final step in peptide elongation, the terminal α-Fmoc (9-fluorenylmethoxycarbonyl) protecting group was converted to Boc (tert-butoxycarbonyl). The peptide resin was washed with DCM and cleaved with 1% TFA/DCM to yield the fully protected peptide with a free carboxylic acid on the C-terminus. The thioester of the peptides was formed by treating the crude protected peptide with DIC/HOBt/DIEA and benzyl mercaptan or thiophenol in DCM overnight. After concentration, the crude protected peptide thioester was precipitated by multiple triturations with cold ether followed by centrifugation. Deprotection was carried out by treatment of the crude protected product with 95:2.5:2.5 TFA/TIS/H$_2$O for 2 hours at room temperature. After precipitation with ice-cold ether the deprotected peptide thioester was purified by preparative RP-HPLC in a H$_2$O-acetonitrile (0.1% TFA) system to afford the final product with 91-95% purity and the desired MS.

Azide-modified Fc6 and alkyne-modified Fc6 were prepared by native chemical ligation as follows. 2-(N-morpholino)ethanesulfonic acid (MES) was obtained from Acros (Morris Plains, N.J.), tris(2-carboxyethyl)phosphine (TCEP) was obtained from Pierce (Rockford, Ill.), and 4-mercaptophenylacetic acid (MPAA) was obtained from Sigma-Aldrich (St. Louis, Mo.). Reactions were carried out by ligating the various thioesters shown in Table 1 with the Fc6 protein as follows. Reactions (100 uL) contained 50 mM MES buffer, pH 6.5, 0.8 mM TCEP, 10 mM MPAA, 4 mg/ml of the peptide thioester, and 0.5 mg/ml of the Fc6 protein. Following overnight incubation at room temperature, reactions were adjusted to pH 7.0 with 0.05 vol/vol of 1.0 M Tris-HCl pH 9.0, purified using Protein A Magnetic Beads from New England BioLabs, dialyzed in 0.1 M phosphate pH 8.0, and concentrated.

Figure 5:
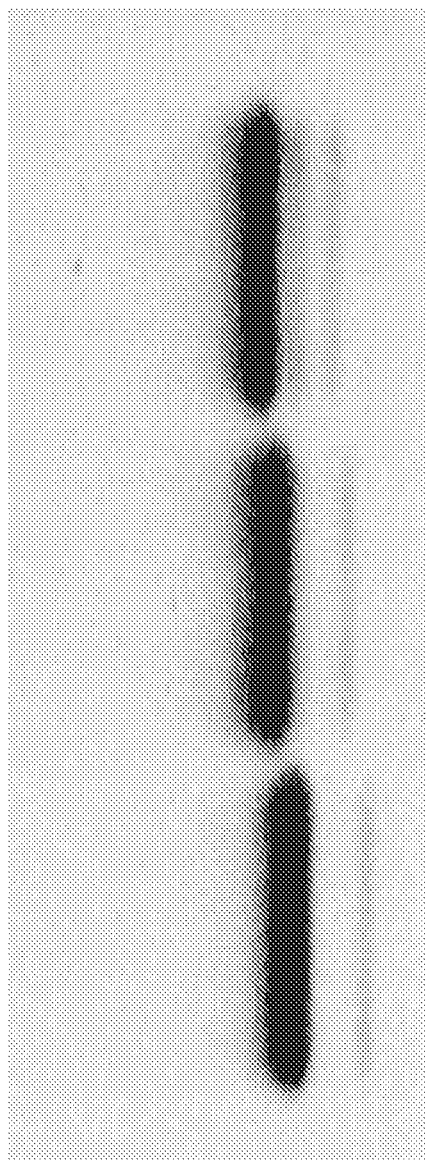
FIG. 5 shows SDS-PAGE analysis (reducing conditions) of (1) unmodified Fc6, (2) the Az-DKTHT-Fc6 reaction product of FIG. 3, and (3) the Az-$PEG_4$-DKTHT-Fc6 reaction product of FIG. 4.

FIG. 5 shows SDS-PAGE analysis demonstrating that Fc6 protein (lane 1) reacted quantitatively with azide-DKTHT-thioester to yield the Az-DKTHT-Fc6 protein (lane 2) and azide-PEG$_4$-DKTHT-thioester to yield the Az-PEG$_4$-DKTHT-Fc6 protein (lane 3). The sequence of the Az-DKTHT-Fc6 protein is shown in SEQ ID NO: 110 and the sequence of the Az-PEG$_4$-DKTHT-Fc6 is shown in SEQ ID NO: 111. The PEG$_4$ oligomer gave an incremental size increase comparable to the 5 amino acid DKTHT sequence. This shows that a single oxyethylene monomer unit makes a contribution to contour length similar to a single amino acid residue, consistent with their having comparable fully extended conformations of ~3.5 to 4 Å (Flory (1969) Statistical Mechanics of Chain Molecules (Interscience Publishers, New York).

Figure 6:
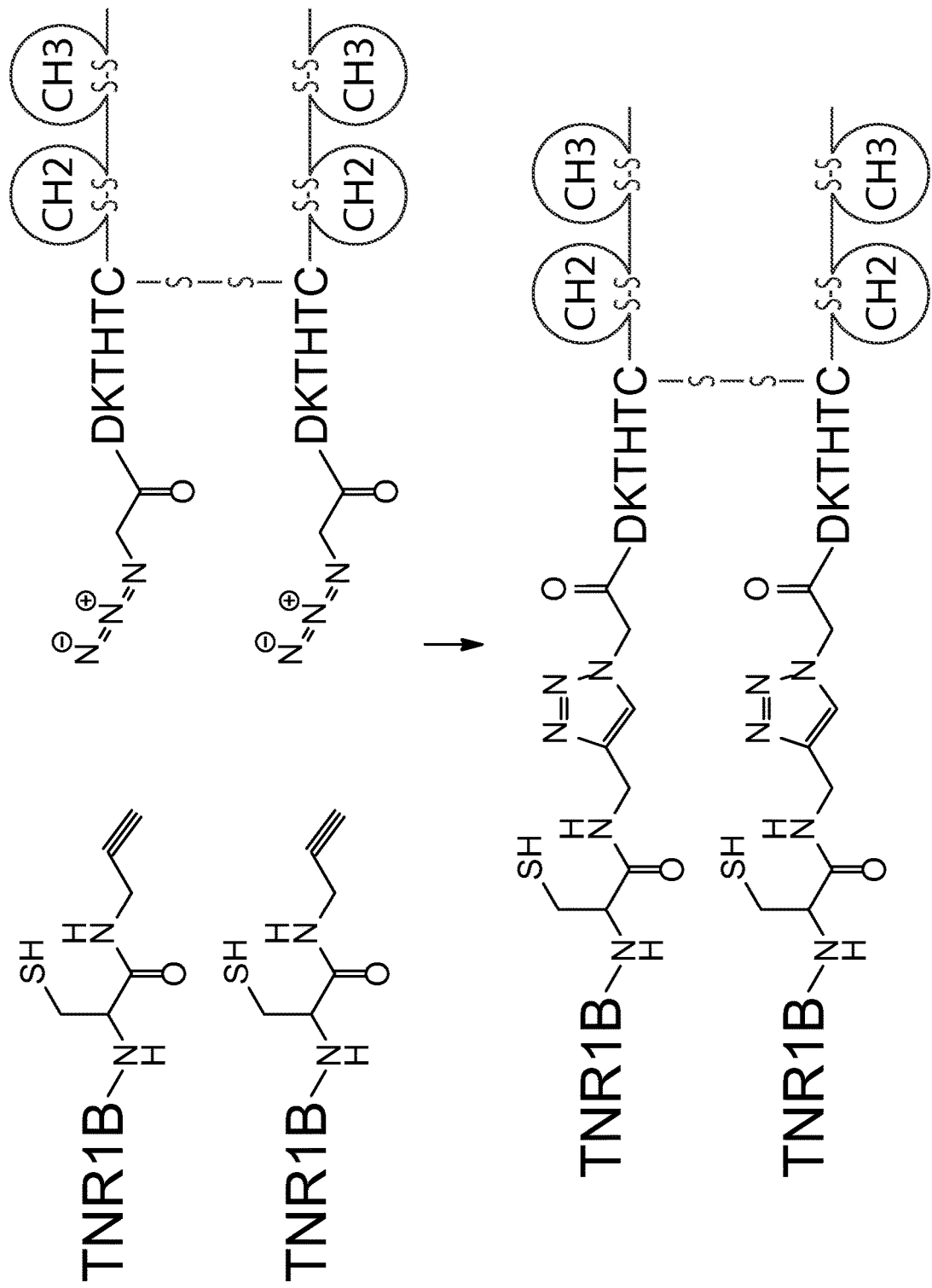
FIG. 6 shows the synthesis of TNR1B-alkyne-azide-Fc6 by ligation (non-peptidyl) of alkyne-modified TNR1B and Az-DKTHT-Fc6.
Figure 7:
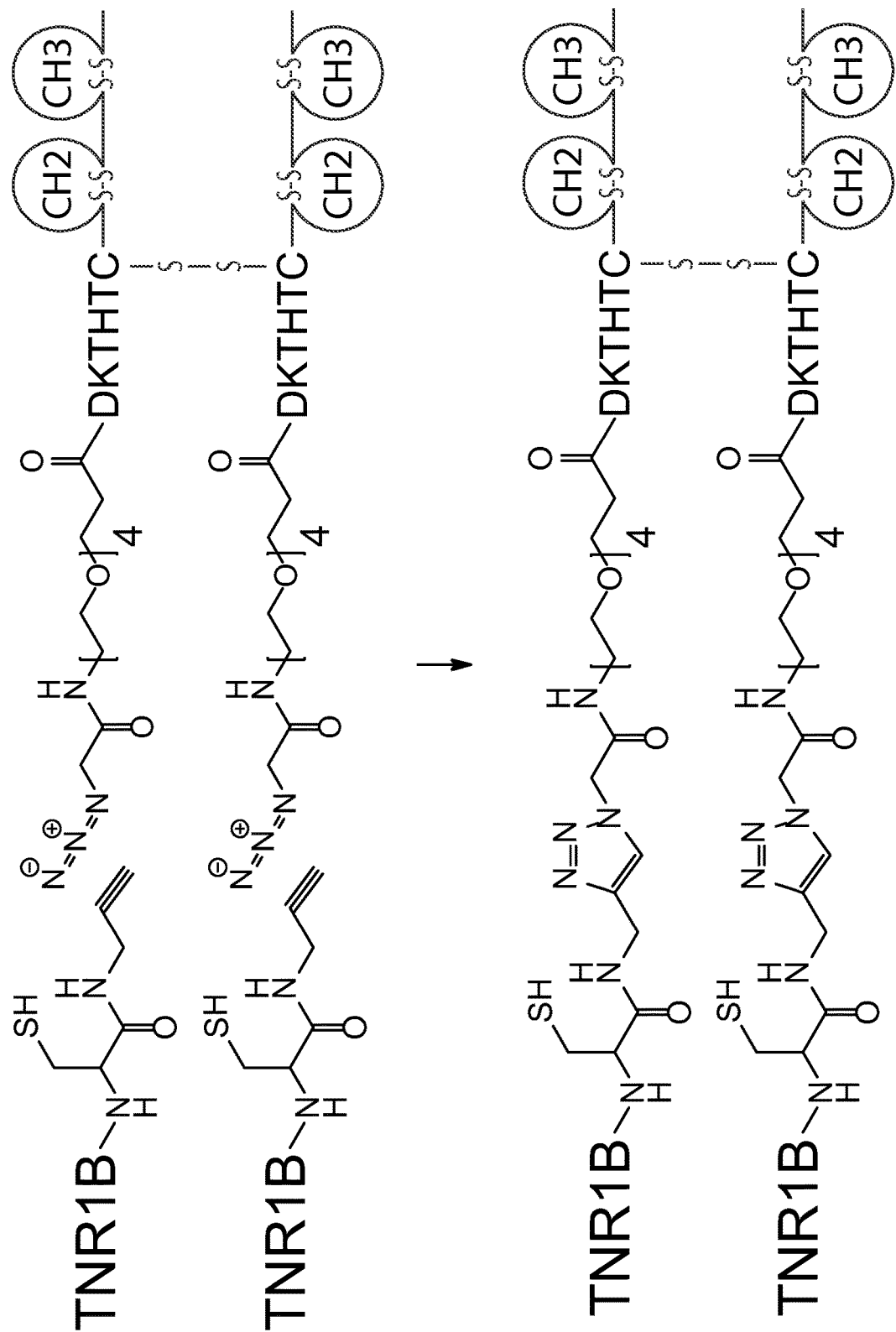
FIG. 7 shows the synthesis of TNR1B-alkyne-azide-$PEG_n$-Fc6 by ligation (non-peptidyl) of alkyne-modified TNR1B and azide-$PEG_n$-DKTHT-Fc6. In this example, n=4.

TNR1B-alkyne-azide-Fc6 was prepared via the reaction of the alkyne-modified TNR1B with the Az-DKTHT-Fc6 protein (FIG. 6) and the Az-PEG$_4$-DKTHT-Fc6 protein (FIG. 7). Sodium phosphate, dibasic (anhydrous) and sodium phosphate, monobasic (monohydrate) were obtained from Acros, TCEP was from Pierce, CuSO$_4$ (pentahydrate) was from Sigma-Aldrich, and Tris[1-benzyl-1H-1,2,3-triazol-4-yl)methyl]amine (TBTA) from AnaSpec (Freemont, Calif.). Reactions (60 uL) contained 0.1 M sodium phoshate, pH 8.0, 1.0 mM CuSO$_4$, 2.0 mM TBTA, the alkyne-modified TNR1B (30 ug), and either the unmodified Fc6 protein, the Az-DKTHT-Fc6 protein, or the Az-PEG$_4$-DKTHT-Fc6 protein (10 ug). Reactions were initiated by the addition of 2.0 mM TCEP, and incubated overnight at room temperature. The reaction products were purified using Protein A Magnetic Beads to remove any unreacted alkyne-modified TNR1B.

Figure 8:
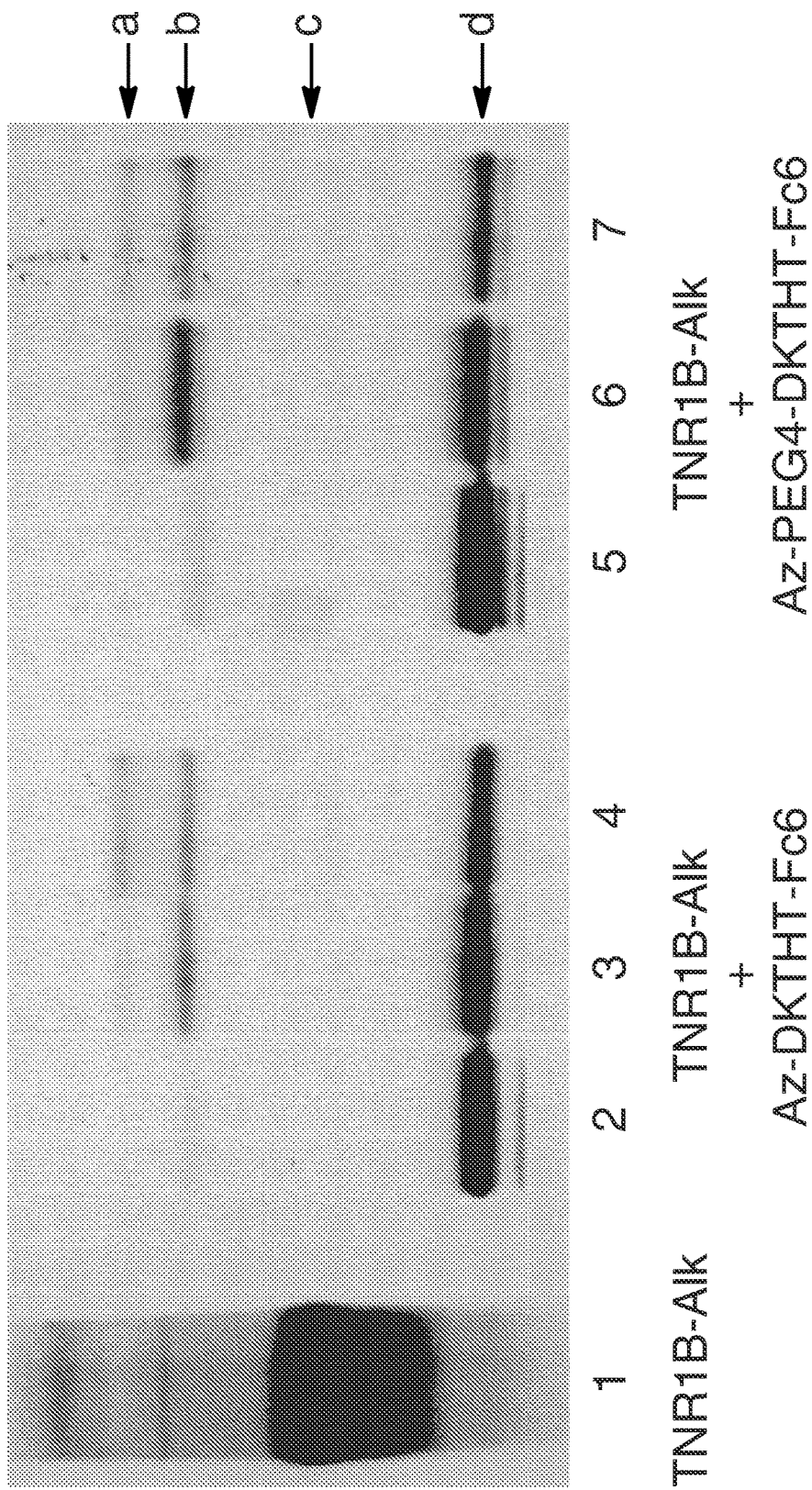
FIG. 8 shows SDS-PAGE analysis (reducing conditions) of (1) alkyne-modified TNR1B alone, (2) alkyne-modified TNR1B+Az-DKTHT-Fc6 in the absence of catalyst, (3) alkyne-modified TNR1B+Az-DKTHT-Fc6+catalyst leading to the product of FIG. 6, and (4) dialyzed alkyne-modified TNR1B+Az-DKTHT-Fc6+catalyst leading to increased formation of the product of FIG. 6, (5) alkyne-modified TNR1B+Az-$PEG_4$-DKTHT-Fc6 in the absence of catalyst, (6) alkyne-modified TNR1B+Az-$PEG_4$-DKTHT-Fc6+catalyst leading to the product of FIG. 7, and (7) dialyzed alkyne-modified TNR1B+Az-$PEG_4$-DKTHT-Fc6+catalyst leading to increased formation of the product of FIG. 7. The arrows correspond to (a) Mr ~75,000, (b) Mr ~65,000, (c) Mr ~43,000, and (d) Mr ~28,000.

FIG. 8 shows SDS-PAGE analysis of the TNR1B-alkyne-azide-Fc6 products under reducing conditions. In the absence of CuSO$_4$, TBTA and TCEP, both Az-DKTHT-Fc6 (lane 2) and Az-PEG$_4$-DKTHT-Fc6 (lane 5) gave a single band of Mr ~28-30,000 daltons (arrow d) corresponding to the input azide-modified Fc6 proteins, with no sign of any product formation. In addition, there was no evidence of any carryover of the input alkyne-modified TNR1B (shown in lane 1) following the Protein A purification. However, in the presence of CuSO$_4$, TBTA and TCEP, the reaction between alkyne-modified TNR1B and Az-DKTHT-Fc6 (lane 3) and the reaction between alkyne-modified TNR1B and Az-PEG$_4$-DKTHT-Fc6 (lane 6) both yielded two new products of Mr ~75,000 daltons (arrow a) and ~65,000 daltons (arrow b). Reactions carried out using a preparation of alkyne-modified TNR1B following buffer-exchange in 0.1 M phosphate pH 8.0 to remove salt gave essentially similar reaction products with both Az-DKTHT-Fc6 (lane 4) and Az-PEG$_4$-DKTHT-Fc6 (lane 6), although there was a significant increase in the yield of the Mr ~75,000 dalton product over the Mr ~65,000 dalton product.

Figure 9:
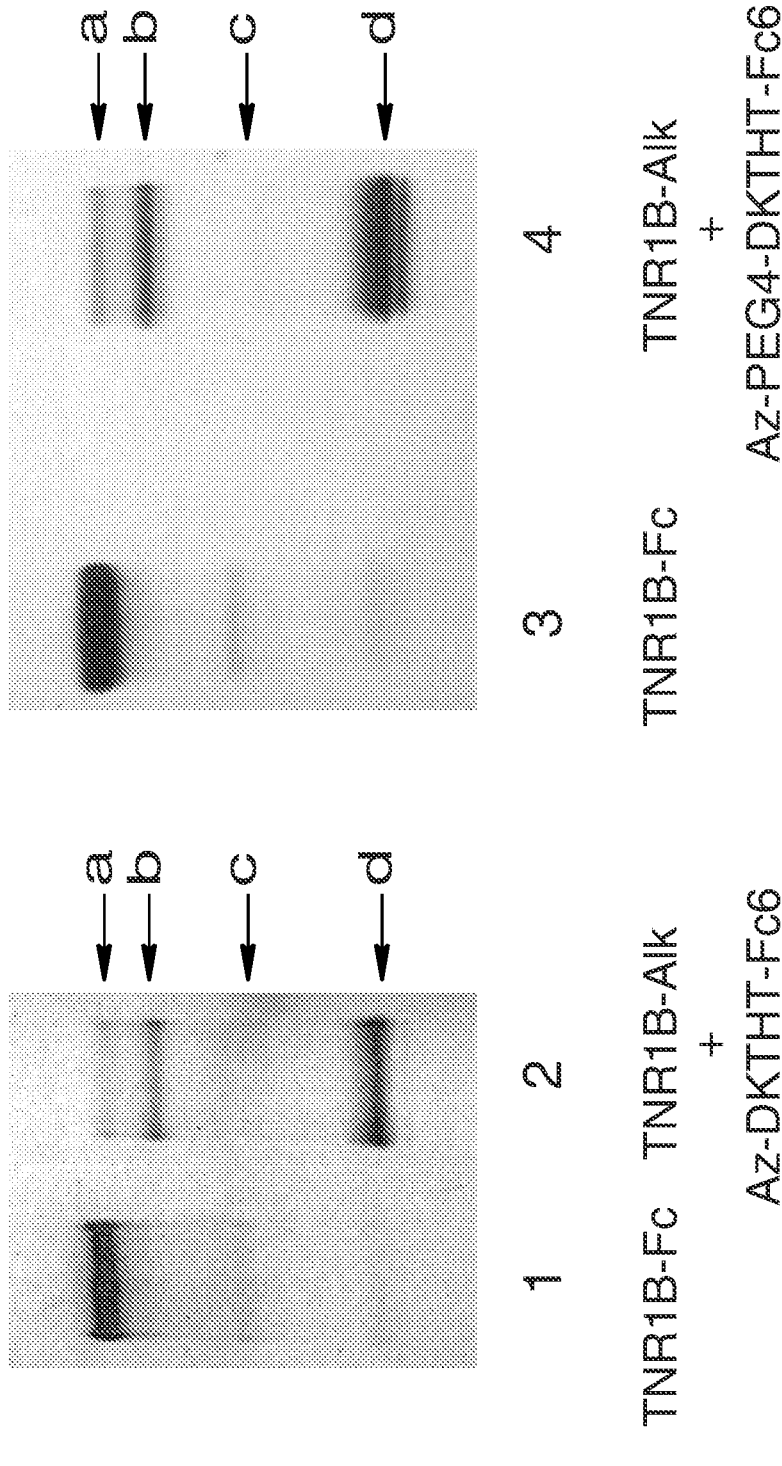
FIG. 9 shows SDS-PAGE analysis (reducing conditions) of (1) TNR1B-Fc fusion protein (etanercept) alone, (2) alkyne-modified TNR1B+Az-DKTHT-Fc6+catalyst leading to the product of FIG. 6, (3) TNR1B-Fc fusion protein (etanercept), and (4) alkyne-modified TNR1B+Az-$PEG_4$-DKTHT-Fc6 leading to the product of FIG. 7. The arrows correspond to (a) Mr ~75,000, (b) Mr ~65,000, (c) Mr ~43,000, and (d) Mr ~28,000.

FIG. 9 shows SDS-PAGE analysis comparing the TNR1B-alkyne-azide-Fc6 reaction products (left panel) and the TNR1B-alkyne-azide-PEG4-Fc6 reaction products (right panel) with TNR1B-Fc fusion protein (etanercept). The TNR1B-alkyne-azide-Fc6 product of Mr ~75,000 daltons (lane 2), having the predicted sequence shown in SEQ ID NO: 112 joined by the alkyne-azide non-peptidyl linker to SEQ ID NO: 113, and the TNR1B-alkyne-azide-PEG4-Fc6 product of Mr ~75,000 daltons (lane 4), having the predicted sequence of shown in SEQ ID NO: 112 joined by the alkyne-azide non-peptidyl and PEG4 linker to SEQ ID NO: 113, are essentially indistinguishable in size from etanercept (lanes 1, 3), the sequence of which is shown in SEQ ID NO: 114.

Figure 10:
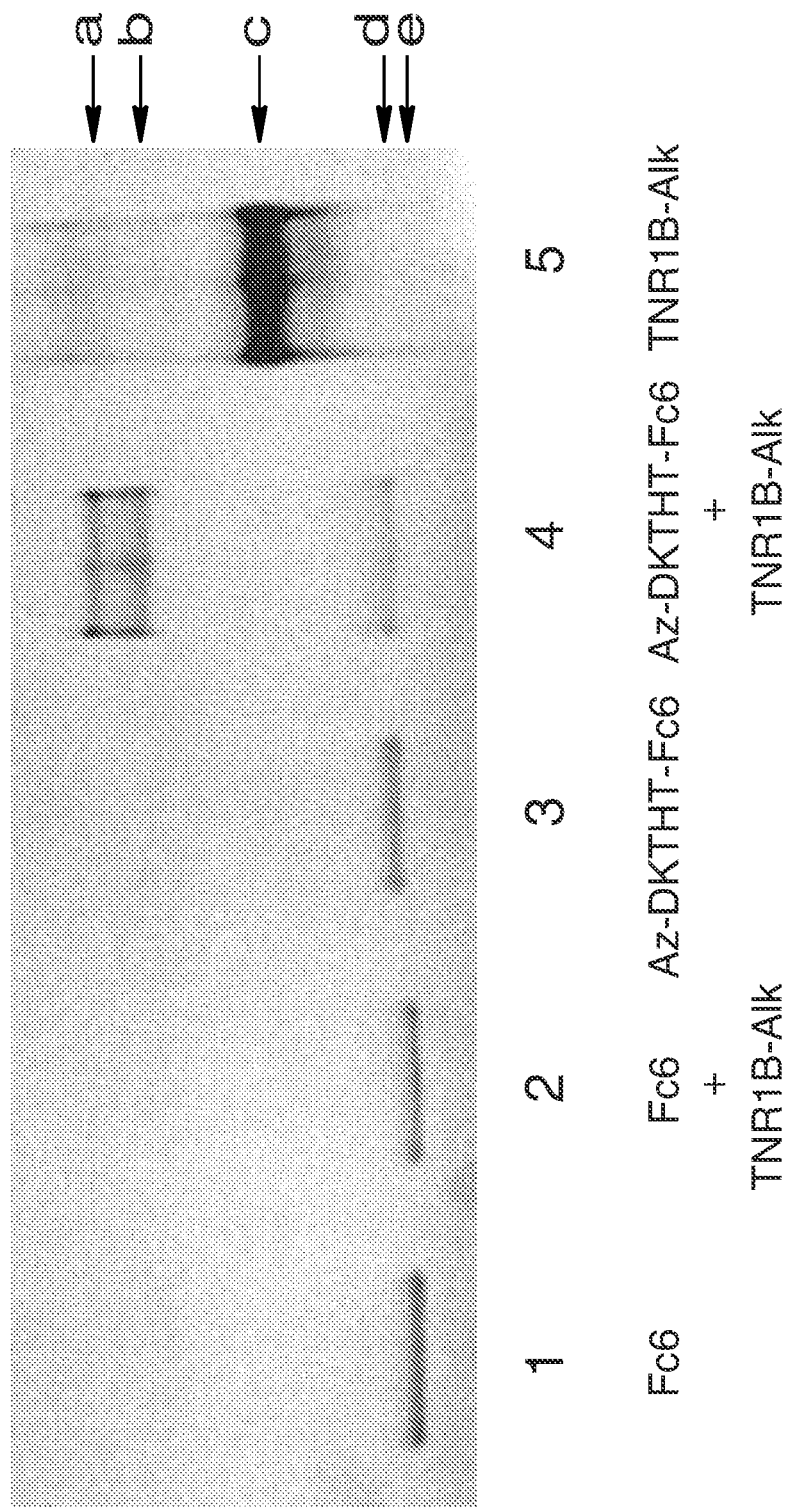
FIG. 10 shows SDS-PAGE analysis (reducing conditions) of (1) unmodified Fc6+catalyst, (2) alkyne-modified TNR1B+unmodified Fc6+catalyst (3) Az-DKTHT-Fc6+catalyst, (4) alkyne-modified TNR1B+Az-DKTHT-Fc6+catalyst leading to the product of FIG. 6, and (5) alkyne-modified TNR1B alone. The arrows correspond to (a) Mr ~75,000, (b) Mr ~65,000, (c) Mr ~43,000, (d) Mr ~28,000, and (e) Mr ~27,000.

FIG. 10 shows SDS-PAGE analysis providing further evidence confirming the requirement of the alkyne and azide groups for reactivity. Reaction mixtures that contained alkyne-modified TNR1B with unmodified Fc6 protein gave no reaction product (lane 2) compared with Fc6 alone (lane 1), while alkyne-modified TNR1B with Az-DKTHT-Fc6 gave the expected products (lane 4) compared with Az-DKTHT-Fc6 alone (lane 3). Again, no carryover of the input alkyne-modified TNR1B (shown in lane 5) was apparent following the Protein A purification.

The TNR1B-alkyne-azide-Fc6 products of FIG. 10 were further characterized by sequencing of their tryptic peptide by LC-MS. Following SDS-PAGE, the gel was Coomassie stained and four gel regions were excised, corresponding to the Mr ~75,000 product (arrow a), the Mr ~65,000 product (arrow b), the unstained region where alkyne-modified TNR1B would migrate (arrow c), and the unreacted Az-DKTHT-Fc6 protein of Mr ~28,000 (arrow d). The four gel slices were diced into small small pieces (~0.5-1.0 mm$^3$) and processed as follows. Ammonium bicarbonate, acetonitrile, dithiothreitol, and iodoacetamide were obtained from Sigma-Aldrich, formic acid was obtained from Pierce, and porcine trypsin (sequencing grade) was obtained from Promega (Madison, Wis.). To remove the Coomassie stain, each gel slice was extracted with 200 uL of 25 mM NH$_4$HCO$_3$ in 50% acetonitrile by vortexing, centrifuged to remove the supernatant, and dehydrated by adding acetonitrile for a few minutes until the gel pieces shrank and turned white. The acetonitrile was discarded, and the gel slices dried in a Speed Vac (Savant Instruments, Farmingdale, N.Y.). Reduction and alkylation was then carried out by rehydrating the gel slices in 40 ul of 10 mM dithiothreitol in 25 mM NH$_4$HCO$_3$, vortexing, and incubated at 56° C. for 45 minutes. The supernatant was then discarded, 40 uL of 55 mM iodoacetamide in 25 mM NH$_4$HCO$_3$ was added, the gel slices vortexed and incubated in the dark for 30 minutes at room temperature. The supernatant was discarded, the gel slices again dehydrated in acetonitrile and dried in a Speed Vac. Trypsin digestion was then carried out by rehydrating the gel slices in 25 uL of trypsin (12.5 ug/mL) in 25 mM NH$_4$HCO$_3$ on ice for 60 minutes. Excess trypsin solution was then removed, the gel slices covered with 25 mM NH$_4$HCO$_3$ and incubated at 37° C. overnight. The supernatant was removed, and the gel then extracted twice with 30 uL of 50% acetonitrile/0.1% formic acid in water. The organic extracts were combined with the aqueous supernatant, reduced to a volume of 10 uL in a Speed Vac, then analysed by LC-MS using a Q-Star Elite mass spectrometer (AB SCIEX, Foster City, Calif.).

FIG. 11 summarizes the characterization of the structure of the TNR1B-alkyne-azide-Fc6 reaction product by mass spectrometry. The Mr ~75,000 product, as expected for the full-length TNR1B-alkyne-azide-Fc6 product, contained peptides from both the alkyne-modified TNR1B and azide-modified Fc6 parent proteins. In addition, the peptide coverage of the alkyne-modified TNR1B sequence (upper panel) extended from the N-terminal region (EYYDQTAQMCCSK, amino acids 22-34 of SEQ ID NO: 114) to the C-terminal region (SMAPGAVHLPQPVST, amino acids 186-200 of SEQ ID NO: 114). Similarly, the peptide coverage of the azide-modified Fc6 protein sequence (lower panel) extended from the N-terminal region (DTLMISR, amino acids 76-83 of SEQ ID NO: 113) to the C-terminal region (TTPPVLDSDGSFFLYSK, amino acids 221-236 of SEQ ID NO: 113). In contrast, the Mr ~65,000 lacked the EYYDQTAQMCCSK (amino acids 22-34 of SEQ ID NO: 114) peptide, suggesting it was an N-terminally deleted version of the expected full-length TNR1B-alkyne-azide-Fc6 product. Sequences derived from the TNR1B protein were not detected in the unstained region of Mr ~43,000 where the alkyne-modified TNR1B would normally migrate (arrow c), while only sequences derived from the Fc6 protein were detected in the unreacted Az-DKTHT-Fc6 protein of Mr ~28,000 (arrow d).

The TNR1B-alkyne-azide-Fc6 and TNR1B-alkyne-azide-PEG$_4$-Fc6 products of FIG. 10 were further characterized for their biological activity by measuring their ability to bind TNF-α using surface plasmon resonance (SPR). Recombinant human TNF-α protein (carrier-free) was obtained from R&D Systems and reconstituted in PBS. SPR studies were carried out using a Biacore T100 instrument from Biacore AB (Uppsala, Sweden). The surface-bound ligands, TNR1B-alkyne-azide-Fc6 and TNR1B-alkyne-azide-PEG$_4$-Fc6, were immobilized onto a CM5 sensor chip, Series S, using a Amine Coupling Kit (BR-1000-50) obtained from GE Healthcare (Piscataway, N.J.) according to the manufacturer's instructions. Binding of TNF-α was carried out at 25° C. in 10 mM Hepes buffer pH 7.4, 150 mM NaCl, 3 mM EDTA, and 0.005% Tween-20. Binding was evaluated in duplicate at TNF-α concentrations of 0.156 nM, 0.312 nM, 0.625 nM, 1.25 nM, 2.5 nM, 5.0 nM, 10.0 nM, 20.0 nM and 40 nM. Data was evaluated using Biacore T100 Evaluation Software, version 2.0.3.

Figure 12:
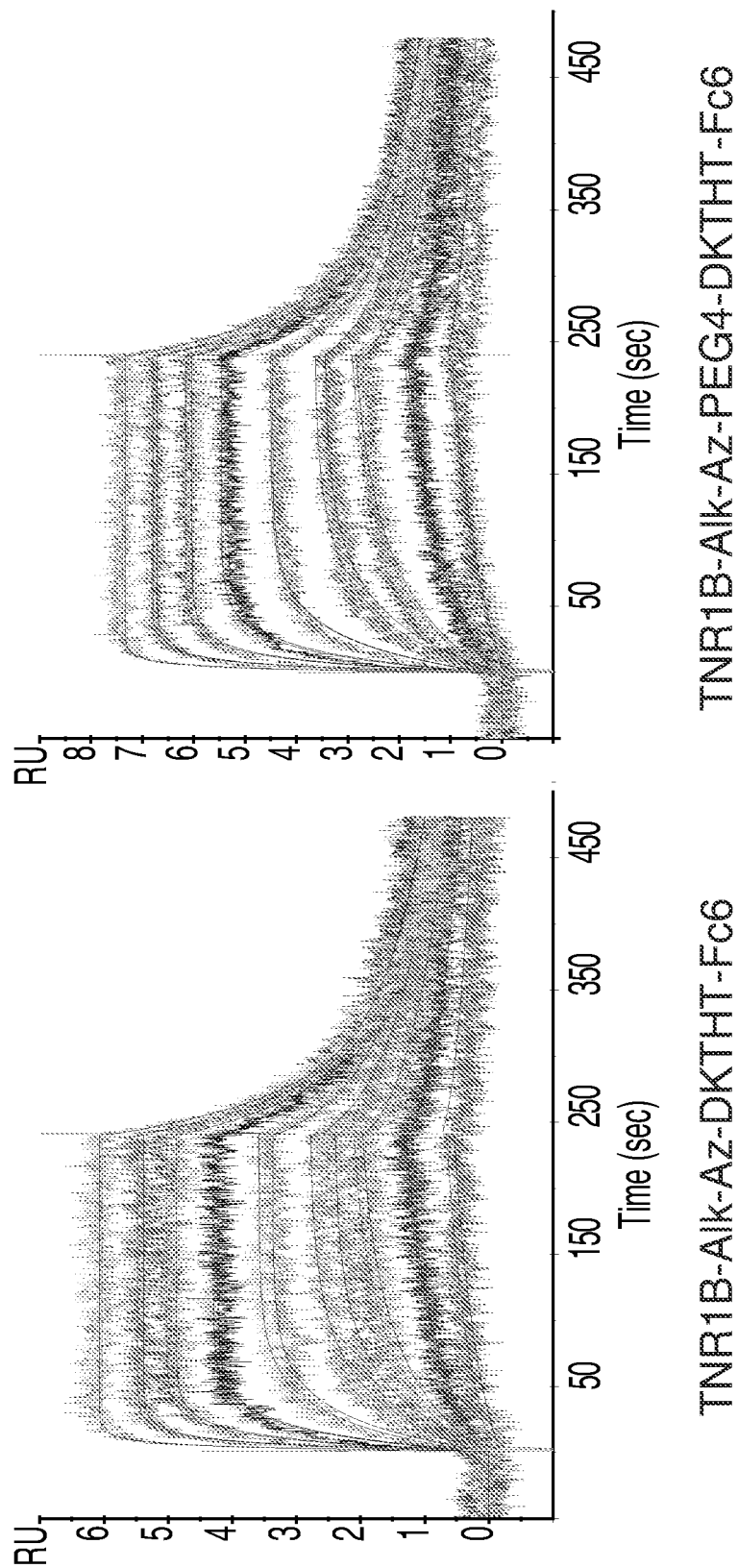
FIG. 12 shows SPR analysis of TNF-α binding by the TNR1B-alkyne-azide-DKTHT-Fc6 (left panel) and TNR1B-alkyne-azide-$PEG_4$-DKTHT-Fc6 (right panel) reaction products of FIG. 9. The kinetic binding data are summarized in Table 2.

FIG. 12 shows the kinetic binding curves for TNR1B-alkyne-azide-Fc6 (left panel) and TNR1B-alkyne-azide-PEG$_4$-Fc6 (right panel). Both products showed saturable TNF-α binding, and an excellent fit was obtained employing a two-exponential model (Chi$^2$ ~0.05). Table 2 summarizes the kinetic binding data. Approximately 40% of the binding sites for each product were higher affinity, with a 1.6-fold greater dissociation constant for TNR1B-alkyne-azide-PEG$_4$-Fc6 ($K_D$=1.86×10$^{-10}$ M) than for TNR1B-alkyne-azide-Fc6 ($K_D$=2.99×10$^{-10}$ M). The remaining 60% of the binding sites were of lower affinity, with the dissociation constants about the same for TNR1B-alkyne-azide-PEG$_4$-Fc6 ($K_D$=5.12×10$^{-9}$ M) and TNR1B-alkyne-azide-Fc6 ($K_D$=5.17×10$^{-9}$ M). The association of the PEG$_4$ linker with increased high affinity binding, but equal low affinity binding, provides compelling evidence for a higher degree of cooperative (two-handed) binding of TNF-α by TNR1B-alkyne-azide-PEG$_4$-Fc6 compared with TNR1B-alkyne-azide-Fc6.

TABLE 1

Azide-containing and Alkyne-Containing Thioesters

| Name | Formula | Mr | MH* | Sequence |
|---|---|---|---|---|
| Az-DKTHT | $C_{33}H_{47}O_{10}N_{11}S$ | 789.86 | 780.60 | Azide-DKTHT-thioester |
| Az-PEG$_4$-DKTHT | $C_{44}H_{68}O_{15}N_{12}S$ | 1037.14 | 1038.20 | Azide-PEG$_4$-DKTHT-thioester |
| Az-PEG$_{12}$-DKTHT | $C_{59}H_{98}O_{23}N_{12}S$ | 1375.53 | 1376.26 | Azide-PEG$_{12}$-DKTHT-thioester |
| Az-PEG$_{24}$-DKTHT | $C_{83}H_{146}O_{35}N_{12}S$ | 1904.18 | 1904.80 | Azide-PEG$_{24}$-DKTHT-thioester |
| Az-PEG$_{36}$-DKTHT | $C_{107}H_{194}O_{47}N_{12}S$ | 2432.82 | 2434.40 | Azide-PEG$_{36}$-DKTHT-thioester |
| Alk-PEG$_{12}$ | $C_{53}H_{74}O_{15}N_2S$ | 1011.22 | 1011.80 | DIBAC-PEG$_{12}$-thioester |

Mr, relative molecular mass; MH*, monoisotypic mass value.

Figure 13:
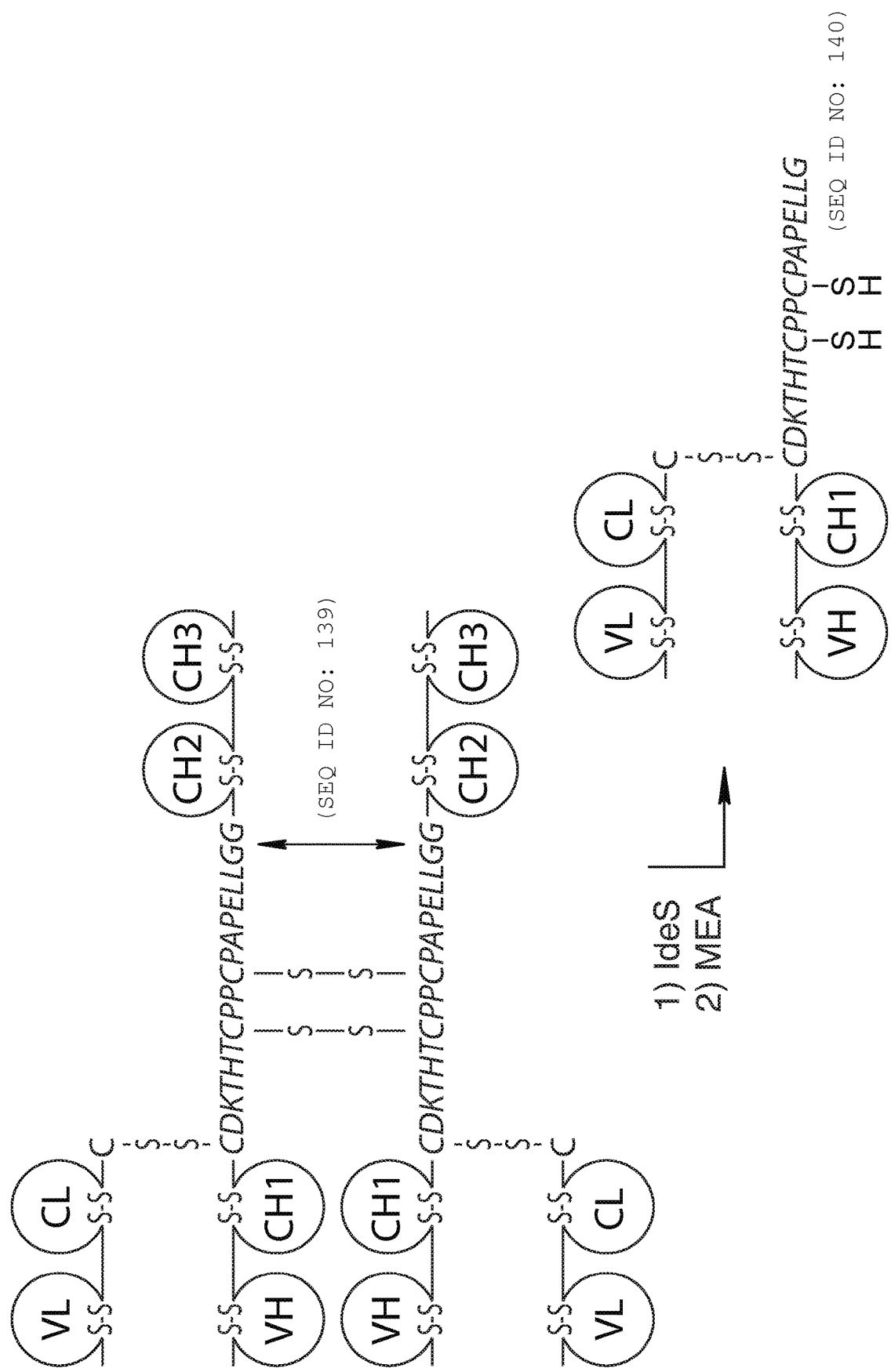
FIG. 13 shows the preparation of adalimumab Fab' in a three-step process: 1) IdeS cleavage to the Fab'2+Fc' fragments, 2) Protein A chromatography to remove the Fc' fragment, and 3) mild reduction of the Fab'2 fragment to the Fab' fragment with 2-mercaptoethylamine (MEA).

Adalimumab (Humira) was obtained as a liquid formulation (50 mg/ml) from Abbott (Abbott Park, Ill.). The Fab' fragment was prepared using IdesS protease to first generate Fab'2 fragment followed by selective reduction of the interchain disulfides with 2-mercaptoethylamine (FIG. 13). Antibody (10 mg) was exchanged into cleavage buffer (50 mM sodium phosphate, 150 mM NaCl, pH 6.6) using a Slide-A-Lyzer Mini Dialysis Unit, 10K MWCO from Pierce (Rockford, Ill.), then incubated with his-tagged recombinant IdeS immobilized on agarose beads (FragIT MidiSpin column) from Genovis (Lund, Sweden) for 1 hour at room temperature with constant mixing. The beads were removed from the digest solution by centrifugation, washed twice with cleavage buffer, and the digest and wash solutions then combined and applied to a HiTrap Protein A HP column from GE Life Sciences (Piscataway, N.J.) to remove Fc' fragment and undigested antibody. Flow-through fractions containing the Fab'2 fragment were reduced to the Fab' fragment by adding 1 mL aliquots to a vial containing 6 mg 2-mercaptoethylamine (MEA) from Pierce. Reductions were carried out with 10 mM EDTA to minimize re-oxidation of the interchain disulfides. Following incubation at 37° C. for 110 min, excess MEA was removed by buffer-exchange into PBS containing 10 mM EDTA using a PD-10 desalting column from GE Life Sciences (Piscataway, N.J.). The eluate containing the Fab' fragment was concentrated using an Amicon Ultracel-3 Centrifugal Filter Unit from Millipore (Billerica, Mass.).

Figure 14:
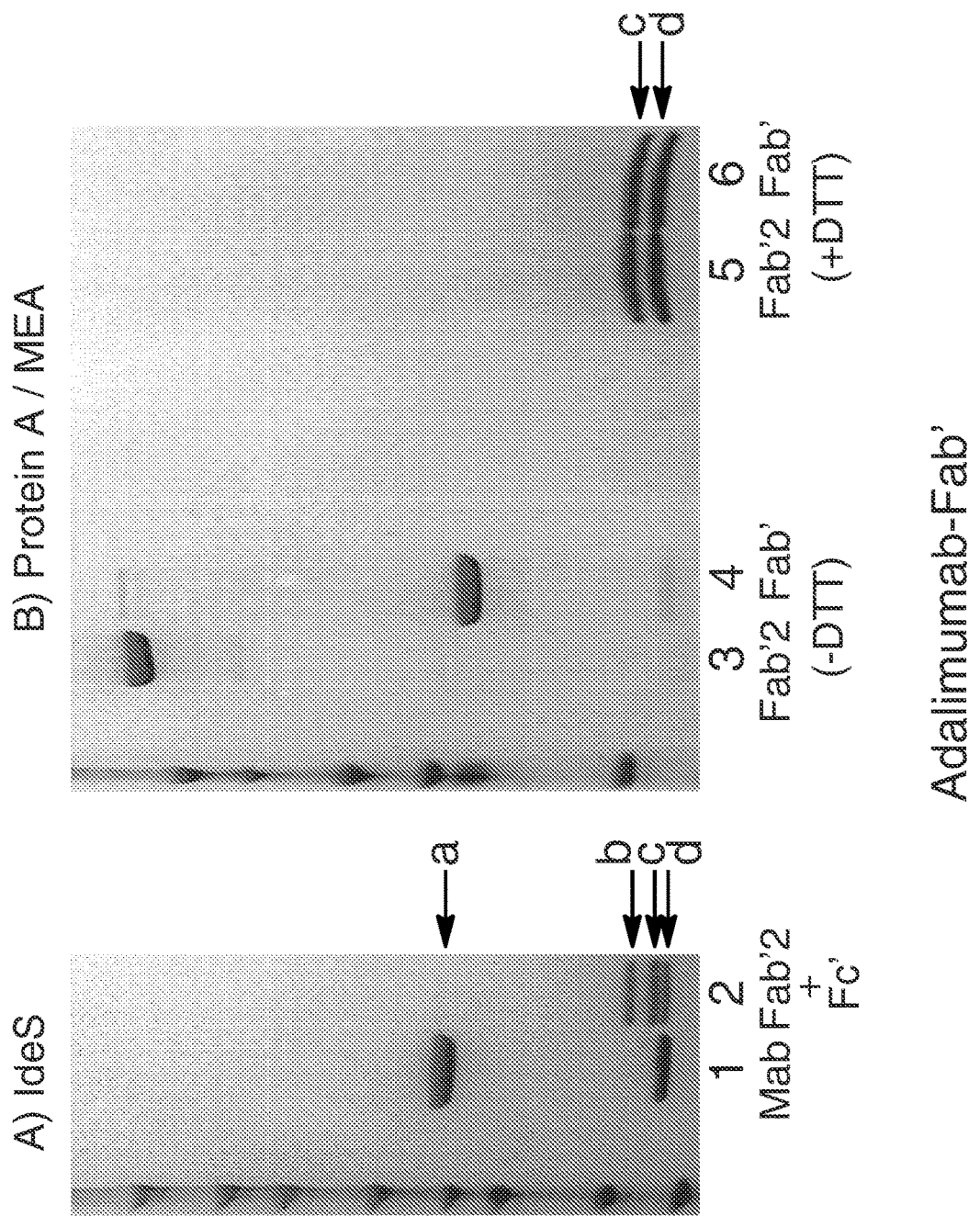
FIG. 14 shows SDS-PAGE analysis of (1) adalimumab, (2) adalimumab after IdeS cleavage, (3) adalimumab Fab'2 after Protein A purification, (4) adalimumab Fab' after MEA treatment of the Protein A purified Fab'2, (5) adalimumab Fab'2 after Protein A purification, and (6) adalimumab Fab' after MEA treatment of the Protein A purified Fab'2. The samples in lanes 1, 2, 5 and 6 were analysis under reducing conditions; while the samples in lanes 3 and 4 were analyzed under non-reducing conditions. The arrows correspond to the (a) heavy chain, (b) heavy chain Fc' fragment, (c) heavy chain Fd' (variable region-containing) fragment, and (d) light chain.

FIG. 14 shows SDS-PAGE analysis of adalimumab after cleavage with IdeS (panel A), followed by Protein A chromatography and mild reduction with MEA (panel B). In the presence of a strong reducing agent (dithiothreitol) in the polyacrylamide gel, the whole antibody (lane 1) migrated as a heavy chain of Mr ~55,000 (arrow a) and a light chain of Mr ~25,000 (arrow d). IdeS cleaved the heavy chain (lane 2) into a C-terminal fragment of Mr ~29,000 (arrow b) and an N-terminal fragment of Mr ~26,000 (arrow c). The light chain and the N-terminal heavy chain fragment comprise the Fab'2 domain, while the C-terminal heavy chain fragment comprises the Fc' domain. The Protein A column efficiently removed the Fc' domain from the Fab' domain (compare lane 2 with lanes 5 and 6). Under non-reducing conditions, the Fab'2 domain migrated as a single species of Mr ~110,000 (lane 3), while the Fab' domain produced by mild reduction with MEA migrated as a single species of Mr ~55,000 (lane 4). Under reducing conditions, the Fab'2 domain (lane 5) and the Fab' domain (lane 6) both yielded the same light chain (arrow d) and N-terminal heavy chain fragment (arrow c), as

TABLE 2

TNF-α binding measured by surface plasmon resonance

| Surface-bound ligand | ka1 (1/Ms) | kd1 (1/s) | KD1 (M) | Rmax1 | ka2 (1/Ms) | kd2 (1/s) | KD2 (M) | Rmax2 | Chi$^2$ |
|---|---|---|---|---|---|---|---|---|---|
| TNR1B-Alk-Az-DKTHT-Fc6 | 1.252E+7 | 0.003744 | 2.990E−10 | 2.5 | 5.176E+6 | 0.03392 | 6.553E−9 | 3.9 | 0.0514 |
| TNR1B-Alk-Az-PEG4-DKTHT-Fc6 | 1.400E+7 | 0.002613 | 1.866E−10 | 3.0 | 5.129E+6 | 0.03021 | 5.890E−9 | 4.8 | 0.0503 |

Abbreviations:
ka, on-rate (measured);
kd, off-rate (measured);
KD, dissociation constant (calculated).

Example 2: Fab'-alkyne-azide-Fc6

Fab'-alkyne-azide-Fc6 was prepared via the reaction of cycloalkyne-modified Fab' with azide-modified Fc6 as follows.

expected. Thus, the Fab' domain obtained by this procedure was essentially free of the Fab'2 and Fc' domains.

Figure 15:
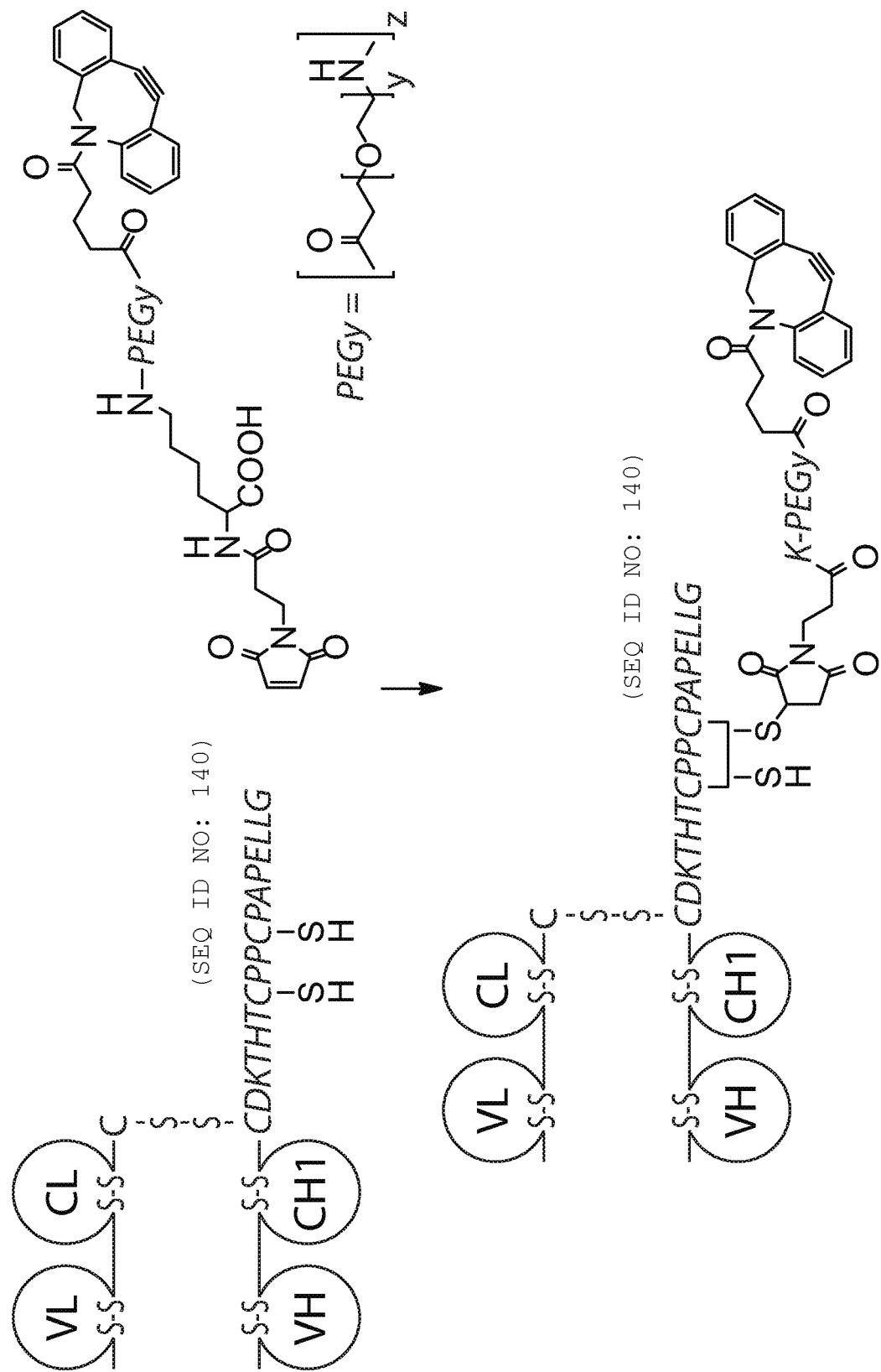
FIG. 15 shows the preparation of cycloalkyne-modified Fab' by the reaction of adalimumab Fab' with DIBAC-$PEG_y$-Lys (Mal). In this example, PEGy=$PEG_{12}$.

Cycloalkyne-modified Fab' was prepared from the adalimumab Fab' domain using a bifunctional linker, DIBAC-PEG$_{12}$-Lys(Mal), which contains a maleimide group capable of reacting with the free thiol groups on the Fab' fragment (FIG. 15). DIBAC-PEG$_{12}$-Lys(Mal) was prepared using an Fmoc solid-phase synthesis strategy. Lys(Mtt)-Wang resin and succinimido 3-maleimidopropanoate (Mpa-OSu) were obtained from CPC Scientific (Sunnyvale, Calif.), Fmoc-N-amido-dPEG$_{12}$-acid was obtained from Quanta BioDesign (Powell, Ohio), and 5-(11,12-Didehydrodibenzo[b,f]azocin-5(6H)-yl)-5-oxopentanoic acid, an acid-functionalised azadibenzocyclooctyne (DIBAC-acid), was synthesized as described by Debets, M. F. et al., Chem. Commun. 46, 97-99 (2010). Fmoc-N-amido-dPEG$_{12}$-acid and DIBAC-acid were sequentially reacted with Lys(Mtt)-Wang resin to obtain DIBAC-PEG$_{12}$-Lys(Mtt)-Wang resin, then treated with TFA/DCM/TIS(1:96:3) to remove the Mtt group. The deprotected resin was reacted with Mpa-OSu on the free amino group on the lysine side chain to obtain DIBAC-PEG12-Lys(Mpa)-Wang resin. Following cleavage with TFA/water (95:5), the crude product was purified by preparative RP-HPLC to afford the DIBAC-PEG$_{12}$-Lys(Mal) product (DPKM) with 93% purity and the desired MS spectra.

Figure 16:
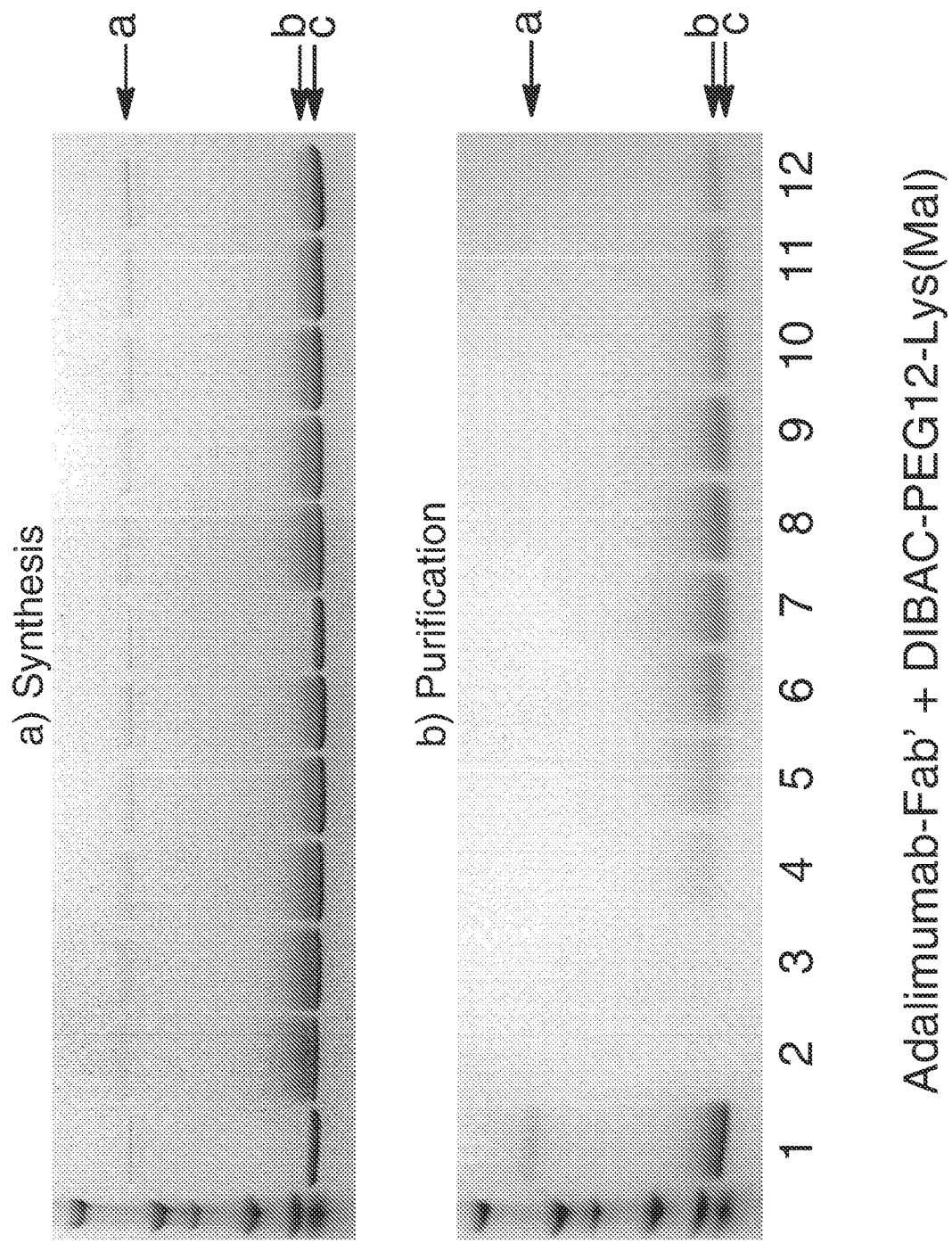
FIG. 16 shows SDS-PAGE analysis (non-reducing conditions) of the synthesis and purification of cycloalkyne-modified adalimumab Fab'. Upper panel shows the reaction at (1-6) pH 7.4 and (7-12) pH 7.0. The DIBAC-$PEG_y$-Lys (Mal) to Fab' ration was (1) 0, (2) 10:1, (3) 5:1, (4) 2.5:1, (5) 1.2:1, (6) 0.6:1, (7) 0, (8) 10, (9) 5, (10) 2.5, (11) 1.2, and (12) 0.6:1. The lower panel shows (1) unreacted Fab', (2) through (12) Protein L flow-through fractions containing only the cycloalkyne-modified Fab'.

FIG. 16 shows the chemical modification of adalimumab Fab' fragment with the DIBAC-PEG$_{12}$-Lys(Mal) linker and the purification of the resulting cycloalkyne-modified Fab'. For purification, reactions (0.535 mL) were carried out in 0.1 M sodium phosphate at pH 7.0 and pH 7.4, each containing 5 mg of Fab' fragment and 10 mg of DIBAC-PEG$_{12}$-Lys (Mal). After 30 hours incubation at room temperature, the two reactions were combined and buffered-exchanged into 20 mM sodium acetate, 20 mM NaCl, pH 5.5 using a PD-10 column. The eluate (3.5 mL) was applied to a HiTrap SP HP cation-exchange column from GE Life Sciences which retained all the unmodified Fab' and residual Fab'2. The flow-through fractions (5.5 mL) containing the purified cycloalkyne-modified Fab' (FIG. 16b) were pooled, adjusted to pH 7.0 with 10x PBS (0.55 mL), and concentrated by affinity chromatography on a Protein L column (Capto L) from GE Life Sciences. The cycloalkyne-modified Fab' was eluted from the Protein L column with 0.1 M glycine HCl pH 2.7 (2.4 mL), neutralized with 1/20 volume 1.0 M Tris HCl pH 9.0, buffered-exchanged into PBS using a PD-10 column (3.5 mL) and concentrated using Amicon Ultracel-3 Centrifugal Filter Unit to a final volume of 70 uL at a concentration of 9.5 mg/mL.

Various azide-modified Fc6 proteins with PEG linkers of different lengths were used in the preparation of the adalimumab Fab'-cycloalkyne-azide-Fc6. Az-DKTHT-Fc6 (FIG. 3) and Az-DKTHT-PEG$_x$-Fc6 derivatives with x=12, 24, and 36 (FIG. 4) were prepared in reactions (2 ml) that contained 50 mM MES pH 6.5, 0.8 mM TCEP, 10 mM MPAA, 5 mg/ml of each of the four Az-DKTHT-PEG$_x$-thioesters, and 2.36 mg/ml of Fc6 protein. After 20 hours at room temperature, the reactions were neutralized with 100 uL of Tris HCl pH 9.0, clarified by centrigugation at 12,000×g, and applied to a 1 ml HiTrap Protein A HP column. The columns were washed with 12 vol of PBS, the azide-modified Fc6 proteins were then eluted with 0.1 M glycine HCl pH 2.7 (2.0 mL), neutralized with 1/20 volume 1.0 M Tris HCl pH 9.0, dialysed against three changes of PBS for 12 hours each using a Slide-A-Lyzer Mini Dialysis Unit, 10K MWCO, and concentrated using Amicon Ultracel-3 Centrifugal Filter Units.

Figure 17:
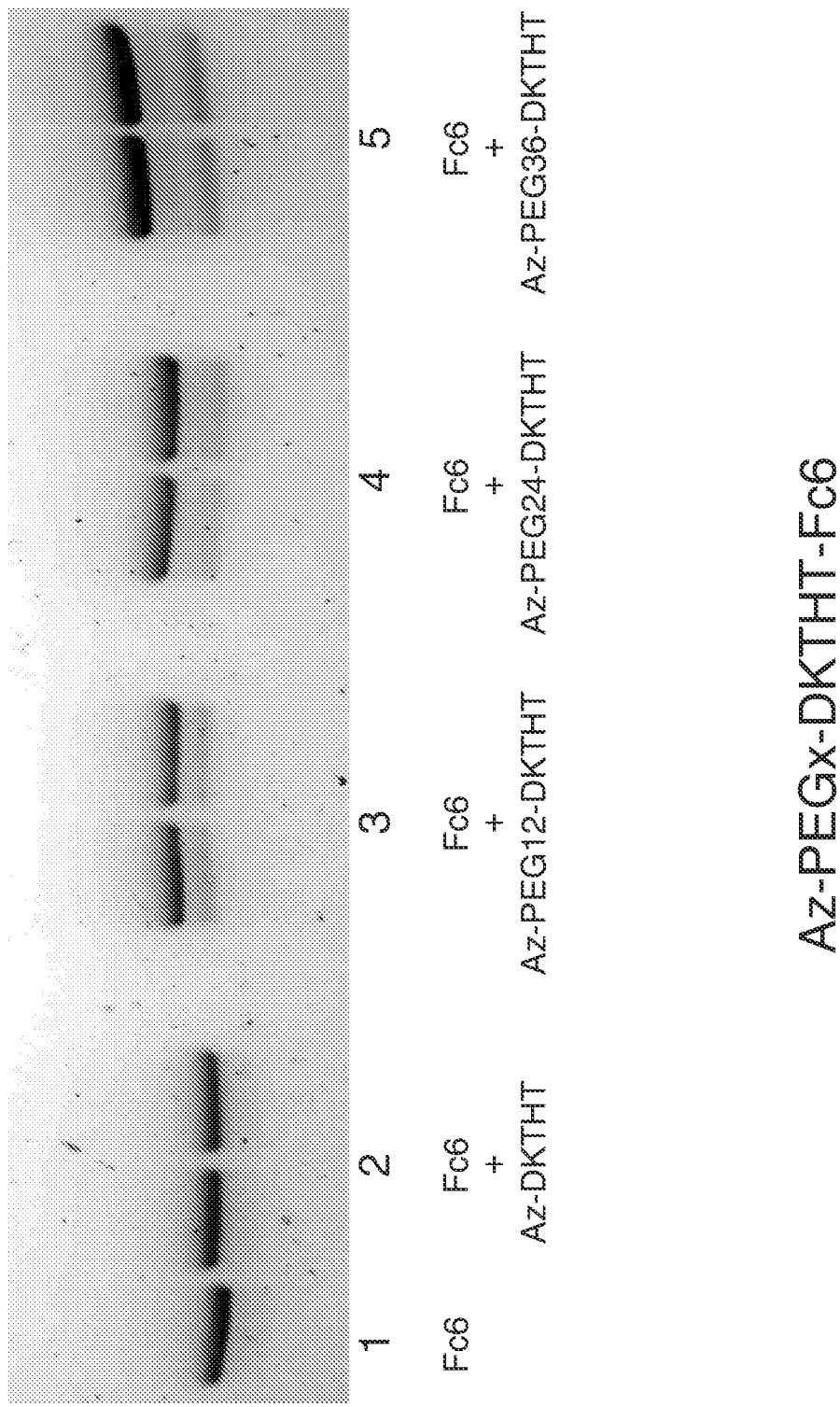
FIG. 17 shows SDS-PAGE analysis (reducing conditions) of (1) Fc6, (2) Az-DKTHT-Fc6, (3) Az-$PEG_{12}$-DKTHT-Fc6, (4) Az-$PEG_{24}$-DKTHT-Fc6, and (5) Az-$PEG_{36}$-DKTHT-Fc6.

FIG. 17 shows analysis by SDS-PAGE under reducing conditions of the Fc6 (lane 1) Az-DKTHT-Fc6 (lane 2), Az-DKTHT-PEG$_{12}$-Fc6 (lane 3), Az-DKTHT-PEG$_{24}$-Fc6 (lane 4), and Az-DKTHT-PEG$_{36}$-Fc6 (lane 5) proteins by SDS-PAGE. The Fc6 protein reacted quantitatively (>90%) with all four thioesters, yielding a ladder of products of increasing size.

Figure 18:
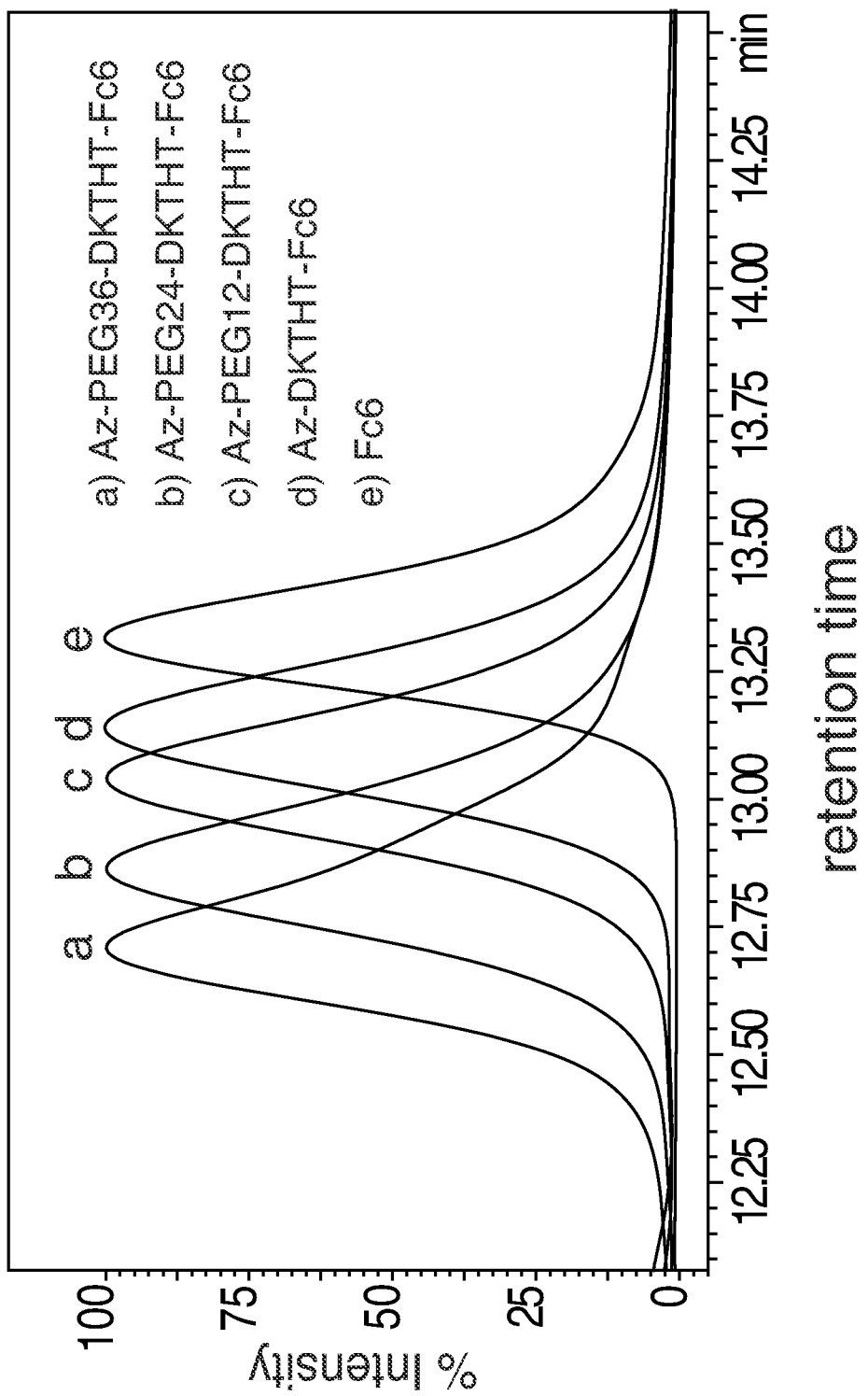
FIG. 18 shows size-exclusion chromatography of (a) Az-$PEG_{36}$-DKTHT-Fc6, (b) Az-$PEG_{24}$-DKTHT-Fc6, (c) Az-$PEG_{12}$-DKTHT-Fc6, (d) Az-DKTHT-Fc6, and (e) Fc6.

FIG. 18 shows analysis by size-exclusion chromatography (SEC) to confirm that the four azide-modified Fc6 protein products had the same dimeric structure as the parent Fc6 molecule. SEC was carried out using a Prominence HPLC System (Shimadzu Corp, Kyoto, Japan). TSKgel Super SW3000 columns (4.6 mm×30 cm column, 4.6 mm×5 cm guard column) were obtained from TOSOH Bioscience (Tokyo, Japan). Mobile phase, flow rate, column temperature, and detection wavelength used were 50 mM sodium phosphate, 300 mM NaCl, pH 7.4, 0.35 mL/min., 30° C., and 280 nm, respectively. The four azide-modified Fc6 protein products displayed a retention time that decreased as the size of PEG linker increased, confirming their dimer structure. All four products also gave essentially a single peak, demonstrating a two-handed structure in which both N-termini of the parent Fc6 dimer were modified by the PEG linker that was confirmed by SDS-PAGE analysis under non-reducing conditions (see below).

Figure 19:
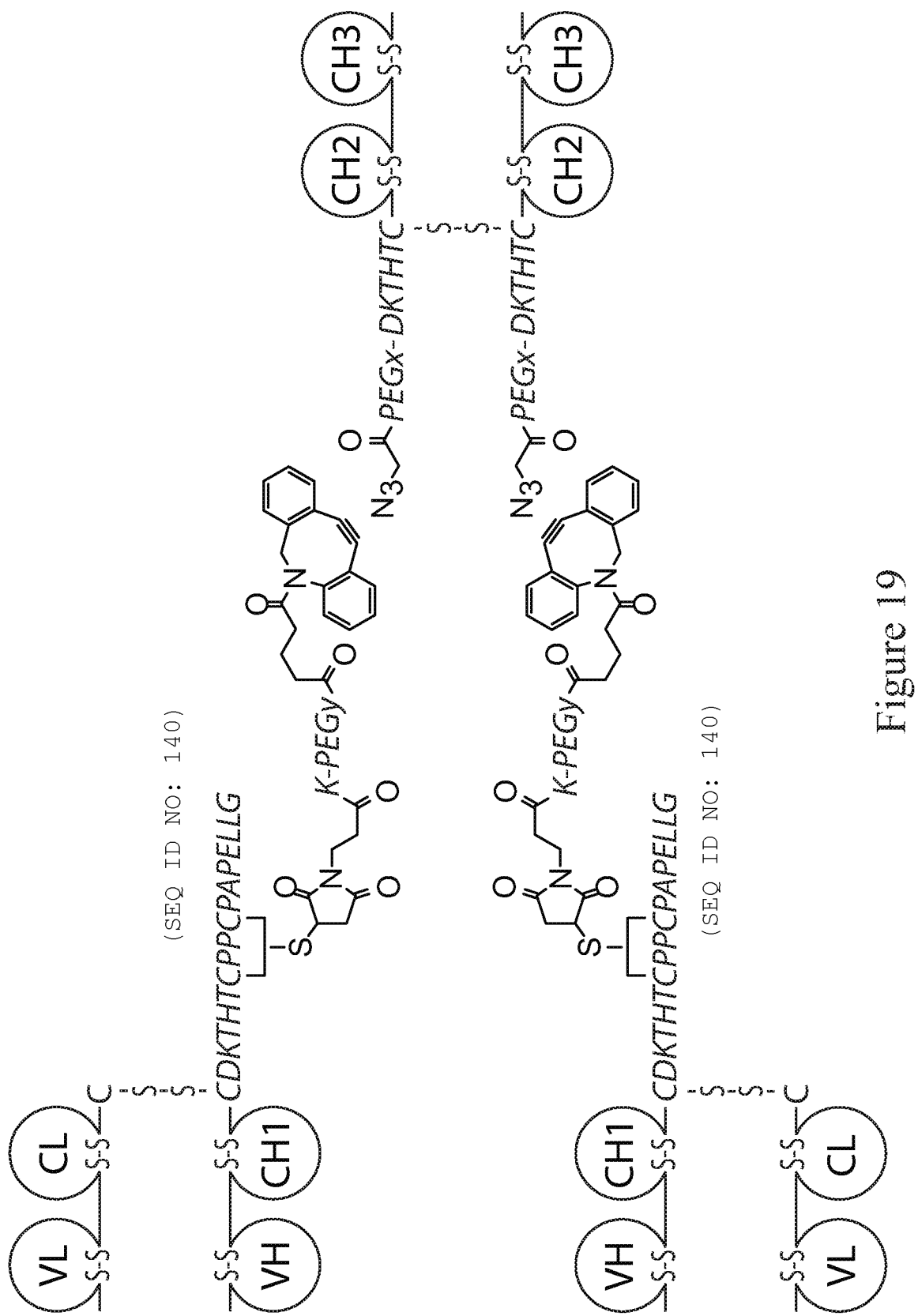
FIG. 19 shows the synthesis of Fab'-PEGy-alkyne-azide-PEGx-Fc6 by ligation (non-peptidyl) of cycloalkyne-modified adalimumab Fab' and azide-modified Fc6.
Figure 20:
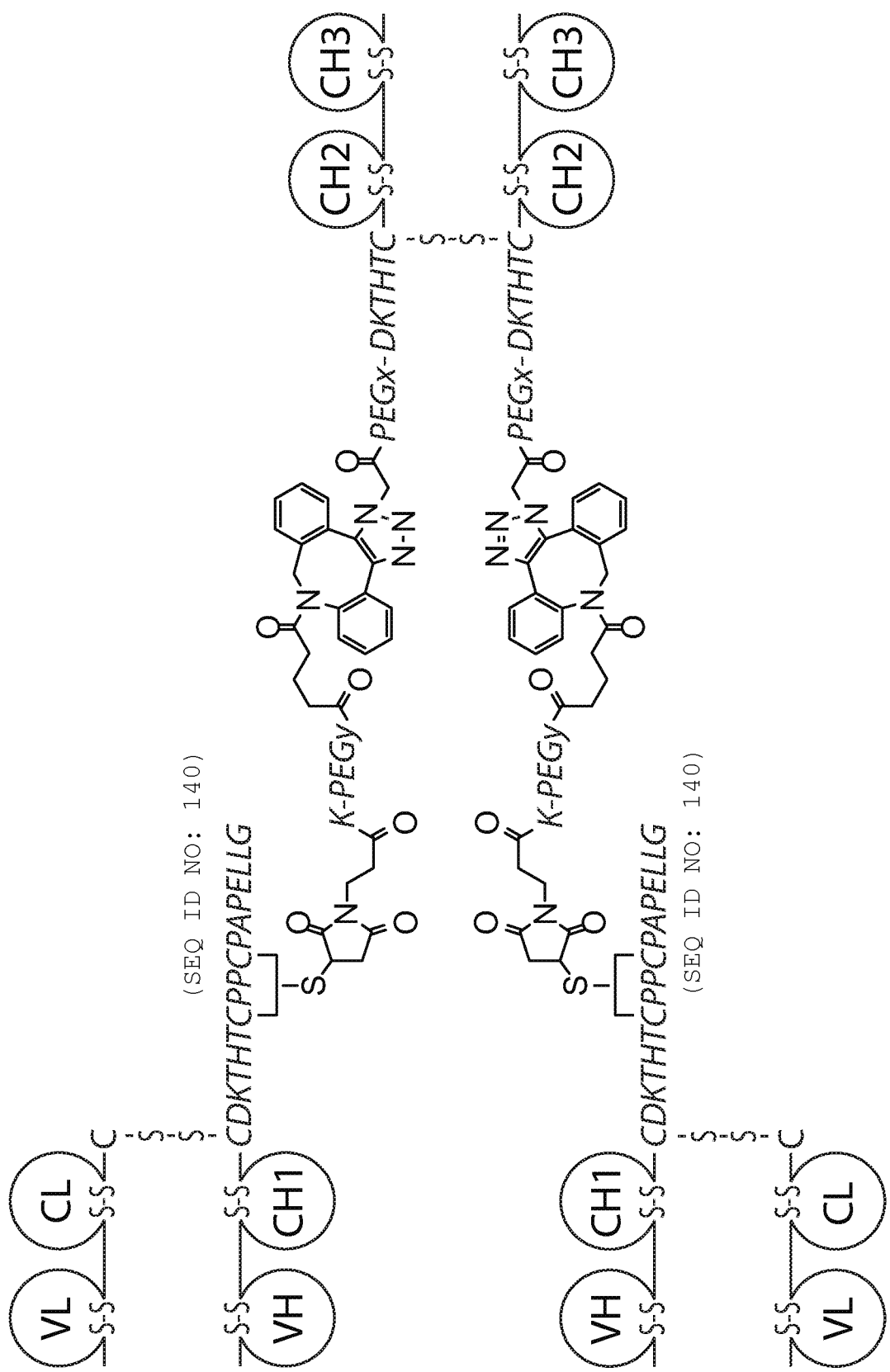
FIG. 20 shows the Fab'-PEGy-alkyne-azide-PEGx-Fc6 product series.

The cyclooctyne-modified Fab' was reacted with all four azide-modified Fc6 molecules (FIG. 19), yielding a family of Fab'-PEG$_y$-cycloalkyne-azide-PEG$_x$-Fc6 structures with arms of increasing length (FIG. 20). The overall lengths of the resulting arms were Fab'-PEG$_{12}$-Fc6 (for x=0, y=12), Fab'-PEG$_{24}$-Fc6 (for x=12, y=12), Fab'-PEG$_{36}$-Fc6 (for x=24, y=12), and Fab'-PEG$_{48}$-Fc6 (for x=36, y=12). The reactions (8 uL) were carried out in 0.1 M sodium phosphate pH 7.0 overnight at room temperature with each of the four azide-modified Fc6 proteins (2.5 mg/ml) in the presence or the absence of the cycloalkyne-modified Fab' (5 mg/ml).

Figure 21:
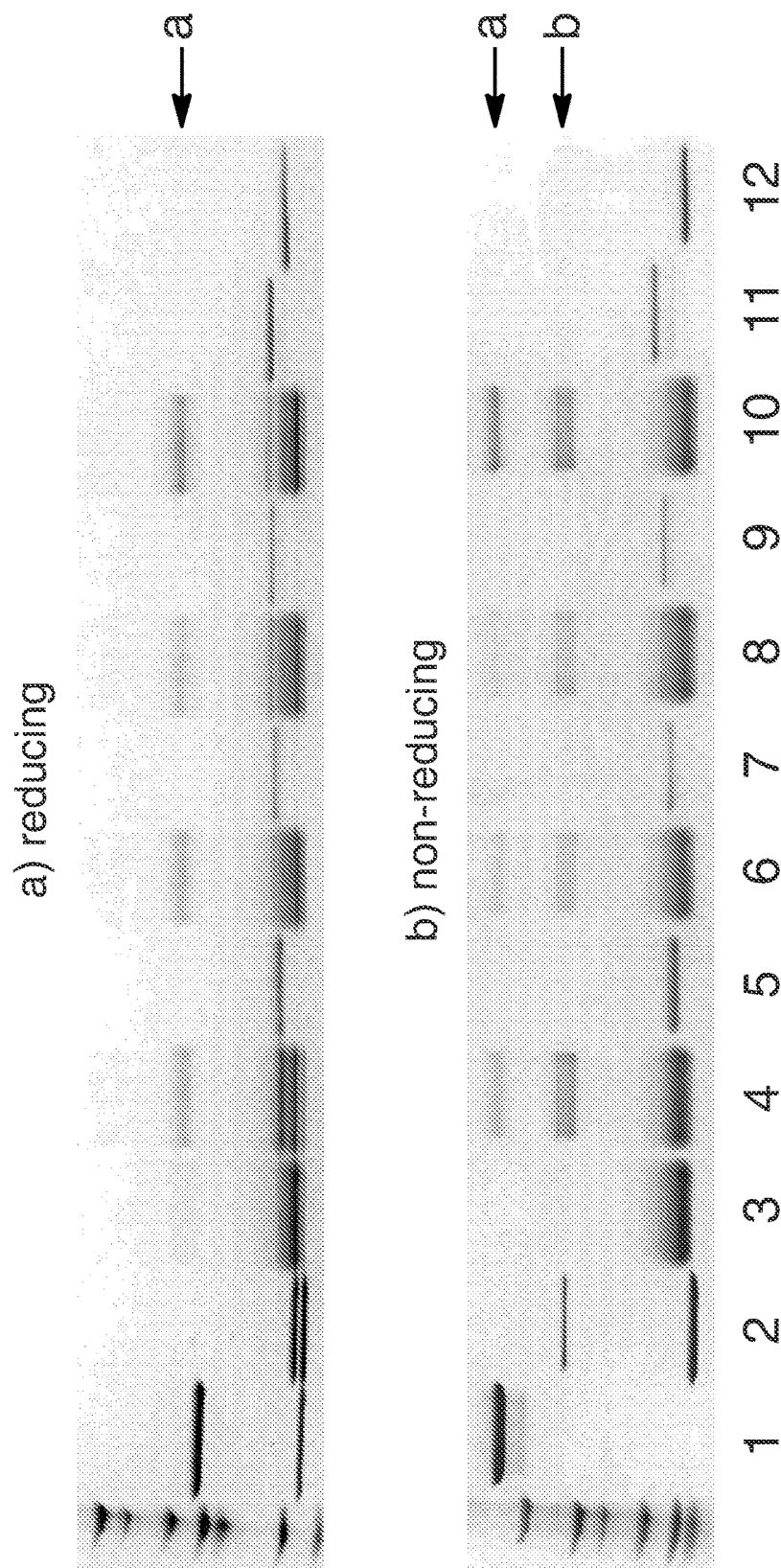
FIG. 21 shows SDS-PAGE analysis of (1) adalimumab whole antibody, (2) adalimumab Fab', (3) Fab'-$PEG_{12}$-alkyne, (4) Fab'-$PEG_{12}$-alkyne+Az-DKTHT-Fc6, (5) Az-DKTHT-Fc6, (6) Fab'-$PEG_{12}$-alkyne+Az-$PEG_{12}$-DKTHT-Fc6, (7) Az-$PEG_{12}$-DKTHT-Fc6, (8) Fab'-$PEG_{12}$-alkyne+Az-$PEG_{24}$-DKTHT-Fc6, (9) Az-$PEG_{24}$-DKTHT-Fc6 alone, (10) Fab'-$PEG_{12}$-alkyne+Az-$PEG_{36}$-DKTHT-Fc6, (11) Az-$PEG_{36}$-DKTHT-Fc6, and (12) Fc6. Samples were run under reducing conditions (upper panel) and non-reducing conditions (lower panel). In the upper panel the arrow shows (a) Fab'-PEGy-alkyne-azide-PEGx-Fc6 heavy chain. In the lower panels the arrows show (a) two-handed Fab'-PEGyalkyne-azide-PEGx-Fc6 molecules, and (b) one-handed Fab'-PEGy-alkyne-azide-PEGx-Fc6 molecules.

FIG. 21 shows SDS-PAGE analysis of the Fab'-cycloalkyne-azide-Fc6 reaction under reducing and non-reducing conditions. In the absence of the cycloalkyne-modified Fab' (lanes 5, 7, 9, and 11), all four of the azide-modified Fc6 proteins gave a single band on both reducing and non-reducing gels, confirming their dimeric, two-handed handed structure. In the presence of the cycloalkyne-modified Fab' (lanes 4, 6, 8, and 10), all four of the azide-modified Fc6 proteins were largely consumed in the resulting reaction. Under reducing conditions, all four reactions gave a product with Mr ~57,000 to 62,000 (arrow a). The size of the Fab'-PEG$_{12}$-Fc6 product (lane 4) was approximately 1-2 kD greater than the wild-type adalimumab heavy chain (lane 1), while the sizes of the Fab'-PEG$_{24}$-Fc6 (lane 6), Fab'-PEG$_{36}$-Fc6 (lane 8), and Fab'-PEG$_{48}$-Fc6 (lane 10) products further increased with the overall length of the PEG linker. Under non-reducing conditions, two products were observed, a first product of Mr ~155,000 to 160,000 (arrow a), and a second of Mr ~110,000 to 115,000 (arrow b). The larger Fab'-PEG$_{12}$-Fc6 product (lane 4) was approximately 5 kD greater than the adalimumab whole antibody (lane 1), consistent with the expected two-handed product, while the larger Fab'-PEG$_{24}$-Fc6 (lane 6), Fab'-PEG$_{36}$-Fc6 (lane 8), and Fab'-PEG$_{48}$-Fc6 (lane 10) products still further increased in size as the overall length of the PEG linker increased.

Figure 22:
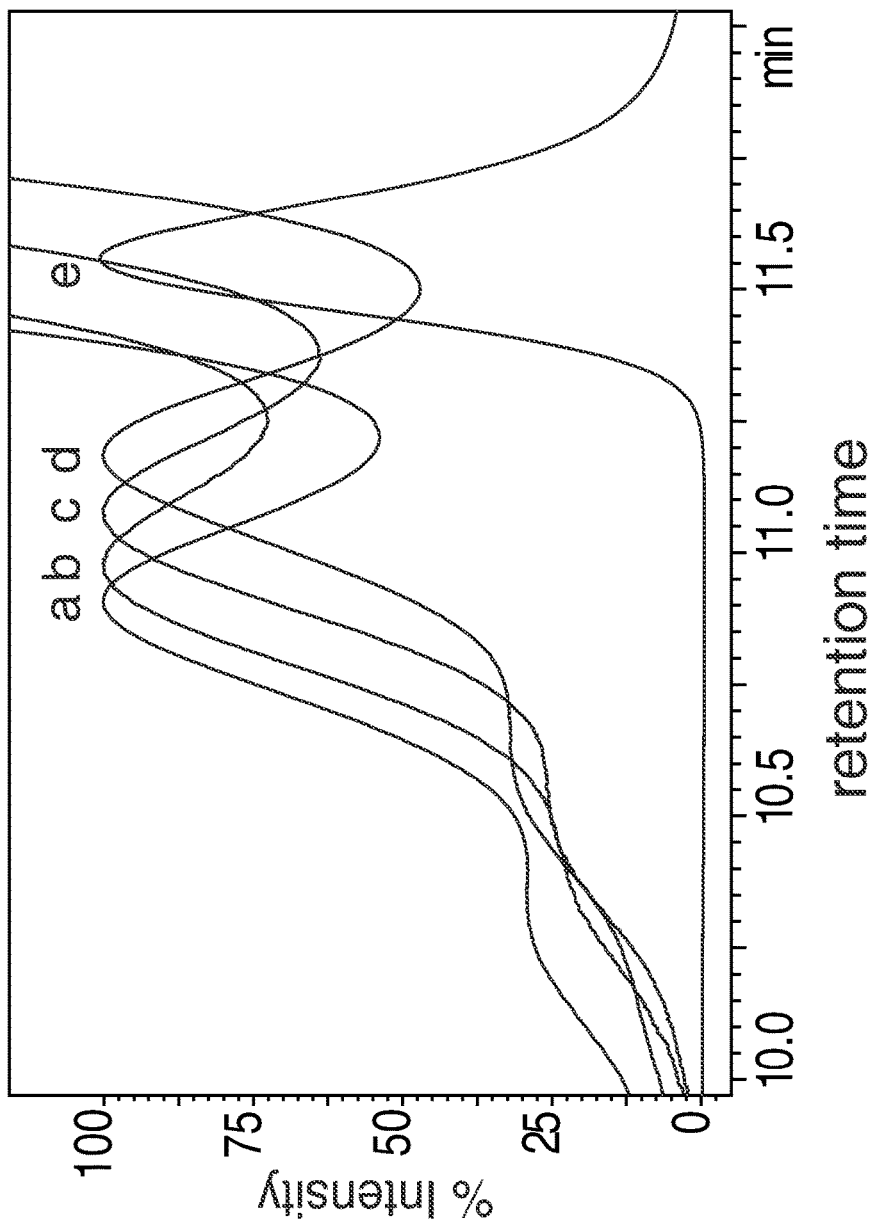
FIG. 22 shows size-exclusion chromatography (SEC) of two-handed reaction products: (a) Fab'-PEG$_{12}$-alkyne-azide-PEG$_{36}$-DKTHT-Fc6, (b) Fab'-PEG$_{12}$-alkyne-azide-PEG$_{24}$-DKTHT-Fc6, (c) Fab'-PEG$_{12}$-alkyne-azide-PEG$_{12}$-DKTHT-Fc6, (d) Fab'-PEG$_{12}$-alkyne-azide-DKTHT-Fc6, and (e) whole adalimumab.

FIG. 22 shows analysis by SEC to confirm the two-handed structure (i.e., two Fab' hands attached to one Fc6 domain.) of the larger reaction product with Mr ~155,000 to 160,000 of the Fab'-PEG$_{12}$-Fc6, Fab'-PEG$_{24}$-Fc6, Fab'-PEG$_{36}$-Fc6, and Fab'-PEG$_{48}$-Fc6 reactions. All four reaction products displayed a shorter retention time than the adalimumab whole antibody that further decreased as the size of PEG linker increased, confirming the two-handed structure observed by SDS-PAGE analysis.

The biological activity of the Fab'-cycloalkyne-azide-Fc6 products evaluated by their ability to neutralize TNF-α-mediated cytotoxicity on murine WEHI cells treated with actinomycin D. The mouse WEHI-13VAR cell line (ATCC CRL-2148) was obtained from the American Type Culture Collection (Rockville, Md.) and grown in Gibco RPMI media 1640 (RPMI-1640) supplemented with 10% fetal bovine serum (FBS) and penicillin and streptomycin (10 U/ml), obtained from Life Technologies (Grand Island, N.Y.). TNF-α cytotoxity assays were carried out as follows. WEHI-13VAR cells were plated in 96-well Nunc white cell culture plates obtained from Thermo Fisher (Waltham, Mass.) at $2 \times 10^4$ cells per well overnight and then treated with actinomycin D (0.5 µg/ml) obtained from Sigma (St Louis, Mo.) and TNF-α (0.2 ng/ml) in the absence or presence of TNFR-IgG or other inhibitors. After 24 hr of incubation at 37° C./5% CO2, the cell viability was determined with CellTiter-Glo Luminescent Cell Viability Assay Systems (Promega, Madison, Wis.) measuring the quantity of the ATP present in metabolically active cells and luminescence measured using a POLARstar luminometer (BMG LABTECH Inc., Cary, N.C.). Each inhibitor was diluted by ten 3-fold serial dilutions starting at 10 µg/ml and measured in duplicate or triplicate. Cytotoxicity data were calculated using the following equations: (1-sample luciferase reading/luciferase reading from cells treated with actinomycin D alone)×100%, and presented as the mean±standard deviation. Enbrel was used as a cytotoxicity positive control and Fc6 as a negative control.

Figure 23:
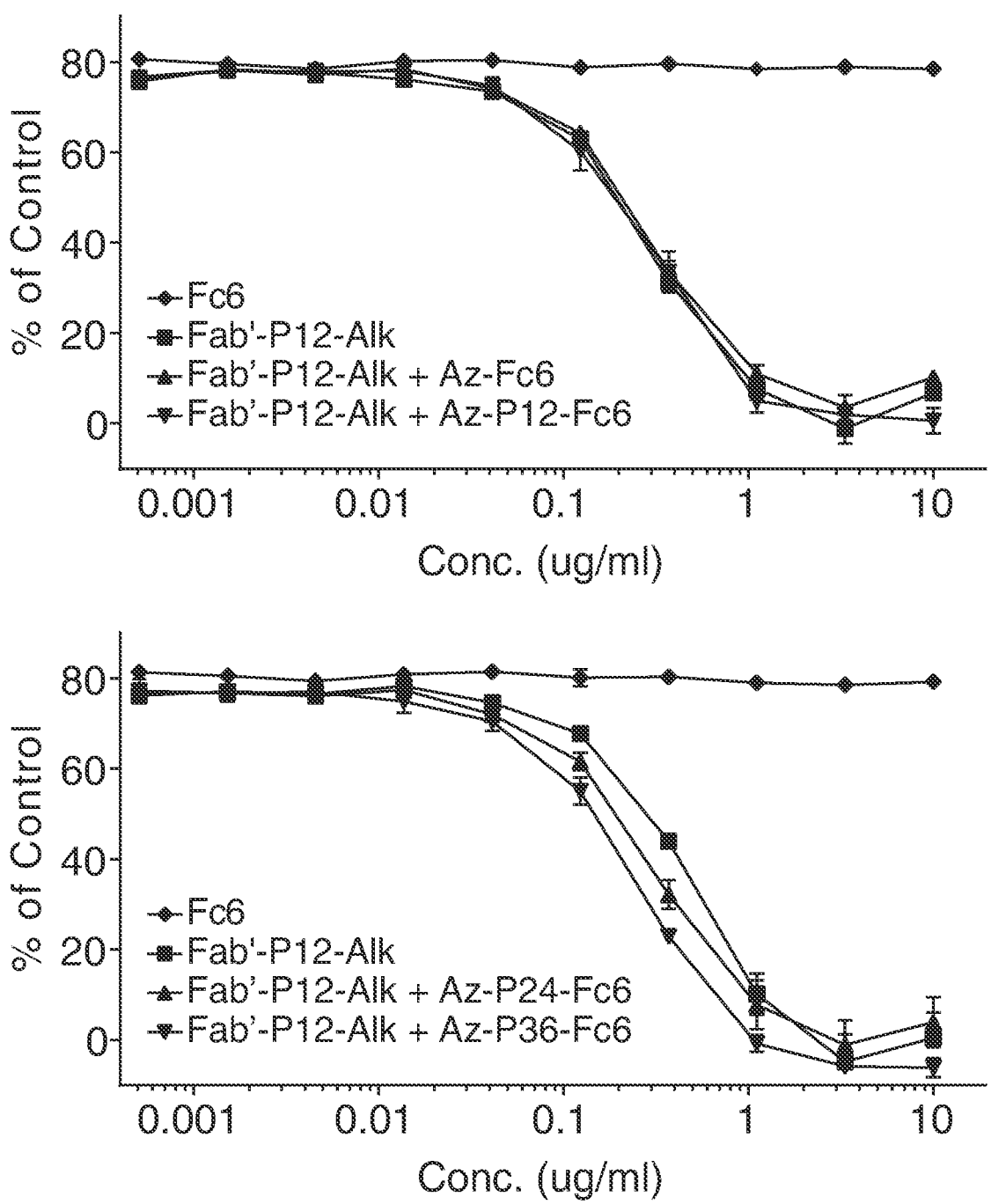
FIG. 23 shows the inhibition of TNF-α cytotoxity on WEHI cells by reaction products. The upper panel shows the (a) Fc6 control, (b) cycloalkyne-modified Fab', (c) Fab'-PEG$_{12}$-alkyne-azide-DKTHT-Fc6, and (d) Fab'-PEG$_{12}$-alkyne-azide-PEG$_{12}$-DKTHT-Fc6. The lower panel shows the (a) Fc6 control, (b) cycloalkyne-modified Fab', (c) Fab'-PEG$_{12}$-alkyne-azide-PEG$_{24}$-DKTHT-Fc6, and (d) Fab'-PEG$_{12}$-alkyne-azide-PEG$_{36}$-DKTHT-Fc6.

FIG. 23 shows the neutralization of TNF-α-mediated cytotoxicity by Fab'-$PEG_{12}$-Fc6, Fab'-$PEG_{24}$-Fc6, Fab'-$PEG_{36}$-Fc6, and Fab'-$PEG_{48}$-Fc6 reaction mixtures compared with the cycloalkyne-modified Fab' (based upon an equal amounts of input cycloalkyne-modified Fab'). The Fab'-$PEG_{12}$-Fc6 and Fab'-$PEG_{24}$-Fc6 reaction mixtures both displayed comparable TNF-α neutralization activity compared with that of the input cycloalkyne-modified Fab' (upper panel), whereas the Fab'-$PEG_{36}$-Fc6 and Fab'-$PEG_{48}$-Fc6 reaction mixtures displayed a 1.5-fold and 2.0-fold increase, respectively, in their TNF-α neutralization activity compared with the input cycloalkyne-modified Fab' (lower panel). Since the amount of two-handed product represented only 10-20% of the total cycloalkyne-modified Fab' in each reaction as estimated by SDS-PAGE (FIG. 22), the two-handed products of the Fab'-$PEG_{36}$-Fc6 and Fab'-$PEG_{48}$-Fc6 reactions are estimated to be at least 7.5-fold and 10-fold greater than the input cycloalkyne-modified Fab', respectively.

Example 3: Fab-alkyne-azide-Fc6

Fab-alkyne-azide-Fc6 is prepared by reacting azide-modified Fc6 with an alkyne-modified or cycloalkyne-modified Fab protein that is produced by cleavage of an Fab-intein fusion protein as follows. Similarly, Fab-azide-alkyne-Fc6 is prepared by reacting alkyne-modified or cycloalkyne-modified Fc6 with an azide-modified Fab protein that is produced by cleavage of an Fab-intein fusion protein.

Adalimumab Fab-intein fusion protein is produced by cotransfecting expression vector pFUSE2ss-DE27-Vκ-CLIg-hk (SEQ ID NO: 115) with pPUSEss-DE27-Vγ1-CHIg-hG1-Mth-1 (SEQ ID NO: 116) or pFUSEss-DE27-Vγ1-CHIg-hG1-Mth-2 (SEQ ID NO: 117).

Vector pFUSE2ss-DE27-Vκ-CLIg-hk directs the expression of the pre-kappa light chain of adalimumab shown in SEQ ID NO: 118. Cleavage of the heterologous IL-2 signal sequence by the cellular signal peptidase provides the mature kappa light chain of adalimumab shown in SEQ ID NO: 119.

Vector pFUSEss-DE27-Vγ1-CHIg-hG1-Mth-1 directs the expression of a first type of pre-heavy chain-intein chimeric polypeptide shown in SEQ ID NO: 120, in which the adalimumab heavy chain VH and CH1 domains are joined at their C-terminus to the N-terminus of an RIR1 self-splicing intein at the autocleavage site. Cleavage of the heterologous IL-2 signal sequence by the cellular signal peptidase provides the mature heavy chain-intein fusion protein shown in SEQ ID NO: 121. Together, the proteins of SEQ ID NO: 119 and SEQ ID NO: 121 comprise the adalimumab Fab-1-intein fusion protein that is secreted into the cell culture fluid.

Vector pFUSEss-DE27-Vγ1-CHIg-hG1-Mth-2 directs the expression of a second type of pre-heavy chain-intein chimeric polypeptide shown in SEQ ID NO: 122, in which the adalimumab heavy chain VH and CH1 domains are joined at their C-terminus to the N-terminus of an RIR1 self-splicing intein at the autocleavage site. Cleavage of the heterologous IL-2 signal sequence by the cellular signal peptidase provides the mature heavy chain-intein fusion protein shown in SEQ ID NO: 123. Together, the proteins of SEQ ID NO: 119 and SEQ ID NO: 123 comprise the adalimumab Fab-2-intein fusion protein that is secreted into the cell culture fluid.

Protein production is executed by transient expression in CHO-DG44 cells essentially as described in Example 1, by the cotransfection of SEQ ID NO: 115 with SEQ ID NO: 116 to produce the adalimumab Fab-1-intein fusion protein, and by cotransfection of SEQ ID NO: 115 with SEQ ID NO: 117 to produce adalimumab Fab-2-intein fusion protein.

Alkyne-modified adalimumab Fab proteins are produced by cleavage of adalimumab Fab-intein fusion proteins with 50 mM cystyl-propargylamide essentially as described in Example 1. The adalimumab Fab-1-intein fusion protein is cleaved with cystyl-propargylamide to produce alkyne-modified adalimumab Fab-1 protein which is a heterodimer protein of SEQ ID NO: 119 and SEQ ID NO: 124. The adalimumab Fab-2-intein fusion protein is cleaved with cystyl-propargylamide to produce alkyne-modified adalimumab Fab-2 protein which is a heterodimer protein of SEQ ID NO: 119 and SEQ ID NO: 125.

Azide-modified adalimumab Fab proteins are produced by cleavage of adalimumab Fab-intein fusion proteins with 50 mM cystyl-3-azidopropylamide essentially as described in Example 1. The adalimumab Fab-1-intein fusion protein is cleaved with cystyl-3-azidopropylamide to produce azide-modified adalimumab Fab-1 protein which is a heterodimer protein of SEQ ID NO: 119 and SEQ ID NO: 126. The adalimumab Fab-2-intein fusion protein is cleaved with cystyl-3-azidopropylamide to produce azide-modified adalimumab Fab-2 protein which is a heterodimer protein of SEQ ID NO: 119 and SEQ ID NO: 127.

Adalimumab Fab-1-alkyne-azide-Fc6 and Adalimumab Fab-2-alkyne-azide-Fc6 are prepared via the reaction of alkyne-modified adalimumab Fab-1 protein or alkyne-modified adalimumab Fab-2 protein with Az-DKTHT-Fc6 protein (FIG. 6) or Az-$PEG_x$-DKTHT-Fc6 proteins (FIG. 7).

Tris(3-hydroxypropyltriazolylmethyl)amine (THTPA) is prepared as described by Hong et al., Angew. Chem. Int. Ed. 48, 1-7 (2009). Reactions are carried out in 0.1 M sodium phosphate, pH 7.0, with the Linker-Fc at a concentration of 5 mgs/mL or greater, and a molar ratio of >2:1 of Fab-A: Linker-Fc. To the reaction is added a final concentration of 0.0001 M $CuSO_4$, 0.0005 M THTPA. The reaction is initiated by adding to a final concentration 0.005 M aminoguanidine and 0.005 M sodium ascorbate. Following incubation at room temperature for 12-18 hours in a closed tube, the reaction mixture is applied to a chromatographic column packed with Protein A (GE Lifesciences, NJ) to remove excess reagent and unreacted Fab-A, washed with PBS, eluted with 0.1 M Glycine-HCl, pH 2.7, and immediately neutralized by adding 1.0 M Tris-HCl, pH 9.0. The eluted Adalimumab Fab-1-alkyne-azide-Fc6 and Adalimumab Fab-2-alkyne-azide-Fc6 products are dialysed against PBS.

Adalimumab Fab-1-azide-alkyne-Fc6 and Adalimumab Fab-2-azide-alkyne-Fc6 are prepared via the reaction of azide-modified adalimumab Fab-1 protein or azide-modified adalimumab Fab-2 protein with cycloalkyne-modified Fc6 protein.

Cycloalkyne-modified Fc6 proteins are prepared essentially as described in Example 1 using DIBAC-PEG$_{12}$-thioester (Table 1) and other DIBAC-PEG$_x$-thioesters and DIBAC-PEG$_x$-DKTHT-thioesters similarly prepared.

DISCUSSION

Aspects of the present invention provides the chemical semisynthesis of antibodies with nonprotein hinges that incorporate large binding domains such as the Fab itself or receptor extracellular domains. The present invention relates to the identification of ligation reactions that are compatible with the native structure and function of the cognate proteins and proceed efficiently. Aspects of the present invention provide compounds having nonprotein chains that are both flexible and extendible. Antibody-like molecules provided in embodiments of the invention have enormous potential as therapeutic candidates with improved binding affinity for their disease targets.

What is claimed is:

1. A compound having the structure:

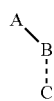

wherein A is a first polypeptide component of the compound;

wherein C is a second polypeptide component of the compound, which polypeptide component has at its N-terminus a sequence of amino acids selected from the group consisting of a cysteine, selenocysteine, CP, CPXCP (where X=P, R, or S) (SEQ ID NOs: 128-130), CDKTHTCPPCP (SEQ ID NO: 131), CVECPPCP (SEQ ID NO: 132), CCVECPPCP (SEQ ID NO: 133) and CDTPPPCPRCP (SEQ ID NO: 134) and comprises consecutive amino acids which (i) are identical to a stretch of consecutive amino acids present in a chain of an $F_c$ domain of an antibody; and (ii) bind to an $F_c$ receptor, wherein B is (a) an organic acid residue or (b) a stretch of consecutive amino acid residues which is, or is present in any of the following sequences: EPKSCDKTH-TCPPCP (SEQ ID NO: 135), ERKCCVECPPCP (SEQ ID NO: 136), ELKTPLGDTTHTCPRCP (EPKSCDTPPPCPRCP)3 (SEQ ID NO: 137), or ESKYGPPCPSC (SEQ ID NO: 138);

wherein the dashed line between B and C represents a peptidyl linkage between B and the N-terminus of C;

wherein the solid line between A and B represents a nonpeptidyl linkage comprising the structure:

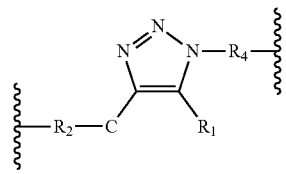

wherein $R_1$ is part of a cyclic structure, $R_2$ is an organic structure which is connected to A, and $R_4$ is an organic structure which is connected to B, wherein the cyclic structure comprises: the carbon attached to $R_2$, $R_1$, and may also comprise (a) $R_2$, or (b) a portion of $R_2$.

2. The compound according to claim 1, wherein $R_1$ and $R_2$ are linked via at least one direct bond so as to form a cyclic structure comprising
i) $R_1$,
ii) a portion of $R_2$,
iii) the carbon attached to $R_2$, and
iv) the alkene double bond in the nonpeptidyl structure.

3. The compound according to claim 2, wherein $R_1$ is selected from the group consisting of:

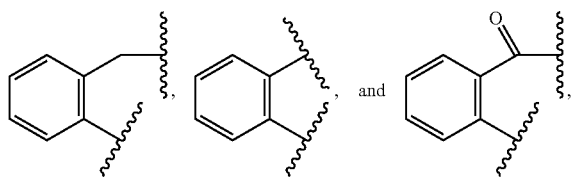

which is optionally substituted at any position.

4. The compound according to claim 1, wherein the carbon attached to $R_2$ is:
(i) directly bonded to $R_2$ via a single bond; or
(ii) directly bonded to $R_2$ via a double bond and a single bond.

5. The compound according to claim 4, wherein the carbon attached to $R_2$ is substituted with two hydrogens and directly bonded to $R_2$ via a single bond.

6. The compound according to claim 4, wherein the carbon attached to $R_2$ is directly bonded to $R_2$ via a double bond and a single bond.

7. The compound according to claim 5, wherein $R_2$ is

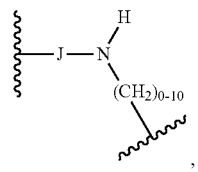

wherein $R_2$ is attached to A via J, and
wherein J is a bond or an organic structure comprising a chain of 2 or more moieties selected from the group consisting of a [PEG(y)]z, polyalkylene glycol, polyoxyalkylated polyol, polyvinyl alcohol, polyvinyl alkyl ether, poly(lactic acid), poly(lactic-glycolic acid), polysaccharide, a branched residue, $C_1$-$C_4$ alkyl, amine, sulfur, oxygen, succinimide, maleimide, glycerol, triazole, isoxazolidine, $C_1$-$C_4$ acyl, succinyl, malonyl, glutaryl, phthalyl, adipoyl and an amino acid,
wherein [PEG(y)]z is:

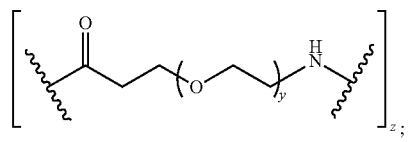

wherein y=1-100 and z=1-10.

8. The compound according to claim 6, wherein $R_2$ is

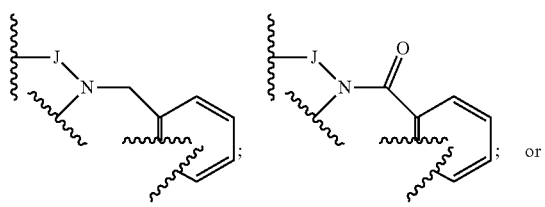

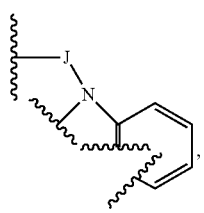

which is optionally substituted at any position,
wherein $R_2$ is attached to $R_1$ via the nitrogen atom of $R_2$, and
wherein J is a bond or an organic structure comprising a chain of 2 or more moieties selected from the group consisting of [PEG(y)]z, polyalkylene glycol, polyoxyalkylated polyol, polyvinyl alcohol, polyvinyl alkyl ether, poly(lactic acid), poly(lactic-glycolic acid), polysaccharide, a branched residue, $C_1$-$C_4$ alkyl, amine, sulfur, oxygen, succinimide, maleimide, glycerol, triazole, isoxazolidine, $C_1$-$C_4$ acyl, succinyl, malonyl, glutaryl, phthalyl, adipoyl and an amino acid,
wherein [PEG(y)]z is:

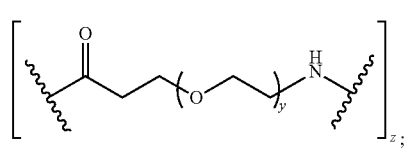

wherein y=1-100 and z=1-10.

9. The compound according to claim 6, wherein the cyclic structure comprises $R_1$ and $R_2$ and is:

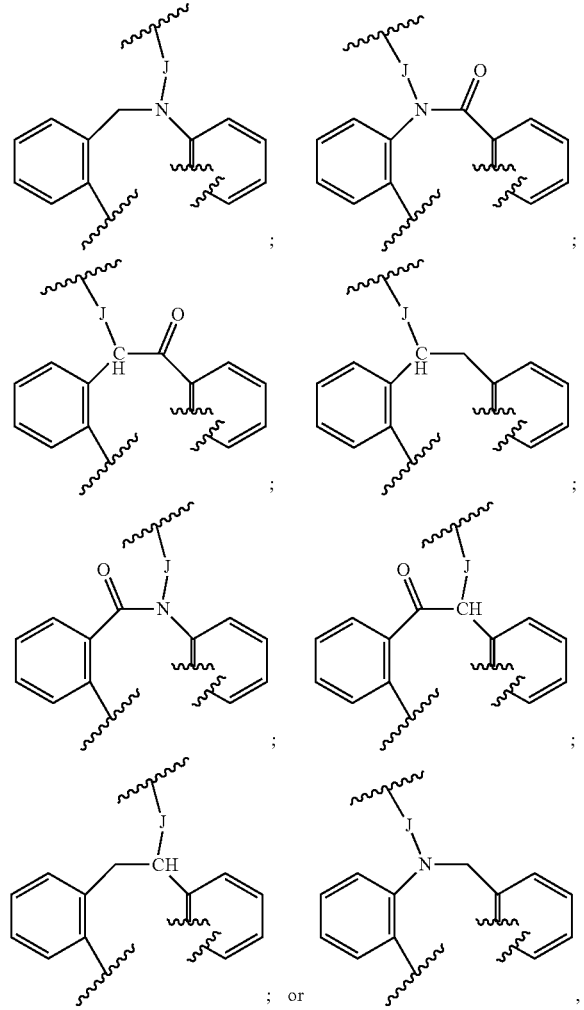

; or

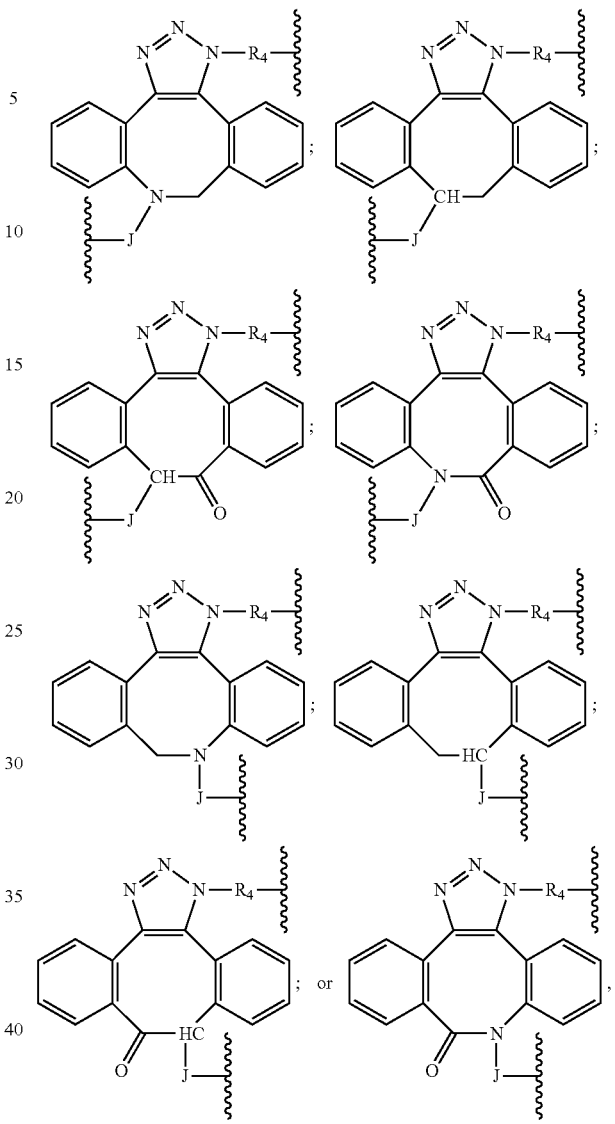

which is optionally substituted at any position, wherein J is a bond or an organic structure comprising a chain of 2 or more moieties selected from the group consisting of [PEG(y)]z, polyalkylene glycol, polyoxyalkylated polyol, polyvinyl alcohol, polyvinyl alkyl ether, poly(lactic acid), poly(lactic-glycolic acid), polysaccharide, a branched residue, $C_1$-$C_4$ alkyl, amine, sulfur, oxygen, succinimide, maleimide, glycerol, triazole, isoxazolidine, $C_1$-$C_4$ acyl, succinyl, malonyl, glutaryl, phthalyl, adipoyl and an amino acid, wherein [PEG(y)]z is:

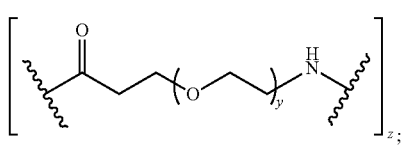

wherein y=1-100 and z=1-10.

10. The compound according to claim 1, wherein the nonpeptidyl linkage comprises the structure:

which is optionally substituted at any position, wherein J is a bond or an organic structure comprising a chain of 2, 3, 4, 5, 6, 7, 8, 9, 10 or more moieties selected from the group consisting of [PEG(y)]z, polyalkylene glycol, polyoxyalkylated polyol, polyvinyl alcohol, polyvinyl alkyl ether, poly(lactic acid), poly(lactic-glycolic acid), polysaccharide, a branched residue, $C_1$-$C_4$ alkyl, amine, sulfur, oxygen, succinimide, maleimide, glycerol, triazole, isoxazolidine, $C_1$-$C_4$ acyl, succinyl, malonyl, glutaryl, phthalyl, adipoyl and an amino acid, wherein [PEG(y)]z is:

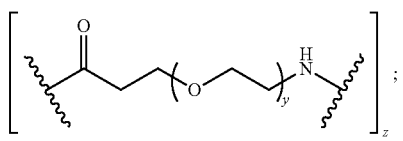

wherein y=1-100 and z=1-10.

11. The compound according to claim 1, wherein C is a second polypeptide component of the compound, which polypeptide component has at its N-terminus a sequence of amino acids consisting of a naturally occurring cysteine selected from the group consisting of CP, CPXCP (where X=P, R, or S) (SEQ ID NOs: 128-130), CDKTHTCPPCP (SEQ ID NO: 131), CVECPPCP (SEQ ID NO: 132), CCVECPPCP (SEQ ID NO: 133) and CDTPPPCPRCP (SEQ ID NO: 134) and comprises consecutive amino acids which (i) are identical to a stretch of consecutive amino acids present in a chain of an $F_c$ domain of an antibody; and (ii) bind to an $F_c$ receptor.

12. The compound according to claim 1, wherein C is a second polypeptide component of the compound, which polypeptide component has at its N-terminus a sequence consisting of a non-naturally occurring cysteine or selenocysteine and comprises consecutive amino acids which (i) are identical to a stretch of consecutive amino acids present in a chain of an $F_c$ domain of an antibody; and (ii) bind to an $F_c$ receptor.

13. The compound according to claim 1, wherein A comprises a secreted protein.

14. The compound according to claim 1, wherein A comprises an extracellular domain of a protein.

15. The compound according to claim 1, wherein A has biological activity.

16. The compound according to claim 1, wherein the A is an independently-folding protein or a portion thereof.

17. The compound according to claim 1, wherein A is a glycosylated protein.

18. The compound according to claim 1, wherein A comprises intra-chain disulfide bonds.

19. The compound according to claim 1, wherein A comprises at least one stretch of consecutive amino acids which are identical to a stretch of consecutive amino acids present in the heavy chain of a Fab or a Fab' of an antibody.

20. The compound according to claim 1, wherein A comprises at least one stretch of consecutive amino acids which are identical to a stretch of consecutive amino acids present in the light chain of a Fab or a Fab' of an antibody.

21. The compound according to claim 1, wherein A comprises at least one Fab or Fab' of an antibody, or a portion of the at least one Fab or Fab'.

22. The compound according to claim 1, wherein A comprises at least 2, 3, 4, 5, 6, 7, 8, 9, or 10 copies of the Fab or Fab' or portion thereof.

23. The compound according to claim 1, wherein A comprises at least one stretch of consecutive amino acids which are identical to a stretch of consecutive amino acids present in a single chain antibody.

24. The compound according to claim 1, wherein A comprises at least one stretch of consecutive amino acids which are identical to a stretch of consecutive amino acids present in a TNFα receptor.

25. A homodimer comprising the compound according to claim 1.

26. A heterodimer comprising the compound according to claim 1, which forms part of a heterodimer.

27. A process for producing a compound having the structure:

wherein A is a first polypeptide component of the compound;

wherein C is a second polypeptide component of the compound, which polypeptide component has at its N-terminus a sequence selected from the group consisting of a cysteine, selenocysteine, CP, CPXCP (where X=P, R, or S) (SEQ ID NOs: 128-130), CDKTHTCPPCP (SEQ ID NO: 131), CVECPPCP (SEQ ID NO: 132), CCVECPPCP (SEQ ID NO: 133) and CDTPPPCPRCP (SEQ ID NO: 134) and comprises consecutive amino acids which (i) are identical to a stretch of consecutive amino acids present in a chain of an $F_c$ domain of an antibody; and (ii) bind to an $F_c$ receptor;

wherein B is (a) an organic acid residue or (b) a stretch of consecutive amino acid residues which is, or is present in any of the following sequences: EPKSCDKTHTCPPCP (SEQ ID NO: 135), ERKCCVECPPCP (SEQ ID NO: 136), ELKTPLGDTTHTCPRCP (EPKSCDTPPPCPRCP)3 (SEQ ID NO: 137), or ESKYGPPCPSC (SEQ ID NO: 138);

wherein the dashed line between B and C represents a peptidyl linkage between B and the N-terminus of C;

wherein the solid line between A and B represents a nonpeptidyl linkage comprising the structure:

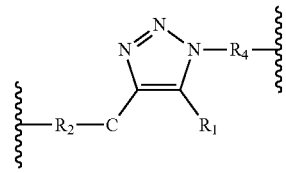

wherein $R_1$ is part of a cyclic structure, $R_2$ is an organic structure which is connected to A, and $R_4$ is an organic structure which is connected to B, wherein the cyclic structure comprises: the carbon attached to $R_2$, $R_1$, and may also comprise (a) $R_2$, or (b) a portion of $R_2$;

which comprises the following steps:
  a) obtaining an A' which comprises A or a derivative of A, and a first terminal reactive group which is an alkyne;
  b) obtaining a B' which comprises B or a derivative of B, a second terminal reactive group and a third terminal reactive group, wherein the second terminal reactive group is an azide capable of reacting with the first terminal reactive group to form a nonpeptidyl linkage, and the third reactive group is a thioester;
  c) obtaining a C' which comprises C or a derivative of C, and a fourth terminal reactive group, wherein the fourth terminal reactive group is an amino acid or amino acid derivative capable of reacting with the third terminal reactive group to form a peptidyl linkage; and
  d) reacting A', B' and C' in any order to produce the compound.

28. The process according to claim 27, wherein the fourth reactive group is cysteine, selenocysteine, homocysteine, or homoselenosysteine, or a derivative of cysteine, selenocysteine, homocysteine, or homoselenosysteine.

29. The compound according to claim 1, wherein $R_4$ is
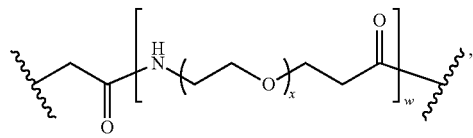
wherein x is 1-100, and w is 0-5.
* * * * *

SEQUENCE LISTING

```
<160> NUMBER OF SEQ ID NOS: 140

<210> SEQ ID NO 1
<211> LENGTH: 228
<212> TYPE: PRT
<213> ORGANISM: Artificial Sequence
<220> FEATURE:
<223> OTHER INFORMATION: Human IgG1 Fc domain having the N-terminal
      sequence CDKTHTCPPCPAPE

<400> SEQUENCE: 1

Cys Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225

<210> SEQ ID NO 2
<211> LENGTH: 684
```

```
<212> TYPE: DNA
<213> ORGANISM: Artificial Sequence
<220> FEATURE:
<223> OTHER INFORMATION: DNA encoding human IgG1 Fc domain having the N-
      terminal sequence CDKTHTCPPCPAPE

<400> SEQUENCE: 2
tgtgacaaaa ctcacacatg cccaccgtgc ccagcacctg aactcctggg ggggccctca      60
gtcttcctct tccccccaaa acccaaggac accctcatga tctcccggac ccctgaggtc     120
acatgcgtgg tggtggacgt gagccacgaa gaccctgagg tcaagttcaa ctggtacgtg     180
gacggcgtgg aggtgcataa tgccaagaca aagccgcggg aggagcagta caacagcacg     240
taccgtgtgg tcagcgtcct caccgtcctg caccaggact ggctgaatgg caaggagtac     300
aagtgcaagg tctccaacaa agccctccca gcccccatcg agaaaaccat ctccaaagcc     360
aaagggcagc cccgagaacc acaggtgtac accctgcccc catcccggga tgagctgacc     420
aagaaccagg tcagcctgac ctgcctggtc aaaggcttct atcccagcga catcgccgtg     480
gagtgggaga gcaatgggca gccggagaac aactacaaga ccacgcctcc cgtgctggac     540
tccgacggct ccttcttcct ctacagcaag ctcaccgtgg acaagagcag gtggcagcag     600
gggaacgtct tctcatgctc cgtgatgcat gaggctctgc acaaccacta cacgcagaag     660
agcctctccc tgtctccggg taaa                                            684

<210> SEQ ID NO 3
<211> LENGTH: 251
<212> TYPE: PRT
<213> ORGANISM: Artificial Sequence
<220> FEATURE:
<223> OTHER INFORMATION: pre-Fc chimeric polypeptide having SHH signal
      peptide

<400> SEQUENCE: 3
```

Met Leu Leu Leu Ala Arg Cys Leu Leu Val Leu Val Ser Ser Leu
1               5                   10                  15

Leu Val Cys Ser Gly Leu Ala Cys Asp Lys Thr His Thr Cys Pro Pro
            20                  25                  30

Cys Pro Ala Pro Glu Leu Leu Gly Gly Pro Ser Val Phe Leu Phe Pro
        35                  40                  45

Pro Lys Pro Lys Asp Thr Leu Met Ile Ser Arg Thr Pro Glu Val Thr
    50                  55                  60

Cys Val Val Val Asp Val Ser His Glu Asp Pro Glu Val Lys Phe Asn
65                  70                  75                  80

Trp Tyr Val Asp Gly Val Glu Val His Asn Ala Lys Thr Lys Pro Arg
                85                  90                  95

Glu Glu Gln Tyr Asn Ser Thr Tyr Arg Val Val Ser Val Leu Thr Val
            100                 105                 110

Leu His Gln Asp Trp Leu Asn Gly Lys Glu Tyr Lys Cys Lys Val Ser
        115                 120                 125

Asn Lys Ala Leu Pro Ala Pro Ile Glu Lys Thr Ile Ser Lys Ala Lys
    130                 135                 140

Gly Gln Pro Arg Glu Pro Gln Val Tyr Thr Leu Pro Pro Ser Arg Asp
145                 150                 155                 160

Glu Leu Thr Lys Asn Gln Val Ser Leu Thr Cys Leu Val Lys Gly Phe
                165                 170                 175

Tyr Pro Ser Asp Ile Ala Val Glu Trp Glu Ser Asn Gly Gln Pro Glu
            180                 185                 190

```
Asn Asn Tyr Lys Thr Thr Pro Pro Val Leu Asp Ser Asp Gly Ser Phe
            195                 200                 205

Phe Leu Tyr Ser Lys Leu Thr Val Asp Lys Ser Arg Trp Gln Gln Gly
        210                 215                 220

Asn Val Phe Ser Cys Ser Val Met His Glu Ala Leu His Asn His Tyr
225                 230                 235                 240

Thr Gln Lys Ser Leu Ser Leu Ser Pro Gly Lys
                245                 250
```

<210> SEQ ID NO 4
<211> LENGTH: 785
<212> TYPE: DNA
<213> ORGANISM: Artificial Sequence
<220> FEATURE:
<223> OTHER INFORMATION: DNA encoding pre-Fc chimeric polypeptide having
     SHH signal peptide

<400> SEQUENCE: 4

```
aagcttgaat tcccaccatg ctgctgctgg cgagatgtct gctgctagtc ctcgtctcct     60
cgctgctggt atgctcggga ctggcgtgtg acaaaactca cacatgccca ccgtgcccag    120
cacctgaact cctgggggg ccctcagtct cctcttccc cccaaaaccc aaggacaccc     180
tcatgatctc ccggaccct gaggtcacat gcgtggtggt ggacgtgagc cacgaagacc    240
ctgaggtcaa gttcaactgg tacgtggacg gcgtggaggt gcataatgcc aagacaaagc    300
cgcgggagga gcagtacaac agcacgtacc gtgtggtcag cgtcctcacc gtcctgcacc    360
aggactggct gaatggcaag gagtacaagt gcaaggtctc caacaaagcc ctcccagccc    420
ccatcgagaa aaccatctcc aaagccaaag ggcagccccg agaaccacag gtgtacaccc    480
tgccccccatc ccgggatgag ctgaccaaga accaggtcag cctgacctgc ctggtcaaag    540
gcttctatcc cagcgacatc gccgtggagt gggagagcaa tgggcagccg gagaacaact    600
acaagaccac gcctcccgtg ctggactccg acggctcctt cttcctctac agcaagctca    660
ccgtggacaa gagcaggtgg cagcagggga acgtcttctc atgctccgtg atgcatgagg    720
ctctgcacaa ccactacacg cagaagagcc tctccctgtc tccgggtaaa tgactcgagc    780
ggccg                                                                785
```

<210> SEQ ID NO 5
<211> LENGTH: 251
<212> TYPE: PRT
<213> ORGANISM: Artificial Sequence
<220> FEATURE:
<223> OTHER INFORMATION: pre-Fc chimeric polypeptide having IFN signal
     peptide

<400> SEQUENCE: 5

```
Met Ala Leu Thr Phe Ala Leu Leu Val Ala Leu Leu Val Leu Ser Cys
1               5                   10                  15

Lys Ser Ser Cys Ser Val Gly Cys Asp Lys Thr His Thr Cys Pro Pro
            20                  25                  30

Cys Pro Ala Pro Glu Leu Leu Gly Gly Pro Ser Val Phe Leu Phe Pro
        35                  40                  45

Pro Lys Pro Lys Asp Thr Leu Met Ile Ser Arg Thr Pro Glu Val Thr
    50                  55                  60

Cys Val Val Val Asp Val Ser His Glu Asp Pro Glu Val Lys Phe Asn
65                  70                  75                  80

Trp Tyr Val Asp Gly Val Glu Val His Asn Ala Lys Thr Lys Pro Arg
                85                  90                  95
```

```
Glu Glu Gln Tyr Asn Ser Thr Tyr Arg Val Val Ser Val Leu Thr Val
            100                 105                 110

Leu His Gln Asp Trp Leu Asn Gly Lys Glu Tyr Lys Cys Lys Val Ser
        115                 120                 125

Asn Lys Ala Leu Pro Ala Pro Ile Glu Lys Thr Ile Ser Lys Ala Lys
    130                 135                 140

Gly Gln Pro Arg Glu Pro Gln Val Tyr Thr Leu Pro Pro Ser Arg Asp
145                 150                 155                 160

Glu Leu Thr Lys Asn Gln Val Ser Leu Thr Cys Leu Val Lys Gly Phe
                165                 170                 175

Tyr Pro Ser Asp Ile Ala Val Glu Trp Glu Ser Asn Gly Gln Pro Glu
            180                 185                 190

Asn Asn Tyr Lys Thr Thr Pro Pro Val Leu Asp Ser Asp Gly Ser Phe
        195                 200                 205

Phe Leu Tyr Ser Lys Leu Thr Val Asp Lys Ser Arg Trp Gln Gln Gly
    210                 215                 220

Asn Val Phe Ser Cys Ser Val Met His Glu Ala Leu His Asn His Tyr
225                 230                 235                 240

Thr Gln Lys Ser Leu Ser Leu Ser Pro Gly Lys
                245                 250

<210> SEQ ID NO 6
<211> LENGTH: 785
<212> TYPE: DNA
<213> ORGANISM: Artificial Sequence
<220> FEATURE:
<223> OTHER INFORMATION: DNA encoding pre-Fc chimeric polypeptide having
      IFN signal peptide

<400> SEQUENCE: 6
aagcttgaat tcccaccatg gccttgacct ttgctttact ggtggccctc ctggtgctca      60
gctgcaagtc aagctgctct gtgggctgtg acaaaactca cacatgccca ccgtgcccag     120
cacctgaact cctgggggg ccctcagtct tcctcttccc cccaaaaccc aaggacaccc     180
tcatgatctc ccggacccct gaggtcacat gcgtggtggt ggacgtgagc cacgaagacc     240
ctgaggtcaa gttcaactgg tacgtggacg gcgtggaggt gcataatgcc aagacaaagc     300
cgcgggagga gcagtacaac agcacgtacc gtgtggtcag cgtcctcacc gtcctgcacc     360
aggactggct gaatggcaag gagtacaagt gcaaggtctc caacaaagcc ctcccagccc     420
ccatcgagaa aaccatctcc aaagccaaag gcagccccg agaaccacag gtgtacaccc     480
tgcccccatc ccgggatgag ctgaccaaga accaggtcag cctgacctgc ctggtcaaag     540
gcttctatcc cagcgacatc gccgtggagt gggagagcaa tgggcagccg gagaacaact     600
acaagaccac gcctcccgtg ctggactccg acggctcctt cttcctctac agcaagctca     660
ccgtggacaa gagcaggtgg cagcagggga acgtcttctc atgctccgtg atgcatgagg     720
ctctgcacaa ccactacacg cagaagagcc tctccctgtc tccgggtaaa tgactcgagc     780
ggccg                                                                785

<210> SEQ ID NO 7
<211> LENGTH: 245
<212> TYPE: PRT
<213> ORGANISM: Artificial Sequence
<220> FEATURE:
<223> OTHER INFORMATION: pre-Fc chimeric polypeptide having CETP signal
      peptide
```

<400> SEQUENCE: 7

```
Met Leu Ala Ala Thr Val Leu Thr Leu Ala Leu Leu Gly Asn Ala His
1               5                   10                  15

Ala Cys Asp Lys Thr His Thr Cys Pro Pro Cys Pro Ala Pro Glu Leu
            20                  25                  30

Leu Gly Gly Pro Ser Val Phe Leu Phe Pro Pro Lys Pro Lys Asp Thr
        35                  40                  45

Leu Met Ile Ser Arg Thr Pro Glu Val Thr Cys Val Val Val Asp Val
    50                  55                  60

Ser His Glu Asp Pro Glu Val Lys Phe Asn Trp Tyr Val Asp Gly Val
65                  70                  75                  80

Glu Val His Asn Ala Lys Thr Lys Pro Arg Glu Glu Gln Tyr Asn Ser
                85                  90                  95

Thr Tyr Arg Val Val Ser Val Leu Thr Val Leu His Gln Asp Trp Leu
            100                 105                 110

Asn Gly Lys Glu Tyr Lys Cys Lys Val Ser Asn Lys Ala Leu Pro Ala
        115                 120                 125

Pro Ile Glu Lys Thr Ile Ser Lys Ala Lys Gly Gln Pro Arg Glu Pro
    130                 135                 140

Gln Val Tyr Thr Leu Pro Pro Ser Arg Asp Glu Leu Thr Lys Asn Gln
145                 150                 155                 160

Val Ser Leu Thr Cys Leu Val Lys Gly Phe Tyr Pro Ser Asp Ile Ala
                165                 170                 175

Val Glu Trp Glu Ser Asn Gly Gln Pro Glu Asn Asn Tyr Lys Thr Thr
            180                 185                 190

Pro Pro Val Leu Asp Ser Asp Gly Ser Phe Phe Leu Tyr Ser Lys Leu
        195                 200                 205

Thr Val Asp Lys Ser Arg Trp Gln Gln Gly Asn Val Phe Ser Cys Ser
    210                 215                 220

Val Met His Glu Ala Leu His Asn His Tyr Thr Gln Lys Ser Leu Ser
225                 230                 235                 240

Leu Ser Pro Gly Lys
            245
```

<210> SEQ ID NO 8
<211> LENGTH: 767
<212> TYPE: DNA
<213> ORGANISM: Artificial Sequence
<220> FEATURE:
<223> OTHER INFORMATION: DNA encoding pre-Fc chimeric polypeptide having CETP signal peptide

<400> SEQUENCE: 8

```
aagcttgaat tcccaccatg ctggctgcca cagtcctgac cctggccctg ctgggcaatg      60
cccatgcctg tgacaaaact cacacatgcc caccgtgccc agcacctgaa ctcctggggg     120 ggcccctcagt cttcctcttc cccccaaaac ccaaggacac cctcatgatc tcccggaccc    180
ctgaggtcac atgcgtggtg gtggacgtga gccacgaaga ccctgaggtc aagttcaact    240
ggtacgtgga cggcgtggag gtgcataatg ccaagacaaa gccgcgggag gagcagtaca    300
acagcacgta ccgtgtggtc agcgtcctca ccgtcctgca ccaggactgg ctgaatggca    360
aggagtacaa gtgcaaggtc tccaacaaag ccctcccagc ccccatcgag aaaaccatct    420
ccaaagccaa agggcagccc cgagaaccac aggtgtacac cctgcccccca tcccgggatg    480 agctgaccaa gaaccaggtc agcctgacct gcctggtcaa aggcttctat cccagcgaca    540
```

-continued

```
tcgccgtgga gtgggagagc aatgggcagc cggagaacaa ctacaagacc acgcctcccg    600
tgctggactc cgacggctcc ttcttcctct acagcaagct caccgtggac aagagcaggt    660
ggcagcaggg gaacgtcttc tcatgctccg tgatgcatga ggctctgcac aaccactaca    720
cgcagaagag cctctccctg tctccgggta aatgactcga gcggccg                  767
```

<210> SEQ ID NO 9
<211> LENGTH: 222
<212> TYPE: PRT
<213> ORGANISM: Artificial Sequence
<220> FEATURE:
<223> OTHER INFORMATION: Human IgG1 Fc domain having the N-terminal sequence CPPCPAPE

<400> SEQUENCE: 9

```
Cys Pro Pro Cys Pro Ala Pro Glu Leu Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
    50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Arg Asp Glu Leu Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly Lys
    210                 215                 220
```

<210> SEQ ID NO 10
<211> LENGTH: 666
<212> TYPE: DNA
<213> ORGANISM: Artificial Sequence
<220> FEATURE:
<223> OTHER INFORMATION: DNA encoding human IgG1 Fc domain having the N-terminal sequence CPPCPAPE

<400> SEQUENCE: 10

```
tgcccaccgt gcccagcacc tgaactcctg ggggggccct cagtcttcct cttccccca    60 aaacccaagg acaccctcat gatctcccgg acccctgagg tcacatgcgt ggtggtggac    120
gtgagccacg aagaccctga ggtcaagttc aactggtacg tggacggcgt ggaggtgcat    180
aatgccaaga caaagccgcg ggaggagcag tacaacagca cgtaccgtgt ggtcagcgtc    240
```

-continued

```
ctcaccgtcc tgcaccagga ctggctgaat ggcaaggagt acaagtgcaa ggtctccaac    300
aaagccctcc cagcccccat cgagaaaacc atctccaaag ccaagggca gccccgagaa    360 ccacaggtgt acaccctgcc cccatcccgg gatgagctga ccaagaacca ggtcagcctg    420
acctgcctgg tcaaaggctt ctatcccagc gacatcgccg tggagtggga gagcaatggg    480
cagccggaga caactacaa gaccacgcct cccgtgctgg actccgacgg ctccttcttc    540
ctctacagca agctcaccgt ggacaagagc aggtggcagc aggggaacgt cttctcatgc    600
tccgtgatgc atgaggctct gcacaaccac tacacgcaga agagcctctc cctgtctccg    660
ggtaaa                                                              666
```

<210> SEQ ID NO 11
<211> LENGTH: 245
<212> TYPE: PRT
<213> ORGANISM: Artificial Sequence
<220> FEATURE:
<223> OTHER INFORMATION: pre-Fc chimeric polypeptide having SHH signal peptide

<400> SEQUENCE: 11

```
Met Leu Leu Leu Ala Arg Cys Leu Leu Leu Val Leu Val Ser Ser Leu
1               5                   10                  15

Leu Val Cys Ser Gly Leu Ala Cys Pro Pro Cys Pro Ala Pro Glu Leu
            20                  25                  30

Leu Gly Gly Pro Ser Val Phe Leu Phe Pro Pro Lys Pro Lys Asp Thr
        35                  40                  45

Leu Met Ile Ser Arg Thr Pro Glu Val Thr Cys Val Val Val Asp Val
    50                  55                  60

Ser His Glu Asp Pro Glu Val Lys Phe Asn Trp Tyr Val Asp Gly Val
65                  70                  75                  80

Glu Val His Asn Ala Lys Thr Lys Pro Arg Glu Glu Gln Tyr Asn Ser
                85                  90                  95

Thr Tyr Arg Val Val Ser Val Leu Thr Val Leu His Gln Asp Trp Leu
            100                 105                 110

Asn Gly Lys Glu Tyr Lys Cys Lys Val Ser Asn Lys Ala Leu Pro Ala
        115                 120                 125

Pro Ile Glu Lys Thr Ile Ser Lys Ala Lys Gly Gln Pro Arg Glu Pro
    130                 135                 140

Gln Val Tyr Thr Leu Pro Pro Ser Arg Asp Glu Leu Thr Lys Asn Gln
145                 150                 155                 160

Val Ser Leu Thr Cys Leu Val Lys Gly Phe Tyr Pro Ser Asp Ile Ala
                165                 170                 175

Val Glu Trp Glu Ser Asn Gly Gln Pro Glu Asn Asn Tyr Lys Thr Thr
            180                 185                 190

Pro Pro Val Leu Asp Ser Asp Gly Ser Phe Phe Leu Tyr Ser Lys Leu
        195                 200                 205

Thr Val Asp Lys Ser Arg Trp Gln Gln Gly Asn Val Phe Ser Cys Ser
    210                 215                 220

Val Met His Glu Ala Leu His Asn His Tyr Thr Gln Lys Ser Leu Ser
225                 230                 235                 240

Leu Ser Pro Gly Lys
                245
```

<210> SEQ ID NO 12
<211> LENGTH: 767

-continued

<212> TYPE: DNA
<213> ORGANISM: Artificial Sequence
<220> FEATURE:
<223> OTHER INFORMATION: DNA encoding pre-Fc chimeric polypeptide having
      SHH signal peptide

<400> SEQUENCE: 12

```
aagcttgaat tcccaccatg ctgctgctgg cgagatgtct gctgctagtc ctcgtctcct      60
cgctgctggt atgctcggga ctggcgtgcc caccgtgccc agcacctgaa ctcctggggg     120
ggccctcagt cttcctcttc cccccaaaac ccaaggacac cctcatgatc tcccggaccc     180
ctgaggtcac atgcgtggtg gtggacgtga gccacgaaga ccctgaggtc aagttcaact     240
ggtacgtgga cggcgtggag gtgcataatg ccaagacaaa gccgcgggag gagcagtaca     300
acagcacgta ccgtgtggtc agcgtcctca ccgtcctgca ccaggactgg ctgaatggca     360
aggagtacaa gtgcaaggtc tccaacaaag ccctcccagc ccccatcgag aaaaccatct     420
ccaaagccaa aggcagcccc gagaaccac aggtgtacac cctgccccca tcccgggatg     480
agctgaccaa gaaccaggtc agcctgacct gcctggtcaa aggcttctat cccagcgaca     540
tcgccgtgga gtgggagagc aatgggcagc cggagaacaa ctacaagacc acgcctcccg     600
tgctggactc cgacggctcc ttcttcctct acagcaagct caccgtggac aagagcaggt     660
ggcagcaggg gaacgtcttc tcatgctccg tgatgcatga ggctctgcac aaccactaca     720
cgcagaagag cctctccctg tctccgggta aatgactcga gcggccg                   767
```

<210> SEQ ID NO 13
<211> LENGTH: 245
<212> TYPE: PRT
<213> ORGANISM: Artificial Sequence
<220> FEATURE:
<223> OTHER INFORMATION: pre-Fc chimeric polypeptide having IFN signal
      peptide

<400> SEQUENCE: 13

```
Met Ala Leu Thr Phe Ala Leu Leu Val Ala Leu Leu Val Leu Ser Cys
1               5                   10                  15

Lys Ser Ser Cys Ser Val Gly Cys Pro Pro Cys Pro Ala Pro Glu Leu
            20                  25                  30

Leu Gly Gly Pro Ser Val Phe Leu Phe Pro Pro Lys Pro Lys Asp Thr
        35                  40                  45

Leu Met Ile Ser Arg Thr Pro Glu Val Thr Cys Val Val Val Asp Val
    50                  55                  60

Ser His Glu Asp Pro Glu Val Lys Phe Asn Trp Tyr Val Asp Gly Val
65                  70                  75                  80

Glu Val His Asn Ala Lys Thr Lys Pro Arg Glu Glu Gln Tyr Asn Ser
                85                  90                  95

Thr Tyr Arg Val Val Ser Val Leu Thr Val Leu His Gln Asp Trp Leu
            100                 105                 110

Asn Gly Lys Glu Tyr Lys Cys Lys Val Ser Asn Lys Ala Leu Pro Ala
        115                 120                 125

Pro Ile Glu Lys Thr Ile Ser Lys Ala Lys Gly Gln Pro Arg Glu Pro
    130                 135                 140

Gln Val Tyr Thr Leu Pro Pro Ser Arg Asp Glu Leu Thr Lys Asn Gln
145                 150                 155                 160

Val Ser Leu Thr Cys Leu Val Lys Gly Phe Tyr Pro Ser Asp Ile Ala
                165                 170                 175

Val Glu Trp Glu Ser Asn Gly Gln Pro Glu Asn Asn Tyr Lys Thr Thr
```

```
                    180                 185                 190
Pro Pro Val Leu Asp Ser Asp Gly Ser Phe Phe Leu Tyr Ser Lys Leu
            195                 200                 205

Thr Val Asp Lys Ser Arg Trp Gln Gln Gly Asn Val Phe Ser Cys Ser
        210                 215                 220

Val Met His Glu Ala Leu His Asn His Tyr Thr Gln Lys Ser Leu Ser
225                 230                 235                 240

Leu Ser Pro Gly Lys
            245

<210> SEQ ID NO 14
<211> LENGTH: 767
<212> TYPE: DNA
<213> ORGANISM: Artificial Sequence
<220> FEATURE:
<223> OTHER INFORMATION: DNA encoding pre-Fc chimeric polypeptide having
      IFN signal peptide

<400> SEQUENCE: 14
aagcttgaat tcccaccatg gccttgacct ttgctttact ggtggccctc ctggtgctca      60
gctgcaagtc aagctgctct gtgggctgcc caccgtgccc agcacctgaa ctcctggggg     120
ggcccctcag tcttcctctt ccccccaaaac ccaaggacac cctcatgatc tcccggaccc    180
ctgaggtcac atgcgtggtg gtggacgtga gccacgaaga ccctgaggtc aagttcaact    240
ggtacgtgga cggcgtggag gtgcataatg ccaagacaaa gccgcgggag gagcagtaca    300
acagcacgta ccgtgtggtc agcgtcctca ccgtcctgca ccaggactgg ctgaatggca    360
aggagtacaa gtgcaaggtc tccaacaaag ccctcccagc ccccatcgag aaaaccatct    420
ccaaagccaa aggcagcccc cgagaaccac aggtgtacac cctgccccca tcccgggatg    480
agctgaccaa gaaccaggtc agcctgacct gcctggtcaa aggcttctat cccagcgaca    540
tcgccgtgga gtgggagagc aatgggcagc cggagaacaa ctacaagacc acgcctcccg    600
tgctggactc cgacggctcc ttcttcctct acagcaagct caccgtggac aagagcaggt    660
ggcagcaggg gaacgtcttc tcatgctccg tgatgcatga ggctctgcac aaccactaca    720
cgcagaagag cctctccctg tctccgggta atgactcga gcggccg                   767

<210> SEQ ID NO 15
<211> LENGTH: 239
<212> TYPE: PRT
<213> ORGANISM: Artificial Sequence
<220> FEATURE:
<223> OTHER INFORMATION: pre-Fc chimeric polypeptide having CETP signal
      peptide

<400> SEQUENCE: 15

Met Leu Ala Ala Thr Val Leu Thr Leu Ala Leu Leu Gly Asn Ala His
1               5                   10                  15

Ala Cys Pro Pro Cys Pro Ala Pro Glu Leu Leu Gly Gly Pro Ser Val
            20                  25                  30

Phe Leu Phe Pro Pro Lys Pro Lys Asp Thr Leu Met Ile Ser Arg Thr
        35                  40                  45

Pro Glu Val Thr Cys Val Val Asp Val Ser His Glu Asp Pro Glu
    50                  55                  60

Val Lys Phe Asn Trp Tyr Val Asp Gly Val Glu Val His Asn Ala Lys
65                  70                  75                  80

Thr Lys Pro Arg Glu Glu Gln Tyr Asn Ser Thr Tyr Arg Val Val Ser
            85                  90                  95
```

Val Leu Thr Val Leu His Gln Asp Trp Leu Asn Gly Lys Glu Tyr Lys
            100                 105                 110

Cys Lys Val Ser Asn Lys Ala Leu Pro Ala Pro Ile Glu Lys Thr Ile
        115                 120                 125

Ser Lys Ala Lys Gly Gln Pro Arg Glu Pro Gln Val Tyr Thr Leu Pro
130                 135                 140

Pro Ser Arg Asp Glu Leu Thr Lys Asn Gln Val Ser Leu Thr Cys Leu
145                 150                 155                 160

Val Lys Gly Phe Tyr Pro Ser Asp Ile Ala Val Glu Trp Glu Ser Asn
                165                 170                 175

Gly Gln Pro Glu Asn Asn Tyr Lys Thr Thr Pro Pro Val Leu Asp Ser
            180                 185                 190

Asp Gly Ser Phe Phe Leu Tyr Ser Lys Leu Thr Val Asp Lys Ser Arg
        195                 200                 205

Trp Gln Gln Gly Asn Val Phe Ser Cys Ser Val Met His Glu Ala Leu
210                 215                 220

His Asn His Tyr Thr Gln Lys Ser Leu Ser Leu Ser Pro Gly Lys
225                 230                 235

<210> SEQ ID NO 16
<211> LENGTH: 749
<212> TYPE: DNA
<213> ORGANISM: Artificial Sequence
<220> FEATURE:
<223> OTHER INFORMATION: DNA encoding pre-Fc chimeric polypeptide having
      CETP signal peptide

<400> SEQUENCE: 16
aagcttgaat tcccaccatg ctggctgcca cagtcctgac cctggccctg ctgggcaatg      60
cccatgcctg cccaccgtgc ccagcacctg aactcctggg ggggccctca gtcttcctct    120
tccccccaaa acccaaggac accctcatga tctcccggac ccctgaggtc acatgcgtgg    180
tggtggacgt gagccacgaa gaccctgagg tcaagttcaa ctggtacgtg gacggcgtgg    240
aggtgcataa tgccaagaca aagccgcggg aggagcagta caacagcacg taccgtgtgg    300
tcagcgtcct caccgtcctg caccaggact ggctgaatgg caaggagtac aagtgcaagg    360
tctccaacaa agcccctccca gcccccatcg agaaaaccat ctccaaagcc aaagggcagc    420
cccgagaacc acaggtgtac accctgcccc catcccggga tgagctgacc aagaaccagg    480
tcagcctgac ctgcctggtc aaaggcttct atcccagcga catcgccgtg gagtgggaga    540
gcaatgggca gccggagaac aactacaaga ccacgcctcc cgtgctggac tccgacggct    600
ccttcttcct ctacagcaag ctcaccgtgg acaagagcag gtggcagcag gggaacgtct    660
tctcatgctc cgtgatgcat gaggctctgc acaaccacta cacgcagaag agcctctccc    720
tgtctccggg taaatgactc gagcggccg                                       749

<210> SEQ ID NO 17
<211> LENGTH: 219
<212> TYPE: PRT
<213> ORGANISM: Artificial Sequence
<220> FEATURE:
<223> OTHER INFORMATION: Human IgG1 Fc domain having the N-terminal
      sequence CPAPE

<400> SEQUENCE: 17

Cys Pro Ala Pro Glu Leu Leu Gly Gly Pro Ser Val Phe Leu Phe Pro
1               5                   10                  15

Pro Lys Pro Lys Asp Thr Leu Met Ile Ser Arg Thr Pro Glu Val Thr
            20                  25                  30

Cys Val Val Asp Val Ser His Glu Asp Pro Glu Val Lys Phe Asn
        35                  40                  45

Trp Tyr Val Asp Gly Val Glu Val His Asn Ala Lys Thr Lys Pro Arg
50                  55                  60

Glu Glu Gln Tyr Asn Ser Thr Tyr Arg Val Val Ser Val Leu Thr Val
65                  70                  75                  80

Leu His Gln Asp Trp Leu Asn Gly Lys Glu Tyr Lys Cys Lys Val Ser
                85                  90                  95

Asn Lys Ala Leu Pro Ala Pro Ile Glu Lys Thr Ile Ser Lys Ala Lys
            100                 105                 110

Gly Gln Pro Arg Glu Pro Gln Val Tyr Thr Leu Pro Pro Ser Arg Asp
            115                 120                 125

Glu Leu Thr Lys Asn Gln Val Ser Leu Thr Cys Leu Val Lys Gly Phe
130                 135                 140

Tyr Pro Ser Asp Ile Ala Val Glu Trp Glu Ser Asn Gly Gln Pro Glu
145                 150                 155                 160

Asn Asn Tyr Lys Thr Thr Pro Pro Val Leu Asp Ser Asp Gly Ser Phe
                165                 170                 175

Phe Leu Tyr Ser Lys Leu Thr Val Asp Lys Ser Arg Trp Gln Gln Gly
            180                 185                 190

Asn Val Phe Ser Cys Ser Val Met His Glu Ala Leu His Asn His Tyr
            195                 200                 205

Thr Gln Lys Ser Leu Ser Leu Ser Pro Gly Lys
210                 215

<210> SEQ ID NO 18
<211> LENGTH: 657
<212> TYPE: DNA
<213> ORGANISM: Artificial Sequence
<220> FEATURE:
<223> OTHER INFORMATION: DNA encoding human IgG1 Fc domain having the N-
      terminal sequence CPAPE

<400> SEQUENCE: 18
tgcccagcac ctgaactcct ggggggaccc tcagtcttcc tcttcccccc aaaacccaag      60
gacaccctca tgatctcccg gacccctgag gtcacatgcg tggtggtgga cgtgagccac     120
gaagaccctg aggtcaagtt caactggtac gtggacggcg tggaggtgca taatgccaag     180
acaaagccgc gggaggagca gtacaacagc acgtaccgtg tggtcagcgt cctcaccgtc     240
ctgcaccagg actggctgaa tggcaaggag tacaagtgca aggtctccaa caaagccctc     300
ccagccccca tcgagaaaac catctccaaa gccaaagggc agccccgaga accacaggtg     360
tacaccctgc cccatcccg ggatgagctg accaagaacc aggtcagcct gacctgcctg      420
gtcaaaggct tctatcccag cgacatcgcc gtggagtggg agagcaatgg gcagccggag     480
aacaactaca agaccacgcc tcccgtgctg gactccgacg gctccttctt cctctacagc     540
aagctcaccg tggacaagag caggtggcag caggggaacg tcttctcatg ctccgtgatg     600
catgaggctc tgcacaacca ctacacgcag aagagcctct ccctgtctcc gggtaaa       657

<210> SEQ ID NO 19
<211> LENGTH: 242
<212> TYPE: PRT
<213> ORGANISM: Artificial Sequence
<220> FEATURE:
<223> OTHER INFORMATION: pre-Fc chimeric polypeptide having SHH signal peptide

<400> SEQUENCE: 19

Met Leu Leu Leu Ala Arg Cys Leu Leu Val Leu Val Ser Ser Leu
1               5                   10                  15

Leu Val Cys Ser Gly Leu Ala Cys Pro Ala Pro Glu Leu Leu Gly Gly
            20                  25                  30

Pro Ser Val Phe Leu Phe Pro Pro Lys Pro Lys Asp Thr Leu Met Ile
        35                  40                  45

Ser Arg Thr Pro Glu Val Thr Cys Val Val Val Asp Val Ser His Glu
    50                  55                  60

Asp Pro Glu Val Lys Phe Asn Trp Tyr Val Asp Gly Val Glu Val His
65                  70                  75                  80

Asn Ala Lys Thr Lys Pro Arg Glu Glu Gln Tyr Asn Ser Thr Tyr Arg
                85                  90                  95

Val Val Ser Val Leu Thr Val Leu His Gln Asp Trp Leu Asn Gly Lys
            100                 105                 110

Glu Tyr Lys Cys Lys Val Ser Asn Lys Ala Leu Pro Ala Pro Ile Glu
        115                 120                 125

Lys Thr Ile Ser Lys Ala Lys Gly Gln Pro Arg Glu Pro Gln Val Tyr
    130                 135                 140

Thr Leu Pro Pro Ser Arg Asp Glu Leu Thr Lys Asn Gln Val Ser Leu
145                 150                 155                 160

Thr Cys Leu Val Lys Gly Phe Tyr Pro Ser Asp Ile Ala Val Glu Trp
                165                 170                 175

Glu Ser Asn Gly Gln Pro Glu Asn Asn Tyr Lys Thr Thr Pro Pro Val
            180                 185                 190

Leu Asp Ser Asp Gly Ser Phe Phe Leu Tyr Ser Lys Leu Thr Val Asp
        195                 200                 205

Lys Ser Arg Trp Gln Gln Gly Asn Val Phe Ser Cys Ser Val Met His
    210                 215                 220

Glu Ala Leu His Asn His Tyr Thr Gln Lys Ser Leu Ser Leu Ser Pro
225                 230                 235                 240

Gly Lys

<210> SEQ ID NO 20
<211> LENGTH: 758
<212> TYPE: DNA
<213> ORGANISM: Artificial Sequence
<220> FEATURE:
<223> OTHER INFORMATION: DNA encoding pre-Fc chimeric polypeptide having
      SHH signal peptide

<400> SEQUENCE: 20
aagcttgaat tcccaccatg ctgctgctgg cgagatgtct gctgctagtc ctcgtctcct      60
cgctgctggt atgctcggga ctggcgtgcc cagcacctga actcctgggg gggccctcag     120
tcttcctctt ccccccaaaa cccaaggaca ccctcatgat ctcccggacc cctgaggtca     180
catgcgtggt ggtggacgtg agccacgaag accctgaggt caagttcaac tggtacgtgg     240
acggcgtgga ggtgcataat gccaagacaa agccgcggga ggagcagtac aacagcacgt     300
accgtgtggt cagcgtcctc accgtcctgc accaggactg gctgaatggc aaggagtaca     360
agtgcaaggt ctccaacaaa gccctcccag ccccatcga gaaaaccatc tccaaagcca     420
aagggcagcc ccgagaacca caggtgtaca ccctgccccc atcccgggat gagctgacca     480
agaaccaggt cagcctgacc tgcctggtca aaggcttcta tcccagcgac atcgccgtgg     540

```
agtgggagag caatgggcag ccggagaaca actacaagac cacgcctccc gtgctggact    600
ccgacggctc cttcttcctc tacagcaagc tcaccgtgga caagagcagg tggcagcagg    660
ggaacgtctt ctcatgctcc gtgatgcatg aggctctgca caaccactac acgcagaaga    720
gcctctccct gtctccgggt aaatgactcg agcggccg                            758
```

<210> SEQ ID NO 21
<211> LENGTH: 242
<212> TYPE: PRT
<213> ORGANISM: Artificial Sequence
<220> FEATURE:
<223> OTHER INFORMATION: pre-Fc chimeric polypeptide having IFN signal peptide

<400> SEQUENCE: 21

```
Met Ala Leu Thr Phe Ala Leu Leu Val Ala Leu Leu Val Leu Ser Cys
1               5                   10                  15

Lys Ser Ser Cys Ser Val Gly Cys Pro Ala Pro Glu Leu Leu Gly Gly
            20                  25                  30

Pro Ser Val Phe Leu Phe Pro Pro Lys Pro Lys Asp Thr Leu Met Ile
        35                  40                  45

Ser Arg Thr Pro Glu Val Thr Cys Val Val Val Asp Val Ser His Glu
    50                  55                  60

Asp Pro Glu Val Lys Phe Asn Trp Tyr Val Asp Gly Val Glu Val His
65                  70                  75                  80

Asn Ala Lys Thr Lys Pro Arg Glu Glu Gln Tyr Asn Ser Thr Tyr Arg
                85                  90                  95

Val Val Ser Val Leu Thr Val Leu His Gln Asp Trp Leu Asn Gly Lys
            100                 105                 110

Glu Tyr Lys Cys Lys Val Ser Asn Lys Ala Leu Pro Ala Pro Ile Glu
        115                 120                 125

Lys Thr Ile Ser Lys Ala Lys Gly Gln Pro Arg Glu Pro Gln Val Tyr
    130                 135                 140

Thr Leu Pro Pro Ser Arg Asp Glu Leu Thr Lys Asn Gln Val Ser Leu
145                 150                 155                 160

Thr Cys Leu Val Lys Gly Phe Tyr Pro Ser Asp Ile Ala Val Glu Trp
                165                 170                 175

Glu Ser Asn Gly Gln Pro Glu Asn Asn Tyr Lys Thr Thr Pro Pro Val
            180                 185                 190

Leu Asp Ser Asp Gly Ser Phe Phe Leu Tyr Ser Lys Leu Thr Val Asp
        195                 200                 205

Lys Ser Arg Trp Gln Gln Gly Asn Val Phe Ser Cys Ser Val Met His
    210                 215                 220

Glu Ala Leu His Asn His Tyr Thr Gln Lys Ser Leu Ser Leu Ser Pro
225                 230                 235                 240

Gly Lys
```

<210> SEQ ID NO 22
<211> LENGTH: 758
<212> TYPE: DNA
<213> ORGANISM: Artificial Sequence
<220> FEATURE:
<223> OTHER INFORMATION: DNA encoding pre-Fc chimeric polypeptide having IFN signal peptide

<400> SEQUENCE: 22

```
aagcttgaat tcccaccatg gccttgacct ttgctttact ggtggccctc ctggtgctca    60
```

-continued

```
gctgcaagtc aagctgctct gtgggctgcc cagcacctga actcctgggg gggcccctcag    120 tcttcctctt cccccaaaa cccaaggaca ccctcatgat ctcccggacc cctgaggtca      180
catgcgtggt ggtggacgtg agccacgaag accctgaggt caagttcaac tggtacgtgg    240
acggcgtgga ggtgcataat gccaagacaa agccgcggga ggagcagtac aacagcacgt    300
accgtgtggt cagcgtcctc accgtcctgc accaggactg gctgaatggc aaggagtaca    360
agtgcaaggt ctccaacaaa gcctcccag ccccatcga gaaaaccatc tccaaagcca      420
aagggcagcc ccgagaacca caggtgtaca ccctgccccc atcccgggat gagctgacca    480
agaaccaggt cagcctgacc tgcctggtca aaggcttcta tcccagcgac atcgccgtgg    540
agtgggagag caatgggcag ccggagaaca actacaagac cacgcctccc gtgctggact    600
ccgacggctc cttcttcctc tacagcaagc tcaccgtgga caagagcagg tggcagcagg    660
ggaacgtctt ctcatgctcc gtgatgcatg aggctctgca caaccactac acgcagaaga    720
gcctctccct gtctccgggt aaatgactcg agcggccg                            758
```

<210> SEQ ID NO 23
<211> LENGTH: 236
<212> TYPE: PRT
<213> ORGANISM: Artificial Sequence
<220> FEATURE:
<223> OTHER INFORMATION: pre-Fc chimeric polypeptide having CETP signal
      peptide

<400> SEQUENCE: 23

```
Met Leu Ala Ala Thr Val Leu Thr Leu Ala Leu Leu Gly Asn Ala His
1               5                   10                  15

Ala Cys Pro Ala Pro Glu Leu Leu Gly Gly Pro Ser Val Phe Leu Phe
                20                  25                  30

Pro Pro Lys Pro Lys Asp Thr Leu Met Ile Ser Arg Thr Pro Glu Val
            35                  40                  45

Thr Cys Val Val Val Asp Val Ser His Glu Asp Pro Glu Val Lys Phe
        50                  55                  60

Asn Trp Tyr Val Asp Gly Val Glu Val His Asn Ala Lys Thr Lys Pro
65                  70                  75                  80

Arg Glu Glu Gln Tyr Asn Ser Thr Tyr Arg Val Val Ser Val Leu Thr
                85                  90                  95

Val Leu His Gln Asp Trp Leu Asn Gly Lys Glu Tyr Lys Cys Lys Val
                100                 105                 110

Ser Asn Lys Ala Leu Pro Ala Pro Ile Glu Lys Thr Ile Ser Lys Ala
            115                 120                 125

Lys Gly Gln Pro Arg Glu Pro Gln Val Tyr Thr Leu Pro Pro Ser Arg
        130                 135                 140

Asp Glu Leu Thr Lys Asn Gln Val Ser Leu Thr Cys Leu Val Lys Gly
145                 150                 155                 160

Phe Tyr Pro Ser Asp Ile Ala Val Glu Trp Glu Ser Asn Gly Gln Pro
                165                 170                 175

Glu Asn Asn Tyr Lys Thr Thr Pro Pro Val Leu Asp Ser Asp Gly Ser
                180                 185                 190

Phe Phe Leu Tyr Ser Lys Leu Thr Val Asp Lys Ser Arg Trp Gln Gln
            195                 200                 205

Gly Asn Val Phe Ser Cys Ser Val Met His Glu Ala Leu His Asn His
        210                 215                 220

Tyr Thr Gln Lys Ser Leu Ser Leu Ser Pro Gly Lys
                225                 230                 235
```

<210> SEQ ID NO 24
<211> LENGTH: 740
<212> TYPE: DNA
<213> ORGANISM: Artificial Sequence
<220> FEATURE:
<223> OTHER INFORMATION: DNA encoding pre-Fc chimeric polypeptide having
      CETP signal peptide

<400> SEQUENCE: 24

```
aagcttgaat tcccaccatg ctggctgcca cagtcctgac cctggccctg ctgggcaatg      60
cccatgcctg cccagcacct gaactcctgg gggggccctc agtcttcctc ttccccccaa     120
aacccaagga caccctcatg atctcccgga ccccctgaggt cacatgcgtg gtggtggacg    180
tgagccacga agaccctgag gtcaagttca actggtacgt ggacggcgtg gaggtgcata    240
atgccaagac aaagccgcgg gaggagcagt acaacagcac gtaccgtgtg gtcagcgtcc    300
tcaccgtcct gcaccaggac tggctgaatg gcaaggagta caagtgcaag gtctccaaca    360
aagccctccc agcccccatc gagaaaacca tctccaaagc caagggcag ccccgagaac     420
cacaggtgta caccctgccc ccatcccggg atgagctgac caagaaccag gtcagcctga    480
cctgcctggt caaaggcttc tatcccagcg acatcgccgt ggagtgggag agcaatgggc    540
agccggagaa caactacaag accacgcctc ccgtgctgga ctccgacggc tccttcttcc    600
tctacagcaa gctcaccgtg gacaagagca ggtggcagca ggggaacgtc ttctcatgct    660
ccgtgatgca tgaggctctg cacaaccact acacgcagaa gagcctctcc ctgtctccgg    720
gtaaatgact cgagcggccg                                                 740
```

<210> SEQ ID NO 25
<211> LENGTH: 225
<212> TYPE: PRT
<213> ORGANISM: Artificial Sequence
<220> FEATURE:
<223> OTHER INFORMATION: Human IgG2 Fc domain having the N-terminal
      sequence CCVECPPCPAPE

<400> SEQUENCE: 25

```
Cys Cys Val Glu Cys Pro Pro Cys Pro Ala Pro Val Ala Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Asp Val Ser His Glu Asp
        35                  40                  45

Pro Glu Val Gln Phe Asn Trp Tyr Val Asp Gly Val Glu Val His Asn
    50                  55                  60

Ala Lys Thr Lys Pro Arg Glu Glu Gln Phe Asn Ser Thr Phe Arg Val
65                  70                  75                  80

Val Ser Val Leu Thr Val Val His Gln Asp Trp Leu Asn Gly Lys Glu
                85                  90                  95

Tyr Lys Cys Lys Val Ser Asn Lys Gly Leu Pro Ala Pro Ile Glu Lys
            100                 105                 110

Thr Ile Ser Lys Thr Lys Gly Gln Pro Arg Glu Pro Gln Val Tyr Thr
        115                 120                 125

Leu Pro Pro Ser Arg Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160
```

```
Ser Asn Gly Gln Pro Glu Asn Asn Tyr Lys Thr Thr Pro Pro Met Leu
            165                 170                 175

Asp Ser Asp Gly Ser Phe Phe Leu Tyr Ser Lys Leu Thr Val Asp Lys
        180                 185                 190

Ser Arg Trp Gln Gln Gly Asn Val Phe Ser Cys Ser Val Met His Glu
    195                 200                 205

Ala Leu His Asn His Tyr Thr Gln Lys Ser Leu Ser Leu Ser Pro Gly
    210                 215                 220

Lys
225

<210> SEQ ID NO 26
<211> LENGTH: 675
<212> TYPE: DNA
<213> ORGANISM: Artificial Sequence
<220> FEATURE:
<223> OTHER INFORMATION: DNA encoding human IgG2 Fc domain having the N-
      terminal sequence CCVECPPCPAPE

<400> SEQUENCE: 26
tgttgtgtcg agtgcccacc gtgcccagca ccacctgtgg caggaccgtc agtcttcctc      60
ttccccccaa acccaaggac accctcatg atctcccgga ccctgaggt cacgtgcgtg      120 gtggtggacg tgagccacga agaccccgag gtccagttca actggtacgt ggacggcgtg     180
gaggtgcata atgccaagac aaagccacgg gaggagcagt tcaacagcac gttccgtgtg     240
gtcagcgtcc tcaccgttgt gcaccaggac tggctgaacg gcaaggagta caagtgcaag     300
gtctccaaca aaggcctccc agcccccatc gagaaaacca tctccaaaac caaagggcag     360
ccccgagaac acaggtgta caccctgccc ccatcccggg aggagatgac caagaaccag     420
gtcagcctga cctgcctggt caaaggcttc taccccagcg acatcgccgt ggagtgggag     480
agcaatgggc agccggagaa caactacaag accacacctc ccatgctgga ctccgacggc     540
tccttcttcc tctacagcaa gctcaccgtg gacaagagca ggtggcagca ggggaacgtc     600
ttctcatgct ccgtgatgca tgaggctctg cacaaccact acacgcagaa gagcctctcc     660
ctgtctccgg gtaaa                                                      675

<210> SEQ ID NO 27
<211> LENGTH: 248
<212> TYPE: PRT
<213> ORGANISM: Artificial Sequence
<220> FEATURE:
<223> OTHER INFORMATION: pre-Fc chimeric polypeptide having SHH signal
      peptide

<400> SEQUENCE: 27

Met Leu Leu Leu Ala Arg Cys Leu Leu Leu Val Leu Val Ser Ser Leu
1               5                   10                  15

Leu Val Cys Ser Gly Leu Ala Cys Cys Val Glu Cys Pro Pro Cys Pro
            20                  25                  30

Ala Pro Pro Val Ala Gly Pro Ser Val Phe Leu Phe Pro Pro Lys Pro
        35                  40                  45

Lys Asp Thr Leu Met Ile Ser Arg Thr Pro Glu Val Thr Cys Val Val
    50                  55                  60

Val Asp Val Ser His Glu Asp Pro Glu Val Gln Phe Asn Trp Tyr Val
65                  70                  75                  80

Asp Gly Val Glu Val His Asn Ala Lys Thr Lys Pro Arg Glu Glu Gln
                85                  90                  95
```

```
Phe Asn Ser Thr Phe Arg Val Ser Val Leu Thr Val His Gln
                100                 105                 110
Asp Trp Leu Asn Gly Lys Glu Tyr Lys Cys Lys Val Ser Asn Lys Gly
            115                 120                 125
Leu Pro Ala Pro Ile Glu Lys Thr Ile Ser Lys Thr Lys Gly Gln Pro
130                 135                 140
Arg Glu Pro Gln Val Tyr Thr Leu Pro Pro Ser Arg Glu Glu Met Thr
145                 150                 155                 160
Lys Asn Gln Val Ser Leu Thr Cys Leu Val Lys Gly Phe Tyr Pro Ser
                165                 170                 175
Asp Ile Ala Val Glu Trp Glu Ser Asn Gly Gln Pro Glu Asn Asn Tyr
            180                 185                 190
Lys Thr Thr Pro Pro Met Leu Asp Ser Asp Gly Ser Phe Phe Leu Tyr
        195                 200                 205
Ser Lys Leu Thr Val Asp Lys Ser Arg Trp Gln Gln Gly Asn Val Phe
210                 215                 220
Ser Cys Ser Val Met His Glu Ala Leu His Asn His Tyr Thr Gln Lys
225                 230                 235                 240
Ser Leu Ser Leu Ser Pro Gly Lys
                245
```

<210> SEQ ID NO 28
<211> LENGTH: 776
<212> TYPE: DNA
<213> ORGANISM: Artificial Sequence
<220> FEATURE:
<223> OTHER INFORMATION: DNA encoding pre-Fc chimeric polypeptide having SHH signal peptide

<400> SEQUENCE: 28

```
aagcttgaat tcccaccatg ctgctgctgg cgagatgtct gctgctagtc ctcgtctcct      60
cgctgctggt atgctcggga ctggcgtgtt gtgtcgagtg cccaccgtgc ccagcaccac     120
ctgtggcagg accgtcagtc ttcctcttcc cccaaaaacc caaggacacc ctcatgatct     180
cccggacccc tgaggtcacg tgcgtggtgg tggacgtgag ccacgaagac cccgaggtcc     240
agttcaactg gtacgtggac ggcgtggagg tgcataatgc caagacaaag ccacgggagg     300
agcagttcaa cagcacgttc cgtgtggtca gcgtcctcac cgttgtgcac caggactggc     360
tgaacggcaa ggagtacaag tgcaaggtct ccaacaaagg cctcccagcc cccatcgaga     420
aaaccatctc caaaccaaa gggcagcccc gagaaccaca ggtgtacacc ctgcccccat     480
cccgggagga gatgaccaag aaccaggtca gcctgacctg cctggtcaaa ggcttctacc     540
ccagcgacat cgccgtggag tgggagagca atgggcagcc ggagaacaac tacaagacca     600
cacctcccat gctggactcc gacggctcct tcttcctcta cagcaagctc accgtggaca     660
agagcaggtg gcagcagggg aacgtcttct catgctccgt gatgcatgag gctctgcaca     720
accactacac gcagaagagc ctctccctgt ctccgggtaa atgactcgag cggccg        776
```

<210> SEQ ID NO 29
<211> LENGTH: 248
<212> TYPE: PRT
<213> ORGANISM: Artificial Sequence
<220> FEATURE:
<223> OTHER INFORMATION: pre-Fc chimeric polypeptide having IFN signal peptide

<400> SEQUENCE: 29

```
Met Ala Leu Thr Phe Ala Leu Leu Val Ala Leu Leu Val Leu Ser Cys
1               5                   10                  15
Lys Ser Ser Cys Ser Val Gly Cys Cys Val Glu Cys Pro Pro Cys Pro
            20                  25                  30
Ala Pro Pro Val Ala Gly Pro Ser Val Phe Leu Phe Pro Pro Lys Pro
            35                  40                  45
Lys Asp Thr Leu Met Ile Ser Arg Thr Pro Glu Val Thr Cys Val Val
50                  55                  60
Val Asp Val Ser His Glu Asp Pro Glu Val Gln Phe Asn Trp Tyr Val
65                  70                  75                  80
Asp Gly Val Glu Val His Asn Ala Lys Thr Lys Pro Arg Glu Glu Gln
            85                  90                  95
Phe Asn Ser Thr Phe Arg Val Val Ser Val Leu Thr Val Val His Gln
            100                 105                 110
Asp Trp Leu Asn Gly Lys Glu Tyr Lys Cys Lys Val Ser Asn Lys Gly
            115                 120                 125
Leu Pro Ala Pro Ile Glu Lys Thr Ile Ser Lys Thr Lys Gly Gln Pro
            130                 135                 140
Arg Glu Pro Gln Val Tyr Thr Leu Pro Pro Ser Arg Glu Glu Met Thr
145                 150                 155                 160
Lys Asn Gln Val Ser Leu Thr Cys Leu Val Lys Gly Phe Tyr Pro Ser
                165                 170                 175
Asp Ile Ala Val Glu Trp Glu Ser Asn Gly Gln Pro Glu Asn Asn Tyr
            180                 185                 190
Lys Thr Thr Pro Pro Met Leu Asp Ser Asp Gly Ser Phe Phe Leu Tyr
            195                 200                 205
Ser Lys Leu Thr Val Asp Lys Ser Arg Trp Gln Gln Gly Asn Val Phe
210                 215                 220
Ser Cys Ser Val Met His Glu Ala Leu His Asn His Tyr Thr Gln Lys
225                 230                 235                 240
Ser Leu Ser Leu Ser Pro Gly Lys
                245
```

<210> SEQ ID NO 30
<211> LENGTH: 776
<212> TYPE: DNA
<213> ORGANISM: Artificial Sequence
<220> FEATURE:
<223> OTHER INFORMATION: DNA encoding pre-Fc chimeric polypeptide having
      IFN signal peptide

<400> SEQUENCE: 30

```
aagcttgaat tcccaccatg gccttgacct ttgctttact ggtggccctc ctggtgctca      60
gctgcaagtc aagctgctct gtgggctgtt gtgtcgagtg cccaccgtgc ccagcaccac     120
ctgtggcagg accgtcagtc ttcctcttcc ccccaaaacc caaggacacc ctcatgatct     180
cccggacccc tgaggtcacg tgcgtggtgg tggacgtgag ccacgaagac cccgaggtcc     240
agttcaactg gtacgtggac ggcgtggagg tgcataatgc caagacaaag ccacgggagg     300
agcagttcaa cagcacgttc cgtgtggtca gcgtcctcac cgttgtgcac caggactggc     360
tgaacggcaa ggagtacaag tgcaaggtct ccaacaaggg cctcccagcc cccatcgaga     420
aaaccatctc caaaaccaaa gggcagcccc gagaaccaca ggtgtacacc ctgcccccat     480
cccgggagga gatgaccaag aaccaggtca gcctgacctg cctggtcaaa ggcttctacc     540
cgagcgacat cgccgtggag tgggagagca atgggcagcc ggagaacaac tacaagacca     600
```

```
cacctcccat gctggactcc gacggctcct tcttcctcta cagcaagctc accgtggaca    660
agagcaggtg gcagcagggg aacgtcttct catgctccgt gatgcatgag gctctgcaca    720
accactacac gcagaagagc ctctccctgt ctccgggtaa atgactcgag cggccg        776
```

<210> SEQ ID NO 31
<211> LENGTH: 242
<212> TYPE: PRT
<213> ORGANISM: Artificial Sequence
<220> FEATURE:
<223> OTHER INFORMATION: pre-Fc chimeric polypeptide having CETP signal
      peptide

<400> SEQUENCE: 31

```
Met Leu Ala Ala Thr Val Leu Thr Leu Ala Leu Leu Gly Asn Ala His
1               5                   10                  15

Ala Cys Cys Val Glu Cys Pro Pro Cys Pro Ala Pro Pro Val Ala Gly
                20                  25                  30

Pro Ser Val Phe Leu Phe Pro Pro Lys Pro Lys Asp Thr Leu Met Ile
            35                  40                  45

Ser Arg Thr Pro Glu Val Thr Cys Val Val Val Asp Val Ser His Glu
        50                  55                  60

Asp Pro Glu Val Gln Phe Asn Trp Tyr Val Asp Gly Val Glu Val His
65                  70                  75                  80

Asn Ala Lys Thr Lys Pro Arg Glu Glu Gln Phe Asn Ser Thr Phe Arg
                85                  90                  95

Val Val Ser Val Leu Thr Val Val His Gln Asp Trp Leu Asn Gly Lys
            100                 105                 110

Glu Tyr Lys Cys Lys Val Ser Asn Lys Gly Leu Pro Ala Pro Ile Glu
        115                 120                 125

Lys Thr Ile Ser Lys Thr Lys Gly Gln Pro Arg Glu Pro Gln Val Tyr
    130                 135                 140

Thr Leu Pro Pro Ser Arg Glu Glu Met Thr Lys Asn Gln Val Ser Leu
145                 150                 155                 160

Thr Cys Leu Val Lys Gly Phe Tyr Pro Ser Asp Ile Ala Val Glu Trp
                165                 170                 175

Glu Ser Asn Gly Gln Pro Glu Asn Asn Tyr Lys Thr Thr Pro Pro Met
            180                 185                 190

Leu Asp Ser Asp Gly Ser Phe Phe Leu Tyr Ser Lys Leu Thr Val Asp
        195                 200                 205

Lys Ser Arg Trp Gln Gln Gly Asn Val Phe Ser Cys Ser Val Met His
    210                 215                 220

Glu Ala Leu His Asn His Tyr Thr Gln Lys Ser Leu Ser Leu Ser Pro
225                 230                 235                 240

Gly Lys
```

<210> SEQ ID NO 32
<211> LENGTH: 758
<212> TYPE: DNA
<213> ORGANISM: Artificial Sequence
<220> FEATURE:
<223> OTHER INFORMATION: DNA encoding pre-Fc chimeric polypeptide having
      CETP signal peptide

<400> SEQUENCE: 32

```
aagcttgaat tcccaccatg ctggctgcca cagtcctgac cctggccctg ctgggcaatg    60
cccatgcctg ttgtgtcgag tgcccaccgt gcccagcacc acctgtggca ggaccgtcag    120
```

```
tcttcctctt ccccccaaaa cccaaggaca ccctcatgat ctcccggacc cctgaggtca      180
cgtgcgtggt ggtggacgtg agccacgaag accccgaggt ccagttcaac tggtacgtgg      240
acggcgtgga ggtgcataat gccaagacaa agccacggga ggagcagttc aacagcacgt      300
tccgtgtggt cagcgtcctc accgttgtgc accaggactg gctgaacggc aaggagtaca      360
agtgcaaggt ctccaacaaa ggcctcccag cccccatcga aaaaccatc tccaaaacca       420 aaggcagcc cgagaacca caggtgtaca ccctgccccc atcccgggag gagatgacca       480
agaaccaggt cagcctgacc tgcctggtca aaggcttcta ccccagcgac atcgccgtgg      540
agtgggagag caatgggcag ccggagaaca actacaagac cacacctccc atgctggact      600
ccgacggctc cttcttcctc tacagcaagc tcaccgtgga caagagcagg tggcagcagg      660
ggaacgtctt ctcatgctcc gtgatgcatg aggctctgca caaccactac acgcagaaga     720 gcctctcccct gtctccgggt aaatgactcg agcggccg                            758
```

<210> SEQ ID NO 33
<211> LENGTH: 224
<212> TYPE: PRT
<213> ORGANISM: Artificial Sequence
<220> FEATURE:
<223> OTHER INFORMATION: Human IgG2 Fc domain having the N-terminal
      sequence CVECPPCPAPE

<400> SEQUENCE: 33

```
Cys Val Glu Cys Pro Pro Cys Pro Ala Pro Val Ala Gly Pro Ser
 1               5                  10                  15

Val Phe Leu Phe Pro Pro Lys Pro Lys Asp Thr Leu Met Ile Ser Arg
            20                  25                  30

Thr Pro Glu Val Thr Cys Val Val Val Asp Val Ser His Glu Asp Pro
        35                  40                  45

Glu Val Gln Phe Asn Trp Tyr Val Asp Gly Val Glu Val His Asn Ala
    50                  55                  60

Lys Thr Lys Pro Arg Glu Glu Gln Phe Asn Ser Thr Phe Arg Val Val
65                  70                  75                  80

Ser Val Leu Thr Val Val His Gln Asp Trp Leu Asn Gly Lys Glu Tyr
                85                  90                  95

Lys Cys Lys Val Ser Asn Lys Gly Leu Pro Ala Pro Ile Glu Lys Thr
            100                 105                 110

Ile Ser Lys Thr Lys Gly Gln Pro Arg Glu Pro Gln Val Tyr Thr Leu
        115                 120                 125

Pro Pro Ser Arg Glu Glu Met Thr Lys Asn Gln Val Ser Leu Thr Cys
    130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Met Leu Asp
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn His Tyr Thr Gln Lys Ser Leu Ser Leu Ser Pro Gly Lys
    210                 215                 220
```

<210> SEQ ID NO 34
<211> LENGTH: 672
<212> TYPE: DNA

<213> ORGANISM: Artificial Sequence
<220> FEATURE:
<223> OTHER INFORMATION: DNA encoding human IgG2 Fc domain having the N-terminal sequence CVECPPCPAPE

<400> SEQUENCE: 34

```
tgtgtcgagt gcccaccgtg cccagcacca cctgtggcag gaccgtcagt cttcctcttc        60
cccccaaaac ccaaggacac cctcatgatc tcccggaccc ctgaggtcac gtgcgtggtg       120
gtggacgtga gccacgaaga ccccgaggtc cagttcaact ggtacgtgga cggcgtggag       180
gtgcataatg ccaagacaaa gccacgggag gagcagttca acagcacgtt ccgtgtggtc       240
agcgtcctca ccgttgtgca ccaggactgg ctgaacggca aggagtacaa gtgcaaggtc       300
tccaacaaag gcctcccagc ccccatcgag aaaaccatct ccaaaaccaa agggcagccc       360
cgagaaccac aggtgtacac cctgccccca tcccgggagg agatgaccaa gaaccaggtc       420
agcctgacct gcctggtcaa aggcttctac cccagcgaca tcgccgtgga gtgggagagc       480
aatgggcagc cggagaacaa ctacaagacc acacctccca tgctggactc cgacggctcc       540
ttcttcctct acagcaagct caccgtggac aagagcaggt ggcagcaggg gaacgtcttc       600
tcatgctccg tgatgcatga ggctctgcac aaccactaca cgcagaagag cctctccctg       660
tctccgggta aa                                                           672
```

<210> SEQ ID NO 35
<211> LENGTH: 247
<212> TYPE: PRT
<213> ORGANISM: Artificial Sequence
<220> FEATURE:
<223> OTHER INFORMATION: pre-Fc chimeric polypeptide having SHH signal peptide

<400> SEQUENCE: 35

```
Met Leu Leu Leu Ala Arg Cys Leu Leu Val Leu Ser Ser Leu
1               5                  10                  15

Leu Val Cys Ser Gly Leu Ala Cys Val Glu Cys Pro Pro Cys Pro Ala
                20                  25                  30

Pro Pro Val Ala Gly Pro Ser Val Phe Leu Phe Pro Pro Lys Pro Lys
            35                  40                  45

Asp Thr Leu Met Ile Ser Arg Thr Pro Glu Val Thr Cys Val Val Val
        50                  55                  60

Asp Val Ser His Glu Asp Pro Glu Val Gln Phe Asn Trp Tyr Val Asp
65                  70                  75                  80

Gly Val Glu Val His Asn Ala Lys Thr Lys Pro Arg Glu Glu Gln Phe
                85                  90                  95

Asn Ser Thr Phe Arg Val Val Ser Val Leu Thr Val Val His Gln Asp
            100                 105                 110

Trp Leu Asn Gly Lys Glu Tyr Lys Cys Lys Val Ser Asn Lys Gly Leu
        115                 120                 125

Pro Ala Pro Ile Glu Lys Thr Ile Ser Lys Thr Lys Gly Gln Pro Arg
    130                 135                 140

Glu Pro Gln Val Tyr Thr Leu Pro Pro Ser Arg Glu Glu Met Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Met Leu Asp Ser Asp Gly Ser Phe Phe Leu Tyr Ser
```

```
              195                 200                 205
Lys Leu Thr Val Asp Lys Ser Arg Trp Gln Gln Gly Asn Val Phe Ser
    210                 215                 220

Cys Ser Val Met His Glu Ala Leu His Asn His Tyr Thr Gln Lys Ser
225                 230                 235                 240

Leu Ser Leu Ser Pro Gly Lys
                245

<210> SEQ ID NO 36
<211> LENGTH: 773
<212> TYPE: DNA
<213> ORGANISM: Artificial Sequence
<220> FEATURE:
<223> OTHER INFORMATION: DNA encoding pre-Fc chimeric polypeptide having
      SHH signal peptide

<400> SEQUENCE: 36
aagcttgaat tcccaccatg ctgctgctgg cgagatgtct gctgctagtc ctcgtctcct      60
cgctgctggt atgctcggga ctggcgtgtg tcgagtgccc accgtgccca gcaccacctg    120
tggcaggacc gtcagtcttc ctcttccccc caaaacccaa ggacaccctc atgatctccc    180 ggaccctga ggtcacgtgc gtggtggtgg acgtgagcca cgaagacccc gaggtccagt     240
tcaactggta cgtggacggc gtggaggtgc ataatgccaa gacaaagcca cgggaggagc    300
agttcaacag cacgttccgt gtggtcagcg tcctcaccgt tgtgcaccag gactggctga    360
acggcaagga gtacaagtgc aaggtctcca acaaaggcct cccagccccc atcgagaaaa    420
ccatctccaa aaccaaaggg cagccccgag aaccacaggt gtacaccctg cccccatccc    480
gggaggagat gaccaagaac caggtcagcc tgacctgcct ggtcaaaggc ttctacccca    540
gcgacatcgc cgtggagtgg gagagcaatg ggcagccgga gaacaactac aagaccacac    600
ctcccatgct ggactccgac ggctccttct cctctacag caagctcacc gtggacaaga    660
gcaggtggca gcaggggaac gtcttctcat gctccgtgat gcatgaggct ctgcacaacc    720
actacacgca gaagagcctc tccctgtctc cgggtaaatg actcgagcgg ccg           773

<210> SEQ ID NO 37
<211> LENGTH: 247
<212> TYPE: PRT
<213> ORGANISM: Artificial Sequence
<220> FEATURE:
<223> OTHER INFORMATION: pre-Fc chimeric polypeptide having IFN signal
      peptide

<400> SEQUENCE: 37

Met Ala Leu Thr Phe Ala Leu Leu Val Ala Leu Leu Val Leu Ser Cys
1               5                   10                  15

Lys Ser Ser Cys Ser Val Gly Cys Val Glu Cys Pro Pro Cys Pro Ala
                20                  25                  30

Pro Pro Val Ala Gly Pro Ser Val Phe Leu Phe Pro Pro Lys Pro Lys
            35                  40                  45

Asp Thr Leu Met Ile Ser Arg Thr Pro Glu Val Thr Cys Val Val Val
        50                  55                  60

Asp Val Ser His Glu Asp Pro Glu Val Gln Phe Asn Trp Tyr Val Asp
65                  70                  75                  80

Gly Val Glu Val His Asn Ala Lys Thr Lys Pro Arg Glu Glu Gln Phe
                85                  90                  95

Asn Ser Thr Phe Arg Val Val Ser Val Leu Thr Val Val His Gln Asp
            100                 105                 110
```

```
Trp Leu Asn Gly Lys Glu Tyr Lys Cys Lys Val Ser Asn Lys Gly Leu
        115                 120                 125

Pro Ala Pro Ile Glu Lys Thr Ile Ser Lys Thr Lys Gly Gln Pro Arg
    130                 135                 140

Glu Pro Gln Val Tyr Thr Leu Pro Pro Ser Arg Glu Glu Met Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Met Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
    210                 215                 220

Cys Ser Val Met His Glu Ala Leu His Asn His Tyr Thr Gln Lys Ser
225                 230                 235                 240

Leu Ser Leu Ser Pro Gly Lys
                245
```

<210> SEQ ID NO 38
<211> LENGTH: 773
<212> TYPE: DNA
<213> ORGANISM: Artificial Sequence
<220> FEATURE:
<223> OTHER INFORMATION: DNA encoding pre-Fc chimeric polypeptide having IFN signal peptide

<400> SEQUENCE: 38

```
aagcttgaat tcccaccatg gccttgacct ttgctttact ggtggccctc ctggtgctca    60
gctgcaagtc aagctgctct gtgggctgtg tcgagtgccc accgtgccca gcaccacctg   120
tggcaggacc gtcagtcttc ctcttccccc caaaacccaa ggacaccctc atgatctccc   180
ggacccctga ggtcacgtgc gtggtggtgg acgtgagcca cgaagacccc gaggtccagt   240
tcaactggta cgtggacggc gtggaggtgc ataatgccaa gacaaagcca cgggaggagc   300
agttcaacag cacgttccgt gtggtcagcg tcctcaccgt tgtgcaccag gactggctga   360
acggcaagga gtacaagtgc aaggtctcca acaaaggcct cccagccccc atcgagaaaa   420
ccatctccaa aaccaaaggg cagccccgag aaccacaggt gtacaccctg cccccatccc   480
gggaggagat gaccaagaac caggtcagcc tgacctgcct ggtcaaaggc ttctacccca   540
gcgacatcgc cgtggagtgg gagagcaatg ggcagccgga gaacaactac aagaccacac   600
ctcccatgct ggactccgac ggctccttct tcctctacag caagctcacc gtggacaaga   660
gcaggtggca gcagggaaac gtcttctcat gctccgtgat gcatgaggct ctgcacaacc   720
actacacgca gaagagcctc tccctgtctc cgggtaaatg actcgagcgg ccg          773
```

<210> SEQ ID NO 39
<211> LENGTH: 241
<212> TYPE: PRT
<213> ORGANISM: Artificial Sequence
<220> FEATURE:
<223> OTHER INFORMATION: pre-Fc chimeric polypeptide having CETP signal peptide

<400> SEQUENCE: 39

```
Met Leu Ala Ala Thr Val Leu Thr Leu Ala Leu Leu Gly Asn Ala His
1               5                   10                  15
```

```
Ala Cys Val Glu Cys Pro Pro Cys Pro Ala Pro Pro Val Ala Gly Pro
             20                  25                  30

Ser Val Phe Leu Phe Pro Pro Lys Pro Lys Asp Thr Leu Met Ile Ser
         35                  40                  45

Arg Thr Pro Glu Val Thr Cys Val Val Val Asp Val Ser His Glu Asp
     50                  55                  60

Pro Glu Val Gln Phe Asn Trp Tyr Val Asp Gly Val Glu Val His Asn
 65                  70                  75                  80

Ala Lys Thr Lys Pro Arg Glu Glu Gln Phe Asn Ser Thr Phe Arg Val
                 85                  90                  95

Val Ser Val Leu Thr Val Val His Gln Asp Trp Leu Asn Gly Lys Glu
            100                 105                 110

Tyr Lys Cys Lys Val Ser Asn Lys Gly Leu Pro Ala Pro Ile Glu Lys
        115                 120                 125

Thr Ile Ser Lys Thr Lys Gly Gln Pro Arg Glu Pro Gln Val Tyr Thr
    130                 135                 140

Leu Pro Pro Ser Arg Glu Glu Met Thr Lys Asn Gln Val Ser Leu Thr
145                 150                 155                 160

Cys Leu Val Lys Gly Phe Tyr Pro Ser Asp Ile Ala Val Glu Trp Glu
                165                 170                 175

Ser Asn Gly Gln Pro Glu Asn Asn Tyr Lys Thr Thr Pro Pro Met Leu
            180                 185                 190

Asp Ser Asp Gly Ser Phe Phe Leu Tyr Ser Lys Leu Thr Val Asp Lys
        195                 200                 205

Ser Arg Trp Gln Gln Gly Asn Val Phe Ser Cys Ser Val Met His Glu
    210                 215                 220

Ala Leu His Asn His Tyr Thr Gln Lys Ser Leu Ser Leu Ser Pro Gly
225                 230                 235                 240

Lys

<210> SEQ ID NO 40
<211> LENGTH: 755
<212> TYPE: DNA
<213> ORGANISM: Artificial Sequence
<220> FEATURE:
<223> OTHER INFORMATION: DNA encoding pre-Fc chimeric polypeptide having
      CETP signal peptide

<400> SEQUENCE: 40
aagcttgaat tcccaccatg ctggctgcca cagtcctgac cctggccctg ctgggcaatg      60
cccatgcctg tgtcgagtgc ccaccgtgcc cagcaccacc tgtggcagga ccgtcagtct     120
tcctcttccc cccaaaaccc aaggacaccc tcatgatctc ccggacccct gaggtcacgt     180
gcgtggtggt ggacgtgagc cacgaagacc ccgaggtcca gttcaactgg tacgtggacg     240
gcgtggaggt gcataatgcc aagacaaagc cacgggagga gcagttcaac agcacgttcc     300
gtgtggtcag cgtcctcacc gttgtgcacc aggactggct gaacggcaag gagtacaagt     360
gcaaggtctc caacaaaggc ctcccagccc ccatcgagaa aaccatctcc aaaaccaaag     420
ggcagccccg agaaccacag gtgtacaccc tgcccccatc ccgggaggag atgaccaaga     480
accaggtcag cctgacctgc ctggtcaaag gcttctaccc cagcgacatc gccgtggagt     540
gggagagcaa tgggcagccg gagaacaact acaagaccac acctcccatg ctggactccg     600
acggctcctt cttcctctac agcaagctca ccgtggacaa gagcaggtgg cagcagggga     660
acgtcttctc atgctccgtg atgcatgagg ctctgcacaa ccactacacg cagaagagcc     720
```
tctccctgtc tccgggtaaa tgactcgagc ggccg                                755

<210> SEQ ID NO 41
<211> LENGTH: 221
<212> TYPE: PRT
<213> ORGANISM: Artificial Sequence
<220> FEATURE:
<223> OTHER INFORMATION: Human IgG2 Fc domain having the N-terminal
      sequence CPPCPAPE

<400> SEQUENCE: 41

Cys Pro Pro Cys Pro Ala Pro Val Ala Gly Pro Ser Val Phe Leu
1               5                   10                  15

Phe Pro Pro Lys Pro Lys Asp Thr Leu Met Ile Ser Arg Thr Pro Glu
                20                  25                  30

Val Thr Cys Val Val Val Asp Val Ser His Glu Asp Pro Glu Val Gln
            35                  40                  45

Phe Asn Trp Tyr Val Asp Gly Val Glu Val His Asn Ala Lys Thr Lys
        50                  55                  60

Pro Arg Glu Glu Gln Phe Asn Ser Thr Phe Arg Val Val Ser Val Leu
65                  70                  75                  80

Thr Val Val His Gln Asp Trp Leu Asn Gly Lys Glu Tyr Lys Cys Lys
                85                  90                  95

Val Ser Asn Lys Gly Leu Pro Ala Pro Ile Glu Lys Thr Ile Ser Lys
                100                 105                 110

Thr Lys Gly Gln Pro Arg Glu Pro Gln Val Tyr Thr Leu Pro Pro Ser
            115                 120                 125

Arg Glu Glu Met Thr Lys Asn Gln Val Ser Leu Thr Cys Leu Val Lys
        130                 135                 140

Gly Phe Tyr Pro Ser Asp Ile Ala Val Glu Trp Glu Ser Asn Gly Gln
145                 150                 155                 160

Pro Glu Asn Asn Tyr Lys Thr Thr Pro Pro Met Leu Asp Ser Asp Gly
                165                 170                 175

Ser Phe Phe Leu Tyr Ser Lys Leu Thr Val Asp Lys Ser Arg Trp Gln
                180                 185                 190

Gln Gly Asn Val Phe Ser Cys Ser Val Met His Glu Ala Leu His Asn
            195                 200                 205

His Tyr Thr Gln Lys Ser Leu Ser Leu Ser Pro Gly Lys
        210                 215                 220

<210> SEQ ID NO 42
<211> LENGTH: 663
<212> TYPE: DNA
<213> ORGANISM: Artificial Sequence
<220> FEATURE:
<223> OTHER INFORMATION: DNA encoding human IgG2 Fc domain having the N-
      terminal sequence CPPCPAPE

<400> SEQUENCE: 42
tgcccaccgt gcccagcacc acctgtggca ggaccgtcag tcttcctctt cccccccaaaa    60 cccaaggaca ccctcatgat ctcccggacc cctgaggtca cgtgcgtggt ggtggacgtg   120
agccacgaag accccgaggt ccagttcaac tggtacgtgg acggcgtgga ggtgcataat   180
gccaagacaa agccacggga ggagcagttc aacagcacgt tccgtgtggt cagcgtcctc   240
accgttgtgc accaggactg gctgaacggc aaggagtaca agtgcaaggt ctccaacaaa   300
ggcctcccag cccccatcga gaaaaccatc tccaaaacca agggcagcc ccgagaacca   360 caggtgtaca ccctgccccc atcccgggag gagatgacca agaaccaggt cagcctgacc   420

```
tgcctggtca aaggcttcta ccccagcgac atcgccgtgg agtgggagag caatgggcag      480
ccggagaaca actacaagac cacacctccc atgctggact ccgacggctc cttcttcctc      540
tacagcaagc tcaccgtgga caagagcagg tggcagcagg ggaacgtctt ctcatgctcc      600
gtgatgcatg aggctctgca caaccactac acgcagaaga gcctctccct gtctccgggt      660
aaa                                                                    663
```

```
<210> SEQ ID NO 43
<211> LENGTH: 244
<212> TYPE: PRT
<213> ORGANISM: Artificial Sequence
<220> FEATURE:
<223> OTHER INFORMATION: pre-Fc chimeric polypeptide having SHH signal
      peptide

<400> SEQUENCE: 43
```

Met Leu Leu Leu Ala Arg Cys Leu Leu Leu Val Leu Val Ser Ser Leu
1               5                   10                  15

Leu Val Cys Ser Gly Leu Ala Cys Pro Pro Cys Pro Ala Pro Pro Val
            20                  25                  30

Ala Gly Pro Ser Val Phe Leu Phe Pro Pro Lys Pro Lys Asp Thr Leu
        35                  40                  45

Met Ile Ser Arg Thr Pro Glu Val Thr Cys Val Val Val Asp Val Ser
    50                  55                  60

His Glu Asp Pro Glu Val Gln Phe Asn Trp Tyr Val Asp Gly Val Glu
65                  70                  75                  80

Val His Asn Ala Lys Thr Lys Pro Arg Glu Glu Gln Phe Asn Ser Thr
                85                  90                  95

Phe Arg Val Val Ser Val Leu Thr Val Val His Gln Asp Trp Leu Asn
            100                 105                 110

Gly Lys Glu Tyr Lys Cys Lys Val Ser Asn Lys Gly Leu Pro Ala Pro
        115                 120                 125

Ile Glu Lys Thr Ile Ser Lys Thr Lys Gly Gln Pro Arg Glu Pro Gln
    130                 135                 140

Val Tyr Thr Leu Pro Pro Ser Arg Glu Glu Met Thr Lys Asn Gln Val
145                 150                 155                 160

Ser Leu Thr Cys Leu Val Lys Gly Phe Tyr Pro Ser Asp Ile Ala Val
                165                 170                 175

Glu Trp Glu Ser Asn Gly Gln Pro Glu Asn Asn Tyr Lys Thr Thr Pro
            180                 185                 190

Pro Met Leu Asp Ser Asp Gly Ser Phe Phe Leu Tyr Ser Lys Leu Thr
        195                 200                 205

Val Asp Lys Ser Arg Trp Gln Gln Gly Asn Val Phe Ser Cys Ser Val
    210                 215                 220

Met His Glu Ala Leu His Asn His Tyr Thr Gln Lys Ser Leu Ser Leu
225                 230                 235                 240

Ser Pro Gly Lys

```
<210> SEQ ID NO 44
<211> LENGTH: 764
<212> TYPE: DNA
<213> ORGANISM: Artificial Sequence
<220> FEATURE:
<223> OTHER INFORMATION: DNA encoding pre-Fc chimeric polypeptide having
      SHH signal peptide

<400> SEQUENCE: 44
```

```
aagcttgaat tcccaccatg ctgctgctgg cgagatgtct gctgctagtc ctcgtctcct      60
cgctgctggt atgctcggga ctggcgtgcc caccgtgccc agcaccacct gtggcaggac     120
cgtcagtctt cctcttcccc ccaaaaccca aggacaccct catgatctcc cggacccctg     180
aggtcacgtg cgtggtggtg gacgtgagcc acgaagaccc cgaggtccag ttcaactggt     240
acgtggacgg cgtggaggtg cataatgcca agacaaagcc acgggaggag cagttcaaca     300
gcacgttccg tgtggtcagc gtcctcaccg ttgtgcacca ggactggctg aacggcaagg     360
agtacaagtg caaggtctcc aacaaagccc tcccagcccc catcgagaaa accatctcca     420
aaaccaaagg gcagccccga gaaccacagg tgtacaccct gcccccatcc cgggaggaga     480
tgaccaagaa ccaggtcagc ctgacctgcc tggtcaaagg cttctacccc agcgacatcg     540
ccgtggagtg ggagagcaat gggcagccgg agaacaacta caagaccaca cctcccatgc     600
tggactccga cggctccttc ttcctctaca gcaagctcac cgtggacaag agcaggtggc     660
agcaggggaa cgtcttctca tgctccgtga tgcatgaggc tctgcacaac cactacacgc     720
agaagagcct ctccctgtct ccgggtaaat gactcgagcg gccg                     764
```

<210> SEQ ID NO 45
<211> LENGTH: 244
<212> TYPE: PRT
<213> ORGANISM: Artificial Sequence
<220> FEATURE:
<223> OTHER INFORMATION: pre-Fc chimeric polypeptide having IFN signal
      peptide

<400> SEQUENCE: 45

Met Ala Leu Thr Phe Ala Leu Leu Val Ala Leu Leu Val Leu Ser Cys
1               5                   10                  15

Lys Ser Ser Cys Ser Val Gly Cys Pro Pro Cys Pro Ala Pro Pro Val
            20                  25                  30

Ala Gly Pro Ser Val Phe Leu Phe Pro Pro Lys Pro Lys Asp Thr Leu
        35                  40                  45

Met Ile Ser Arg Thr Pro Glu Val Thr Cys Val Val Val Asp Val Ser
    50                  55                  60

His Glu Asp Pro Glu Val Gln Phe Asn Trp Tyr Val Asp Gly Val Glu
65                  70                  75                  80

Val His Asn Ala Lys Thr Lys Pro Arg Glu Glu Gln Phe Asn Ser Thr
                85                  90                  95

Phe Arg Val Val Ser Val Leu Thr Val Val His Gln Asp Trp Leu Asn
            100                 105                 110

Gly Lys Glu Tyr Lys Cys Lys Val Ser Asn Lys Gly Leu Pro Ala Pro
        115                 120                 125

Ile Glu Lys Thr Ile Ser Lys Thr Lys Gly Gln Pro Arg Glu Pro Gln
    130                 135                 140

Val Tyr Thr Leu Pro Pro Ser Arg Glu Glu Met Thr Lys Asn Gln Val
145                 150                 155                 160

Ser Leu Thr Cys Leu Val Lys Gly Phe Tyr Pro Ser Asp Ile Ala Val
                165                 170                 175

Glu Trp Glu Ser Asn Gly Gln Pro Glu Asn Asn Tyr Lys Thr Thr Pro
            180                 185                 190

Pro Met Leu Asp Ser Asp Gly Ser Phe Phe Leu Tyr Ser Lys Leu Thr
        195                 200                 205

Val Asp Lys Ser Arg Trp Gln Gln Gly Asn Val Phe Ser Cys Ser Val
    210                 215                 220

Met His Glu Ala Leu His Asn His Tyr Thr Gln Lys Ser Leu Ser Leu
225                 230                 235                 240

Ser Pro Gly Lys

<210> SEQ ID NO 46
<211> LENGTH: 764
<212> TYPE: DNA
<213> ORGANISM: Artificial Sequence
<220> FEATURE:
<223> OTHER INFORMATION: DNA encoding pre-Fc chimeric polypeptide having
      IFN signal peptide

<400> SEQUENCE: 46
aagcttgaat tcccaccatg gccttgacct ttgctttact ggtggccctc ctggtgctca      60
gctgcaagtc aagctgctct gtgggctgcc caccgtgccc agcaccacct gtggcaggac     120
cgtcagtctt cctcttcccc ccaaaaccca aggacaccct catgatctcc cggacccctg     180
aggtcacgtg cgtggtggtg gacgtgagcc acgaagaccc cgaggtccag ttcaactggt     240
acgtggacgg cgtggaggtg cataatgcca agacaaagcc acgggaggag cagttcaaca     300
gcacgttccg tgtggtcagc gtcctcaccg ttgtgcacca ggactggctg aacggcaagg     360
agtacaagtg caaggtctcc aacaaaggcc tcccagcccc catcgagaaa accatctcca     420
aaaccaaagg gcagccccga gaaccacagg tgtacaccct gcccccatcc cgggaggaga     480
tgaccaagaa ccaggtcagc ctgacctgcc tggtcaaagg cttctacccc agcgacatcg     540
ccgtggagtg ggagagcaat gggcagccgg agaacaacta caagaccaca cctcccatgc     600
tggactccga cggctccttc ttcctctaca gcaagctcac cgtggacaag agcaggtggc     660
agcaggggaa cgtcttctca tgctccgtga tgcatgaggc tctgcacaac cactacacgc     720
agaagagcct ctccctgtct ccgggtaaat gactcgagcg ccg                       764

<210> SEQ ID NO 47
<211> LENGTH: 238
<212> TYPE: PRT
<213> ORGANISM: Artificial Sequence
<220> FEATURE:
<223> OTHER INFORMATION: pre-Fc chimeric polypeptide having CETP signal
      peptide

<400> SEQUENCE: 47

Met Leu Ala Ala Thr Val Leu Thr Leu Ala Leu Leu Gly Asn Ala His
1               5                   10                  15

Ala Cys Pro Pro Cys Pro Ala Pro Val Ala Gly Pro Ser Val Phe
                20                  25                  30

Leu Phe Pro Pro Lys Pro Lys Asp Thr Leu Met Ile Ser Arg Thr Pro
            35                  40                  45

Glu Val Thr Cys Val Val Val Asp Val Ser His Glu Asp Pro Glu Val
        50                  55                  60

Gln Phe Asn Trp Tyr Val Asp Gly Val Glu Val His Asn Ala Lys Thr
65                  70                  75                  80

Lys Pro Arg Glu Glu Gln Phe Asn Ser Thr Phe Arg Val Val Ser Val
                85                  90                  95

Leu Thr Val Val His Gln Asp Trp Leu Asn Gly Lys Glu Tyr Lys Cys
            100                 105                 110

Lys Val Ser Asn Lys Gly Leu Pro Ala Pro Ile Glu Lys Thr Ile Ser
        115                 120                 125

Lys Thr Lys Gly Gln Pro Arg Glu Pro Gln Val Tyr Thr Leu Pro Pro

```
                     130                 135                 140
Ser Arg Glu Glu Met Thr Lys Asn Gln Val Ser Leu Thr Cys Leu Val
145                 150                 155                 160

Lys Gly Phe Tyr Pro Ser Asp Ile Ala Val Glu Trp Glu Ser Asn Gly
                165                 170                 175

Gln Pro Glu Asn Asn Tyr Lys Thr Thr Pro Pro Met Leu Asp Ser Asp
            180                 185                 190

Gly Ser Phe Phe Leu Tyr Ser Lys Leu Thr Val Asp Lys Ser Arg Trp
        195                 200                 205

Gln Gln Gly Asn Val Phe Ser Cys Ser Val Met His Glu Ala Leu His
    210                 215                 220

Asn His Tyr Thr Gln Lys Ser Leu Ser Leu Ser Pro Gly Lys
225                 230                 235

<210> SEQ ID NO 48
<211> LENGTH: 746
<212> TYPE: DNA
<213> ORGANISM: Artificial Sequence
<220> FEATURE:
<223> OTHER INFORMATION: DNA encoding pre-Fc chimeric polypeptide having
      CETP signal peptide

<400> SEQUENCE: 48
aagcttgaat tcccaccatg ctggctgcca cagtcctgac cctggccctg ctgggcaatg    60
cccatgcctg cccaccgtgc ccagcaccac ctgtggcagg accgtcagtc ttcctcttcc   120
ccccaaaacc caaggacacc ctcatgatct cccggacccc tgaggtcacg tgcgtggtgg   180
tggacgtgag ccacgaagac cccgaggtcc agttcaactg gtacgtggac ggcgtggagg   240
tgcataatgc caagacaaag ccacgggagg agcagttcaa cagcacgttc cgtgtggtca   300
gcgtcctcac cgttgtgcac caggactggc tgaacggcaa ggagtacaag tgcaaggtct   360
ccaacaaagg cctcccagcc cccatcgaga aaaccatctc caaaaccaaa gggcagcccc   420
gagaaccaca ggtgtacacc ctgcccccat cccgggagga gatgaccaag aaccaggtca   480
gcctgacctg cctggtcaaa ggcttctacc ccagcgacat cgccgtggag tgggagagca   540
atgggcagcc ggagaacaac tacaagacca cacctcccat gctggactcc gacggctcct   600
tcttcctcta cagcaagctc accgtggaca agagcaggtg gcagcagggg aacgtcttct   660
catgctccgt gatgcatgag gctctgcaca accactacac gcagaagagc ctctccctgt   720
ctccgggtaa atgactcgag cggccg                                        746

<210> SEQ ID NO 49
<211> LENGTH: 218
<212> TYPE: PRT
<213> ORGANISM: Artificial Sequence
<220> FEATURE:
<223> OTHER INFORMATION: Human IgG2 Fc domain having the N-terminal
      sequence CPAPE

<400> SEQUENCE: 49

Cys Pro Ala Pro Pro Val Ala Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser His Glu Asp Pro Glu Val Gln Phe Asn Trp
        35                  40                  45

Tyr Val Asp Gly Val Glu Val His Asn Ala Lys Thr Lys Pro Arg Glu
    50                  55                  60
```

```
Glu Gln Phe Asn Ser Thr Phe Arg Val Val Ser Val Leu Thr Val Val
 65                  70                  75                  80

His Gln Asp Trp Leu Asn Gly Lys Glu Tyr Lys Cys Lys Val Ser Asn
                 85                  90                  95

Lys Gly Leu Pro Ala Pro Ile Glu Lys Thr Ile Ser Lys Thr Lys Gly
            100                 105                 110

Gln Pro Arg Glu Pro Gln Val Tyr Thr Leu Pro Pro Ser Arg Glu Glu
        115                 120                 125

Met Thr Lys Asn Gln Val Ser Leu Thr Cys Leu Val Lys Gly Phe Tyr
    130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Met Leu Asp Ser Asp Gly Ser Phe Phe
                165                 170                 175

Leu Tyr Ser Lys Leu Thr Val Asp Lys Ser Arg Trp Gln Gln Gly Asn
            180                 185                 190

Val Phe Ser Cys Ser Val Met His Glu Ala Leu His Asn His Tyr Thr
        195                 200                 205

Gln Lys Ser Leu Ser Leu Ser Pro Gly Lys
    210                 215

<210> SEQ ID NO 50
<211> LENGTH: 654
<212> TYPE: DNA
<213> ORGANISM: Artificial Sequence
<220> FEATURE:
<223> OTHER INFORMATION: DNA encoding human IgG2 Fc domain having the N-
      terminal sequence CPAPE

<400> SEQUENCE: 50
tgcccagcac cacctgtggc aggaccgtca gtcttcctct tccccccaaa acccaaggac     60
accctcatga tctcccggac ccctgaggtc acgtgcgtgg tggtggacgt gagccacgaa    120
gaccccgagg tccagttcaa ctggtacgtg gacggcgtgg aggtgcataa tgccaagaca    180
aagccacggg aggagcagtt caacagcacg ttccgtgtgg tcagcgtcct caccgttgtg    240
caccaggact ggctgaacgg caaggagtac aagtgcaagg tctccaacaa aggcctccca    300
gcccccatcg agaaaaccat ctccaaaacc aaagggcagc ccgagaacc acaggtgtac     360 accctgcccc catcccggga ggagatgacc aagaaccagg tcagcctgac ctgcctggtc    420
aaaggcttct accccagcga catcgccgtg gagtgggaga gcaatgggca gccggagaac    480
aactacaaga ccacacctcc catgctggac tccgacggct ccttcttcct ctacagcaag    540
ctcaccgtgg acaagagcag gtggcagcag gggaacgtct tctcatgctc cgtgatgcat    600
gaggctctgc acaaccacta cacgcagaag agcctctccc tgtctccggg taaa          654

<210> SEQ ID NO 51
<211> LENGTH: 241
<212> TYPE: PRT
<213> ORGANISM: Artificial Sequence
<220> FEATURE:
<223> OTHER INFORMATION: pre-Fc chimeric polypeptide having SHH signal
      peptide

<400> SEQUENCE: 51

Met Leu Leu Leu Ala Arg Cys Leu Leu Leu Val Leu Val Ser Ser Leu
 1               5                  10                  15

Leu Val Cys Ser Gly Leu Ala Cys Pro Ala Pro Pro Val Ala Gly Pro
```

```
            20                  25                  30
Ser Val Phe Leu Phe Pro Pro Lys Pro Lys Asp Thr Leu Met Ile Ser
        35                  40                  45

Arg Thr Pro Glu Val Thr Cys Val Val Val Asp Val Ser His Glu Asp
    50                  55                  60

Pro Glu Val Gln Phe Asn Trp Tyr Val Asp Gly Val Glu Val His Asn
65                  70                  75                  80

Ala Lys Thr Lys Pro Arg Glu Glu Gln Phe Asn Ser Thr Phe Arg Val
                85                  90                  95

Val Ser Val Leu Thr Val Val His Gln Asp Trp Leu Asn Gly Lys Glu
            100                 105                 110

Tyr Lys Cys Lys Val Ser Asn Lys Gly Leu Pro Ala Pro Ile Glu Lys
        115                 120                 125

Thr Ile Ser Lys Thr Lys Gly Gln Pro Arg Glu Pro Gln Val Tyr Thr
    130                 135                 140

Leu Pro Pro Ser Arg Glu Glu Met Thr Lys Asn Gln Val Ser Leu Thr
145                 150                 155                 160

Cys Leu Val Lys Gly Phe Tyr Pro Ser Asp Ile Ala Val Glu Trp Glu
                165                 170                 175

Ser Asn Gly Gln Pro Glu Asn Asn Tyr Lys Thr Thr Pro Pro Met Leu
            180                 185                 190

Asp Ser Asp Gly Ser Phe Phe Leu Tyr Ser Lys Leu Thr Val Asp Lys
        195                 200                 205

Ser Arg Trp Gln Gln Gly Asn Val Phe Ser Cys Ser Val Met His Glu
    210                 215                 220

Ala Leu His Asn His Tyr Thr Gln Lys Ser Leu Ser Leu Ser Pro Gly
225                 230                 235                 240

Lys

<210> SEQ ID NO 52
<211> LENGTH: 755
<212> TYPE: DNA
<213> ORGANISM: Artificial Sequence
<220> FEATURE:
<223> OTHER INFORMATION: DNA encoding pre-Fc chimeric polypeptide having
      SHH signal peptide

<400> SEQUENCE: 52
aagcttgaat tcccaccatg ctgctgctgg cgagatgtct gctgctagtc ctcgtctcct    60
cgctgctggt atgctcggga ctggcgtgcc cagcaccacc tgtggcagga ccgtcagtct   120
tcctcttccc cccaaaaccc aaggacaccc tcatgatctc ccggacccct gaggtcacgt   180
gcgtggtggt ggacgtgagc cacgaagacc ccgaggtcca gttcaactgg tacgtggacg   240
gcgtggaggt gcataatgcc aagacaaagc cacgggagga gcagttcaac agcacgttcc   300
gtgtggtcag cgtcctcacc gttgtgcacc aggactggct gaacggcaag gagtacaagt   360
gcaaggtctc caacaaaggc ctcccagccc ccatcgagaa aaccatctcc aaaaccaaag   420
ggcagccccg agaaccacag gtgtacaccc tgcccccatc ccgggaggag atgaccaaga   480
accaggtcag cctgacctgc ctggtcaaag gcttctaccc cagcgacatc gccgtggagt   540
gggagagcaa tgggcagccg gagaacaact acaagaccac acctcccatg ctggactccg   600
acggctcctt cttcctctac agcaagctca ccgtggacaa gagcaggtgg cagcagggga   660
acgtcttctc atgctccgtg atgcatgagg ctctgcacaa ccactacacg cagaagagcc   720
tctccctgtc tccgggtaaa tgactcgagc ggccg                              755
```

<210> SEQ ID NO 53
<211> LENGTH: 241
<212> TYPE: PRT
<213> ORGANISM: Artificial Sequence
<220> FEATURE:
<223> OTHER INFORMATION: pre-Fc chimeric polypeptide having IFN signal peptide

<400> SEQUENCE: 53

Met Ala Leu Thr Phe Ala Leu Leu Val Ala Leu Leu Val Leu Ser Cys
1               5                   10                  15

Lys Ser Ser Cys Ser Val Gly Cys Pro Ala Pro Pro Val Ala Gly Pro
            20                  25                  30

Ser Val Phe Leu Phe Pro Pro Lys Pro Lys Asp Thr Leu Met Ile Ser
        35                  40                  45

Arg Thr Pro Glu Val Thr Cys Val Val Val Asp Val Ser His Glu Asp
    50                  55                  60

Pro Glu Val Gln Phe Asn Trp Tyr Val Asp Gly Val Glu Val His Asn
65                  70                  75                  80

Ala Lys Thr Lys Pro Arg Glu Glu Gln Phe Asn Ser Thr Phe Arg Val
                85                  90                  95

Val Ser Val Leu Thr Val Val His Gln Asp Trp Leu Asn Gly Lys Glu
            100                 105                 110

Tyr Lys Cys Lys Val Ser Asn Lys Gly Leu Pro Ala Pro Ile Glu Lys
        115                 120                 125

Thr Ile Ser Lys Thr Lys Gly Gln Pro Arg Glu Pro Gln Val Tyr Thr
    130                 135                 140

Leu Pro Pro Ser Arg Glu Glu Met Thr Lys Asn Gln Val Ser Leu Thr
145                 150                 155                 160

Cys Leu Val Lys Gly Phe Tyr Pro Ser Asp Ile Ala Val Glu Trp Glu
                165                 170                 175

Ser Asn Gly Gln Pro Glu Asn Asn Tyr Lys Thr Thr Pro Pro Met Leu
            180                 185                 190

Asp Ser Asp Gly Ser Phe Phe Leu Tyr Ser Lys Leu Thr Val Asp Lys
        195                 200                 205

Ser Arg Trp Gln Gln Gly Asn Val Phe Ser Cys Ser Val Met His Glu
    210                 215                 220

Ala Leu His Asn His Tyr Thr Gln Lys Ser Leu Ser Leu Ser Pro Gly
225                 230                 235                 240

Lys

<210> SEQ ID NO 54
<211> LENGTH: 755
<212> TYPE: DNA
<213> ORGANISM: Artificial Sequence
<220> FEATURE:
<223> OTHER INFORMATION: DNA encoding pre-Fc chimeric polypeptide having IFN signal peptide

<400> SEQUENCE: 54
aagcttgaat tcccaccatg gccttgacct ttgctttact ggtggccctc ctggtgctca      60
gctgcaagtc aagctgctct gtgggctgcc cagcaccacc tgtggcagga ccgtcagtct     120
tcctcttccc cccaaaaccc aaggacaccc tcatgatctc ccggacccct gaggtcacgt     180
gcgtggtggt ggacgtgagc cacgaagacc ccgaggtcca gttcaactgg tacgtggacg     240
gcgtggaggt gcataatgcc aagacaaagc cacgggagga gcagttcaac agcacgttcc     300

-continued

```
gtgtggtcag cgtcctcacc gttgtgcacc aggactggct gaacggcaag gagtacaagt    360
gcaaggtctc caacaaaggc ctcccagccc ccatcgagaa aaccatctcc aaaaccaaag    420
ggcagccccg agaaccacag gtgtacaccc tgcccccatc ccgggaggag atgaccaaga    480
accaggtcag cctgacctgc ctggtcaaag gcttctaccc cagcgacatc gccgtggagt    540
gggagagcaa tgggcagccg gagaacaact acaagaccac acctcccatg ctggactccg    600
acggctcctt cttcctctac agcaagctca ccgtggacaa gagcaggtgg cagcagggga    660
acgtcttctc atgctccgtg atgcatgagg ctctgcacaa ccactacacg cagaagagcc    720
tctccctgtc tccgggtaaa tgactcgagc ggccg                               755
```

<210> SEQ ID NO 55
<211> LENGTH: 235
<212> TYPE: PRT
<213> ORGANISM: Artificial Sequence
<220> FEATURE:
<223> OTHER INFORMATION: pre-Fc chimeric polypeptide having CETP signal peptide
<400> SEQUENCE: 55

```
Met Leu Ala Ala Thr Val Leu Thr Leu Ala Leu Leu Gly Asn Ala His
1               5                   10                  15

Ala Cys Pro Ala Pro Pro Val Ala Gly Pro Ser Val Phe Leu Phe Pro
                20                  25                  30

Pro Lys Pro Lys Asp Thr Leu Met Ile Ser Arg Thr Pro Glu Val Thr
            35                  40                  45

Cys Val Val Val Asp Val Ser His Glu Asp Pro Glu Val Gln Phe Asn
        50                  55                  60

Trp Tyr Val Asp Gly Val Glu Val His Asn Ala Lys Thr Lys Pro Arg
    65                  70                  75                  80

Glu Glu Gln Phe Asn Ser Thr Phe Arg Val Val Ser Val Leu Thr Val
                85                  90                  95

Val His Gln Asp Trp Leu Asn Gly Lys Glu Tyr Lys Cys Lys Val Ser
                100                 105                 110

Asn Lys Gly Leu Pro Ala Pro Ile Glu Lys Thr Ile Ser Lys Thr Lys
            115                 120                 125

Gly Gln Pro Arg Glu Pro Gln Val Tyr Thr Leu Pro Pro Ser Arg Glu
        130                 135                 140

Glu Met Thr Lys Asn Gln Val Ser Leu Thr Cys Leu Val Lys Gly Phe
145                 150                 155                 160

Tyr Pro Ser Asp Ile Ala Val Glu Trp Glu Ser Asn Gly Gln Pro Glu
                165                 170                 175

Asn Asn Tyr Lys Thr Thr Pro Pro Met Leu Asp Ser Asp Gly Ser Phe
            180                 185                 190

Phe Leu Tyr Ser Lys Leu Thr Val Asp Lys Ser Arg Trp Gln Gln Gly
        195                 200                 205

Asn Val Phe Ser Cys Ser Val Met His Glu Ala Leu His Asn His Tyr
    210                 215                 220

Thr Gln Lys Ser Leu Ser Leu Ser Pro Gly Lys
225                 230                 235
```

<210> SEQ ID NO 56
<211> LENGTH: 737
<212> TYPE: DNA
<213> ORGANISM: Artificial Sequence
<220> FEATURE:

<223> OTHER INFORMATION: DNA encoding pre-Fc chimeric polypeptide having
      CETP signal peptide

<400> SEQUENCE: 56

```
aagcttgaat tcccaccatg ctggctgcca cagtcctgac cctggccctg ctgggcaatg    60
cccatgcctg cccagcacca cctgtggcag gaccgtcagt cttcctcttc cccccaaaac   120
ccaaggacac cctcatgatc tcccggaccc ctgaggtcac gtgcgtggtg gtggacgtga   180
gccacgaaga ccccgaggtc cagttcaact ggtacgtgga cggcgtggag gtgcataatg   240
ccaagacaaa gccacgggag gagcagttca acagcacgtt ccgtgtggtc agcgtcctca   300
ccgttgtgca ccaggactgg ctgaacggca aggagtacaa gtgcaaggtc tccaacaaag   360
gcctcccagc ccccatcgag aaaaccatct ccaaaaccaa agggcagccc cgagaaccac   420
aggtgtacac cctgccccca tcccgggagg agatgaccaa gaaccaggtc agcctgacct   480
gcctggtcaa aggcttctac cccagcgaca tcgccgtgga gtgggagagc aatgggcagc   540
cggagaacaa ctacaagacc acacctccca tgctggactc cgacggctcc ttcttcctct   600
acagcaagct caccgtggac aagagcaggt ggcagcaggg gaacgtcttc tcatgctccg   660
tgatgcatga ggctctgcac aaccactaca cgcagaagag cctctccctg tctccgggta   720
aatgactcga gcggccg                                                  737
```

<210> SEQ ID NO 57
<211> LENGTH: 267
<212> TYPE: PRT
<213> ORGANISM: Artificial Sequence
<220> FEATURE:
<223> OTHER INFORMATION: Human IgG3 Fc domain having the N-terminal
      sequence (CPRCPEPKSDTPPP)3-CPRCPAPE

<400> SEQUENCE: 57

```
Cys Pro Arg Cys Pro Glu Pro Lys Ser Cys Asp Thr Pro Pro Cys
1               5                   10                  15

Pro Arg Cys Pro Glu Pro Lys Ser Cys Asp Thr Pro Pro Cys Pro
                20                  25                  30

Arg Cys Pro Glu Pro Lys Ser Cys Asp Thr Pro Pro Cys Pro Arg
            35                  40                  45

Cys Pro Ala Pro Glu Leu Leu Gly Gly Pro Ser Val Phe Leu Phe Pro
        50                  55                  60

Pro Lys Pro Lys Asp Thr Leu Met Ile Ser Arg Thr Pro Glu Val Thr
65                  70                  75                  80

Cys Val Val Val Asp Val Ser His Glu Asp Pro Glu Val Gln Phe Lys
                85                  90                  95

Trp Tyr Val Asp Gly Val Glu Val His Asn Ala Lys Thr Lys Pro Arg
            100                 105                 110

Glu Glu Gln Tyr Asn Ser Thr Phe Arg Val Val Ser Val Leu Thr Val
        115                 120                 125

Leu His Gln Asp Trp Leu Asn Gly Lys Glu Tyr Lys Cys Lys Val Ser
    130                 135                 140

Asn Lys Ala Leu Pro Ala Pro Ile Glu Lys Thr Ile Ser Lys Thr Lys
145                 150                 155                 160

Gly Gln Pro Arg Glu Pro Gln Val Tyr Thr Leu Pro Pro Ser Arg Glu
                165                 170                 175

Glu Met Thr Lys Asn Gln Val Ser Leu Thr Cys Leu Val Lys Gly Phe
            180                 185                 190

Tyr Pro Ser Asp Ile Ala Val Glu Trp Glu Ser Ser Gly Gln Pro Glu
```

```
                195                 200                 205
Asn Asn Tyr Asn Thr Thr Pro Pro Met Leu Asp Ser Asp Gly Ser Phe
        210                 215                 220

Phe Leu Tyr Ser Lys Leu Thr Val Asp Lys Ser Arg Trp Gln Gln Gly
225                 230                 235                 240

Asn Ile Phe Ser Cys Ser Val Met His Glu Ala Leu His Asn Arg Phe
                245                 250                 255

Thr Gln Lys Ser Leu Ser Leu Ser Pro Gly Lys
            260                 265
```

<210> SEQ ID NO 58
<211> LENGTH: 801
<212> TYPE: DNA
<213> ORGANISM: Artificial Sequence
<220> FEATURE:
<223> OTHER INFORMATION: DNA encoding human IgG3 Fc domain having the N-terminal sequence (CPRCPEPKSDTPPP)3-CPRCPAPE

<400> SEQUENCE: 58

```
tgcccacggt gcccagagcc caaatcttgt gacacacctc ccccgtgccc acggtgccca      60
gagcccaaat cttgtgacac acctccccca tgcccacggt gcccagagcc caaatcttgt     120
gacacacctc ccccgtgccc aaggtgccca gcacctgaac tcctgggagg accgtcagtc     180
ttcctcttcc ccccaaaacc caaggatacc cttatgattt cccggacccc tgaggtcacg     240
tgcgtggtgg tggacgtgag ccacgaagac cccgaggtcc agttcaagtg gtacgtggac     300
ggcgtggagg tgcataatgc caagacaaag ccgcgggagg agcagtacaa cagcacgttc     360
cgtgtggtca gcgtcctcac cgtcctgcac caggactggc tgaacggcaa ggagtacaag     420
tgcaaggtct ccaacaaagc cctcccagcc cccatcgaga aaaccatctc caaaaccaaa     480
ggacagcccc gagaaccaca ggtgtacacc ctgcccccat cccgggagga gatgaccaag     540
aaccaggtca gcctgacctg cctggtcaaa ggcttctacc ccagcgacat cgccgtggag     600
tgggagagca gcgggcagcc ggagaacaac tacaacacca cgcctcccat gctggactcc     660
gacggctcct tcttcctcta cagcaagctc accgtggaca agagcaggtg gcagcagggg     720
aacatcttct catgctccgt gatgcatgag gctctgcaca accgcttcac gcagaagagc     780
ctctccctgt ctccgggtaa a                                               801
```

<210> SEQ ID NO 59
<211> LENGTH: 290
<212> TYPE: PRT
<213> ORGANISM: Artificial Sequence
<220> FEATURE:
<223> OTHER INFORMATION: pre-Fc chimeric polypeptide having SHH signal peptide

<400> SEQUENCE: 59

```
Met Leu Leu Leu Ala Arg Cys Leu Leu Leu Val Leu Val Ser Ser Leu
1               5                   10                  15

Leu Val Cys Ser Gly Leu Ala Cys Pro Arg Cys Pro Glu Pro Lys Ser
                20                  25                  30

Cys Asp Thr Pro Pro Pro Cys Pro Arg Cys Pro Glu Pro Lys Ser Cys
            35                  40                  45

Asp Thr Pro Pro Pro Cys Pro Arg Cys Pro Glu Pro Lys Ser Cys Asp
        50                  55                  60

Thr Pro Pro Pro Cys Pro Arg Cys Pro Ala Pro Glu Leu Leu Gly Gly
65                  70                  75                  80
```

```
Pro Ser Val Phe Leu Phe Pro Pro Lys Pro Lys Asp Thr Leu Met Ile
            85                  90                  95

Ser Arg Thr Pro Glu Val Thr Cys Val Val Asp Val Ser His Glu
            100                 105                 110

Asp Pro Glu Val Gln Phe Lys Trp Tyr Val Asp Gly Val Glu Val His
            115                 120                 125

Asn Ala Lys Thr Lys Pro Arg Glu Glu Gln Tyr Asn Ser Thr Phe Arg
        130                 135                 140

Val Val Ser Val Leu Thr Val Leu His Gln Asp Trp Leu Asn Gly Lys
145                 150                 155                 160

Glu Tyr Lys Cys Lys Val Ser Asn Lys Ala Leu Pro Ala Pro Ile Glu
                165                 170                 175

Lys Thr Ile Ser Lys Thr Lys Gly Gln Pro Arg Glu Pro Gln Val Tyr
            180                 185                 190

Thr Leu Pro Pro Ser Arg Glu Glu Met Thr Lys Asn Gln Val Ser Leu
        195                 200                 205

Thr Cys Leu Val Lys Gly Phe Tyr Pro Ser Asp Ile Ala Val Glu Trp
    210                 215                 220

Glu Ser Ser Gly Gln Pro Glu Asn Asn Tyr Asn Thr Thr Pro Pro Met
225                 230                 235                 240

Leu Asp Ser Asp Gly Ser Phe Phe Leu Tyr Ser Lys Leu Thr Val Asp
                245                 250                 255

Lys Ser Arg Trp Gln Gln Gly Asn Ile Phe Ser Cys Ser Val Met His
            260                 265                 270

Glu Ala Leu His Asn Arg Phe Thr Gln Lys Ser Leu Ser Leu Ser Pro
        275                 280                 285

Gly Lys
    290

<210> SEQ ID NO 60
<211> LENGTH: 902
<212> TYPE: DNA
<213> ORGANISM: Artificial Sequence
<220> FEATURE:
<223> OTHER INFORMATION: DNA encoding pre-Fc chimeric polypeptide
      having SHH signal peptide

<400> SEQUENCE: 60
aagcttgaat tcccaccatg ctgctgctgg cgagatgtct gctgctagtc ctcgtctcct      60
cgctgctggt atgctcggga ctggcgtgcc acggtgccc agagcccaaa tcttgtgaca     120
cacctccccc gtgcccacgg tgcccagagc ccaaatcttg tgacacacct ccccatgcc     180 cacggtgccc agagcccaaa tcttgtgaca cacctccccc gtgcccaagg tgcccagcac     240
ctgaactcct gggaggaccg tcagtcttcc tcttcccccc aaaacccaag gatacccta    300 tgatttcccg gaccctgag gtcacgtgcg tggtggtgga cgtgagccac gaagaccccg     360
aggtccagtt caagtggtac gtggacggcg tggaggtgca taatgccaag acaaagccgc     420
gggaggagca gtacaacagc acgttccgtg tggtcagcgt cctcaccgtc ctgcaccagg     480
actggctgaa cggcaaggag tacaagtgca aggtctccaa caaagccctc ccagccccca     540
tcgagaaaac catctccaaa accaaaggac agccccgaga ccacaggtg tacaccctgc     600 ccccatcccg ggaggagatg accaagaacc aggtcagcct gacctgcctg gtcaaaggct     660
tctaccccag cgacatcgcc gtggagtggg agagcagcgg gcagccggag aacaactaca     720
acaccacgcc tcccatgctg gactccgacg gctccttctt cctctacagc aagctcaccg     780
```

```
tggacaagag caggtggcag caggggaaca tcttctcatg ctccgtgatg catgaggctc    840
tgcacaaccg cttcacgcag aagagcctct ccctgtctcc gggtaaatga ctcgagcggc    900
cg                                                                   902
```

<210> SEQ ID NO 61
<211> LENGTH: 290
<212> TYPE: PRT
<213> ORGANISM: Artificial Sequence
<220> FEATURE:
<223> OTHER INFORMATION: pre-Fc chimeric polypeptide having IFN signal
      peptide

<400> SEQUENCE: 61

Met Ala Leu Thr Phe Ala Leu Leu Val Ala Leu Leu Val Leu Ser Cys
1               5                   10                  15

Lys Ser Ser Cys Ser Val Gly Cys Pro Arg Cys Pro Glu Pro Lys Ser
            20                  25                  30

Cys Asp Thr Pro Pro Pro Cys Pro Arg Cys Pro Glu Pro Lys Ser Cys
        35                  40                  45

Asp Thr Pro Pro Pro Cys Pro Arg Cys Pro Glu Pro Lys Ser Cys Asp
    50                  55                  60

Thr Pro Pro Pro Cys Pro Arg Cys Pro Ala Pro Glu Leu Leu Gly Gly
65                  70                  75                  80

Pro Ser Val Phe Leu Phe Pro Pro Lys Pro Lys Asp Thr Leu Met Ile
                85                  90                  95

Ser Arg Thr Pro Glu Val Thr Cys Val Val Val Asp Val Ser His Glu
            100                 105                 110

Asp Pro Glu Val Gln Phe Lys Trp Tyr Val Asp Gly Val Glu Val His
        115                 120                 125

Asn Ala Lys Thr Lys Pro Arg Glu Glu Gln Tyr Asn Ser Thr Phe Arg
    130                 135                 140

Val Val Ser Val Leu Thr Val Leu His Gln Asp Trp Leu Asn Gly Lys
145                 150                 155                 160

Glu Tyr Lys Cys Lys Val Ser Asn Lys Ala Leu Pro Ala Pro Ile Glu
                165                 170                 175

Lys Thr Ile Ser Lys Thr Lys Gly Gln Pro Arg Glu Pro Gln Val Tyr
            180                 185                 190

Thr Leu Pro Pro Ser Arg Glu Glu Met Thr Lys Asn Gln Val Ser Leu
        195                 200                 205

Thr Cys Leu Val Lys Gly Phe Tyr Pro Ser Asp Ile Ala Val Glu Trp
    210                 215                 220

Glu Ser Ser Gly Gln Pro Glu Asn Asn Tyr Asn Thr Thr Pro Pro Met
225                 230                 235                 240

Leu Asp Ser Asp Gly Ser Phe Phe Leu Tyr Ser Lys Leu Thr Val Asp
                245                 250                 255

Lys Ser Arg Trp Gln Gln Gly Asn Ile Phe Ser Cys Ser Val Met His
            260                 265                 270

Glu Ala Leu His Asn Arg Phe Thr Gln Lys Ser Leu Ser Leu Ser Pro
        275                 280                 285

Gly Lys
    290

<210> SEQ ID NO 62
<211> LENGTH: 902
<212> TYPE: DNA
<213> ORGANISM: Artificial Sequence

```
<220> FEATURE:
<223> OTHER INFORMATION: DNA encoding pre-Fc chimeric polypeptide having
      IFN signal peptide

<400> SEQUENCE: 62
aagcttgaat cccaccatg gccttgacct ttgctttact ggtggccctc ctggtgctca        60
gctgcaagtc aagctgctct gtgggctgcc cacggtgccc agagcccaaa tcttgtgaca      120
cacctccccc gtgcccacgg tgcccagagc ccaaatcttg tgacacacct ccccccatgcc    180 cacggtgccc agagcccaaa tcttgtgaca cacctccccc gtgcccaagg tgcccagcac     240
ctgaactcct gggaggaccg tcagtcttcc tcttcccccc aaaacccaag gataccctta    300
tgatttcccg daccctgag gtcacgtgcg tggtggtgga cgtgagccac gaagaccccg     360
aggtccagtt caagtggtac gtggacggcg tggaggtgca taatgccaag acaaagccgc   420
gggaggagca gtacaacagc acgttccgtg tggtcagcgt cctcaccgtc ctgcaccagg   480
actggctgaa cggcaaggag tacaagtgca aggtctccaa caaagccctc ccagccccca    540
tcgagaaaac catctccaaa accaaaggac agccccgaga ccacaggtg tacaccctgc     600 ccccatcccg ggaggagatg accaagaacc aggtcagcct gacctgcctg gtcaaaggct    660
tctaccccag cgacatcgcc gtggagtggg agagcagcgg gcagccggag aacaactaca   720
acaccacgcc tcccatgctg gactccgacg gctccttctt cctctacagc aagctcaccg   780
tggacaagag caggtggcag caggggaaca tcttctcatg ctccgtgatg catgaggctc    840
tgcacaaccg cttcacgcag aagagcctct ccctgtctcc gggtaaatga ctcgagcggc   900
cg                                                                   902

<210> SEQ ID NO 63
<211> LENGTH: 284
<212> TYPE: PRT
<213> ORGANISM: Artificial Sequence
<220> FEATURE:
<223> OTHER INFORMATION: pre-Fc chimeric polypeptide having CETP signal
      peptide

<400> SEQUENCE: 63

Met Leu Ala Ala Thr Val Leu Thr Leu Ala Leu Leu Gly Asn Ala His
1               5                   10                  15

Ala Cys Pro Arg Cys Pro Glu Pro Lys Ser Cys Asp Thr Pro Pro
                20                  25                  30

Cys Pro Arg Cys Pro Glu Pro Lys Ser Cys Asp Thr Pro Pro Cys
        35                  40                  45

Pro Arg Cys Pro Glu Pro Lys Ser Cys Asp Thr Pro Pro Cys Pro
    50                  55                  60

Arg Cys Pro Ala Pro Glu Leu Leu Gly Gly Pro Ser Val Phe Leu Phe
65                  70                  75                  80

Pro Pro Lys Pro Lys Asp Thr Leu Met Ile Ser Arg Thr Pro Glu Val
                85                  90                  95

Thr Cys Val Val Val Asp Val Ser His Glu Asp Pro Glu Val Gln Phe
                100                 105                 110

Lys Trp Tyr Val Asp Gly Val Glu Val His Asn Ala Lys Thr Lys Pro
            115                 120                 125

Arg Glu Glu Gln Tyr Asn Ser Thr Phe Arg Val Val Ser Val Leu Thr
        130                 135                 140

Val Leu His Gln Asp Trp Leu Asn Gly Lys Glu Tyr Lys Cys Lys Val
145                 150                 155                 160
```

```
Ser Asn Lys Ala Leu Pro Ala Pro Ile Glu Lys Thr Ile Ser Lys Thr
                165                 170                 175
Lys Gly Gln Pro Arg Glu Pro Gln Val Tyr Thr Leu Pro Pro Ser Arg
            180                 185                 190
Glu Glu Met Thr Lys Asn Gln Val Ser Leu Thr Cys Leu Val Lys Gly
        195                 200                 205
Phe Tyr Pro Ser Asp Ile Ala Val Glu Trp Glu Ser Ser Gly Gln Pro
    210                 215                 220
Glu Asn Asn Tyr Asn Thr Thr Pro Pro Met Leu Asp Ser Asp Gly Ser
225                 230                 235                 240
Phe Phe Leu Tyr Ser Lys Leu Thr Val Asp Lys Ser Arg Trp Gln Gln
                245                 250                 255
Gly Asn Ile Phe Ser Cys Ser Val Met His Glu Ala Leu His Asn Arg
            260                 265                 270
Phe Thr Gln Lys Ser Leu Ser Leu Ser Pro Gly Lys
        275                 280
```

<210> SEQ ID NO 64
<211> LENGTH: 884
<212> TYPE: DNA
<213> ORGANISM: Artificial Sequence
<220> FEATURE:
<223> OTHER INFORMATION: DNA encoding pre-Fc chimeric polypeptide having CETP signal peptide

<400> SEQUENCE: 64

```
aagcttgaat tcccaccatg ctggctgcca cagtcctgac cctggccctg ctgggcaatg      60
cccatgcctg cccacggtgc ccagagccca atcttgtga cacacctccc ccgtgcccac     120
ggtgcccaga gcccaaatct tgtgacacac ctcccccgtg cccacggtgc ccagagccca     180
aatcttgtga cacacctccc ccgtgcccaa ggtgcccagc acctgaactc ctgggaggac     240
cgtcagtctt cctcttcccc ccaaaaccca aggatacccc tatgatttcc cggacccctg     300
aggtcacgtg cgtggtggtg gacgtgagcc acgaagaccc cgaggtccag ttcaagtggt     360
acgtggacgg cgtggaggtg cataatgcca agacaaagcc gcgggaggag cagtacaaca     420
gcacgttccg tgtggtcagc gtcctcaccg tcctgcacca ggactggctg aacggcaagg     480
agtacaagtg caaggtctcc aacaaagccc tcccagcccc catcgagaaa accatctcca     540
aaaccaaagg acagccccga gaaccacagg tgtacaccct gcccccatcc cgggaggaga     600
tgaccaagaa ccaggtcagc ctgacctgcc tggtcaaagg cttctacccc agcgacatcg     660
ccgtggagtg ggagagcagc gggcagccgg agaacaacta caacaccacg cctcccatgc     720
tggactccga cggctccttc ttcctctaca gcaagctcac cgtggacaag agcaggtggc     780
agcagggaa catcttctca tgctccgtga tgcatgagge tctgcacaac cgcttcacgc     840
agaagagcct ctccctgtct ccgggtaaat gactcgagcg gccg                     884
```

<210> SEQ ID NO 65
<211> LENGTH: 222
<212> TYPE: PRT
<213> ORGANISM: Artificial Sequence
<220> FEATURE:
<223> OTHER INFORMATION: Human IgG3 Fc domain having the N-terminal sequence CPRCPAPE

<400> SEQUENCE: 65

```
Cys Pro Arg Cys Pro Ala Pro Glu Leu Leu Gly Gly Pro Ser Val Phe
1               5                   10                  15
```

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Gln Phe Lys Trp Tyr Val Asp Gly Val Glu Val His Asn Ala Lys Thr
    50                  55                  60

Lys Pro Arg Glu Glu Gln Tyr Asn Ser Thr Phe Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
            100                 105                 110

Lys Thr Lys Gly Gln Pro Arg Glu Pro Gln Val Tyr Thr Leu Pro Pro
        115                 120                 125

Ser Arg Glu Glu Met Thr Lys Asn Gln Val Ser Leu Thr Cys Leu Val
    130                 135                 140

Lys Gly Phe Tyr Pro Ser Asp Ile Ala Val Glu Trp Glu Ser Ser Gly
145                 150                 155                 160

Gln Pro Glu Asn Asn Tyr Asn Thr Thr Pro Pro Met Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Ile Phe Ser Cys Ser Val Met His Glu Ala Leu His
        195                 200                 205

Asn Arg Phe Thr Gln Lys Ser Leu Ser Leu Ser Pro Gly Lys
    210                 215                 220

<210> SEQ ID NO 66
<211> LENGTH: 681
<212> TYPE: DNA
<213> ORGANISM: Artificial Sequence
<220> FEATURE:
<223> OTHER INFORMATION: DNA encoding human IgG3 Fc domain having the
      N-terminal sequence CPRCPAPE

<400> SEQUENCE: 66
tgcccaaggt gcccagcacc tgaactcctg ggaggaccgt cagtcttcct cttccccca       60 aaacccaagg ataccttat gatttcccgg acccctgagg tcacgtgcgt ggtggtggac     120
gtgagccacg aagaccccga ggtccagttc aagtggtacg tggacggcgt ggaggtgcat     180
aatgccaaga caaagccgcg ggaggagcag tacaacagca cgttccgtgt ggtcagcgtc     240
ctcaccgtcc tgcaccagga ctggctgaac ggcaaggagt acaagtgcaa ggtctccaac     300
aaagccctcc cagcccccat cgagaaaacc atctccaaaa ccaaggaca gccccgagaa      360 ccacaggtgt acaccctgcc cccatcccgg gaggagatga ccaagaacca ggtcagcctg     420
acctgcctgg tcaaaggctt ctaccccagc gacatcgccg tggagtggga gagcagcggg     480
cagccggaga acaactacaa caccacgcct cccatgctgg actccgacgg ctccttcttc     540
ctctacagca agctcaccgt ggacaagagc aggtggcagc aggggaacat cttctcatgc     600
tccgtgatgc atgaggctct gcacaaccgc ttcacgcaga gagcctctc cctgtctccg      660 ggtaaatgac tcgagcggcc g                                                681

<210> SEQ ID NO 67
<211> LENGTH: 245
<212> TYPE: PRT
<213> ORGANISM: Artificial Sequence

```
<220> FEATURE:
<223> OTHER INFORMATION: pre-Fc chimeric polypeptide having SHH signal
      peptide

<400> SEQUENCE: 67

Met Leu Leu Leu Ala Arg Cys Leu Leu Leu Val Leu Val Ser Ser Leu
1               5                   10                  15

Leu Val Cys Ser Gly Leu Ala Cys Pro Arg Cys Pro Ala Pro Glu Leu
            20                  25                  30

Leu Gly Gly Pro Ser Val Phe Leu Phe Pro Pro Lys Pro Lys Asp Thr
        35                  40                  45

Leu Met Ile Ser Arg Thr Pro Glu Val Thr Cys Val Val Val Asp Val
    50                  55                  60

Ser His Glu Asp Pro Glu Val Gln Phe Lys Trp Tyr Val Asp Gly Val
65                  70                  75                  80

Glu Val His Asn Ala Lys Thr Lys Pro Arg Glu Glu Gln Tyr Asn Ser
                85                  90                  95

Thr Phe Arg Val Val Ser Val Leu Thr Val Leu His Gln Asp Trp Leu
            100                 105                 110

Asn Gly Lys Glu Tyr Lys Cys Lys Val Ser Asn Lys Ala Leu Pro Ala
        115                 120                 125

Pro Ile Glu Lys Thr Ile Ser Lys Thr Lys Gly Gln Pro Arg Glu Pro
    130                 135                 140

Gln Val Tyr Thr Leu Pro Pro Ser Arg Glu Glu Met Thr Lys Asn Gln
145                 150                 155                 160

Val Ser Leu Thr Cys Leu Val Lys Gly Phe Tyr Pro Ser Asp Ile Ala
                165                 170                 175

Val Glu Trp Glu Ser Ser Gly Gln Pro Glu Asn Asn Tyr Asn Thr Thr
            180                 185                 190

Pro Pro Met Leu Asp Ser Asp Gly Ser Phe Phe Leu Tyr Ser Lys Leu
        195                 200                 205

Thr Val Asp Lys Ser Arg Trp Gln Gln Gly Asn Ile Phe Ser Cys Ser
    210                 215                 220

Val Met His Glu Ala Leu His Asn Arg Phe Thr Gln Lys Ser Leu Ser
225                 230                 235                 240

Leu Ser Pro Gly Lys
                245

<210> SEQ ID NO 68
<211> LENGTH: 767
<212> TYPE: DNA
<213> ORGANISM: Artificial Sequence
<220> FEATURE:
<223> OTHER INFORMATION: DNA encoding pre-Fc chimeric polypeptide having
      SHH signal peptide

<400> SEQUENCE: 68
aagcttgaat cccaccatg  ctgctgctgg cgagatgtct gctgctagtc ctcgtctcct    60
cgctgctggt atgctcggga ctggcgtgcc caaggtgccc agcacctgaa ctcctgggag   120
gaccgtcagt cttcctcttc cccccaaaac ccaaggatac ccttatgatt tcccggaccc   180
ctgaggtcac gtgcgtggtg gtggacgtga gccacgaaga ccccgaggtc cagttcaagt   240
ggtacgtgga cggcgtggag gtgcataatg ccaagacaaa gccgcgggag gagcagtaca   300
acagcacgtt ccgtgtggtc agcgtcctca ccgtcctgca ccaggactgg ctgaacggca   360
aggagtacaa gtgcaaggtc tccaacaaag ccctcccagc ccccatcgag aaaaccatct   420
```

```
ccaaaaccaa aggacagccc cgagaaccac aggtgtacac cctgccccca tcccgggagg    480
agatgaccaa gaaccaggtc agcctgacct gcctggtcaa aggcttctac cccagcgaca    540
tcgccgtgga gtgggagagc agcgggcagc cggagaacaa ctacaacacc acgcctccca    600
tgctggactc cgacggctcc ttcttcctct acagcaagct caccgtggac aagagcaggt    660
ggcagcaggg gaacatcttc tcatgctccg tgatgcatga ggctctgcac aaccgcttca    720
cgcagaagag cctctccctg tctccgggta aatgactcga gcggccg                 767
```

<210> SEQ ID NO 69
<211> LENGTH: 245
<212> TYPE: PRT
<213> ORGANISM: Artificial Sequence
<220> FEATURE:
<223> OTHER INFORMATION: pre-Fc chimeric polypeptide having IFN signal peptide

<400> SEQUENCE: 69

```
Met Ala Leu Thr Phe Ala Leu Leu Val Ala Leu Leu Val Leu Ser Cys
1               5                   10                  15

Lys Ser Ser Cys Ser Val Gly Cys Pro Arg Cys Pro Ala Pro Glu Leu
            20                  25                  30

Leu Gly Gly Pro Ser Val Phe Leu Phe Pro Pro Lys Pro Lys Asp Thr
        35                  40                  45

Leu Met Ile Ser Arg Thr Pro Glu Val Thr Cys Val Val Val Asp Val
    50                  55                  60

Ser His Glu Asp Pro Glu Val Gln Phe Lys Trp Tyr Val Asp Gly Val
65                  70                  75                  80

Glu Val His Asn Ala Lys Thr Lys Pro Arg Glu Glu Gln Tyr Asn Ser
                85                  90                  95

Thr Phe Arg Val Val Ser Val Leu Thr Val Leu His Gln Asp Trp Leu
            100                 105                 110

Asn Gly Lys Glu Tyr Lys Cys Lys Val Ser Asn Lys Ala Leu Pro Ala
        115                 120                 125

Pro Ile Glu Lys Thr Ile Ser Lys Thr Lys Gly Gln Pro Arg Glu Pro
    130                 135                 140

Gln Val Tyr Thr Leu Pro Pro Ser Arg Glu Glu Met Thr Lys Asn Gln
145                 150                 155                 160

Val Ser Leu Thr Cys Leu Val Lys Gly Phe Tyr Pro Ser Asp Ile Ala
                165                 170                 175

Val Glu Trp Glu Ser Ser Gly Gln Pro Glu Asn Asn Tyr Asn Thr Thr
            180                 185                 190

Pro Pro Met Leu Asp Ser Asp Gly Ser Phe Phe Leu Tyr Ser Lys Leu
        195                 200                 205

Thr Val Asp Lys Ser Arg Trp Gln Gln Gly Asn Ile Phe Ser Cys Ser
    210                 215                 220

Val Met His Glu Ala Leu His Asn Arg Phe Thr Gln Lys Ser Leu Ser
225                 230                 235                 240

Leu Ser Pro Gly Lys
            245
```

<210> SEQ ID NO 70
<211> LENGTH: 767
<212> TYPE: DNA
<213> ORGANISM: Artificial Sequence
<220> FEATURE:
<223> OTHER INFORMATION: DNA encoding pre-Fc chimeric polypeptide having IFN signal peptide

<400> SEQUENCE: 70

```
aagcttgaat tcccaccatg gccttgacct ttgctttact ggtggccctc ctggtgctca      60
gctgcaagtc aagctgctct gtgggctgcc caaggtgccc agcacctgaa ctcctgggag     120
gaccgtcagt cttcctcttc ccccaaaaac ccaaggatac ccttatgatt tcccggaccc     180
ctgaggtcac gtgcgtggtg gtggacgtga gccacgaaga ccccgaggtc cagttcaagt     240
ggtacgtgga cggcgtggag gtgcataatg ccaagacaaa gccgcgggag gagcagtaca     300
acagcacgtt ccgtgtggtc agcgtcctca ccgtcctgca ccaggactgg ctgaacggca     360
aggagtacaa gtgcaaggtc tccaacaaag ccctcccagc ccccatcgag aaaaccatct     420
ccaaaaccaa aggacagccc cgagaaccac aggtgtacac cctgcccca tcccgggagg     480
agatgaccaa gaaccaggtc agcctgacct gcctggtcaa aggcttctac cccagcgaca     540
tcgccgtgga gtgggagagc agcgggcagc cggagaacaa ctacaacacc acgcctccca     600
tgctggactc cgacggctcc ttcttcctct acagcaagct caccgtggac aagagcaggt     660
ggcagcaggg gaacatcttc tcatgctccg tgatgcatga ggctctgcac aaccgcttca     720
cgcagaagag cctctccctg tctccgggta aatgactcga gcggccg                  767
```

<210> SEQ ID NO 71
<211> LENGTH: 239
<212> TYPE: PRT
<213> ORGANISM: Artificial Sequence
<220> FEATURE:
<223> OTHER INFORMATION: pre-Fc chimeric polypeptide having CETP signal peptide

<400> SEQUENCE: 71

```
Met Leu Ala Ala Thr Val Leu Thr Leu Ala Leu Leu Gly Asn Ala His
1               5                   10                  15

Ala Cys Pro Arg Cys Pro Ala Pro Glu Leu Leu Gly Gly Pro Ser Val
                20                  25                  30

Phe Leu Phe Pro Pro Lys Pro Lys Asp Thr Leu Met Ile Ser Arg Thr
            35                  40                  45

Pro Glu Val Thr Cys Val Val Asp Val Ser His Glu Asp Pro Glu
        50                  55                  60

Val Gln Phe Lys Trp Tyr Val Asp Gly Val Glu Val His Asn Ala Lys
65                  70                  75                  80

Thr Lys Pro Arg Glu Glu Gln Tyr Asn Ser Thr Phe Arg Val Val Ser
                85                  90                  95

Val Leu Thr Val Leu His Gln Asp Trp Leu Asn Gly Lys Glu Tyr Lys
            100                 105                 110

Cys Lys Val Ser Asn Lys Ala Leu Pro Ala Pro Ile Glu Lys Thr Ile
        115                 120                 125

Ser Lys Thr Lys Gly Gln Pro Arg Glu Pro Gln Val Tyr Thr Leu Pro
    130                 135                 140

Pro Ser Arg Glu Glu Met Thr Lys Asn Gln Val Ser Leu Thr Cys Leu
145                 150                 155                 160

Val Lys Gly Phe Tyr Pro Ser Asp Ile Ala Val Glu Trp Glu Ser Ser
                165                 170                 175

Gly Gln Pro Glu Asn Asn Tyr Asn Thr Thr Pro Pro Met Leu Asp Ser
            180                 185                 190

Asp Gly Ser Phe Phe Leu Tyr Ser Lys Leu Thr Val Asp Lys Ser Arg
        195                 200                 205
```

Trp Gln Gln Gly Asn Ile Phe Ser Cys Ser Val Met His Glu Ala Leu
    210                 215                 220

His Asn Arg Phe Thr Gln Lys Ser Leu Ser Leu Ser Pro Gly Lys
225                 230                 235

<210> SEQ ID NO 72
<211> LENGTH: 749
<212> TYPE: DNA
<213> ORGANISM: Artificial Sequence
<220> FEATURE:
<223> OTHER INFORMATION: DNA encoding pre-Fc chimeric polypeptide having
      CETP signal peptide

<400> SEQUENCE: 72

```
aagcttgaat tcccaccatg ctggctgcca cagtcctgac cctggccctg ctgggcaatg      60
cccatgcctg cccaaggtgc ccagcacctg aactcctggg aggaccgtca gtcttcctct     120
tccccccaaa acccaaggat acccttatga tttcccggac ccctgaggtc acgtgcgtgg     180
tggtggacgt gagccacgaa gaccccgagg tccagttcaa gtggtacgtg gacggcgtgg     240
aggtgcataa tgccaagaca aagccgcggg aggagcagta caacagcacg ttccgtgtgg     300
tcagcgtcct caccgtcctg caccaggact ggctgaacgg caaggagtac aagtgcaagg     360
tctccaacaa agccctccca gcccccatcg agaaaaccat ctccaaaacc aaggacagc      420
cccgagaacc acaggtgtac accctgcccc catcccggga ggagatgacc aagaaccagg     480
tcagcctgac ctgcctggtc aaaggcttct accccagcga catcgccgtg gagtgggaga     540
gcagcgggca gccggagaac aactacaaca ccacgcctcc catgctggac tccgacggct     600
ccttcttcct ctacagcaag ctcaccgtgg acaagagcag gtggcagcag gggaacatct     660
tctcatgctc cgtgatgcat gaggctctgc acaaccgctt cacgcagaag agcctctccc     720
tgtctccggg taaatgactc gagcggccg                                       749
```

<210> SEQ ID NO 73
<211> LENGTH: 219
<212> TYPE: PRT
<213> ORGANISM: Artificial Sequence
<220> FEATURE:
<223> OTHER INFORMATION: Human IgG3 Fc domain having the N-terminal
      sequence CPAPE

<400> SEQUENCE: 73

Cys Pro Ala Pro Glu Leu Leu Gly Gly Pro Ser Val Phe Leu Phe Pro
1               5                   10                  15

Pro Lys Pro Lys Asp Thr Leu Met Ile Ser Arg Thr Pro Glu Val Thr
            20                  25                  30

Cys Val Val Val Asp Val Ser His Glu Asp Pro Glu Val Gln Phe Lys
        35                  40                  45

Trp Tyr Val Asp Gly Val Glu Val His Asn Ala Lys Thr Lys Pro Arg
    50                  55                  60

Glu Glu Gln Tyr Asn Ser Thr Phe Arg Val Val Ser Val Leu Thr Val
65                  70                  75                  80

Leu His Gln Asp Trp Leu Asn Gly Lys Glu Tyr Lys Cys Lys Val Ser
                85                  90                  95

Asn Lys Ala Leu Pro Ala Pro Ile Glu Lys Thr Ile Ser Lys Thr Lys
            100                 105                 110

Gly Gln Pro Arg Glu Pro Gln Val Tyr Thr Leu Pro Pro Ser Arg Glu
        115                 120                 125

Glu Met Thr Lys Asn Gln Val Ser Leu Thr Cys Leu Val Lys Gly Phe

Tyr Pro Ser Asp Ile Ala Val Glu Trp Glu Ser Ser Gly Gln Pro Glu
145                 150                 155                 160

Asn Asn Tyr Asn Thr Thr Pro Pro Met Leu Asp Ser Asp Gly Ser Phe
            165                 170                 175

Phe Leu Tyr Ser Lys Leu Thr Val Asp Lys Ser Arg Trp Gln Gln Gly
            180                 185                 190

Asn Ile Phe Ser Cys Ser Val Met His Glu Ala Leu His Asn Arg Phe
            195                 200                 205

Thr Gln Lys Ser Leu Ser Leu Ser Pro Gly Lys
            210                 215

<210> SEQ ID NO 74
<211> LENGTH: 672
<212> TYPE: DNA
<213> ORGANISM: Artificial Sequence
<220> FEATURE:
<223> OTHER INFORMATION: DNA encoding human IgG3 Fc domain having the N-
      terminal sequence CPAPE

<400> SEQUENCE: 74
tgcccagcac ctgaactcct gggaggaccg tcagtcttcc tcttcccccc aaaacccaag     60
gataccctta tgatttcccg gaccccctgag gtcacgtgcg tggtggtgga cgtgagccac    120
gaagaccccg aggtccagtt caagtggtac gtggacggcg tggaggtgca taatgccaag    180
acaaagccgc gggaggagca gtacaacagc acgttccgtg tggtcagcgt cctcaccgtc    240
ctgcaccagg actggctgaa cggcaaggag tacaagtgca aggtctccaa caaagccctc    300
ccagccccca tcgagaaaac catctccaaa accaaaggac agccccgaga accacaggtg    360
tacaccctgc ccccatcccg ggaggagatg accaagaacc aggtcagcct gacctgcctg    420
gtcaaaggct tctaccccag cgacatcgcc gtggagtggg agagcagcgg gcagccggag    480
aacaactaca acaccacgcc tcccatgctg gactccgacg gctccttctt cctctacagc    540
aagctcaccg tggacaagag caggtggcag caggggaaca tcttctcatg ctccgtgatg    600
catgaggctc tgcacaaccg cttcacgcag aagagcctct ccctgtctcc gggtaaatga    660
ctcgagcggc cg                                                        672

<210> SEQ ID NO 75
<211> LENGTH: 242
<212> TYPE: PRT
<213> ORGANISM: Artificial Sequence
<220> FEATURE:
<223> OTHER INFORMATION: pre-Fc chimeric polypeptide having SHH signal
      peptide

<400> SEQUENCE: 75

Met Leu Leu Leu Ala Arg Cys Leu Leu Leu Val Leu Val Ser Ser Leu
1               5                   10                  15

Leu Val Cys Ser Gly Leu Ala Cys Pro Ala Pro Glu Leu Leu Gly Gly
                20                  25                  30

Pro Ser Val Phe Leu Phe Pro Pro Lys Pro Lys Asp Thr Leu Met Ile
            35                  40                  45

Ser Arg Thr Pro Glu Val Thr Cys Val Val Val Asp Val Ser His Glu
        50                  55                  60

Asp Pro Glu Val Gln Phe Lys Trp Tyr Val Asp Gly Val Glu Val His
65                  70                  75                  80

Asn Ala Lys Thr Lys Pro Arg Glu Glu Gln Tyr Asn Ser Thr Phe Arg

```
                    85                  90                  95
Val Val Ser Val Leu Thr Val Leu His Gln Asp Trp Leu Asn Gly Lys
                100                 105                 110

Glu Tyr Lys Cys Lys Val Ser Asn Lys Ala Leu Pro Ala Pro Ile Glu
            115                 120                 125

Lys Thr Ile Ser Lys Thr Lys Gly Gln Pro Arg Glu Pro Gln Val Tyr
130                 135                 140

Thr Leu Pro Pro Ser Arg Glu Glu Met Thr Lys Asn Gln Val Ser Leu
145                 150                 155                 160

Thr Cys Leu Val Lys Gly Phe Tyr Pro Ser Asp Ile Ala Val Glu Trp
                165                 170                 175

Glu Ser Ser Gly Gln Pro Glu Asn Asn Tyr Asn Thr Thr Pro Pro Met
            180                 185                 190

Leu Asp Ser Asp Gly Ser Phe Phe Leu Tyr Ser Lys Leu Thr Val Asp
        195                 200                 205

Lys Ser Arg Trp Gln Gln Gly Asn Ile Phe Ser Cys Ser Val Met His
    210                 215                 220

Glu Ala Leu His Asn Arg Phe Thr Gln Lys Ser Leu Ser Leu Ser Pro
225                 230                 235                 240

Gly Lys

<210> SEQ ID NO 76
<211> LENGTH: 758
<212> TYPE: DNA
<213> ORGANISM: Artificial Sequence
<220> FEATURE:
<223> OTHER INFORMATION: DNA encoding pre-Fc chimeric polypeptide having
      SHH signal peptide

<400> SEQUENCE: 76
aagcttgaat tcccaccatg ctgctgctgg cgagatgtct gctgctagtc ctcgtctcct      60
cgctgctggt atgctcggga ctggcgtgcc cagcacctga actcctggga ggaccgtcag     120
tcttcctctt cccccccaaa acccaaggata cccttatgat ttcccggacc cctgaggtca    180
cgtgcgtggt ggtggacgtg agccacgaag accccgaggt ccagttcaag tggtacgtgg    240
acggcgtgga ggtgcataat gccaagacaa agccgcggga ggagcagtac aacagcacgt    300
tccgtgtggt cagcgtcctc accgtcctgc accaggactg gctgaacggc aaggagtaca    360
agtgcaaggt ctccaacaaa gccctcccag cccccatcga gaaaaccatc tccaaaacca    420
aaggacagcc ccgagaacca caggtgtaca ccctgccccc atcccgggag gagatgacca    480
agaaccaggt cagcctgacc tgcctggtca aaggcttcta ccccagcgac atcgccgtgg    540
agtgggagag cagcgggcag ccggagaaca actacaacac cacgcctccc atgctggact    600
ccgacggctc cttcttcctc tacagcaagc tcaccgtgga caagagcagg tggcagcagg    660
ggaacatctt ctcatgctcc gtgatgcatg aggctctgca caaccgcttc acgcagaaga    720
gcctctccct gtctccgggt aaatgactcg agcggccg                            758

<210> SEQ ID NO 77
<211> LENGTH: 242
<212> TYPE: PRT
<213> ORGANISM: Artificial Sequence
<220> FEATURE:
<223> OTHER INFORMATION: pre-Fc chimeric polypeptide having IFN signal
      peptide

<400> SEQUENCE: 77
```

Met Ala Leu Thr Phe Ala Leu Leu Val Ala Leu Val Leu Ser Cys
1               5                   10                  15

Lys Ser Ser Cys Ser Val Gly Cys Pro Ala Pro Glu Leu Leu Gly Gly
            20                  25                  30

Pro Ser Val Phe Leu Phe Pro Pro Lys Pro Lys Asp Thr Leu Met Ile
            35                  40                  45

Ser Arg Thr Pro Glu Val Thr Cys Val Val Val Asp Val Ser His Glu
50                  55                  60

Asp Pro Glu Val Gln Phe Lys Trp Tyr Val Asp Gly Val Glu Val His
65                  70                  75                  80

Asn Ala Lys Thr Lys Pro Arg Glu Glu Gln Tyr Asn Ser Thr Phe Arg
            85                  90                  95

Val Val Ser Val Leu Thr Val Leu His Gln Asp Trp Leu Asn Gly Lys
            100                 105                 110

Glu Tyr Lys Cys Lys Val Ser Asn Lys Ala Leu Pro Ala Pro Ile Glu
            115                 120                 125

Lys Thr Ile Ser Lys Thr Lys Gly Gln Pro Arg Glu Pro Gln Val Tyr
            130                 135                 140

Thr Leu Pro Pro Ser Arg Glu Glu Met Thr Lys Asn Gln Val Ser Leu
145                 150                 155                 160

Thr Cys Leu Val Lys Gly Phe Tyr Pro Ser Asp Ile Ala Val Glu Trp
            165                 170                 175

Glu Ser Ser Gly Gln Pro Glu Asn Asn Tyr Asn Thr Thr Pro Pro Met
            180                 185                 190

Leu Asp Ser Asp Gly Ser Phe Phe Leu Tyr Ser Lys Leu Thr Val Asp
            195                 200                 205

Lys Ser Arg Trp Gln Gln Gly Asn Ile Phe Ser Cys Ser Val Met His
            210                 215                 220

Glu Ala Leu His Asn Arg Phe Thr Gln Lys Ser Leu Ser Leu Ser Pro
225                 230                 235                 240

Gly Lys

<210> SEQ ID NO 78
<211> LENGTH: 758
<212> TYPE: DNA
<213> ORGANISM: Artificial Sequence
<220> FEATURE:
<223> OTHER INFORMATION: DNA encoding pre-Fc chimeric polypeptide having
      IFN signal peptide

<400> SEQUENCE: 78
aagcttgaat tcccaccatg gccttgacct tgctttact ggtggccctc ctggtgctca      60
gctgcaagtc aagctgctct gtgggctgcc cagcacctga actcctggga ggaccgtcag    120
tcttcctctt ccccccaaaa cccaaggata cccttatgat ttcccggacc cctgaggtca    180
cgtgcgtggt ggtggacgtg agccacgaag accccgaggt ccagttcaag tggtacgtgg    240
acggcgtgga ggtgcataat gccaagacaa agccgcggga ggagcagtac aacagcacgt    300
tccgtgtggt cagcgtcctc accgtcctgc accaggactg gctgaacggc aaggagtaca    360
agtgcaaggt ctccaacaaa gccctcccag ccccatcga gaaaaccatc tccaaaacca    420
aaggacagcc ccgagaacca caggtgtaca ccctgccccc atcccgggag gagatgacca    480
agaaccaggt cagcctgacc tgcctggtca aaggcttcta ccccagcgac atcgccgtgg    540
agtgggagag cagcgggcag ccggagaaca actacaacac cacgcctccc atgctggact    600
ccgacggctc cttcttcctc tacagcaagc tcaccgtgga caagagcagg tggcagcagg    660
ggaacatctt ctcatgctcc gtgatgcatg aggctctgca caaccgcttc acgcagaaga    720
gcctctccct gtctccgggt aaatgactcg agcggccg    758

<210> SEQ ID NO 79
<211> LENGTH: 235
<212> TYPE: PRT
<213> ORGANISM: Artificial Sequence
<220> FEATURE:
<223> OTHER INFORMATION: pre-Fc chimeric polypeptide having CETP signal
      peptide

<400> SEQUENCE: 79

Met Leu Ala Ala Thr Val Leu Thr Leu Ala Leu Leu Gly Asn Ala His
1               5                   10                  15

Ala Cys Pro Ala Pro Glu Leu Leu Gly Gly Pro Ser Val Phe Leu Phe
            20                  25                  30

Pro Pro Lys Pro Lys Asp Thr Leu Met Ile Ser Arg Thr Pro Glu Val
        35                  40                  45

Thr Cys Val Val Val Asp Val Ser His Glu Asp Pro Glu Val Gln Phe
    50                  55                  60

Lys Trp Tyr Val Asp Gly Val Glu Val His Asn Ala Lys Thr Lys Pro
65                  70                  75                  80

Arg Glu Glu Gln Tyr Asn Ser Thr Phe Arg Val Val Ser Val Leu Thr
                85                  90                  95

Val Leu His Gln Asp Trp Leu Asn Gly Lys Glu Tyr Lys Cys Lys Val
            100                 105                 110

Ser Asn Lys Ala Leu Pro Ala Pro Ile Glu Lys Thr Ile Ser Lys Thr
        115                 120                 125

Lys Gly Gln Pro Arg Glu Pro Gln Val Tyr Thr Leu Pro Pro Ser Arg
    130                 135                 140

Glu Glu Met Thr Lys Asn Gln Val Ser Leu Thr Cys Leu Val Lys Gly
145                 150                 155                 160

Phe Tyr Pro Ser Asp Ile Ala Val Glu Trp Glu Ser Ser Gly Gln Pro
                165                 170                 175

Glu Asn Asn Tyr Asn Thr Thr Pro Pro Met Leu Asp Ser Asp Gly Ser
            180                 185                 190

Phe Phe Leu Tyr Ser Lys Leu Thr Val Asp Lys Ser Arg Trp Gln Gln
        195                 200                 205

Gly Asn Ile Phe Ser Cys Ser Val Met His Glu Ala Leu His Asn Arg
    210                 215                 220

Phe Thr Gln Lys Ser Leu Ser Leu Ser Pro Gly
225                 230                 235

<210> SEQ ID NO 80
<211> LENGTH: 740
<212> TYPE: DNA
<213> ORGANISM: Artificial Sequence
<220> FEATURE:
<223> OTHER INFORMATION: DNA encoding pre-Fc chimeric polypeptide having
      CETP signal peptide

<400> SEQUENCE: 80
aagcttgaat tcccaccatg ctggctgcca cagtcctgac cctggccctg ctgggcaatg    60
cccatgcctg cccagcacct gaactcctgg gaggaccgtc agtcttcctc ttccccccaa   120
aacccaagga tacccttatg atttccggga cccctgaggt cacgtgcgtg gtggtggacg   180
tgagccacga agaccccgag gtccagttca gtggtacgt ggacggcgtg gaggtgcata   240

```
atgccaagac aaagccgcgg gaggagcagt acaacagcac gttccgtgtg gtcagcgtcc    300
tcaccgtcct gcaccaggac tggctgaacg gcaaggagta caagtgcaag gtctccaaca    360
aagccctccc agcccccatc gagaaaacca tctccaaaac caaggacag ccccgagaac     420 cacaggtgta caccctgccc ccatcccggg aggagatgac caagaaccag gtcagcctga    480
cctgcctggt caaaggcttc taccccagcg acatcgccgt ggagtgggag agcagcgggc    540
agccggagaa caactacaac accacgcctc ccatgctgga ctccgacggc tccttcttcc    600
tctacagcaa gctcaccgtg gacaagagca ggtggcagca ggggaacatc ttctcatgct    660
ccgtgatgca tgaggctctg cacaaccgct tcacgcagaa gagcctctcc ctgtctccgg    720
gtaaatgact cgagcggccg                                                 740
```

```
<210> SEQ ID NO 81
<211> LENGTH: 222
<212> TYPE: PRT
<213> ORGANISM: Artificial Sequence
<220> FEATURE:
<223> OTHER INFORMATION: Human IgG4 Fc domain having the N-terminal
      sequence CPSCPAPE

<400> SEQUENCE: 81
```

Cys Pro Ser Cys Pro Ala Pro Glu Phe Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser Gln Glu Asp Pro Glu Val
        35                  40                  45

Gln Phe Asn Trp Tyr Val Asp Gly Val Glu Val His Asn Ala Lys Thr
    50                  55                  60

Lys Pro Arg Glu Glu Gln Phe Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Gly Leu Pro Ser Ser Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Gln Glu Glu Met Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Arg Leu Thr Val Asp Lys Ser Arg Trp
            180                 185                 190

Gln Glu Gly Asn Val Phe Ser Cys Ser Val Met His Glu Ala Leu His
        195                 200                 205

Asn His Tyr Thr Gln Lys Ser Leu Ser Leu Ser Leu Gly Lys
    210                 215                 220

```
<210> SEQ ID NO 82
<211> LENGTH: 666
<212> TYPE: DNA
<213> ORGANISM: Artificial Sequence
<220> FEATURE:
<223> OTHER INFORMATION: DNA encoding human IgG4 Fc domain having the N-
``` terminal sequence CPSCPAPE

<400> SEQUENCE: 82

```
tgcccatcat gcccagcacc tgagttcctg gggggaccat cagtcttcct gttcccccca      60
aaacccaagg acactctcat gatctcccgg acccctgagg tcacgtgcgt ggtggtggac     120
gtgagccagg aagaccccga ggtccagttc aactggtacg tggatggcgt ggaggtgcat     180
aatgccaaga caaagccgcg ggaggagcag ttcaacagca cgtaccgtgt ggtcagcgtc     240
ctcaccgtcc tgcaccagga ctggctgaac ggcaaggagt acaagtgcaa ggtctccaac     300
aaaggcctcc cgtcctccat cgagaaaacc atctccaaag ccaaagggca gccccgagag     360
ccacaggtgt acaccctgcc cccatcccag gaggagatga ccaagaacca ggtcagcctg     420
acctgcctgg tcaaaggctt ctaccccagc gacatcgccg tggagtggga gagcaatggg     480
cagccggaga acaactacaa gaccacgcct cccgtgctgg actccgacgg ctccttcttc     540
ctctacagca ggctaaccgt ggacaagagc aggtggcagg aggggaatgt cttctcatgc     600
tccgtgatgc atgaggctct gcacaaccac tacacacaga gagcctctc cctgtctctg      660
ggtaaa                                                                 666
```

<210> SEQ ID NO 83
<211> LENGTH: 245
<212> TYPE: PRT
<213> ORGANISM: Artificial Sequence
<220> FEATURE:
<223> OTHER INFORMATION: pre-Fc chimeric polypeptide having a SHH signal peptide

<400> SEQUENCE: 83

```
Met Leu Leu Leu Ala Arg Cys Leu Leu Leu Val Leu Val Ser Ser Leu
1               5                   10                  15

Leu Val Cys Ser Gly Leu Ala Cys Pro Ser Cys Pro Ala Pro Glu Phe
            20                  25                  30

Leu Gly Gly Pro Ser Val Phe Leu Phe Pro Pro Lys Pro Lys Asp Thr
        35                  40                  45

Leu Met Ile Ser Arg Thr Pro Glu Val Thr Cys Val Val Val Asp Val
    50                  55                  60

Ser Gln Glu Asp Pro Glu Val Gln Phe Asn Trp Tyr Val Asp Gly Val
65                  70                  75                  80

Glu Val His Asn Ala Lys Thr Lys Pro Arg Glu Gln Phe Asn Ser
                85                  90                  95

Thr Tyr Arg Val Val Ser Val Leu Thr Val Leu His Gln Asp Trp Leu
            100                 105                 110

Asn Gly Lys Glu Tyr Lys Cys Lys Val Ser Asn Lys Gly Leu Pro Ser
        115                 120                 125

Ser Ile Glu Lys Thr Ile Ser Lys Ala Lys Gly Gln Pro Arg Glu Pro
    130                 135                 140

Gln Val Tyr Thr Leu Pro Pro Ser Gln Glu Glu Met Thr Lys Asn Gln
145                 150                 155                 160

Val Ser Leu Thr Cys Leu Val Lys Gly Phe Tyr Pro Ser Asp Ile Ala
                165                 170                 175

Val Glu Trp Glu Ser Asn Gly Gln Pro Glu Asn Asn Tyr Lys Thr Thr
            180                 185                 190

Pro Pro Val Leu Asp Ser Asp Gly Ser Phe Phe Leu Tyr Ser Arg Leu
        195                 200                 205

Thr Val Asp Lys Ser Arg Trp Gln Glu Gly Asn Val Phe Ser Cys Ser
```

Val Met His Glu Ala Leu His Asn His Tyr Thr Gln Lys Ser Leu Ser
225                 230                 235                 240

Leu Ser Leu Gly Lys
            245

<210> SEQ ID NO 84
<211> LENGTH: 767
<212> TYPE: DNA
<213> ORGANISM: Artificial Sequence
<220> FEATURE:
<223> OTHER INFORMATION: DNA encoding pre-Fc chimeric polypeptide having
      a SHH signal peptide

<400> SEQUENCE: 84
aagcttgaat tcccaccatg ctgctgctgg cgagatgtct gctgctagtc ctcgtctcct      60
cgctgctggt atgctcggga ctggcgtgcc catcatgccc agcacctgag ttcctggggg     120
gaccatcagt cttcctgttc cccccaaaac ccaaggacac tctcatgatc tcccggaccc     180
ctgaggtcac gtgcgtggtg gtggacgtga gccaggaaga ccccgaggtc cagttcaact     240
ggtacgtgga tggcgtggag gtgcataatg ccaagacaaa gccgcgggag gagcagttca     300
acagcacgta ccgtgtggtc agcgtcctca ccgtcctgca ccaggactgg ctgaacggca     360
aggagtacaa gtgcaaggtc tccaacaaag gcctcccgtc ctccatcgag aaaaccatct     420
ccaaagccaa agggcagccc cgagagccac aggtgtacac cctgcccca tcccaggagg      480 agatgaccaa gaaccaggtc agcctgacct gcctggtcaa aggcttctac cccagcgaca     540
tcgccgtgga gtgggagagc aatgggcagc cggagaacaa ctacaagacc acgcctcccg     600
tgctggactc cgacggctcc ttcttcctct acagcaggct aaccgtggac aagagcaggt     660
ggcaggaggg gaatgtcttc tcatgctccg tgatgcatga ggctctgcac aaccactaca     720
cacagaagag cctctccctg tctctgggta atgactcga gcggccg                    767

<210> SEQ ID NO 85
<211> LENGTH: 245
<212> TYPE: PRT
<213> ORGANISM: Artificial Sequence
<220> FEATURE:
<223> OTHER INFORMATION: pre-Fc chimeric polypeptide having a IFN signal
      peptide

<400> SEQUENCE: 85

Met Ala Leu Thr Phe Ala Leu Leu Val Ala Leu Leu Val Leu Ser Cys
1               5                   10                  15

Lys Ser Ser Cys Ser Val Gly Cys Pro Ser Cys Pro Ala Pro Glu Phe
            20                  25                  30

Leu Gly Gly Pro Ser Val Phe Leu Phe Pro Pro Lys Pro Lys Asp Thr
        35                  40                  45

Leu Met Ile Ser Arg Thr Pro Glu Val Thr Cys Val Val Val Asp Val
    50                  55                  60

Ser Gln Glu Asp Pro Glu Val Gln Phe Asn Trp Tyr Val Asp Gly Val
65                  70                  75                  80

Glu Val His Asn Ala Lys Thr Lys Pro Arg Glu Glu Gln Phe Asn Ser
                85                  90                  95

Thr Tyr Arg Val Val Ser Val Leu Thr Val Leu His Gln Asp Trp Leu
            100                 105                 110

Asn Gly Lys Glu Tyr Lys Cys Lys Val Ser Asn Lys Gly Leu Pro Ser
        115                 120                 125

```
Ser Ile Glu Lys Thr Ile Ser Lys Ala Lys Gly Gln Pro Arg Glu Pro
        130                 135                 140

Gln Val Tyr Thr Leu Pro Pro Ser Gln Glu Glu Met Thr Lys Asn Gln
145                 150                 155                 160

Val Ser Leu Thr Cys Leu Val Lys Gly Phe Tyr Pro Ser Asp Ile Ala
                165                 170                 175

Val Glu Trp Glu Ser Asn Gly Gln Pro Glu Asn Asn Tyr Lys Thr Thr
            180                 185                 190

Pro Pro Val Leu Asp Ser Asp Gly Ser Phe Phe Leu Tyr Ser Arg Leu
        195                 200                 205

Thr Val Asp Lys Ser Arg Trp Gln Glu Gly Asn Val Phe Ser Cys Ser
        210                 215                 220

Val Met His Glu Ala Leu His Asn His Tyr Thr Gln Lys Ser Leu Ser
225                 230                 235                 240

Leu Ser Leu Gly Lys
            245
```

<210> SEQ ID NO 86
<211> LENGTH: 767
<212> TYPE: DNA
<213> ORGANISM: Artificial Sequence
<220> FEATURE:
<223> OTHER INFORMATION: DNA encoding pre-Fc chimeric polypeptide having a IFN signal peptide

<400> SEQUENCE: 86

```
aagcttgaat tcccaccatg gccttgacct ttgctttact ggtggccctc ctggtgctca    60
gctgcaagtc aagctgctct gtgggctgcc catcatgccc agcacctgag ttcctggggg   120
gaccatcagt cttcctgttc cccccaaaac ccaaggacac tctcatgatc tcccggaccc   180
ctgaggtcac gtgcgtggtg gtggacgtga gccaggaaga ccccgaggtc cagttcaact   240
ggtacgtgga tggcgtggag gtgcataatg ccaagacaaa gccgcgggag gagcagttca   300
acagcacgta ccgtgtggtc agcgtcctca ccgtcctgca ccaggactgg ctgaacggca   360
aggagtacaa gtgcaaggtc tccaacaaag gcctcccgtc ctccatcgag aaaaccatct   420
ccaaagccaa agggcagccc cgagagccac aggtgtacac cctgccccca tcccaggagg   480
agatgaccaa gaaccaggtc agcctgacct gcctggtcaa aggcttctac ccagcgaca   540 tcgccgtgga gtgggagagc aatgggcagc cggagaacaa ctacaagacc acgcctcccg   600
tgctggactc cgacggctcc ttcttcctct acagcaggct aaccgtggac aagagcaggt   660
ggcaggaggg gaatgtcttc tcatgctccg tgatgcatga ggctctgcac aaccactaca   720
cacagaagag cctctccctg tctctgggta aatgactcga gcggccg              767
```

<210> SEQ ID NO 87
<211> LENGTH: 239
<212> TYPE: PRT
<213> ORGANISM: Artificial Sequence
<220> FEATURE:
<223> OTHER INFORMATION: pre-Fc chimeric polypeptide having a CETP signal peptide

<400> SEQUENCE: 87

```
Met Leu Ala Ala Thr Val Leu Thr Leu Ala Leu Leu Gly Asn Ala His
1               5                   10                  15

Ala Cys Pro Ser Cys Pro Ala Pro Glu Phe Leu Gly Gly Pro Ser Val
            20                  25                  30
```

```
Phe Leu Phe Pro Pro Lys Pro Lys Asp Thr Leu Met Ile Ser Arg Thr
             35                  40                  45

Pro Glu Val Thr Cys Val Val Val Asp Val Ser Gln Glu Asp Pro Glu
 50                  55                  60

Val Gln Phe Asn Trp Tyr Val Asp Gly Val Glu Val His Asn Ala Lys
 65                  70                  75                  80

Thr Lys Pro Arg Glu Glu Gln Phe Asn Ser Thr Tyr Arg Val Val Ser
                 85                  90                  95

Val Leu Thr Val Leu His Gln Asp Trp Leu Asn Gly Lys Glu Tyr Lys
                100                 105                 110

Cys Lys Val Ser Asn Lys Gly Leu Pro Ser Ser Ile Glu Lys Thr Ile
                115                 120                 125

Ser Lys Ala Lys Gly Gln Pro Arg Glu Pro Gln Val Tyr Thr Leu Pro
                130                 135                 140

Pro Ser Gln Glu Glu Met Thr Lys Asn Gln Val Ser Leu Thr Cys Leu
145                 150                 155                 160

Val Lys Gly Phe Tyr Pro Ser Asp Ile Ala Val Glu Trp Glu Ser Asn
                165                 170                 175

Gly Gln Pro Glu Asn Asn Tyr Lys Thr Thr Pro Pro Val Leu Asp Ser
                180                 185                 190

Asp Gly Ser Phe Phe Leu Tyr Ser Arg Leu Thr Val Asp Lys Ser Arg
                195                 200                 205

Trp Gln Glu Gly Asn Val Phe Ser Cys Ser Val Met His Glu Ala Leu
                210                 215                 220

His Asn His Tyr Thr Gln Lys Ser Leu Ser Leu Ser Leu Gly Lys
225                 230                 235
```

<210> SEQ ID NO 88
<211> LENGTH: 749
<212> TYPE: DNA
<213> ORGANISM: Artificial Sequence
<220> FEATURE:
<223> OTHER INFORMATION: DNA encoding pre-Fc chimeric polypeptide having
      a CETP signal peptide

<400> SEQUENCE: 88

```
aagcttgaat tcccaccatg ctggctgcca cagtcctgac cctggccctg ctgggcaatg     60
cccatgcctg cccatcatgc ccagcacctg agttcctggg gggaccatca gtcttcctgt    120 tcccccaaa acccaaggac actctcatga tctcccggac ccctgaggtc acgtgcgtgg    180
tggtggacgt gagccaggaa gaccccgagg tccagttcaa ctggtacgtg gatggcgtgg    240
aggtgcataa tgccaagaca aagccgcggg aggagcagtt caacagcacg taccgtgtgg    300
tcagcgtcct caccgtcctg caccaggact ggctgaacgg caaggagtac aagtgcaagg    360
tctccaacaa aggcctcccg tcctccatcg agaaaaccat ctccaaagcc aaagggcagc    420
cccgagagcc acaggtgtac accctgcccc catcccagga ggagatgacc aagaaccagg    480
tcagcctgac ctgcctggtc aaaggcttct accccagcga catcgccgtg gagtgggaga    540
gcaatgggca gccggagaac aactacaaga ccacgcctcc cgtgctggac tccgacggct    600
ccttcttcct ctacagcagg ctaaccgtgg acaagagcag gtggcaggag gggaatgtct    660
tctcatgctc cgtgatgcat gaggctctgc acaaccacta cacacagaag agcctctccc    720
tgtctctggg taaatgactc gagcggccg                                     749
```

<210> SEQ ID NO 89
<211> LENGTH: 219

<212> TYPE: PRT
<213> ORGANISM: Artificial Sequence
<220> FEATURE:
<223> OTHER INFORMATION: Human IgG4 Fc domain having the N-terminal sequence CPAPE

<400> SEQUENCE: 89

Cys Pro Ala Pro Glu Phe Leu Gly Gly Pro Ser Val Phe Leu Phe Pro
1               5                   10                  15

Pro Lys Pro Lys Asp Thr Leu Met Ile Ser Arg Thr Pro Glu Val Thr
            20                  25                  30

Cys Val Val Val Asp Val Ser Gln Glu Asp Pro Glu Val Gln Phe Asn
        35                  40                  45

Trp Tyr Val Asp Gly Val Glu Val His Asn Ala Lys Thr Lys Pro Arg
    50                  55                  60

Glu Glu Gln Phe Asn Ser Thr Tyr Arg Val Val Ser Val Leu Thr Val
65                  70                  75                  80

Leu His Gln Asp Trp Leu Asn Gly Lys Glu Tyr Lys Cys Lys Val Ser
                85                  90                  95

Asn Lys Gly Leu Pro Ser Ser Ile Glu Lys Thr Ile Ser Lys Ala Lys
            100                 105                 110

Gly Gln Pro Arg Glu Pro Gln Val Tyr Thr Leu Pro Pro Ser Gln Glu
        115                 120                 125

Glu Met Thr Lys Asn Gln Val Ser Leu Thr Cys Leu Val Lys Gly Phe
    130                 135                 140

Tyr Pro Ser Asp Ile Ala Val Glu Trp Glu Ser Asn Gly Gln Pro Glu
145                 150                 155                 160

Asn Asn Tyr Lys Thr Thr Pro Pro Val Leu Asp Ser Asp Gly Ser Phe
                165                 170                 175

Phe Leu Tyr Ser Arg Leu Thr Val Asp Lys Ser Arg Trp Gln Glu Gly
            180                 185                 190

Asn Val Phe Ser Cys Ser Val Met His Glu Ala Leu His Asn His Tyr
        195                 200                 205

Thr Gln Lys Ser Leu Ser Leu Ser Leu Gly Lys
    210                 215

<210> SEQ ID NO 90
<211> LENGTH: 657
<212> TYPE: DNA
<213> ORGANISM: Artificial Sequence
<220> FEATURE:
<223> OTHER INFORMATION: DNA encoding human IgG4 Fc domain having the N-terminal sequence CPAPE

<400> SEQUENCE: 90
tgcccagcac ctgagttcct ggggggacca tcagtcttcc tgttcccccc aaaacccaag      60
gacactctca tgatctcccg gacccctgag gtcacgtgcg tggtggtgga cgtgagccag     120
gaagaccccg aggtccagtt caactggtac gtggatggcg tggaggtgca taatgccaag     180
acaaagccgc gggaggagca gttcaacagc acgtaccgtg tggtcagcgt cctcaccgtc     240
ctgcaccagg actggctgaa cggcaaggag tacaagtgca aggtctccaa caaaggcctc     300
ccgtcctcca tcgagaaaac catctccaaa gccaaagggc agccccgaga gccacaggtg     360
tacaccctgc ccccatccca ggaggagatg accaagaacc aggtcagcct gacctgcctg     420
gtcaaaggct tctaccccag cgacatcgcc gtggagtggg agagcaatgg gcagccggag     480
aacaactaca agaccacgcc tcccgtgctg gactccgacg gctccttctt cctctacagc     540

```
aggctaaccg tggacaagag caggtggcag gaggggaatg tcttctcatg ctccgtgatg     600
catgaggctc tgcacaacca ctacacacag aagagcctct ccctgtctct gggtaaa        657
```

<210> SEQ ID NO 91
<211> LENGTH: 242
<212> TYPE: PRT
<213> ORGANISM: Artificial Sequence
<220> FEATURE:
<223> OTHER INFORMATION: pre-Fc chimeric polypeptide having a SHH signal peptide

<400> SEQUENCE: 91

```
Met Leu Leu Leu Ala Arg Cys Leu Leu Leu Val Leu Val Ser Ser Leu
1               5                   10                  15

Leu Val Cys Ser Gly Leu Ala Cys Pro Ala Pro Glu Phe Leu Gly Gly
            20                  25                  30

Pro Ser Val Phe Leu Phe Pro Pro Lys Pro Lys Asp Thr Leu Met Ile
        35                  40                  45

Ser Arg Thr Pro Glu Val Thr Cys Val Val Val Asp Val Ser Gln Glu
    50                  55                  60

Asp Pro Glu Val Gln Phe Asn Trp Tyr Val Asp Gly Val Glu Val His
65                  70                  75                  80

Asn Ala Lys Thr Lys Pro Arg Glu Glu Gln Phe Asn Ser Thr Tyr Arg
                85                  90                  95

Val Val Ser Val Leu Thr Val Leu His Gln Asp Trp Leu Asn Gly Lys
            100                 105                 110

Glu Tyr Lys Cys Lys Val Ser Asn Lys Gly Leu Pro Ser Ser Ile Glu
        115                 120                 125

Lys Thr Ile Ser Lys Ala Lys Gly Gln Pro Arg Glu Pro Gln Val Tyr
    130                 135                 140

Thr Leu Pro Pro Ser Gln Glu Glu Met Thr Lys Asn Gln Val Ser Leu
145                 150                 155                 160

Thr Cys Leu Val Lys Gly Phe Tyr Pro Ser Asp Ile Ala Val Glu Trp
                165                 170                 175

Glu Ser Asn Gly Gln Pro Glu Asn Asn Tyr Lys Thr Thr Pro Pro Val
            180                 185                 190

Leu Asp Ser Asp Gly Ser Phe Phe Leu Tyr Ser Arg Leu Thr Val Asp
        195                 200                 205

Lys Ser Arg Trp Gln Glu Gly Asn Val Phe Ser Cys Ser Val Met His
    210                 215                 220

Glu Ala Leu His Asn His Tyr Thr Gln Lys Ser Leu Ser Leu Ser Leu
225                 230                 235                 240

Gly Lys
```

<210> SEQ ID NO 92
<211> LENGTH: 758
<212> TYPE: DNA
<213> ORGANISM: Artificial Sequence
<220> FEATURE:
<223> OTHER INFORMATION: DNA encoding pre-Fc chimeric polypeptide having a SHH signal peptide

<400> SEQUENCE: 92

```
aagcttgaat tcccaccatg ctgctgctgg cgagatgtct gctgctagtc ctcgtctcct     60
cgctgctggt atgctcggga ctggcgtgcc cagcacctga gttcctgggg ggaccatcag    120
tcttcctgtt ccccccaaaa cccaaggaca ctctcatgat ctcccggacc cctgaggtca    180
```

```
cgtgcgtggt ggtggacgtg agccaggaag accccgaggt ccagttcaac tggtacgtgg    240
atggcgtgga ggtgcataat gccaagacaa agccgcggga ggagcagttc aacagcacgt    300
accgtgtggt cagcgtcctc accgtcctgc accaggactg gctgaacggc aaggagtaca    360
agtgcaaggt ctccaacaaa ggcctcccgt cctccatcga gaaaaccatc tccaaagcca    420
aagggcagcc ccgagagcca caggtgtaca ccctgccccc atcccaggag gagatgacca    480
agaaccaggt cagcctgacc tgcctggtca aaggcttcta ccccagcgac atcgccgtgg    540
agtgggagag caatgggcag ccggagaaca actacaagac cacgcctccc gtgctggact    600
ccgacggctc cttcttcctc tacagcaggc taaccgtgga caagagcagg tggcaggagg    660
ggaatgtctt ctcatgctcc gtgatgcatg aggctctgca caaccactac acacagaaga    720
gcctctccct gtctctgggt aaatgactcg agcggccg                            758
```

<210> SEQ ID NO 93
<211> LENGTH: 242
<212> TYPE: PRT
<213> ORGANISM: Artificial Sequence
<220> FEATURE:
<223> OTHER INFORMATION: pre-Fc chimeric polypeptide having a IFN signal
      peptide

<400> SEQUENCE: 93

Met Ala Leu Thr Phe Ala Leu Leu Val Ala Leu Leu Val Leu Ser Cys
1               5                   10                  15

Lys Ser Ser Cys Ser Val Gly Cys Pro Ala Pro Glu Phe Leu Gly Gly
            20                  25                  30

Pro Ser Val Phe Leu Phe Pro Pro Lys Pro Lys Asp Thr Leu Met Ile
        35                  40                  45

Ser Arg Thr Pro Glu Val Thr Cys Val Val Val Asp Val Ser Gln Glu
    50                  55                  60

Asp Pro Glu Val Gln Phe Asn Trp Tyr Val Asp Gly Val Glu Val His
65                  70                  75                  80

Asn Ala Lys Thr Lys Pro Arg Glu Glu Gln Phe Asn Ser Thr Tyr Arg
                85                  90                  95

Val Val Ser Val Leu Thr Val Leu His Gln Asp Trp Leu Asn Gly Lys
            100                 105                 110

Glu Tyr Lys Cys Lys Val Ser Asn Lys Gly Leu Pro Ser Ser Ile Glu
        115                 120                 125

Lys Thr Ile Ser Lys Ala Lys Gly Gln Pro Arg Glu Pro Gln Val Tyr
    130                 135                 140

Thr Leu Pro Pro Ser Gln Glu Glu Met Thr Lys Asn Gln Val Ser Leu
145                 150                 155                 160

Thr Cys Leu Val Lys Gly Phe Tyr Pro Ser Asp Ile Ala Val Glu Trp
                165                 170                 175

Glu Ser Asn Gly Gln Pro Glu Asn Asn Tyr Lys Thr Thr Pro Pro Val
            180                 185                 190

Leu Asp Ser Asp Gly Ser Phe Phe Leu Tyr Ser Arg Leu Thr Val Asp
        195                 200                 205

Lys Ser Arg Trp Gln Glu Gly Asn Val Phe Ser Cys Ser Val Met His
    210                 215                 220

Glu Ala Leu His Asn His Tyr Thr Gln Lys Ser Leu Ser Leu Ser Leu
225                 230                 235                 240

Gly Lys

<210> SEQ ID NO 94
<211> LENGTH: 758
<212> TYPE: DNA
<213> ORGANISM: Artificial Sequence
<220> FEATURE:
<223> OTHER INFORMATION: DNA encoding pre-Fc chimeric polypeptide having a IFN signal peptide

<400> SEQUENCE: 94

```
aagcttgaat tcccaccatg gccttgacct ttgctttact ggtggccctc ctggtgctca    60
gctgcaagtc aagctgctct gtgggctgcc cagcacctga gttcctgggg ggaccatcag   120
tcttcctgtt cccccaaaa cccaaggaca ctctcatgat ctcccggacc cctgaggtca   180
cgtgcgtggt ggtggacgtg agccaggaag accccgaggt ccagttcaac tggtacgtgg   240
atggcgtgga ggtgcataat gccaagacaa agccgcggga ggagcagttc aacagcacgt   300
accgtgtggt cagcgtcctc accgtcctgc accaggactg gctgaacggc aaggagtaca   360
agtgcaaggt ctccaacaaa ggcctcccgt cctccatcga gaaaaccatc tccaaagcca   420
aagggcagcc ccgagagcca caggtgtaca ccctgccccc atcccaggag gagatgacca   480
agaaccaggt cagcctgacc tgcctggtca aaggcttcta ccccagcgac atcgccgtgg   540
agtgggagag caatgggcag ccggagaaca actacaagac cacgcctccc gtgctggact   600
ccgacggctc cttcttcctc tacagcaggc taaccgtgga caagagcagg tggcaggagg   660
ggaatgtctt ctcatgctcc gtgatgcatg aggctctgca caaccactac acacagaaga   720
gcctctccct gtctctgggt aaatgactcg agcggccg                             758
```

<210> SEQ ID NO 95
<211> LENGTH: 236
<212> TYPE: PRT
<213> ORGANISM: Artificial Sequence
<220> FEATURE:
<223> OTHER INFORMATION: pre-Fc chimeric polypeptide having a CETP signal peptide

<400> SEQUENCE: 95

```
Met Leu Ala Ala Thr Val Leu Thr Leu Ala Leu Leu Gly Asn Ala His
1               5                   10                  15

Ala Cys Pro Ala Pro Glu Phe Leu Gly Gly Pro Ser Val Phe Leu Phe
                20                  25                  30

Pro Pro Lys Pro Lys Asp Thr Leu Met Ile Ser Arg Thr Pro Glu Val
            35                  40                  45

Thr Cys Val Val Val Asp Val Ser Gln Glu Asp Pro Glu Val Gln Phe
        50                  55                  60

Asn Trp Tyr Val Asp Gly Val Glu Val His Asn Ala Lys Thr Lys Pro
65                  70                  75                  80

Arg Glu Glu Gln Phe Asn Ser Thr Tyr Arg Val Val Ser Val Leu Thr
                85                  90                  95

Val Leu His Gln Asp Trp Leu Asn Gly Lys Glu Tyr Lys Cys Lys Val
                100                 105                 110

Ser Asn Lys Gly Leu Pro Ser Ser Ile Glu Lys Thr Ile Ser Lys Ala
            115                 120                 125

Lys Gly Gln Pro Arg Glu Pro Gln Val Tyr Thr Leu Pro Pro Ser Gln
        130                 135                 140

Glu Glu Met Thr Lys Asn Gln Val Ser Leu Thr Cys Leu Val Lys Gly
145                 150                 155                 160

Phe Tyr Pro Ser Asp Ile Ala Val Glu Trp Glu Ser Asn Gly Gln Pro
                165                 170                 175
```

```
Glu Asn Asn Tyr Lys Thr Thr Pro Pro Val Leu Asp Ser Asp Gly Ser
                180                 185                 190

Phe Phe Leu Tyr Ser Arg Leu Thr Val Asp Lys Ser Arg Trp Gln Glu
            195                 200                 205

Gly Asn Val Phe Ser Cys Ser Val Met His Glu Ala Leu His Asn His
        210                 215                 220

Tyr Thr Gln Lys Ser Leu Ser Leu Ser Leu Gly Lys
225                 230                 235

<210> SEQ ID NO 96
<211> LENGTH: 740
<212> TYPE: DNA
<213> ORGANISM: Artificial Sequence
<220> FEATURE:
<223> OTHER INFORMATION: DNA encoding pre-Fc chimeric polypeptide having
      a CETP signal peptide

<400> SEQUENCE: 96
aagcttgaat tcccaccatg ctggctgcca cagtcctgac cctggccctg ctgggcaatg     60
cccatgcctg cccagcacct gagttcctgg ggggaccatc agtcttcctg ttccccccaa   120
aacccaagga cactctcatg atctcccgga cccctgaggt cacgtgcgtg gtggtggacg   180
tgagccagga agaccccgag gtccagttca actggtacgt ggatggcgtg gaggtgcata   240
atgccaagac aaagccgcgg gaggagcagt tcaacagcac gtaccgtgtg gtcagcgtcc   300
tcaccgtcct gcaccaggac tggctgaacg gcaaggagta caagtgcaag gtctccaaca   360
aaggcctccc gtcctccatc gagaaaacca tctccaaagc caaagggcag ccccgagagc   420
cacaggtgta caccctgccc ccatcccagg aggagatgac caagaaccag gtcagcctga   480
cctgcctggt caaaggcttc taccccagcg acatcgccgt ggagtgggag agcaatgggc   540
agccggagaa caactacaag accacgcctc ccgtgctgga ctccgacggc tccttcttcc   600
tctacagcag gctaaccgtg gacaagagca ggtggcagga ggggaatgtc ttctcatgct   660
ccgtgatgca tgaggctctg cacaaccact acacacagaa gagcctctcc ctgtctctgg   720
gtaaatgact cgagcggccg                                                740

<210> SEQ ID NO 97
<211> LENGTH: 5428
<212> TYPE: DNA
<213> ORGANISM: Artificial Sequence
<220> FEATURE:
<223> OTHER INFORMATION: pCDNA3.1(+)

<400> SEQUENCE: 97
gacggatcgg gagatctccc gatcccctat ggtgcactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
```

```
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aaatgtcgta acaactccgc cccattgacg caaatgggcg     780
gtaggcgtgt acggtgggag gtctatataa gcagagctct ctggctaact agagaaccca     840
ctgcttactg gcttatcgaa attaatacga ctcactatag ggagacccaa gctggctagc     900
gtttaaactt aagcttggta ccgagctcgg atccactagt ccagtgtggt ggaattctgc     960
agatatccag cacagtggcg gccgctcgag tctagagggc ccgtttaaac ccgctgatca    1020
gcctcgactg tgccttctag ttgccagcca tctgttgttt gcccctcccc cgtgccttcc    1080
ttgaccctgg aaggtgccac tcccactgtc ctttcctaat aaaatgagga aattgcatcg    1140
cattgtctga gtaggtgtca ttctattctg ggggtgggg tggggcagga cagcaagggg    1200
gaggattggg aagacaatag caggcatgct ggggatgcgg tgggctctat ggcttctgag    1260
gcggaaagaa ccagctgggg ctctaggggg tatccccacg cgccctgtag cggcgcatta    1320
agcgcggcgg gtgtggtggt tacgcgcagc gtgaccgcta cacttgccag cgccctagcg    1380
cccgctcctt tcgctttctt cccttccttt ctcgccacgt tcgccggctt tccccgtcaa    1440
gctctaaatc gggggctccc tttagggttc cgatttagtg ctttacggca cctcgacccc    1500
aaaaaacttg attagggtga tggttcacgt agtgggccat cgccctgata gacggttttt    1560
cgccctttga cgttggagtc cacgttcttt aatagtggac tcttgttcca aactggaaca    1620
acactcaacc ctatctcggt ctattctttt gatttataag gattttgcc gatttcggcc    1680 tattggttaa aaaatgagct gatttaacaa aaatttaacg cgaattaatt ctgtggaatg    1740
tgtgtcagtt agggtgtgga aagtccccag gctccccagc aggcagaagt atgcaaagca    1800
tgcatctcaa ttagtcagca accaggtgtg gaaagtcccc aggctcccca gcaggcagaa    1860
gtatgcaaag catgcatctc aattagtcag caaccatagt cccgccccta actccgccca    1920
tcccgcccct aactccgccc agttccgccc attctccgcc ccatggctga ctaatttttt    1980
ttatttatgc agaggccgag gccgcctctg cctctgagct attccagaag tagtgaggag    2040
gcttttttgg aggcctaggc ttttgcaaaa agctcccggg agcttgtata tccatttcg    2100 gatctgatca agagacagga tgaggatcgt ttcgcatgat tgaacaagat ggattgcacg    2160
caggttctcc ggccgcttgg gtggagaggc tattcggcta tgactggca caacagacaa    2220 tcggctgctc tgatgccgcc gtgttccggc tgtcagcgca ggggcgcccg gttcttttg    2280 tcaagaccga cctgtccggt gccctgaatg aactgcagga cgaggcagcg cggctatcgt    2340
ggctggccac gacgggcgtt ccttgcgcag ctgtgctcga cgttgtcact gaagcgggaa    2400
gggactggct gctattgggc gaagtgccgg ggcaggatct cctgtcatct caccttgctc    2460
ctgccgagaa agtatccatc atggctgatg caatgcggcg gctgcatacg cttgatccgg    2520
ctacctgccc attcgaccac caagcgaaac atcgcatcga gcgagcacgt actcggatgg    2580
aagccggtct tgtcgatcag gatgatctgg acgaagagca tcagggctc gcgccagccg    2640 aactgttcgc caggctcaag gcgcgcatgc ccgacggcga ggatctcgtc gtgacccatg    2700
gcgatgcctg cttgccgaat atcatggtgg aaaatggccg cttttctgga ttcatcgact    2760
gtggccggct gggtgtggcg gaccgctatc aggacatagc gttggctacc cgtgatattg    2820
ctgaagagct tggcggcgaa tgggctgacc gcttcctcgt gctttacggt atcgccgctc    2880
ccgattcgca gcgcatcgcc ttctatcgcc ttcttgacga gttcttctga gcgggactct    2940
```

```
ggggttcgaa atgaccgacc aagcgacgcc caacctgcca tcacgagatt tcgattccac   3000
cgccgccttc tatgaaaggt tgggcttcgg aatcgttttc cgggacgccg gctggatgat   3060
cctccagcgc ggggatctca tgctggagtt cttcgcccac cccaacttgt ttattgcagc   3120
ttataatggt tacaaataaa gcaatagcat cacaaatttc acaaataaag cattttttc   3180 actgcattct agttgtggtt tgtccaaact catcaatgta tcttatcatg tctgtatacc   3240
gtcgacctct agctagagct tggcgtaatc atggtcatag ctgtttcctg tgtgaaattg   3300
ttatccgctc acaattccac acaacatacg agccggaagc ataaagtgta aagcctgggg   3360
tgcctaatga gtgagctaac tcacattaat tgcgttgcgc tcactgcccg ctttccagtc   3420
gggaaacctg tcgtgccagc tgcattaatg aatcggccaa cgcgcgggga gaggcggttt   3480
gcgtattggg cgctcttccg cttcctcgct cactgactcg ctgcgctcgg tcgttcggct   3540
gcggcgagcg gtatcagctc actcaaaggc ggtaatacgg ttatccacag aatcagggga   3600
taacgcagga aagaacatgt gagcaaaagg ccagcaaaag gccaggaacc gtaaaaaggc   3660
cgcgttgctg gcgttttcc ataggctccg ccccctgac gagcatcaca aaaatcgacg   3720
ctcaagtcag aggtggcgaa acccgacagg actataaaga taccaggcgt ttccccctgg   3780
aagctccctc gtgcgctctc ctgttccgac cctgccgctt accggatacc tgtccgcctt   3840
tctcccttcg ggaagcgtgg cgctttctca tagctcacgc tgtaggtatc tcagttcggt   3900
gtaggtcgtt cgctccaagc tgggctgtgt gcacgaaccc cccgttcagc ccgaccgctg   3960
cgccttatcc ggtaactatc gtcttgagtc aacccggta agacacgact tatcgccact   4020
ggcagcagcc actggtaaca ggattagcag agcgaggtat gtaggcggtg ctacagagtt   4080
cttgaagtgg tggcctaact acggctacac tagaagaaca gtatttggta tctgcgctct   4140
gctgaagcca gttaccttcg gaaaaagagt tggtagctct tgatccggca aacaaaccac   4200
cgctggtagc ggtttttttg tttgcaagca gcagattacg cgcagaaaaa aaggatctca   4260
agaagatcct ttgatctttt ctacggggtc tgacgctcag tggaacgaaa actcacgtta   4320
agggattttg gtcatgagat tatcaaaaag gatcttcacc tagatccttt taaattaaaa   4380
atgaagtttt aaatcaatct aaagtatata tgagtaaact tggtctgaca gttaccaatg   4440
cttaatcagt gaggcaccta tctcagcgat ctgtctattt cgttcatcca tagttgcctg   4500
actccccgtc gtgtagataa ctacgatacg ggagggctta ccatctggcc ccagtgctgc   4560
aatgataccg cgagacccac gctcaccggc tccagattta tcagcaataa accagccagc   4620
cggaagggcc gagcgcagaa gtggtcctgc aactttatcc gcctccatcc agtctattaa   4680
ttgttgccgg gaagctagag taagtagttc gccagttaat agtttgcgca acgttgttgc   4740
cattgctaca ggcatcgtgg tgtcacgctc gtcgtttggt atggcttcat tcagctccgg   4800
ttcccaacga tcaaggcgag ttacatgatc ccccatgttg tgcaaaaaag cggttagctc   4860
cttcggtcct ccgatcgttg tcagaagtaa gttggccgca gtgttatcac tcatggttat   4920
ggcagcactg cataattctc ttactgtcat gccatccgta agatgctttt ctgtgactgg   4980
tgagtactca accaagtcat tctgagaata gtgtatgcgg cgaccgagtt gctcttgccc   5040
ggcgtcaata cggataata ccgcgccaca tagcagaact ttaaaagtgc tcatcattgg   5100
aaaacgttct cggggcgaa aactctcaag gatcttaccg ctgttgagat ccagttcgat   5160
gtaacccact cgtgcaccca actgatcttc agcatctttt actttcacca gcgtttctgg   5220
gtgagcaaaa acaggaaggc aaaatgccgc aaaaaaggga ataagggcga cacggaaatg   5280
ttgaatactc atactcttcc ttttcaata ttattgaagc atttatcagg gttattgtct   5340
```

```
catgagcgga tacatatttg aatgtattta gaaaaataaa caaataggggg ttccgcgcac     5400 atttccccga aaagtgccac ctgacgtc                                        5428

<210> SEQ ID NO 98
<211> LENGTH: 4195
<212> TYPE: DNA
<213> ORGANISM: Artificial Sequence
<220> FEATURE:
<223> OTHER INFORMATION: pSA

<400> SEQUENCE: 98
ctaaattgta agcgttaata ttttgttaaa attcgcgtta aattttttgtt aaatcagctc       60 attttttaac caataggccg aaatcggcaa atcccttat aaatcaaaag aatagaccga      120 gataggttg agtgttgttc cagttttgaa caagagtcca ctattaaaga acgtggactc      180
caacgtcaaa gggcgaaaaa ccgtctatca gggcgatggc ccactacgtg aaccatcacc      240
ctaatcaagt ttttgggggt cgaggtgccg taaagcacta atcggaacc ctaaagggag      300 cccccgattt agagcttgac ggggaaagcc ggcgaacgtg gcgagaaagg aagggaagaa      360
agcgaaagga gcgggcgcta gggcgctggc aagtgtagcg gtcacgctgc gcgtaaccac      420
cacacccgcc gcgcttaatg cgccgctaca gggcgcgtcc cattcgccat tcaggctgcg      480
caactgttgg gaagggcgat cggtgcgggc ctcttcgcta ttacgccagc tggcgaaagg      540
gggatgtgct gcaaggcgat taagttgggt aacgccaggg ttttcccagt cacgacgttg      600
taaaacgacg gccagtgagc gcgcaagcgg ccgcaacccg ggaaaagctt ggccattgca      660
tacgttgtat ccatatcata atatgtacat ttatattggc tcatgtccaa cattaccgcc      720
atgttgacat tgattattga ctagttatta atagtaatca attacggggt cattagttca      780
tagcccatat atggagttcc gcgttacata acttacggta aatggcccgc ctggctgacc      840
gcccaacgac ccccgcccat tgacgtcaat aatgacgtat gttcccatag taacgccaat      900
agggactttc cattgacgtc aatgggtgga gtatttacgg taaactgccc acttggcagt      960
acatcaagtg tatcatatgc caagtacgcc ccctattgac gtcaatgacg gtaaatggcc     1020
cgcctggcat tatgcccagt acatgacctt atgggacttt cctacttggc agtacatcta     1080
cgtattagtc atcgctatta ccatggtgat gcggttttgg cagtacatca atgggcgtgg     1140
atagcggttt gactcacggg gatttccaag tctccacccc attgacgtca atgggagttt     1200
gttttggcac caaaatcaac gggactttcc aaaatgtcgt aacaactccg ccccattgac     1260
gcaaatgggc ggtaggcgtg tacggtggga ggtctatata agcagagctc gtttagtgaa     1320
ccgtcagatc gcctggagac gccatccacg ctgttttgac ctccatagaa gacaccggga     1380
ccgatccagc ctccgcggcc gggaacggtg cattggaacg cggattcccc gtgccaagag     1440
tgacgtaagt accgcctata gagtctatag gcccaccccc ttggcttctt atgcatgctc     1500
ccctgctccg acccgggctc ctcgcccgcc cggacccaca ggccaccctc aaccgtcctg     1560
gccccggacc caaaccccac ccctcactct gcttctcccc gcaggagaat tcaatcgcga     1620
aagggcccaa agatctgcca taccacattt gtagaggttt tacttgcttt aaaaaacctc     1680
ccacacctcc ccctgaacct gaaacataaa atgaatgcaa ttgttgttgt taacttgttt     1740
attgcagctt ataatggtta caaataaagc aatagcatca caaatttcac aaataaagca     1800
tttttttcac tgcattctag ttgtggtttg tccaaactca tcaatgtatc ttatcatgtc     1860
tggagctagc atcccgcccc taactccgcc ctgttccgcc cattctccgc ccatggctg     1920
```

```
actaattttt tttatttatg cagaggccga ggccgcctcg gcctctgagc tattccagaa    1980
gtagtgagga ggcttttttg gaggcctagg cttttgcgtc gagaagcgcg cttggcgtaa    2040
tcatggtcat agctgtttcc tgtgtgaaat tgttatccgc tcacaattcc acacaacata    2100
cgagccggaa gcataaagtg taaagcctgg ggtgcctaat gagtgagcta actcacatta    2160
attgcgttgc gctcactgcc cgctttccag tcgggaaacc tgtcgtgcca gctgcattaa    2220
tgaatcggcc aacgcgcggg gagaggcggt ttgcgtattg ggcgctcttc cgcttcctcg    2280
ctcactgact cgctgcgctc ggtcgttcgg ctgcggcgag cggtatcagc tcactcaaag    2340
gcggtaatac ggttatccac agaatcaggg gataacgcag gaaagaacat gtgagcaaaa    2400
ggccagcaaa aggccaggaa ccgtaaaaag gccgcgttgc tggcgttttt ccataggctc    2460
cgcccccctg acgagcatca caaaaatcga cgctcaagtc agaggtggcg aaacccgaca    2520
ggactataaa gataccaggc gtttccccct ggaagctccc tcgtgcgctc tcctgttccg    2580
accctgccgc ttaccggata cctgtccgcc tttctccctt cgggaagcgt ggcgctttct    2640
catagctcac gctgtaggta tctcagttcg gtgtaggtcg ttcgctccaa gctgggctgt    2700
gtgcacgaac cccccgttca gcccgaccgc tgcgccttat ccggtaacta tcgtcttgag    2760
tccaacccgg taagacacga cttatcgcca ctggcagcag ccactggtaa caggattagc    2820
agagcgaggt atgtaggcgg tgctacagag ttcttgaagt ggtggcctaa ctacggctac    2880
actagaagga cagtatttgg tatctgcgct ctgctgaagc cagttacctt cggaaaaaga    2940
gttggtagct cttgatccgg caaacaaacc accgctggta gcggtggttt ttttgtttgc    3000
aagcagcaga ttacgcgcag aaaaaaagga tctcaagaag atcctttgat cttttctacg    3060
gggtctgacg ctcagtggaa cgaaaactca cgttaaggga ttttggtcat gagattatca    3120
aaaaggatct tcacctagat ccttttaaat taaaaatgaa gttttaaatc aatctaaagt    3180
atatatgagt aaacttggtc tgacagttac caatgcttaa tcagtgaggc acctatctca    3240
gcgatctgtc tatttcgttc atccatagtt gcctgactcc ccgtcgtgta gataactacg    3300
atacgggagg gcttaccatc tggccccagt gctgcaatga taccgcgaga cccacgctca    3360
ccggctccag atttatcagc aataaaccag ccagccggaa gggccgagcg cagaagtggt    3420
cctgcaactt tatccgcctc catccagtct attaattgtt gccgggaagc tagagtaagt    3480
agttcgccag ttaatagttt gcgcaacgtt gttgccattg ctacaggcat cgtggtgtca    3540
cgctcgtcgt ttggtatggc ttcattcagc tccggttccc aacgatcaag gcgagttaca    3600
tgatccccca tgttgtgcaa aaaagcggtt agctccttcg gtcctccgat cgttgtcaga    3660
agtaagttgg ccgcagtgtt atcactcatg gttatggcag cactgcataa ttctcttact    3720
gtcatgccat ccgtaagatg cttttctgtg actggtgagt actcaaccaa gtcattctga    3780
gaatagtgta tgcggcgacc gagttgctct tgcccggcgt caatacggga taataccgcg    3840
ccacatagca gaactttaaa agtgctcatc attggaaaac gttcttcggg gcgaaaactc    3900
tcaaggatct taccgctgtt gagatccagt tcgatgtaac ccactcgtgc acccaactga    3960
tcttcagcat cttttacttt caccagcgtt tctgggtgag caaaaacagg aaggcaaaat    4020
gccgcaaaaa agggaataag ggcgacacgg aaatgttgaa tactcatact cttccttttt    4080
caatattatt gaagcattta tcagggttat tgtctcatga gcggatacat atttgaatgt    4140
atttagaaaa ataaacaaat aggggttccg cgcacatttc cccgaaaagt gccac         4195
```

<210> SEQ ID NO 99
<211> LENGTH: 824

```
<212> TYPE: DNA
<213> ORGANISM: Artificial Sequence
<220> FEATURE:
<223> OTHER INFORMATION: Artificial Construct

<400> SEQUENCE: 99
gttaacgaat cccaccatg attgaacaag atggattgca cgcaggttct ccggccgctt      60
gggtggagag gctattcggc tatgactggg cacaacagac aatcggctgc tctgatgccg     120
ccgtgttccg gctgtcagcg caggggcgcc cggttctttt tgtcaagacc gacctgtccg     180
gtgccctgaa tgaactgcag gacgaggcag cgcggctatc gtggctggcc acgacgggcg     240
ttccttgcgc agctgtgctc gacgttgtca ctgaagcggg aagggactgg ctgctattgg     300
gcgaagtgcc ggggcaggat ctcctgtcat ctcaccttgc tcctgccgag aaagtatcca     360
tcatggctga tgcaatgcgg cggctgcata cgcttgatcc ggctacctgc ccattcgacc     420
accaagcgaa acatcgcatc gagcgagcac gtactcggat ggaagccggt cttgtcgatc     480
aggatgatct ggacgaagag catcaggggc tcgcgccagc cgaactgttc gccaggctca     540
aggcgcgcat gcccgacggc gaggatctcg tcgtgaccca tggcgatgcc tgcttgccga     600
atatcatggt ggaaaatggc cgcttttctg gattcatcga ctgtggccgg ctgggtgtgg     660
cggaccgcta tcaggacata gcgttggcta cccgtgatat tgctgaagag cttggcggcg     720
aatgggctga ccgcttcctc gtgctttacg gtatcgccgc tcccgattcg cagcgcatcg     780
ccttctatcg ccttcttgac gagttcttct gaagatctgt taac                      824

<210> SEQ ID NO 100
<211> LENGTH: 6739
<212> TYPE: DNA
<213> ORGANISM: Artificial Sequence
<220> FEATURE:
<223> OTHER INFORMATION: pCDNA3-TNR1B-Mth

<400> SEQUENCE: 100
gacggatcgg gagatctccc gatcccctat ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggag tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aaatgtcgta acaactccgc cccattgacg caaatgggcg     780
gtaggcgtgt acggtgggag gtctatataa gcagagctct ctggctaact agagaaccca     840
ctgcttactg gcttatcgaa attaatacga ctcactatag ggagacccaa gctggctagc     900
gtttaaactt aagcttgaat tcccaccatg gcgcccgtcg ccgtctgggc cgcgctggcc     960
gtcggactgg agctctgggc tgcggcgcac gccttgcccg cccaggtggc atttacaccc    1020
```

-continued

```
tacgccccgg agcccgggag cacatgccgg ctcagagaat actatgacca gacagctcag    1080
atgtgctgca gcaaatgctc gccgggccaa catgcaaaag tcttctgtac caagacctcg    1140
gacaccgtgt gtgactcctg tgaggacagc acatacaccc agctctggaa ctgggttccc    1200
gagtgcttga gctgtggctc ccgctgtagc tctgaccagg tggaaactca agcctgcact    1260
cgggaacaga accgcatctg cacctgcagg cccggctggt actgcgcgct gagcaagcag    1320
gaggggtgcc ggctgtgcgc gccgctgcgc aagtgccgcc cgggcttcgg cgtggccaga    1380
ccaggaactg aaacatcaga cgtggtgtgc aagccctgtg ccccggggac gttctccaac    1440
acgacttcat ccacggatat ttgcaggccc accagatct gtaacgtggt ggccatccct    1500
gggaatgcaa gcatggatgc agtctgcacg tccacgtccc ccacccggag tatggcccca    1560
ggggcagtac acttacccca gccagtgtcc cacgatccc aacacacgca gccaactcca     1620
gaacccagca ctgctccaag cacctccttc ctgctcccaa tggggccag cccccagct      1680
gaagggagca ctggcgacgg gtgcgtatcc ggtgacacca ttgtaatgac tagtggcggg    1740
ccccgcactg tggctgaact ggagggcaaa ccgttcaccg cactgattcg cggctctggc    1800
tacccatgcc cctcaggttt cttccgcacc tgtgaacgtg acgtatatga tctgcgtaca    1860
cgtgagggtc attgcttacg tttgacccat gatcaccgtg ttctggtgat ggatggtggc    1920
ctggaatggc gtgccgcggg tgaactggaa cgcggcgacc gcctggtgat ggatgatgca    1980
gctggcgagt ttccggcact ggcaaccttc cgtggcctgc gtggcgctgg ccgccaggat    2040
gtttatgacg ctactgttta cggtgctagc gcattcactg ctaatggctt cattgtacac    2100
gcatgtggcg agcagcccgg gaccggtctg aactcaggcc tcacgacaaa tcctggtgta    2160
tccgcttggc aggtcaacac agcttatact gcgggacaat tggtcacata taacggcaag    2220
acgtataaat gtttgcagcc ccacacctcc ttggcaggat gggaaccatc caacgttcct    2280
gccttgtggc agcttcaatg actcgagcgg cccgtttaaa cccgctgatc agcctcgact    2340
gtgccttcta gttgccagcc atctgttgtt tgccctccc ccgtgccttc cttgaccctg     2400
gaaggtgcca ctcccactgt cctttcctaa taaaatgagg aaattgcatc gcattgtctg    2460
agtaggtgtc attctattct ggggggtggg gtggggcagg acagcaaggg ggaggattgg    2520
gaagacaata gcaggcatgc tggggatgcg gtgggctcta tggcttctga ggcggaaaga    2580
accagctggg gctctagggg gtatccccac gcgccctgta gcggcgcatt aagcgcggcg    2640
ggtgtggtgg ttacgcgcag cgtgaccgct acacttgcca gcgccctagc gcccgctcct    2700
ttcgctttct tcccttcctt tctcgccacg ttcgccggct ttccccgtca agctctaaat    2760
cgggggctcc ctttagggtt ccgatttagt gctttacggc acctcgaccc caaaaaactt    2820
gattagggtg atggttcacg tagtgggcca tcgccctgat agacggtttt tcgccctttg    2880
acgttggagt ccacgttctt taatagtgga ctcttgttcc aaactggaac aacactcaac    2940
cctatctcgg tctattcttt tgatttataa gggattttgc cgatttcggc ctattggtta    3000
aaaaatgagc tgatttaaca aaaatttaac gcgaattaat tctgtggaat gtgtgtcagt    3060
tagggtgtgg aaagtcccca ggctcccag caggcagaag tatgcaaagc atgcatctca     3120
attagtcagc aaccaggtgt ggaaagtccc caggctcccc agcaggcaga agtatgcaaa    3180
gcatgcatct caattagtca gcaaccatag tcccgcccct aactccgccc atcccgcccc    3240
taactccgcc cagttccgcc cattctccgc cccatggctg actaattttt tttatttatg    3300
cagaggccga ggccgcctct gcctctgagc tattccagaa gtagtgagga ggcttttttg    3360
gaggcctagg cttttgcaaa aagctcccgg gagcttgtat atccattttc ggatctgatc    3420
```

```
aagagacagg atgaggatcg tttcgcatga ttgaacaaga tggattgcac gcaggttctc    3480
cggccgcttg ggtggagagg ctattcggct atgactgggc acaacagaca atcggctgct    3540
ctgatgccgc cgtgttccgg ctgtcagcgc aggggcgccc ggttctttt gtcaagaccg     3600 acctgtccgg tgccctgaat gaactgcagg acgaggcagc gcggctatcg tggctggcca    3660
cgacgggcgt tccttgcgca gctgtgctcg acgttgtcac tgaagcggga agggactggc    3720
tgctattggg cgaagtgccg gggcaggatc tcctgtcatc tcaccttgct cctgccgaga    3780
aagtatccat catggctgat gcaatgcggc ggctgcatac gcttgatccg gctacctgcc    3840
cattcgacca ccaagcgaaa catcgcatcg agcgagcacg tactcggatg aagccggtc     3900 ttgtcgatca ggatgatctg gacgaagagc atcaggggct cgcgccagcc gaactgttcg    3960
ccaggctcaa ggcgcgcatg cccgacggcg aggatctcgt cgtgacccat ggcgatgcct    4020
gcttgccgaa tatcatggtg gaaaatggcc gcttttctgg attcatcgac tgtggccggc    4080
tgggtgtggc ggaccgctat caggacatag cgttggctac ccgtgatatt gctgaagagc    4140
ttggcggcga atgggctgac cgcttcctcg tgctttacgg tatcgccgct cccgattcgc    4200
agcgcatcgc cttctatcgc cttcttgacg agttcttctg agcgggactc tggggttcga    4260
aatgaccgac caagcgacgc ccaacctgcc atcacgagat tcgattcca ccgccgcctt     4320 ctatgaaagg ttgggcttcg gaatcgtttt ccgggacgcc ggctggatga tcctccagcg    4380
cggggatctc atgctggagt tcttcgccca ccccaacttg tttattgcag cttataatgg    4440
ttacaaataa agcaatagca tcacaaattt cacaaataaa gcatttttt cactgcattc     4500 tagttgtggt ttgtccaaac tcatcaatgt atcttatcat gtctgtatac cgtcgacctc    4560
tagctagagc ttggcgtaat catggtcata gctgtttcct gtgtgaaatt gttatccgct    4620
cacaattcca cacaacatac gagccggaag cataaagtgt aaagcctggg gtgcctaatg    4680
agtgagctaa ctcacattaa ttgcgttgcg ctcactgccc gctttccagt cgggaaacct    4740
gtcgtgccag ctgcattaat gaatcggcca acgcgcgggg agaggcggtt tgcgtattgg    4800
gcgctcttcc gcttcctcgc tcactgactc gctgcgctcg tcgttcggc tgcggcgagc     4860 ggtatcagct cactcaaagg cggtaatacg gttatccaca gaatcagggg ataacgcagg    4920
aaagaacatg tgagcaaaag gccagcaaaa ggccaggaac cgtaaaaagg ccgcgttgct    4980
ggcgtttttc cataggctcc gcccccctga cgagcatcac aaaaatcgac gctcaagtca    5040
gaggtggcga aacccgacag gactataaag ataccaggcg tttccccctg gaagctccct    5100
cgtgcgctct cctgttccga ccctgccgct taccggatac ctgtccgcct ttctcccttc    5160
gggaagcgtg gcgctttctc atagctcacg ctgtaggtat ctcagttcgg tgtaggtcgt    5220
tcgctccaag ctgggctgtg tgcacgaacc ccccgttcag cccgaccgct gcgccttatc    5280
cggtaactat cgtcttgagt ccaacccggt aagacacgac ttatcgccac tggcagcagc    5340
cactggtaac aggattagca gagcgaggta tgtaggcggt gctacagagt tcttgaagtg    5400
gtggcctaac tacggctaca ctagaagaac agtatttggt atctgcgctc tgctgaagcc    5460
agttaccttc ggaaaaagag ttggtagctc ttgatccggc aaacaaacca ccgctggtag    5520 cggtttttt gtttgcaagc agcagattac gcgcagaaaa aaggatctc aagaagatcc      5580 tttgatcttt tctacggggt ctgacgctca gtggaacgaa aactcacgtt aagggatttt    5640
ggtcatgaga ttatcaaaaa ggatcttcac ctagatcctt ttaaattaaa aatgaagttt    5700
taaatcaatc taaagtatat atgagtaaac ttggtctgac agttaccaat gcttaatcag    5760
```

-continued

```
tgaggcacct atctcagcga tctgtctatt tcgttcatcc atagttgcct gactccccgt    5820
cgtgtagata actacgatac gggagggctt accatctggc cccagtgctg caatgatacc    5880
gcgagaccca cgctcaccgg ctccagattt atcagcaata aaccagccag ccggaagggc    5940
cgagcgcaga agtggtcctg caactttatc cgcctccatc cagtctatta attgttgccg    6000
ggaagctaga gtaagtagtt cgccagttaa tagtttgcgc aacgttgttg ccattgctac    6060
aggcatcgtg gtgtcacgct cgtcgtttgg tatggcttca ttcagctccg gttcccaacg    6120
atcaaggcga gttacatgat cccccatgtt gtgcaaaaaa gcggttagct ccttcggtcc    6180
tccgatcgtt gtcagaagta agttggccgc agtgttatca ctcatggtta tggcagcact    6240
gcataattct cttactgtca tgccatccgt aagatgcttt tctgtgactg gtgagtactc    6300
aaccaagtca ttctgagaat agtgtatgcg gcgaccgagt tgctcttgcc cggcgtcaat    6360
acgggataat accgcgccac atagcagaac tttaaaagtg ctcatcattg gaaaacgttc    6420
ttcggggcga aaactctcaa ggatcttacc gctgttgaga tccagttcga tgtaacccac    6480
tcgtgcaccc aactgatctt cagcatcttt tactttcacc agcgtttctg ggtgagcaaa    6540
aacaggaagg caaaatgccg caaaaaaggg aataagggcg acacggaaat gttgaatact    6600
catactcttc ctttttcaat attattgaag catttatcag ggttattgtc tcatgagcgg    6660
atacatattt gaatgtattt agaaaaataa acaataggg gttccgcgca catttccccg     6720
aaaagtgcca cctgacgtc                                                 6739
```

<210> SEQ ID NO 101
<211> LENGTH: 457
<212> TYPE: PRT
<213> ORGANISM: Artificial Sequence
<220> FEATURE:
<223> OTHER INFORMATION: pre-TNR1B-intein chimeric polypeptide
<400> SEQUENCE: 101

```
Met Ala Pro Val Ala Val Trp Ala Ala Leu Ala Val Gly Leu Glu Leu
1               5                   10                  15

Trp Ala Ala Ala His Ala Leu Pro Ala Gln Val Ala Phe Thr Pro Tyr
            20                  25                  30

Ala Pro Glu Pro Gly Ser Thr Cys Arg Leu Arg Glu Tyr Tyr Asp Gln
        35                  40                  45

Thr Ala Gln Met Cys Cys Ser Lys Cys Ser Pro Gly Gln His Ala Lys
    50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Trp Val Pro Glu Cys Leu Ser Cys
                85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
        115                 120                 125

Ser Lys Gln Glu Gly Cys Arg Leu Cys Ala Pro Leu Arg Lys Cys Arg
    130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180                 185                 190
```

Asn Ala Ser Met Asp Ala Val Cys Thr Ser Thr Ser Pro Thr Arg Ser
        195                 200                 205

Met Ala Pro Gly Ala Val His Leu Pro Gln Pro Val Ser Thr Arg Ser
    210                 215                 220

Gln His Thr Gln Pro Thr Pro Glu Pro Ser Thr Ala Pro Ser Thr Ser
225                 230                 235                 240

Phe Leu Leu Pro Met Gly Pro Ser Pro Ala Glu Gly Ser Thr Gly
                245                 250                 255

Asp Gly Cys Val Ser Gly Asp Thr Ile Val Met Thr Ser Gly Gly Pro
                260                 265                 270

Arg Thr Val Ala Glu Leu Glu Gly Lys Pro Phe Thr Ala Leu Ile Arg
                275                 280                 285

Gly Ser Gly Tyr Pro Cys Pro Ser Gly Phe Phe Arg Thr Cys Glu Arg
                290                 295                 300

Asp Val Tyr Asp Leu Arg Thr Arg Glu Gly His Cys Leu Arg Leu Thr
305                 310                 315                 320

His Asp His Arg Val Leu Val Met Asp Gly Leu Glu Trp Arg Ala
                325                 330                 335

Ala Gly Glu Leu Glu Arg Gly Asp Arg Leu Val Met Asp Ala Ala
                340                 345                 350

Gly Glu Phe Pro Ala Leu Ala Thr Phe Arg Gly Leu Arg Gly Ala Gly
                355                 360                 365

Arg Gln Asp Val Tyr Asp Ala Thr Val Tyr Gly Ala Ser Ala Phe Thr
    370                 375                 380

Ala Asn Gly Phe Ile Val His Ala Cys Gly Glu Gln Pro Gly Thr Gly
385                 390                 395                 400

Leu Asn Ser Gly Leu Thr Thr Asn Pro Gly Val Ser Ala Trp Gln Val
                405                 410                 415

Asn Thr Ala Tyr Thr Ala Gly Gln Leu Val Thr Tyr Asn Gly Lys Thr
                420                 425                 430

Tyr Lys Cys Leu Gln Pro His Thr Ser Leu Ala Gly Trp Glu Pro Ser
                435                 440                 445

Asn Val Pro Ala Leu Trp Gln Leu Gln
    450                 455

<210> SEQ ID NO 102
<211> LENGTH: 435
<212> TYPE: PRT
<213> ORGANISM: Artificial Sequence
<220> FEATURE:
<223> OTHER INFORMATION: mature TNR1B-intein fusion protein

<400> SEQUENCE: 102

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
                20                  25                  30

Ser Lys Cys Ser Pro Gly Gln His Ala Lys Val Phe Cys Thr Lys Thr
                35                  40                  45

Ser Asp Thr Val Cys Asp Ser Cys Glu Asp Ser Thr Tyr Thr Gln Leu
            50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
            115                 120                 125

Arg Pro Gly Thr Glu Thr Ser Asp Val Val Cys Lys Pro Cys Ala Pro
130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
            165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
            195                 200                 205

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp Gly Cys Val Ser Gly
225                 230                 235                 240

Asp Thr Ile Val Met Thr Ser Gly Gly Pro Arg Thr Val Ala Glu Leu
            245                 250                 255

Glu Gly Lys Pro Phe Thr Ala Leu Ile Arg Gly Ser Gly Tyr Pro Cys
            260                 265                 270

Pro Ser Gly Phe Phe Arg Thr Cys Glu Arg Asp Val Tyr Asp Leu Arg
    275                 280                 285

Thr Arg Glu Gly His Cys Leu Arg Leu Thr His Asp His Arg Val Leu
    290                 295                 300

Val Met Asp Gly Gly Leu Glu Trp Arg Ala Ala Gly Glu Leu Glu Arg
305                 310                 315                 320

Gly Asp Arg Leu Val Met Asp Ala Ala Gly Glu Phe Pro Ala Leu
            325                 330                 335

Ala Thr Phe Arg Gly Leu Arg Gly Ala Gly Arg Gln Asp Val Tyr Asp
            340                 345                 350

Ala Thr Val Tyr Gly Ala Ser Ala Phe Thr Ala Asn Gly Phe Ile Val
            355                 360                 365

His Ala Cys Gly Glu Gln Pro Gly Thr Gly Leu Asn Ser Gly Leu Thr
    370                 375                 380

Thr Asn Pro Gly Val Ser Ala Trp Gln Val Asn Thr Ala Tyr Thr Ala
385                 390                 395                 400

Gly Gln Leu Val Thr Tyr Asn Gly Lys Thr Tyr Lys Cys Leu Gln Pro
            405                 410                 415

His Thr Ser Leu Ala Gly Trp Glu Pro Ser Asn Val Pro Ala Leu Trp
            420                 425                 430

Gln Leu Gln
    435

<210> SEQ ID NO 103
<211> LENGTH: 6103
<212> TYPE: DNA
<213> ORGANISM: Artificial Sequence
<220> FEATURE:
<223> OTHER INFORMATION: pCDNA3-SHH-IgG1-Fc11

<400> SEQUENCE: 103
gacggatcgg gagatctccc gatcccctat ggtgcactct cagtacaatc tgctctgatg    60

```
ccgcatagtt aagccagtat ctgctccctg cttgtgtgtt ggaggtcgct gagtagtgcg      120
cgagcaaaat ttaagctaca acaaggcaag gcttgaccga caattgcatg aagaatctgc      180
ttagggttag gcgttttgcg ctgcttcgcg atgtacgggc cagatatacg cgttgacatt      240
gattattgac tagttattaa tagtaatcaa ttacggggtc attagttcat agcccatata      300
tggagttccg cgttacataa cttacggtaa atggcccgcc tggctgaccg cccaacgacc      360
cccgcccatt gacgtcaata atgacgtatg ttcccatagt aacgccaata gggactttcc      420
attgacgtca atgggtggag tatttacggt aaactgccca cttggcagta catcaagtgt      480
atcatatgcc aagtacgccc cctattgacg tcaatgacgg taaatggccc gcctggcatt      540
atgcccagta catgacctta tgggactttc ctacttggca gtacatctac gtattagtca      600
tcgctattac catggtgatg cggttttggc agtacatcaa tgggcgtgga tagcggtttg      660
actcacgggg atttccaagt ctccacccca ttgacgtcaa tgggagtttg ttttggcacc      720
aaaatcaacg ggactttcca aaatgtcgta acaactccgc cccattgacg caaatgggcg      780
gtaggcgtgt acggtgggag gtctatataa gcagagctct ctggctaact agagaaccca      840
ctgcttactg gcttatcgaa attaatacga ctcactatag ggagacccaa gctggctagc      900
gtttaaactt aagcttgaat cccaccatgc tgctgctgg cgagatgtct gctgctagtc      960
ctcgtctcct cgctgctggt atgctcggga ctggcgtgcc caccgtgccc agcacctgaa     1020
ctcctggggg ggccctcagt cttcctcttc cccccaaaac ccaaggacac cctcatgatc     1080
tcccggaccc ctgaggtcac atgcgtggtg gtggacgtga gccacgaaga ccctgaggtc     1140
aagttcaact ggtacgtgga cggcgtggag gtgcataatg ccaagacaaa gccgcgggag     1200
gagcagtaca acagcacgta ccgtgtggtc agcgtcctca ccgtcctgca ccaggactgg     1260
ctgaatggca aggagtacaa gtgcaaggtc tccaacaaag cccctcccagc ccccatcgag     1320 aaaaccatct ccaaagccaa agggcagccc cgagaaccac aggtgtacac cctgcccca     1380 tcccgggatg agctgaccaa gaaccaggtc agcctgacct gcctggtcaa aggcttctat     1440
cccagcgaca tcgccgtgga gtgggagagc aatgggcagc cggagaacaa ctacaagacc     1500
acgcctcccg tgctggactc cgacggctcc ttcttcctct acagcaagct caccgtggac     1560
aagagcaggt ggcagcaggg gaacgtcttc tcatgctccg tgatgcatga ggctctgcac     1620
aaccactaca cgcagaagag cctctccctg tctccgggta aatgactcga gcggccgtt     1680 taaacccgct gatcagcctc gactgtgcct tctagttgcc agccatctgt tgtttgcccc     1740
tcccccgtgc cttccttgac cctggaaggt gccactccca ctgtcctttc ctaataaaat     1800
gaggaaattg catcgcattg tctgagtagg tgtcattcta ttctgggggg tggggtgggg     1860
caggacagca agggggagga ttgggaagac aatagcaggc atgctgggga tgcggtgggc     1920
tctatggctt ctgaggcgga agaaccagc tggggctcta gggggtatcc ccacgcgccc     1980
tgtagcggcg cattaagcgc ggcgggtgtg tggttacgc gcagcgtgac cgctacactt     2040
gccagcgccc tagcgcccgc tcctttcgct ttcttccctt cctttctcgc cacgttcgcc     2100
ggctttcccc gtcaagctct aaatcggggg ctcccttag ggttccgatt tagtgcttta     2160
cggcacctcg accccaaaaa acttgattag ggtgatggtt cacgtagtgg gccatcgccc     2220
tgatagacgg ttttcgccc tttgacgttg gagtccacgt tctttaatag tggactcttg     2280
ttccaaactg gaacaacact caaccctatc tcggtctatt cttttgattt ataagggatt     2340
ttgccgattt cggcctattg gttaaaaaat gagctgattt aacaaaaatt taacgcgaat     2400
taattctgtg gaatgtgtgt cagttagggt gtggaaagtc cccaggctcc ccagcaggca     2460
```

| | |
|---|---|
| gaagtatgca aagcatgcat ctcaattagt cagcaaccag gtgtggaaag tccccaggct | 2520 |
| ccccagcagg cagaagtatg caaagcatgc atctcaatta gtcagcaacc atagtcccgc | 2580 |
| ccctaactcc gcccatcccg cccctaactc cgcccagttc cgcccattct ccgccccatg | 2640 |
| gctgactaat ttttttatt tatgcagagg ccgaggccgc ctctgcctct gagctattcc | 2700 |
| agaagtagtg aggaggcttt tttggaggcc taggcttttg caaaaagctc ccgggagctt | 2760 |
| gtatatccat tttcggatct gatcaagaga caggatgagg atcgtttcgc atgattgaac | 2820 |
| aagatggatt gcacgcaggt tctccggccg cttgggtgga gaggctattc ggctatgact | 2880 |
| gggcacaaca gacaatcggc tgctctgatg ccgccgtgtt ccggctgtca gcgcaggggc | 2940 |
| gcccggttct ttttgtcaag accgacctgt ccggtgccct gaatgaactg caggacgagg | 3000 |
| cagcgcggct atcgtggctg gccacgacgg gcgttccttg cgcagctgtg ctcgacgttg | 3060 |
| tcactgaagc gggaagggac tggctgctat tgggcgaagt gccggggcag gatctcctgt | 3120 |
| catctcacct tgctcctgcc gagaaagtat ccatcatggc tgatgcaatg cggcggctgc | 3180 |
| atacgcttga tccggctacc tgcccattcg accaccaagc gaaacatcgc atcgagcgag | 3240 |
| cacgtactcg gatggaagcc ggtcttgtcg atcaggatga tctggacgaa gagcatcagg | 3300 |
| ggctcgcgcc agccgaactg ttcgccaggc tcaaggcgcg catgcccgac ggcgaggatc | 3360 |
| tcgtcgtgac ccatggcgat gcctgcttgc cgaatatcat ggtggaaaat ggccgctttt | 3420 |
| ctggattcat cgactgtggc cggctgggtg tggcggaccg ctatcaggac atagcgttgg | 3480 |
| ctacccgtga tattgctgaa gagcttggcg gcgaatgggc tgaccgcttc ctcgtgcttt | 3540 |
| acggtatcgc cgctcccgat tcgcagcgca tcgccttcta tcgccttctt gacgagttct | 3600 |
| tctgagcggg actctggggt tcgaaatgac cgaccaagcg acgcccaacc tgccatcacg | 3660 |
| agatttcgat tccaccgccg ccttctatga aggttgggc ttcggaatcg ttttccggga | 3720 |
| cgccggctgg atgatcctcc agcgcgggga tctcatgctg gagttcttcg ccacccccaa | 3780 |
| cttgtttatt gcagcttata atggttacaa ataaagcaat agcatcacaa atttcacaaa | 3840 |
| taaagcattt ttttcactgc attctagttg tggtttgtcc aaactcatca atgtatctta | 3900 |
| tcatgtctgt ataccgtcga cctctagcta gagcttggcg taatcatggt catagctgtt | 3960 |
| tcctgtgtga aattgttatc cgctcacaat tccacacaac atacgagccg aagcataaa | 4020 |
| gtgtaaagcc tggggtgcct aatgagtgag ctaactcaca ttaattgcgt tgcgctcact | 4080 |
| gcccgctttc cagtcgggaa acctgtcgtg ccagctgcat taatgaatcg gccaacgcgc | 4140 |
| ggggagaggc ggtttgcgta ttgggcgctc ttccgcttcc tcgctcactg actcgctgcg | 4200 |
| ctcggtcgtt cggctgcggc gagcggtatc agctcactca aaggcggtaa tacggttatc | 4260 |
| cacagaatca ggggataacg caggaaagaa catgtgagca aaaggccagc aaaaggccag | 4320 |
| gaaccgtaaa aaggccgcgt tgctggcgtt tttccatagg ctccgccccc ctgacgagca | 4380 |
| tcacaaaaat cgacgctcaa gtcagaggtg gcgaaacccg acaggactat aaagatacca | 4440 |
| ggcgtttccc cctggaagct ccctcgtgcg ctctcctgtt ccgaccctgc cgcttaccgg | 4500 |
| atacctgtcc gcctttctcc cttcgggaag cgtggcgctt tctcatagct cacgctgtag | 4560 |
| gtatctcagt tcggtgtagg tcgttcgctc caagctgggc tgtgtgcacg aaccccccgt | 4620 |
| tcagcccgac cgctgcgcct tatccggtaa ctatcgtctt gagtccaacc cggtaagaca | 4680 |
| cgacttatcg ccactggcag cagccactgg taacaggatt agcagagcga ggtatgtagg | 4740 |
| cggtgctaca gagttcttga agtggtggcc taactacggc tacactagaa gaacagtatt | 4800 |

```
tggtatctgc gctctgctga agccagttac cttcggaaaa agagttggta gctcttgatc    4860
cggcaaacaa accaccgctg gtagcggttt ttttgtttgc aagcagcaga ttacgcgcag    4920
aaaaaaagga tctcaagaag atcctttgat cttttctacg gggtctgacg ctcagtggaa    4980
cgaaaactca cgttaaggga ttttggtcat gagattatca aaaaggatct tcacctagat    5040
ccttttaaat taaaaatgaa gttttaaatc aatctaaagt atatatgagt aaacttggtc    5100
tgacagttac caatgcttaa tcagtgaggc acctatctca gcgatctgtc tatttcgttc    5160
atccatagtt gcctgactcc ccgtcgtgta gataactacg atacgggagg gcttaccatc    5220
tggccccagt gctgcaatga taccgcgaga cccacgctca ccggctccag atttatcagc    5280
aataaaccag ccagccggaa gggccgagcg cagaagtggt cctgcaactt tatccgcctc    5340
catccagtct attaattgtt gccgggaagc tagagtaagt agttcgccag ttaatagttt    5400
gcgcaacgtt gttgccattg ctacaggcat cgtggtgtca cgctcgtcgt ttggtatggc    5460
ttcattcagc tccggttccc aacgatcaag gcgagttaca tgatccccca tgttgtgcaa    5520
aaaagcggtt agctccttcg gtcctccgat cgttgtcaga agtaagttgg ccgcagtgtt    5580
atcactcatg gttatggcag cactgcataa ttctcttact gtcatgccat ccgtaagatg    5640
cttttctgtg actggtgagt actcaaccaa gtcattctga atagtgta tgcggcgacc    5700 gagttgctct tgcccggcgt caatacggga taataccgcg ccacatagca gaactttaaa    5760
agtgctcatc attggaaaac gttcttcggg gcgaaaactc tcaaggatct taccgctgtt    5820
gagatccagt tcgatgtaac ccactcgtgc acccaactga tcttcagcat cttttacttt    5880
caccagcgtt tctgggtgag caaaaacagg aaggcaaaat gccgcaaaaa agggaataag    5940
ggcgacacgg aaatgttgaa tactcatact cttccttttt caatattatt gaagcattta    6000
tcagggttat tgtctcatga gcggatacat atttgaatgt atttagaaaa ataaacaaat    6060 agggggttccg cgcacatttc cccgaaaagt gccacctgac gtc    6103
```

<210> SEQ ID NO 104
<211> LENGTH: 245
<212> TYPE: PRT
<213> ORGANISM: Artificial Sequence
<220> FEATURE:
<223> OTHER INFORMATION: pre-Fc6 polypeptide

<400> SEQUENCE: 104

```
Met Leu Leu Leu Ala Arg Cys Leu Leu Leu Val Leu Val Ser Ser Leu
1               5                   10                  15

Leu Val Cys Ser Gly Leu Ala Cys Pro Pro Cys Pro Ala Pro Glu Leu
            20                  25                  30

Leu Gly Gly Pro Ser Val Phe Leu Phe Pro Pro Lys Pro Lys Asp Thr
        35                  40                  45

Leu Met Ile Ser Arg Thr Pro Glu Val Thr Cys Val Val Val Asp Val
    50                  55                  60

Ser His Glu Asp Pro Glu Val Lys Phe Asn Trp Tyr Val Asp Gly Val
65                  70                  75                  80

Glu Val His Asn Ala Lys Thr Lys Pro Arg Glu Glu Gln Tyr Asn Ser
                85                  90                  95

Thr Tyr Arg Val Val Ser Val Leu Thr Val Leu His Gln Asp Trp Leu
            100                 105                 110

Asn Gly Lys Glu Tyr Lys Cys Lys Val Ser Asn Lys Ala Leu Pro Ala
        115                 120                 125

Pro Ile Glu Lys Thr Ile Ser Lys Ala Lys Gly Gln Pro Arg Glu Pro
```

```
            130                 135                 140
Gln Val Tyr Thr Leu Pro Pro Ser Arg Asp Glu Leu Thr Lys Asn Gln
145                 150                 155                 160

Val Ser Leu Thr Cys Leu Val Lys Gly Phe Tyr Pro Ser Asp Ile Ala
                165                 170                 175

Val Glu Trp Glu Ser Asn Gly Gln Pro Glu Asn Asn Tyr Lys Thr Thr
            180                 185                 190

Pro Pro Val Leu Asp Ser Asp Gly Ser Phe Phe Leu Tyr Ser Lys Leu
            195                 200                 205

Thr Val Asp Lys Ser Arg Trp Gln Gln Gly Asn Val Phe Ser Cys Ser
        210                 215                 220

Val Met His Glu Ala Leu His Asn His Tyr Thr Gln Lys Ser Leu Ser
225                 230                 235                 240

Leu Ser Pro Gly Lys
                245

<210> SEQ ID NO 105
<211> LENGTH: 222
<212> TYPE: PRT
<213> ORGANISM: Artificial Sequence
<220> FEATURE:
<223> OTHER INFORMATION: mature Fc6 protein

<400> SEQUENCE: 105

Cys Pro Pro Cys Pro Ala Pro Glu Leu Leu Gly Gly Pro Ser Val Phe
1               5                   10                  15

Leu Phe Pro Pro Lys Pro Lys Asp Thr Leu Met Ile Ser Arg Thr Pro
                20                  25                  30

Glu Val Thr Cys Val Val Val Asp Val Ser His Glu Asp Pro Glu Val
            35                  40                  45

Lys Phe Asn Trp Tyr Val Asp Gly Val Glu Val His Asn Ala Lys Thr
        50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Arg Asp Glu Leu Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly Lys
    210                 215                 220

<210> SEQ ID NO 106
<211> LENGTH: 237
<212> TYPE: PRT
```

```
<213> ORGANISM: Artificial Sequence
<220> FEATURE:
<223> OTHER INFORMATION: cleaved alkyne-modified TNR1B
<220> FEATURE:
<221> NAME/KEY: Xaa
<222> LOCATION: (237)..(237)
<223> OTHER INFORMATION: cysteine-alkyne

<400> SEQUENCE: 106

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
    130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp Gly Xaa
225                 230                 235

<210> SEQ ID NO 107
<211> LENGTH: 237
<212> TYPE: PRT
<213> ORGANISM: Artificial Sequence
<220> FEATURE:
<223> OTHER INFORMATION: azide-modified TNR1B protein
<220> FEATURE:
<221> NAME/KEY: Xaa
<222> LOCATION: (237)..(237)
<223> OTHER INFORMATION: cysteine-azide

<400> SEQUENCE: 107

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
```

```
            50                  55                  60
Trp Asn Trp Val Pro Glu Cys Leu Ser Cys Gly Ser Arg Cys Ser Ser
 65                  70                  75                  80

Asp Gln Val Glu Thr Gln Ala Cys Thr Arg Glu Gln Asn Arg Ile Cys
                     85                  90                  95

Thr Cys Arg Pro Gly Trp Tyr Cys Ala Leu Ser Lys Gln Glu Gly Cys
                100                 105                 110

Arg Leu Cys Ala Pro Leu Arg Lys Cys Arg Pro Gly Phe Gly Val Ala
            115                 120                 125

Arg Pro Gly Thr Glu Thr Ser Asp Val Val Cys Lys Pro Cys Ala Pro
        130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp Gly Xaa
225                 230                 235
```

<210> SEQ ID NO 108
<211> LENGTH: 237
<212> TYPE: PRT
<213> ORGANISM: Artificial Sequence
<220> FEATURE:
<223> OTHER INFORMATION: cysteine-modified TNR1B

<400> SEQUENCE: 108

```
Leu Pro Ala Gln Val Ala Phe Thr Pro Tyr Ala Pro Glu Pro Gly Ser
  1               5                  10                  15

Thr Cys Arg Leu Arg Glu Tyr Tyr Asp Gln Thr Ala Gln Met Cys Cys
                 20                  25                  30

Ser Lys Cys Ser Pro Gly Gln His Ala Lys Val Phe Cys Thr Lys Thr
             35                  40                  45

Ser Asp Thr Val Cys Asp Ser Cys Glu Asp Ser Thr Tyr Thr Gln Leu
 50                  55                  60

Trp Asn Trp Val Pro Glu Cys Leu Ser Cys Gly Ser Arg Cys Ser Ser
 65                  70                  75                  80

Asp Gln Val Glu Thr Gln Ala Cys Thr Arg Glu Gln Asn Arg Ile Cys
                     85                  90                  95

Thr Cys Arg Pro Gly Trp Tyr Cys Ala Leu Ser Lys Gln Glu Gly Cys
                100                 105                 110

Arg Leu Cys Ala Pro Leu Arg Lys Cys Arg Pro Gly Phe Gly Val Ala
            115                 120                 125

Arg Pro Gly Thr Glu Thr Ser Asp Val Val Cys Lys Pro Cys Ala Pro
        130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
```

```
                    180                 185                 190

His Leu Pro Gln Pro Val Ser Thr Arg Ser Gln His Thr Gln Pro Thr
            195                 200                 205

Pro Glu Pro Ser Thr Ala Pro Ser Thr Ser Phe Leu Leu Pro Met Gly
        210                 215                 220

Pro Ser Pro Pro Ala Glu Gly Ser Thr Gly Asp Gly Cys
225                 230                 235

<210> SEQ ID NO 109
<211> LENGTH: 236
<212> TYPE: PRT
<213> ORGANISM: Artificial Sequence
<220> FEATURE:
<223> OTHER INFORMATION: thioester-modified TNR1B
<220> FEATURE:
<221> NAME/KEY: Xaa
<222> LOCATION: (236)..(236)
<223> OTHER INFORMATION: glycine-thioester

<400> SEQUENCE: 109

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
    130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp Xaa
225                 230                 235

<210> SEQ ID NO 110
<211> LENGTH: 227
<212> TYPE: PRT
<213> ORGANISM: Artificial Sequence
<220> FEATURE:
<223> OTHER INFORMATION: Az-DKTHT-Fc6 protein
<220> FEATURE:
<221> NAME/KEY: Xaa
```

<222> LOCATION: (1)..(1)
<223> OTHER INFORMATION: azide-aspartic acid

<400> SEQUENCE: 110

Xaa Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 111
<211> LENGTH: 227
<212> TYPE: PRT
<213> ORGANISM: Artificial Sequence
<220> FEATURE:
<223> OTHER INFORMATION: Az-PEG4-DKTHT-Fc6
<220> FEATURE:
<221> NAME/KEY: Xaa
<222> LOCATION: (1)..(1)
<223> OTHER INFORMATION: zide-PEG4-aspartic acid

<400> SEQUENCE: 111

Xaa Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

```
Arg Val Val Ser Val Leu Thr Val Leu His Gln Asp Trp Leu Asn Gly
                85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
            115                 120                 125
Tyr Thr Leu Pro Pro Ser Arg Asp Glu Leu Thr Lys Asn Gln Val Ser
            130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
            180                 185                 190
Asp Lys Ser Arg Trp Gln Gln Gly Asn Val Phe Ser Cys Ser Val Met
            195                 200                 205
His Glu Ala Leu His Asn His Tyr Thr Gln Lys Ser Leu Ser Leu Ser
    210                 215                 220
Pro Gly Lys
225

<210> SEQ ID NO 112
<211> LENGTH: 190
<212> TYPE: PRT
<213> ORGANISM: Artificial Sequence
<220> FEATURE:
<223> OTHER INFORMATION: Polypeptide with internal non-peptidyl moiety.
      TNR1B-alkyne-azide-Fc6

<400> SEQUENCE: 112

Leu Pro Ala Gln Val Ala Phe Thr Pro Tyr Ala Pro Glu Pro Gly Ser
1               5                   10                  15
Thr Cys Arg Leu Arg Glu Tyr Tyr Asp Gln Thr Ala Gln Met Cys Cys
            20                  25                  30
Ser Lys Cys Ser Pro Gly Gln His Ala Lys Val Phe Cys Thr Lys Thr
            35                  40                  45
Ser Asp Thr Val Cys Asp Ser Cys Glu Asp Ser Thr Tyr Thr Gln Leu
    50                  55                  60
Trp Asn Trp Val Pro Glu Cys Leu Ser Cys Gly Ser Arg Cys Ser Ser
65                  70                  75                  80
Asp Gln Val Glu Thr Gln Ala Cys Thr Arg Glu Gln Asn Arg Ile Cys
                85                  90                  95
Thr Cys Arg Pro Gly Trp Tyr Cys Ala Leu Ser Lys Gln Glu Gly Cys
            100                 105                 110
Arg Leu Cys Ala Pro Leu Arg Lys Cys Arg Pro Gly Phe Gly Val Ala
            115                 120                 125
Arg Pro Gly Thr Glu Thr Ser Asp Val Val Cys Lys Pro Cys Ala Pro
            130                 135                 140
Gly Thr Phe Ser Asn Thr Thr Ser Ser Thr Asp Ile Cys Arg Pro His
145                 150                 155                 160
Gln Ile Cys Asn Val Val Ala Ile Pro Gly Asn Ala Ser Met Asp Ala
                165                 170                 175
Val Cys Thr Ser Thr Ser Pro Thr Arg Ser Met Ala Pro Gly
            180                 185                 190

<210> SEQ ID NO 113
```

<211> LENGTH: 275
<212> TYPE: PRT
<213> ORGANISM: Artificial Sequence
<220> FEATURE:
<223> OTHER INFORMATION: Polypeptide with internal non-peptidyl moiety.
      TNR1B-alkyne-azide-PEG4-Fc6
<220> FEATURE:
<221> NAME/KEY: misc_feature
<222> LOCATION: (48)..(48)
<223> OTHER INFORMATION: Xaa can be any naturally occurring amino acid

<400> SEQUENCE: 113

Ala Val His Leu Pro Gln Pro Val Ser Thr Arg Ser Gln His Thr Gln
1               5                   10                  15

Pro Thr Pro Glu Pro Ser Thr Ala Pro Ser Thr Ser Phe Leu Leu Pro
            20                  25                  30

Met Gly Pro Ser Pro Pro Ala Glu Gly Ser Thr Gly Asp Gly Cys Xaa
        35                  40                  45

Asp Lys Thr His Thr Cys Pro Pro Cys Pro Ala Pro Glu Leu Leu Gly
    50                  55                  60

Gly Pro Ser Val Phe Leu Phe Pro Pro Lys Pro Lys Asp Thr Leu Met
65                  70                  75                  80

Ile Ser Arg Thr Pro Glu Val Thr Cys Val Val Val Asp Val Ser His
                85                  90                  95

Glu Asp Pro Glu Val Lys Phe Asn Trp Tyr Val Asp Gly Val Glu Val
            100                 105                 110

His Asn Ala Lys Thr Lys Pro Arg Glu Glu Gln Tyr Asn Ser Thr Tyr
        115                 120                 125

Arg Val Val Ser Val Leu Thr Val Leu His Gln Asp Trp Leu Asn Gly
    130                 135                 140

Lys Glu Tyr Lys Cys Lys Val Ser Asn Lys Ala Leu Pro Ala Pro Ile
145                 150                 155                 160

Glu Lys Thr Ile Ser Lys Ala Lys Gly Gln Pro Arg Glu Pro Gln Val
                165                 170                 175

Tyr Thr Leu Pro Pro Ser Arg Asp Glu Leu Thr Lys Asn Gln Val Ser
            180                 185                 190

Leu Thr Cys Leu Val Lys Gly Phe Tyr Pro Ser Asp Ile Ala Val Glu
        195                 200                 205

Trp Glu Ser Asn Gly Gln Pro Glu Asn Asn Tyr Lys Thr Thr Pro Pro
    210                 215                 220

Val Leu Asp Ser Asp Gly Ser Phe Phe Leu Tyr Ser Lys Leu Thr Val
225                 230                 235                 240

Asp Lys Ser Arg Trp Gln Gln Gly Asn Val Phe Ser Cys Ser Val Met
                245                 250                 255

His Glu Ala Leu His Asn His Tyr Thr Gln Lys Ser Leu Ser Leu Ser
            260                 265                 270

Pro Gly Lys
        275

<210> SEQ ID NO 114
<211> LENGTH: 467
<212> TYPE: PRT
<213> ORGANISM: Artificial Sequence
<220> FEATURE:
<223> OTHER INFORMATION: Etanercept

<400> SEQUENCE: 114

Leu Pro Ala Gln Val Ala Phe Thr Pro Tyr Ala Pro Glu Pro Gly Ser
1               5                   10                  15

-continued

Thr Cys Arg Leu Arg Glu Tyr Tyr Asp Gln Thr Ala Gln Met Cys Cys
             20                  25                  30

Ser Lys Cys Ser Pro Gly Gln His Ala Lys Val Phe Cys Thr Lys Thr
         35                  40                  45

Ser Asp Thr Val Cys Asp Ser Cys Glu Asp Ser Thr Tyr Thr Gln Leu
 50                  55                  60

Trp Asn Trp Val Pro Glu Cys Leu Ser Cys Gly Ser Arg Cys Ser Ser
 65                  70                  75                  80

Asp Gln Val Glu Thr Gln Ala Cys Thr Arg Glu Gln Asn Arg Ile Cys
             85                  90                  95

Thr Cys Arg Pro Gly Trp Tyr Cys Ala Leu Ser Lys Gln Glu Gly Cys
             100                 105                 110

Arg Leu Cys Ala Pro Leu Arg Lys Cys Arg Pro Gly Phe Gly Val Ala
         115                 120                 125

Arg Pro Gly Thr Glu Thr Ser Asp Val Val Cys Lys Pro Cys Ala Pro
 130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
             165                 170                 175

Val Cys Thr Ser Thr Ser Pro Thr Arg Ser Met Ala Pro Gly Ala Val
         180                 185                 190

His Leu Pro Gln Pro Val Ser Thr Arg Ser Gln His Thr Gln Pro Thr
         195                 200                 205

Pro Glu Pro Ser Thr Ala Pro Ser Thr Ser Phe Leu Leu Pro Met Gly
 210                 215                 220

Pro Ser Pro Pro Ala Glu Gly Ser Thr Gly Asp Glu Pro Lys Ser Cys
225                 230                 235                 240

Asp Lys Thr His Thr Cys Pro Pro Cys Pro Ala Pro Glu Leu Leu Gly
             245                 250                 255

Gly Pro Ser Val Phe Leu Phe Pro Pro Lys Pro Lys Asp Thr Leu Met
         260                 265                 270

Ile Ser Arg Thr Pro Glu Val Thr Cys Val Val Val Asp Val Ser His
         275                 280                 285

Glu Asp Pro Glu Val Lys Phe Asn Trp Tyr Val Asp Gly Val Glu Val
 290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
             325                 330                 335

Lys Glu Tyr Lys Cys Lys Val Ser Asn Lys Ala Leu Pro Ala Pro Ile
         340                 345                 350

Glu Lys Thr Ile Ser Lys Ala Lys Gly Gln Pro Arg Glu Pro Gln Val
         355                 360                 365

Tyr Thr Leu Pro Pro Ser Arg Asp Glu Leu Thr Lys Asn Gln Val Ser
 370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
             405                 410                 415

Val Leu Asp Ser Asp Gly Ser Phe Phe Leu Tyr Ser Lys Leu Thr Val
         420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465

<210> SEQ ID NO 115
<211> LENGTH: 4175
<212> TYPE: DNA
<213> ORGANISM: Artificial Sequence
<220> FEATURE:
<223> OTHER INFORMATION: pFUSE2ss-DE27-V -CLIg-hk

<400> SEQUENCE: 115

| | | | | | |
|---|---|---|---|---|---|
| ggatctgcga | tcgctccggt | gcccgtcagt | gggcagagcg | cacatcgccc | acagtccccg | 60 |
| agaagttggg | gggaggggtc | ggcaattgaa | cgggtgccta | gagaaggtgg | cgcggggtaa | 120 |
| actgggaaag | tgatgtcgtg | tactggctcc | gccttttcc | cgagggtggg | ggagaaccgt | 180 |
| atataagtgc | agtagtcgcc | gtgaacgttc | tttttcgcaa | cgggtttgcc | gccagaacac | 240 |
| agctgaagct | cgaggggct | cgcatctctc | cttcacgcgc | ccgccgccct | acctgaggcc | 300 |
| gccatccacg | ccggttgagt | cgcgttctgc | cgcctcccgc | ctgtggtgcc | tcctgaactg | 360 |
| cgtccgccgt | ctaggtaagt | ttaaagctca | ggtcgagacc | gggcctttgt | ccggcgctcc | 420 |
| cttggagcct | acctagactc | agccggctct | ccacgctttg | cctgaccctg | cttgctcaac | 480 |
| tctacgtctt | tgtttcgttt | tctgttctgc | gccgttacag | atccaagctg | taccggcgc | 540 |
| ctacctgaga | tcaacatgta | caggatgcaa | ctcctgtctt | gcattgcact | aagtcttgca | 600 |
| cttgtcacga | attcagacat | ccagatgacc | cagtctccat | cctccctgtc | tgcatctgta | 660 |
| ggggacagag | tcaccatcac | ttgtcgggca | agtcagggca | tcagaaatta | cttagcctgg | 720 |
| tatcagcaaa | aaccagggaa | agcccctaag | ctcctgatct | atgctgcatc | cactttgcaa | 780 |
| tcaggggtcc | catctcggtt | cagtggcagt | ggatctggga | cagatttcac | tctcaccatc | 840 |
| agcagcctac | agcctgaaga | tgttgcaact | tattactgtc | aaaggtataa | ccgtgcaccg | 900 |
| tatactttg | gccagggac | caaggtggaa | atcaaacgta | cggtggctgc | accatctgtc | 960 |
| ttcatcttcc | cgccatctga | tgagcagttg | aaatctggaa | ctgcctctgt | tgtgtgcctg | 1020 |
| ctgaataact | tctatcccag | agaggccaaa | gtacagtgga | aggtggataa | cgccctccaa | 1080 |
| tcgggtaact | cccaggagag | tgtcacagag | caggacagca | aggacagcac | ctacagcctc | 1140 |
| agcagcaccc | tgacgctgag | caaagcagac | tacgagaaac | acaaagtcta | cgcctgcgaa | 1200 |
| gtcacccatc | agggcctgag | ctcgcccgtc | acaaagagct | tcaacagggg | agagtgttag | 1260 |
| agggagctag | ctcgacatga | taagatacat | tgatgagttt | ggacaaacca | caactagaat | 1320 |
| gcagtgaaaa | aaatgcttta | tttgtgaaat | ttgtgatgct | attgctttat | ttgtgaaatt | 1380 |
| tgtgatgcta | ttgctttatt | tgtaaccatt | ataagctgca | ataaacaagt | taacaacaac | 1440 |
| aattgcattc | attttatgtt | tcaggttcag | ggggaggtgt | gggaggtttt | ttaaagcaag | 1500 |
| taaaacctct | acaaatgtgg | tatggaatta | attctaaaat | acagcatagc | aaaactttaa | 1560 |
| cctccaaatc | aagcctctac | ttgaatcctt | ttctgaggga | tgaataaggc | ataggcatca | 1620 |
| ggggctgttg | ccaatgtgca | ttagctgttt | gcagcctcac | cttctttcat | ggagtttaag | 1680 |
| atatagtgta | ttttcccaag | gtttgaacta | gctcttcatt | tctttatgtt | ttaaatgcac | 1740 |
| tgacctccca | cattcccttt | ttagtaaaat | attcagaaat | aatttaaata | catcattgca | 1800 |

```
atgaaaataa atgttttta ttaggcagaa tccagatgct caaggccctt cataatatcc    1860
cccagtttag tagttggact tagggaacaa aggaaccttt aatagaaatt ggacagcaag    1920
aaagcgagct tctagcttta gttcctggtg tacttgaggg ggatgagttc ctcaatggtg    1980
gttttgacca gcttgccatt catctcaatg agcacaaagc agtcaggagc atagtcagag    2040
atgagctctc tgcacatgcc acaggggctg accaccctga tggatctgtc cacctcatca    2100
gagtaggggt gcctgacagc acaatggtgt caaagtcct tctgcccgtt gctcacagca     2160
gacccaatgg caatggcttc agcacagaca gtgaccctgc caatgtaggc ctcaatgtgg    2220
acagcagaga tgatctcccc agtcttggtc ctgatggccg ccccgacatg gtgcttgttg    2280
tcctcataga gcatggtgat cttctcagtg gcgacctcca ccagctccag atcctgctga    2340
gagatgttga aggtcttcat gatggctcct cctgtcagga gaggaaagag aagaaggtta    2400
gtacaattgc tatagtgagt tgtattatac tatgcttatg attaattgtc aaactagggc    2460
tgcagggttc atagtgccac tttcctgca ctgccccatc tcctgccac cctttcccag      2520
gcatagacag tcagtgactt accaaactca caggagggag aaggcagaag cttgagacag    2580
acccgcggga ccgccgaact gcgagggac gtggctaggg cggcttcttt tatggtgcgc     2640
cggccctcgg aggcagggcg ctcggggagg cctagcggcc aatctgcggt ggcaggaggc    2700
ggggccgaag gccgtgcctg accaatccgg agcacatagg agtctcagcc ccccgcccca    2760
aagcaagggg aagtcacgcg cctgtagcgc cagcgtgttg tgaaatgggg gcttgggggg    2820
gttggggccc tgactagtca aaacaaactc ccattgacgt caatggggtg gagacttgga    2880
aatccccgtg agtcaaaccg ctatccacgc ccattgatgt actgccaaaa ccgcatcatc    2940
atggtaatag cgatgactaa tacgtagatg tactgccaag taggaaagtc ccataaggtc    3000
atgtactggg cataatgcca ggcgggccat ttaccgtcat tgacgtcaat aggggggcgta   3060
cttggcatat gatacacttg atgtactgcc aagtgggcag tttaccgtaa atactccacc    3120
cattgacgtc aatggaaagt ccctattggc gttactatgg gaacatacgt cattattgac    3180
gtcaatgggc gggggtcgtt gggcggtcag ccaggcgggc catttaccgt aagttatgta    3240
acgcctgcag gttaattaag aacatgtgag caaaaggcca gcaaaaggcc aggaaccgta    3300
aaaaggccgc gttgctggcg tttttccata ggctccgccc cctgacgag catcacaaaa     3360
atcgacgctc aagtcagagg tggcgaaacc cgacaggact ataaagatac caggcgtttc    3420
ccctggaag ctccctcgtg cgctctcctg ttccgaccct gccgcttacc ggatacctgt     3480
ccgcctttct cccttcggga agcgtggcgc tttctcatag ctcacgctgt aggtatctca    3540
gttcggtgta ggtcgttcgc tccaagctgg gctgtgtgca cgaaccccc gttcagcccg     3600
accgctgcgc cttatccggt aactatcgtc ttgagtccaa cccggtaaga cacgacttat    3660
cgccactggc agcagccact ggtaacagga ttagcagagc gaggtatgta ggcggtgcta    3720
cagagttctt gaagtggtgg cctaactacg gctacactag aagaacagta tttggtatct    3780
gcgctctgct gaagccagtt accttcggaa aaagagttgg tagctcttga tccggcaaac    3840
aaaccaccgc tggtagcggt ggttttttg tttgcaagca gcagattacg cgcagaaaaa     3900
aaggatctca agaagatcct ttgatctttt ctacggggtc tgacgctcag tggaacgaaa    3960
actcacgtta agggattttg gtcatggcta gttaattaac atttaaatca gcggccgcaa    4020
taaaatatct ttattttcat tacatctgtg tgttggtttt tgtgtgaat cgtaactaac     4080
atacgctctc catcaaaaca aaacgaaaca aacaaaacta gcaaaatagg ctgtccccag    4140
tgcaagtgca ggtgccagaa catttctcta tcgaa                               4175
```

<210> SEQ ID NO 116
<211> LENGTH: 4776
<212> TYPE: DNA
<213> ORGANISM: Artificial Sequence
<220> FEATURE:
<223> OTHER INFORMATION: pPUSEss-DE27-V 1-CHIg-hG1-Mth-1

<400> SEQUENCE: 116

| | | | | | |
|---|---|---|---|---|---|
| ggatctgcga | tcgctccggt | gcccgtcagt | gggcagagcg | cacatcgccc | acagtccccg | 60 |
| agaagttggg | gggaggggtc | ggcaattgaa | cgggtgccta | gagaaggtgg | cgcggggtaa | 120 |
| actgggaaag | tgatgtcgtg | tactggctcc | gcctttttcc | cgagggtggg | ggagaaccgt | 180 |
| atataagtgc | agtagtcgcc | gtgaacgttc | tttttcgcaa | cgggtttgcc | gccagaacac | 240 |
| agctgaagct | cgaggggct | cgcatctctc | cttcacgcgc | ccgccgccct | acctgaggcc | 300 |
| gccatccacg | ccggttgagt | cgcgttctgc | cgcctcccgc | ctgtggtgcc | tcctgaactg | 360 |
| cgtccgccgt | ctaggtaagt | ttaaagctca | ggtcgagacc | gggcctttgt | ccggcgctcc | 420 |
| cttggagcct | acctagactc | agccggctct | ccacgctttg | cctgaccctg | cttgctcaac | 480 |
| tctacgtctt | tgtttcgttt | tctgttctgc | gccgttacag | atccaagctg | tgaccggcgc | 540 |
| ctacctgaga | tcaccggcga | aggagggcca | ccatgtacag | gatgcaactc | ctgtcttgca | 600 |
| ttgcactaag | tcttgcactt | gtcacgaatt | cggaggtgca | gctggtggag | tctggggag | 660 |
| gcttggtaca | gcccggcagg | tccctgagac | tctcctgtgc | ggcctctgga | ttcacctttg | 720 |
| atgattatgc | catgcactgg | gtccggcaag | ctccagggaa | gggcctggaa | tgggtctcag | 780 |
| ctatcacttg | gaatagtggt | cacatagact | atgcggactc | tgtggagggc | cgattcacca | 840 |
| tctccagaga | caacgccaag | aactccctgt | atctgcaaat | gaacagtctg | agagctgagg | 900 |
| atacggccgt | atattactgt | gcgaaagtct | cgtaccttag | caccgcgtcc | tcccttgact | 960 |
| attggggcca | aggtaccctg | gtcaccgtct | cgagtgctag | caccaagggc | ccatcggtct | 1020 |
| tccccctggc | accctcctcc | aagagcacct | ctgggggcac | agcggccctg | ggctgcctgg | 1080 |
| tcaaggacta | cttccccgaa | ccggtgacgg | tgtcgtggaa | ctcaggcgcc | ctgaccagcg | 1140 |
| gcgtgcacac | cttcccggct | gtcctacagt | cctcaggact | ctactccctc | agcagcgtgg | 1200 |
| tgaccgtgcc | ctccagcagc | ttgggcaccc | agacctacat | ctgcaacgtg | aatcacaagc | 1260 |
| ccagcaacac | caaggtggac | aagaaagttg | agcccaaatc | ttgtgacaaa | actcacacat | 1320 |
| gcgtatccgg | tgacaccatt | gtaatgacta | gtggcgggcc | ccgcactgtg | ctgaactgg | 1380 |
| agggcaaacc | gttcaccgca | ctgattcgcg | gctctggcta | cccatgcccc | tcaggtttct | 1440 |
| tccgcacctg | tgaacgtgac | gtatatgatc | tgcgtacacg | tgagggtcat | tgcttacgtt | 1500 |
| tgacccatga | tcaccgtgtt | ctggtgatgg | atggtgcct | ggaatggcgt | gccgcgggtg | 1560 |
| aactggaacg | cggcgaccgc | ctggtgatgg | atgatgcagc | tggcgagttt | ccggcactgg | 1620 |
| caaccttccg | tggcctgcgt | ggcgctggcc | gccaggatgt | ttatgacgct | actgtttacg | 1680 |
| gtgctagcgc | attcactgct | aatggcttca | ttgtacacgc | atgtggcgag | cagcccggga | 1740 |
| ccggtctgaa | ctcaggcctc | acgacaaatc | tggtgtatc | cgcttggcag | gtcaacacag | 1800 |
| cttatactgc | gggacaattg | gtcacatata | acggcaagac | gtataaatgt | ttgcagcccc | 1860 |
| acacctcctt | ggcaggatgg | gaaccatcca | acgttcctgc | cttgtggcag | cttcaatgag | 1920 |
| tcctagctgg | ccagacatga | taagatacat | tgatgagttt | ggacaaacca | caactagaat | 1980 |
| gcagtgaaaa | aaatgcttta | tttgtgaaat | ttgtgatgct | attgctttat | ttgtaaccat | 2040 |

```
tataagctgc aataaacaag ttaacaacaa caattgcatt cattttatgt ttcaggttca    2100
gggggaggtg tgggaggttt tttaaagcaa gtaaaacctc tacaaatgtg gtatggaatt    2160
aattctaaaa tacagcatag caaaacttta acctccaaat caagcctcta cttgaatcct    2220
tttctgaggg atgaataagg cataggcatc aggggctgtt gccaatgtgc attagctgtt    2280
tgcagcctca ccttctttca tggagtttaa gatatagtgt attttcccaa ggtttgaact    2340
agctcttcat ttctttatgt tttaaatgca ctgacctccc acattccctt tttagtaaaa    2400
tattcagaaa taatttaaat acatcattgc aatgaaaata aatgtttttt attaggcaga    2460
atccagatgc tcaaggccct tcataatatc ccccagttta gtagttggac ttagggaaca    2520
aaggaacctt aatagaaat tggacagcaa gaaagcgagc ttctagctta tcctcagtcc    2580
tgctcctctg ccacaaagtg cacgcagttg ccggccgggt cgcgcagggc gaactcccgc    2640
ccccacggct gctcgccgat ctcggtcatg gccgccccgg aggcgtcccg gaagttcgtg    2700
gacacgacct ccgaccactc ggcgtacagc tcgtccaggc cgcgcaccca cacccaggcc    2760
agggtgttgt ccggcaccac ctggtcctgg accgcgctga tgaacagggt cacgtcgtcc    2820
cggaccacac cggcgaagtc gtcctccacg aagtcccggg agaacccgag ccggtcggtc    2880
cagaactcga ccgctccggc gacgtcgcgc gcggtgagca ccggaacggc actggtcaac    2940
ttggccatga tggctcctcc tgtcaggaga ggaaagagaa gaaggttagt acaattgcta    3000
tagtgagttg tattatacta tgcagatata ctatgccaat gattaattgt caaactaggg    3060
ctgcagggtt catagtgcca cttttcctgc actgccccat ctcctgccca cccttttccca    3120
ggcatagaca gtcagtgact taccaaactc acaggaggga gaaggcagaa gcttgagaca    3180
gacccgcggg accgccgaac tgcgagggga cgtggctagg gcggcttctt ttatggtgcg    3240
ccggccctcg gaggcagggc gctcggggag gcctagcggc caatctgcgg tgcaggagg    3300
cggggccgaa ggccgtgcct gaccaatccg gagcacatag gagtctcagc cccccgcccc    3360
aaagcaaggg gaagtcacgc gcctgtagcg ccagcgtgtt gtgaaatggg ggcttggggg    3420
ggttggggcc ctgactagtc aaaacaaact cccattgacg tcaatggggt ggagacttgg    3480
aaatccccgt gagtcaaacc gctatccacg cccattgatg tactgccaaa accgcatcat    3540
catggtaata gcgatgacta atacgtagat gtactgccaa gtaggaaagt cccataaggt    3600
catgtactgg gcataatgcc aggcgggcca tttaccgtca ttgacgtcaa tagggggcgt    3660
acttggcata tgatacactt gatgtactgc caagtgggca gtttaccgta aatactccac    3720
ccattgacgt caatggaaag tccctattgg cgttactatg ggaacatacg tcattattga    3780
cgtcaatggg cggggtcgt tgggcggtca gccaggcggg ccatttaccg taagttatgt    3840
aacgcctgca ggttaattaa gaacatgtga gcaaaaggcc agcaaaaggc caggaaccgt    3900
aaaaaggccg cgttgctggc gtttttccat aggctccgcc ccctgacga gcatcacaaa    3960
aatcgacgct caagtcagag gtggcgaaac ccgacaggac tataaagata ccaggcgttt    4020
cccccctggaa gctccctcgt gcgctctcct gttccgaccc tgccgcttac cggatacctg    4080
tccgcctttc tcccttcggg aagcgtggcg ctttctcata gctcacgctg taggtatctc    4140
agttcggtgt aggtcgttcg ctccaagctg ggctgtgtgc acgaaccccc cgttcagccc    4200
gaccgctgcg ccttatccgg taactatcgt cttgagtcca acccggtaag acacgactta    4260
tcgccactgg cagcagccac tggtaacagg attagcagag cgaggtatgt aggcggtgct    4320
acagagttct tgaagtggtg gcctaactac ggctacacta agagaacagt atttggtatc    4380
tgcgctctgc tgaagccagt taccttcgga aaaagagttg gtagctcttg atccggcaaa    4440
```

```
caaaccaccg ctggtagcgg tggttttttt gtttgcaagc agcagattac gcgcagaaaa    4500
aaaggatctc aagaagatcc tttgatcttt tctacggggt ctgacgctca gtggaacgaa    4560
aactcacgtt aagggatttt ggtcatggct agttaattaa catttaaatc agcggccgca    4620
ataaaatatc tttattttca ttacatctgt gtgttggttt tttgtgtgaa tcgtaactaa    4680
catacgctct ccatcaaaac aaaacgaaac aaaacaaact agcaaaatag gctgtcccca    4740
gtgcaagtgc aggtgccaga acatttctct atcgaa                              4776
```

<210> SEQ ID NO 117
<211> LENGTH: 4779
<212> TYPE: DNA
<213> ORGANISM: Artificial Sequence
<220> FEATURE:
<223> OTHER INFORMATION: pFUSEss-DE27-V 1-CHIg-hG1-Mth-2

<400> SEQUENCE: 117

```
ggatctgcga tcgctccggt gcccgtcagt gggcagagcg cacatcgccc acagtccccg      60
agaagttggg gggaggggtc ggcaattgaa cgggtgccta gagaaggtgg cgcggggtaa     120
actgggaaag tgatgtcgtg tactggctcc gcctttttcc cgagggtggg ggagaaccgt     180
atataagtgc agtagtcgcc gtgaacgttc tttttcgcaa cgggtttgcc gccagaacac     240
agctgaagct cgagggggct cgcatctctc cttcacgcgc ccgccgccct acctgaggcc     300
gccatccacg ccggttgagt cgcgttctgc cgcctcccgc ctgtggtgcc tcctgaactg     360
cgtccgccgt ctaggtaagt ttaaagctca ggtcgagacc gggcctttgt ccggcgctcc     420
cttggagcct acctagactc agccggctct ccacgctttg cctgaccctg cttgctcaac     480
tctacgtctt tgtttcgttt tctgttctgc gccgttacag atccaagctg tgaccggcgc     540
ctacctgaga tcaccggcga aggagggcca ccatgtacag gatgcaactc ctgtcttgca     600
ttgcactaag tcttgcactt gtcacgaatt cggaggtgca gctggtggag tctgggggag     660
gcttggtaca gcccggcagg tccctgagac tctcctgtgc ggcctctgga ttcacctttg     720
atgattatgc catgcactgg gtccggcaag ctccagggaa gggcctggaa tgggtctcag     780
ctatcacttg gaatagtggt cacatagact atgcggactc tgtggagggc cgattcacca     840
tctccagaga caacgccaag aactccctgt atctgcaaat gaacagtctg agagctgagg     900
atacggccgt atattactgt gcgaaagtct cgtaccttag caccgcgtcc tcccttgact     960
attggggcca aggtaccctg gtcaccgtct cgagtgctag caccaagggc ccatcggtct    1020
tccccctggc accctcctcc aagagcacct ctggggcac agcggccctg ggctgcctgg    1080
tcaaggacta cttccccgaa ccggtgacgg tgtcgtggaa ctcaggcgcc ctgaccagcg    1140
gcgtgcacac cttcccggct gtcctacagt cctcaggact ctactccctc agcagcgtgg    1200
tgaccgtgcc ctccagcagc ttgggcaccc agacctacat ctgcaacgtg aatcacaagc    1260
ccagcaacac caaggtggac aagaaagttg agcccaaatc ttgtgacaaa actcacacag    1320
ggtgcgtatc cggtgacacc attgtaatga ctagtggcgg ccccgcact gtggctgaac    1380 tgagggcaa accgttcacc gcactgatc gcggctctgg ctacccatgc ccctcaggtt    1440
tcttccgcac ctgtgaacgt gacgtatatg atctgcgtac acgtgagggt cattgcttac    1500
gtttgaccca tgatcaccgt gttctggtga tggatggtgg cctggaatgg cgtgccgcgg    1560
gtgaactgga acgcgcgac cgcctggtga tggatgatgc agctggcgag tttcggcac    1620 tggcaacctt ccgtggcctg cgtggcgctg gccgccagga tgtttatgac gctactgttt    1680
```

```
acggtgctag cgcattcact gctaatggct tcattgtaca cgcatgtggc gagcagcccg   1740
ggaccggtct gaactcaggc ctcacgacaa atcctggtgt atccgcttgg caggtcaaca   1800
cagcttatac tgcgggacaa ttggtcacat ataacggcaa gacgtataaa tgtttgcagc   1860
cccacacctc cttggcagga tgggaaccat ccaacgttcc tgccttgtgg cagcttcaat   1920
gagtcctagc tggccagaca tgataagata cattgatgag tttggacaaa ccacaactag   1980
aatgcagtga aaaaaatgct ttatttgtga aatttgtgat gctattgctt tatttgtaac   2040
cattataagc tgcaataaac aagttaacaa caacaattgc attcatttta tgtttcaggt   2100
tcaggggag gtgtgggagg tttttttaaag caagtaaaac ctctacaaat gtggtatgga   2160
attaattcta aaatacagca tagcaaaact ttaacctcca aatcaagcct ctacttgaat   2220
cctttctga gggatgaata aggcataggc atcaggggct gttgccaatg tgcattagct   2280
gtttgcagcc tcaccttctt tcatggagtt taagatatag tgtattttcc caaggtttga   2340
actagctctt catttcttta tgttttaaat gcactgacct cccacattcc cttttagta   2400
aaatattcag aaataattta atacatcat tgcaatgaaa ataaatgttt tttattaggc   2460
agaatccaga tgctcaaggc ccttcataat atccccccagt ttagtagttg gacttaggga   2520
acaaaggaac ctttaataga aattggacag caagaaagcg agcttctagc ttatcctcag   2580
tcctgctcct ctgccacaaa gtgcacgcag ttgccggccg ggtcgcgcag ggcgaactcc   2640
cgcccccacg gctgctcgcc gatctcggtc atggccggcc cggaggcgtc ccggaagttc   2700
gtggacacga cctccgacca ctcggcgtac agctcgtcca ggccgcgcac ccacacccag   2760
gccagggtgt tgtccggcac cacctggtcc tggaccgcgc tgatgaacag ggtcacgtcg   2820
tcccggacca caccggcgaa gtcgtcctcc acgaagtccc gggagaaccc gagccggtcg   2880
gtccagaact cgaccgctcc ggcgacgtcg cgcgcggtga gcaccggaac ggcactggtc   2940
aacttggcca tgatggctcc tcctgtcagg agaggaaaga gaagaaggtt agtacaattg   3000
ctatagtgag ttgtattata ctatgcagat atactatgcc aatgattaat tgtcaaacta   3060
gggctgcagg gttcatagtg ccacttttcc tgcactgccc catctcctgc ccacccttc   3120
ccaggcatag acagtcagtg acttaccaaa ctcacaggag ggagaaggca gaagcttgag   3180
acagacccgc gggaccgccg aactgcgagg ggacgtggct agggcggctt ctttatggt   3240
gcgccggcc tcgaggcag ggcgctcggg gaggcctagc ggccaatctg cggtggcagg   3300
aggcggggcc gaaggccgtg cctgaccaat ccggagcaca taggagtctc agcccccgc   3360
cccaaagcaa gggaagtca cgcgcctgta gcgccagcgt gttgtgaaat gggggcttgg   3420
ggggggttggg gccctgacta gtcaaaacaa actcccattg acgtcaatgg ggtggagact   3480
tggaaatccc cgtgagtcaa accgctatcc acgcccattg atgtactgcc aaaaccgcat   3540
catcatggta atagcgatga ctaatacgta gatgtactgc caagtaggaa agtcccataa   3600
ggtcatgtac tgggcataat gccaggcggg ccatttaccg tcattgacgt caatagggg   3660
cgtacttggc atatgataca cttgatgtac tgccaagtgg gcagtttacc gtaaatactc   3720
cacccattga cgtcaatgga aagtccctat tggcgttact atgggaacat acgtcattat   3780
tgacgtcaat gggcggggt cgttggcgg tcagccaggc gggccattta ccgtaagtta   3840
tgtaacgcct gcaggttaat taagaacatg tgagcaaaag gccagcaaaa ggccaggaac   3900
cgtaaaaagg ccgcgttgct ggcgtttttc cataggctcc gccccctga cgagcatcac   3960
aaaaatcgac gctcaagtca gaggtggcga acccgacag gactataaag ataccaggcg   4020
tttccccctg gaagctccct cgtgcgctct cctgttccga ccctgccgct taccggatac   4080
```

```
ctgtccgcct ttctcccttc gggaagcgtg gcgctttctc atagctcacg ctgtaggtat    4140
ctcagttcgg tgtaggtcgt tcgctccaag ctgggctgtg tgcacgaacc ccccgttcag    4200
cccgaccgct gcgccttatc cggtaactat cgtcttgagt ccaacccggt aagacacgac    4260
ttatcgccac tggcagcagc cactggtaac aggattagca gagcgaggta tgtaggcggt    4320
gctacagagt tcttgaagtg gtggcctaac tacggctaca ctagaagaac agtatttggt    4380
atctgcgctc tgctgaagcc agttaccttc ggaaaaagag ttggtagctc ttgatccggc    4440
aaacaaacca ccgctggtag cggtggtttt tttgtttgca agcagcagat tacgcgcaga    4500
aaaaaaggat ctcaagaaga tcctttgatc ttttctacgg ggtctgacgc tcagtggaac    4560
gaaaactcac gttaagggat tttggtcatg gctagttaat taacatttaa atcagcggcc    4620
gcaataaaat atctttattt tcattacatc tgtgtgttgg ttttttgtgt gaatcgtaac    4680
taacatacgc tctccatcaa aacaaaacga aacaaaacaa actagcaaaa taggctgtcc    4740
ccagtgcaag tgcaggtgcc agaacatttc tctatcgaa                          4779

<210> SEQ ID NO 118
<211> LENGTH: 234
<212> TYPE: PRT
<213> ORGANISM: Artificial Sequence
<220> FEATURE:
<223> OTHER INFORMATION: pre-kappa light chain of adalimumab

<400> SEQUENCE: 118

Met Tyr Arg Met Gln Leu Leu Ser Cys Ile Ala Leu Ser Leu Ala Leu
 1               5                  10                  15

Val Thr Asn Ser Asp Ile Gln Met Thr Gln Ser Pro Ser Ser Leu Ser
             20                  25                  30

Ala Ser Val Gly Asp Arg Val Thr Ile Thr Cys Arg Ala Ser Gln Gly
         35                  40                  45

Ile Arg Asn Tyr Leu Ala Trp Tyr Gln Gln Lys Pro Gly Lys Ala Pro
     50                  55                  60

Lys Leu Leu Ile Tyr Ala Ala Ser Thr Leu Gln Ser Gly Val Pro Ser
 65                  70                  75                  80

Arg Phe Ser Gly Ser Gly Ser Gly Thr Asp Phe Thr Leu Thr Ile Ser
                 85                  90                  95

Ser Leu Gln Pro Glu Asp Val Ala Thr Tyr Tyr Cys Gln Arg Tyr Asn
            100                 105                 110

Arg Ala Pro Tyr Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

```
<210> SEQ ID NO 119
<211> LENGTH: 214
<212> TYPE: PRT
<213> ORGANISM: Artificial Sequence
<220> FEATURE:
<223> OTHER INFORMATION: mature kappa light chain of adalimumab

<400> SEQUENCE: 119
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

```
<210> SEQ ID NO 120
<211> LENGTH: 448
<212> TYPE: PRT
<213> ORGANISM: Artificial Sequence
<220> FEATURE:
<223> OTHER INFORMATION: pre-heavy chain-intein chimeric polypeptide

<400> SEQUENCE: 120
```

Met Tyr Arg Met Gln Leu Leu Ser Cys Ile Ala Leu Ser Leu Ala Leu
1               5                   10                  15

Val Thr Asn Ser Glu Val Gln Leu Val Glu Ser Gly Gly Gly Leu Val
            20                  25                  30

Gln Pro Gly Arg Ser Leu Arg Leu Ser Cys Ala Ala Ser Gly Phe Thr
        35                  40                  45

Phe Asp Asp Tyr Ala Met His Trp Val Arg Gln Ala Pro Gly Lys Gly
50                  55                  60

Leu Glu Trp Val Ser Ala Ile Thr Trp Asn Ser Gly His Ile Asp Tyr
65                  70                  75                  80

Ala Asp Ser Val Glu Gly Arg Phe Thr Ile Ser Arg Asp Asn Ala Lys

```
                    85                  90                  95
Asn Ser Leu Tyr Leu Gln Met Asn Ser Leu Arg Ala Glu Asp Thr Ala
                100                 105                 110

Val Tyr Tyr Cys Ala Lys Val Ser Tyr Leu Ser Thr Ala Ser Ser Leu
                115                 120                 125

Asp Tyr Trp Gly Gln Gly Thr Leu Val Thr Val Ser Ser Ala Ser Thr
            130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
                180                 185                 190

Thr Phe Pro Ala Val Leu Gln Ser Ser Gly Leu Tyr Ser Leu Ser Ser
                195                 200                 205

Val Val Thr Val Pro Ser Ser Ser Leu Gly Thr Gln Thr Tyr Ile Cys
                210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Val Ser Gly Asp Thr Ile
                245                 250                 255

Val Met Thr Ser Gly Gly Pro Arg Thr Val Ala Glu Leu Glu Gly Lys
                260                 265                 270

Pro Phe Thr Ala Leu Ile Arg Gly Ser Gly Tyr Pro Cys Pro Ser Gly
                275                 280                 285

Phe Phe Arg Thr Cys Glu Arg Asp Val Tyr Asp Leu Arg Thr Arg Glu
                290                 295                 300

Gly His Cys Leu Arg Leu Thr His Asp His Arg Val Leu Val Met Asp
305                 310                 315                 320

Gly Gly Leu Glu Trp Arg Ala Ala Gly Glu Leu Glu Arg Gly Asp Arg
                325                 330                 335

Leu Val Met Asp Asp Ala Ala Gly Glu Phe Pro Ala Leu Ala Thr Phe
                340                 345                 350

Arg Gly Leu Arg Gly Ala Gly Arg Gln Asp Val Tyr Asp Ala Thr Val
                355                 360                 365

Tyr Gly Ala Ser Ala Phe Thr Ala Asn Gly Phe Ile Val His Ala Cys
            370                 375                 380

Gly Glu Gln Pro Gly Thr Gly Leu Asn Ser Gly Leu Thr Thr Asn Pro
385                 390                 395                 400

Gly Val Ser Ala Trp Gln Val Asn Thr Ala Tyr Thr Ala Gly Gln Leu
                405                 410                 415

Val Thr Tyr Asn Gly Lys Thr Tyr Lys Cys Leu Gln Pro His Thr Ser
                420                 425                 430

Leu Ala Gly Trp Glu Pro Ser Asn Val Pro Ala Leu Trp Gln Leu Gln
                435                 440                 445

<210> SEQ ID NO 121
<211> LENGTH: 428
<212> TYPE: PRT
<213> ORGANISM: Artificial Sequence
<220> FEATURE:
<223> OTHER INFORMATION: mature heavy chain-intein fusion protein

<400> SEQUENCE: 121

Glu Val Gln Leu Val Glu Ser Gly Gly Gly Leu Val Gln Pro Gly Arg
```

-continued

```
1               5                   10                  15
Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
            35                  40                  45

Ser Ala Ile Thr Trp Asn Ser Gly His Ile Asp Tyr Ala Asp Ser Val
 50                  55                  60

Glu Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Val Glu Pro Lys Ser Cys
 210                 215                 220

Asp Lys Thr His Thr Cys Val Ser Gly Asp Thr Ile Val Met Thr Ser
225                 230                 235                 240

Gly Gly Pro Arg Thr Val Ala Glu Leu Glu Gly Lys Pro Phe Thr Ala
                245                 250                 255

Leu Ile Arg Gly Ser Gly Tyr Pro Cys Pro Ser Gly Phe Phe Arg Thr
            260                 265                 270

Cys Glu Arg Asp Val Tyr Asp Leu Arg Thr Arg Glu Gly His Cys Leu
            275                 280                 285

Arg Leu Thr His Asp His Arg Val Leu Val Met Asp Gly Gly Leu Glu
            290                 295                 300

Trp Arg Ala Ala Gly Glu Leu Glu Arg Gly Asp Arg Leu Val Met Asp
305                 310                 315                 320

Asp Ala Ala Gly Glu Phe Pro Ala Leu Ala Thr Phe Arg Gly Leu Arg
                325                 330                 335

Gly Ala Gly Arg Gln Asp Val Tyr Asp Ala Thr Val Tyr Gly Ala Ser
            340                 345                 350

Ala Phe Thr Ala Asn Gly Phe Ile Val His Ala Cys Gly Glu Gln Pro
            355                 360                 365

Gly Thr Gly Leu Asn Ser Gly Leu Thr Thr Asn Pro Gly Val Ser Ala
            370                 375                 380

Trp Gln Val Asn Thr Ala Tyr Thr Ala Gly Gln Leu Val Thr Tyr Asn
385                 390                 395                 400

Gly Lys Thr Tyr Lys Cys Leu Gln Pro His Thr Ser Leu Ala Gly Trp
                405                 410                 415

Glu Pro Ser Asn Val Pro Ala Leu Trp Gln Leu Gln
            420                 425
```

<210> SEQ ID NO 122
<211> LENGTH: 449
<212> TYPE: PRT
<213> ORGANISM: Artificial Sequence
<220> FEATURE:
<223> OTHER INFORMATION: pre-heavy chain-intein chimeric polypeptide

<400> SEQUENCE: 122

```
Met Tyr Arg Met Gln Leu Leu Ser Cys Ile Ala Leu Ser Leu Ala Leu
1               5                   10                  15

Val Thr Asn Ser Glu Val Gln Leu Val Glu Ser Gly Gly Gly Leu Val
            20                  25                  30

Gln Pro Gly Arg Ser Leu Arg Leu Ser Cys Ala Ala Ser Gly Phe Thr
        35                  40                  45

Phe Asp Asp Tyr Ala Met His Trp Val Arg Gln Ala Pro Gly Lys Gly
    50                  55                  60

Leu Glu Trp Val Ser Ala Ile Thr Trp Asn Ser Gly His Ile Asp Tyr
65                  70                  75                  80

Ala Asp Ser Val Glu Gly Arg Phe Thr Ile Ser Arg Asp Asn Ala Lys
                85                  90                  95

Asn Ser Leu Tyr Leu Gln Met Asn Ser Leu Arg Ala Glu Asp Thr Ala
            100                 105                 110

Val Tyr Tyr Cys Ala Lys Val Ser Tyr Leu Ser Thr Ala Ser Ser Leu
        115                 120                 125

Asp Tyr Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Gly Cys Val Ser Gly Asp Thr
                245                 250                 255

Ile Val Met Thr Ser Gly Gly Pro Arg Thr Val Ala Glu Leu Glu Gly
            260                 265                 270

Lys Pro Phe Thr Ala Leu Ile Arg Gly Ser Gly Tyr Pro Cys Pro Ser
        275                 280                 285

Gly Phe Phe Arg Thr Cys Glu Arg Asp Val Tyr Asp Leu Arg Thr Arg
    290                 295                 300

Glu Gly His Cys Leu Arg Leu Thr His Asp His Arg Val Leu Val Met
305                 310                 315                 320

Asp Gly Gly Leu Glu Trp Arg Ala Ala Gly Glu Leu Glu Arg Gly Asp
                325                 330                 335

Arg Leu Val Met Asp Asp Ala Ala Gly Glu Phe Pro Ala Leu Ala Thr
            340                 345                 350

Phe Arg Gly Leu Arg Gly Ala Gly Arg Gln Asp Val Tyr Asp Ala Thr
        355                 360                 365
```

```
Val Tyr Gly Ala Ser Ala Phe Thr Ala Asn Gly Phe Ile Val His Ala
    370                 375                 380

Cys Gly Glu Gln Pro Gly Thr Gly Leu Asn Ser Gly Leu Thr Thr Asn
385                 390                 395                 400

Pro Gly Val Ser Ala Trp Gln Val Asn Thr Ala Tyr Thr Ala Gly Gln
                405                 410                 415

Leu Val Thr Tyr Asn Gly Lys Thr Tyr Lys Cys Leu Gln Pro His Thr
            420                 425                 430

Ser Leu Ala Gly Trp Glu Pro Ser Asn Val Pro Ala Leu Trp Gln Leu
        435                 440                 445

Gln

<210> SEQ ID NO 123
<211> LENGTH: 429
<212> TYPE: PRT
<213> ORGANISM: Artificial Sequence
<220> FEATURE:
<223> OTHER INFORMATION: mature heavy chain-intein fusion protein

<400> SEQUENCE: 123

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Gly Cys Val Ser Gly Asp Thr Ile Val Met Thr
225                 230                 235                 240

Ser Gly Gly Pro Arg Thr Val Ala Glu Leu Glu Gly Lys Pro Phe Thr
                245                 250                 255

Ala Leu Ile Arg Gly Ser Gly Tyr Pro Cys Pro Ser Gly Phe Phe Arg
            260                 265                 270
```

```
Thr Cys Glu Arg Asp Val Tyr Asp Leu Arg Thr Arg Glu Gly His Cys
            275                 280                 285

Leu Arg Leu Thr His Asp His Arg Val Leu Val Met Asp Gly Gly Leu
        290                 295                 300

Glu Trp Arg Ala Ala Gly Glu Leu Glu Arg Gly Asp Arg Leu Val Met
305                 310                 315                 320

Asp Asp Ala Ala Gly Glu Phe Pro Ala Leu Ala Thr Phe Arg Gly Leu
                325                 330                 335

Arg Gly Ala Gly Arg Gln Asp Val Tyr Asp Ala Thr Val Tyr Gly Ala
            340                 345                 350

Ser Ala Phe Thr Ala Asn Gly Phe Ile Val His Ala Cys Gly Glu Gln
        355                 360                 365

Pro Gly Thr Gly Leu Asn Ser Gly Leu Thr Thr Asn Pro Gly Val Ser
    370                 375                 380

Ala Trp Gln Val Asn Thr Ala Tyr Thr Ala Gly Gln Leu Val Thr Tyr
385                 390                 395                 400

Asn Gly Lys Thr Tyr Lys Cys Leu Gln Pro His Thr Ser Leu Ala Gly
                405                 410                 415

Trp Glu Pro Ser Asn Val Pro Ala Leu Trp Gln Leu Gln
                420                 425

<210> SEQ ID NO 124
<211> LENGTH: 230
<212> TYPE: PRT
<213> ORGANISM: Artificial Sequence
<220> FEATURE:
<223> OTHER INFORMATION: Part of alkyne-modified adalimumab Fab-1
      protein. Modified at C-Terminus.
<220> FEATURE:
<221> NAME/KEY: Xaa
<222> LOCATION: (230)..(230)
<223> OTHER INFORMATION: cysteine-alkyne

<400> SEQUENCE: 124

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
```

```
                       180                 185                 190
Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
    210                 215                 220

Asp Lys Thr His Thr Xaa
225                 230

<210> SEQ ID NO 125
<211> LENGTH: 231
<212> TYPE: PRT
<213> ORGANISM: Artificial Sequence
<220> FEATURE:
<223> OTHER INFORMATION: Part of alkyne-modified adalimumab Fab-2
      protein. Motified at C-Terminus
<220> FEATURE:
<221> NAME/KEY: Xaa
<222> LOCATION: (131)..(131)
<223> OTHER INFORMATION: cysteine-alkyne
<220> FEATURE:
<221> NAME/KEY: misc_feature
<222> LOCATION: (231)..(231)
<223> OTHER INFORMATION: Xaa can be any naturally occurring amino acid

<400> SEQUENCE: 125

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Gly Xaa
225                 230

<210> SEQ ID NO 126
<211> LENGTH: 230
<212> TYPE: PRT
```

<213> ORGANISM: Artificial Sequence
<220> FEATURE:
<223> OTHER INFORMATION: Part of azide-modified adalimumab Fab-1
      protein. Modified C-Terminus
<220> FEATURE:
<221> NAME/KEY: Xaa
<222> LOCATION: (230)..(230)
<223> OTHER INFORMATION: cysteine-azide

<400> SEQUENCE: 126

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Ala Ile Thr Trp Asn Ser Gly His Ile Asp Tyr Ala Asp Ser Val
50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Xaa
225                 230

<210> SEQ ID NO 127
<211> LENGTH: 231
<212> TYPE: PRT
<213> ORGANISM: Artificial Sequence
<220> FEATURE:
<223> OTHER INFORMATION: Part of azide-modified adalimumab Fab-2
      protein. Modified C-Terminus
<220> FEATURE:
<221> NAME/KEY: Xaa
<222> LOCATION: (231)..(231)
<223> OTHER INFORMATION: cysteine-azide

<400> SEQUENCE: 127

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

```
Ser Ala Ile Thr Trp Asn Ser Gly His Ile Asp Tyr Ala Asp Ser Val
 50                  55                  60

Glu Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Lys Val Ser Tyr Leu Ser Thr Ala Ser Ser Leu Asp Tyr Trp Gly
                100                 105                 110

Gln Gly Thr Leu Val Thr Val Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Val Glu Pro Lys Ser Cys
210                 215                 220

Asp Lys Thr His Thr Gly Xaa
225                 230

<210> SEQ ID NO 128
<211> LENGTH: 5
<212> TYPE: PRT
<213> ORGANISM: Artificial Sequence
<220> FEATURE:
<223> OTHER INFORMATION: N-Terminal Sequence

<400> SEQUENCE: 128

Cys Pro Pro Cys Pro
1               5

<210> SEQ ID NO 129
<211> LENGTH: 5
<212> TYPE: PRT
<213> ORGANISM: Artificial
<220> FEATURE:
<223> OTHER INFORMATION: N-Terminal Sequence

<400> SEQUENCE: 129

Cys Pro Arg Cys Pro
1               5

<210> SEQ ID NO 130
<211> LENGTH: 5
<212> TYPE: PRT
<213> ORGANISM: Artificial
<220> FEATURE:
<223> OTHER INFORMATION: N-Terminal Sequence

<400> SEQUENCE: 130

Cys Pro Ser Cys Pro
1               5

<210> SEQ ID NO 131
<211> LENGTH: 11
```

<212> TYPE: PRT
<213> ORGANISM: Artificial
<220> FEATURE:
<223> OTHER INFORMATION: N-Terminal Sequence

<400> SEQUENCE: 131

Cys Asp Lys Thr His Thr Cys Pro Pro Cys Pro
1               5                   10

<210> SEQ ID NO 132
<211> LENGTH: 8
<212> TYPE: PRT
<213> ORGANISM: Artificial
<220> FEATURE:
<223> OTHER INFORMATION: N-Terminal Sequence

<400> SEQUENCE: 132

Cys Val Glu Cys Pro Pro Cys Pro
1               5

<210> SEQ ID NO 133
<211> LENGTH: 9
<212> TYPE: PRT
<213> ORGANISM: Artificial
<220> FEATURE:
<223> OTHER INFORMATION: N-Terminal Sequence

<400> SEQUENCE: 133

Cys Cys Val Glu Cys Pro Pro Cys Pro
1               5

<210> SEQ ID NO 134
<211> LENGTH: 11
<212> TYPE: PRT
<213> ORGANISM: Artificial
<220> FEATURE:
<223> OTHER INFORMATION: N-Terminal Sequence

<400> SEQUENCE: 134

Cys Asp Thr Pro Pro Pro Cys Pro Arg Cys Pro
1               5                   10

<210> SEQ ID NO 135
<211> LENGTH: 15
<212> TYPE: PRT
<213> ORGANISM: Artificial
<220> FEATURE:
<223> OTHER INFORMATION: Stretch of consecutive amino acids in B

<400> SEQUENCE: 135

Glu Pro Lys Ser Cys Asp Lys Thr His Thr Cys Pro Pro Cys Pro
1               5                   10                  15

<210> SEQ ID NO 136
<211> LENGTH: 12
<212> TYPE: PRT
<213> ORGANISM: Artificial
<220> FEATURE:
<223> OTHER INFORMATION: Stretch of consecutive amino acids in B

<400> SEQUENCE: 136

Glu Arg Lys Cys Cys Val Glu Cys Pro Pro Cys Pro
1               5                   10

<210> SEQ ID NO 137
<211> LENGTH: 62
<212> TYPE: PRT

```
<213> ORGANISM: Artificial
<220> FEATURE:
<223> OTHER INFORMATION: Stretch of consecutive amino acids in B

<400> SEQUENCE: 137

Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
            20                  25                  30

Glu Pro Lys Ser Cys Asp Thr Pro Pro Cys Pro Arg Cys Pro Glu
        35                  40                  45

Pro Lys Ser Cys Asp Thr Pro Pro Cys Pro Arg Cys Pro
    50                  55                  60

<210> SEQ ID NO 138
<211> LENGTH: 12
<212> TYPE: PRT
<213> ORGANISM: Artificial
<220> FEATURE:
<223> OTHER INFORMATION: Stretch of consecutive amino acids in B

<400> SEQUENCE: 138

Glu Ser Lys Tyr Gly Pro Pro Cys Pro Ser Cys Pro
1               5                   10

<210> SEQ ID NO 139
<211> LENGTH: 18
<212> TYPE: PRT
<213> ORGANISM: Artificial
<220> FEATURE:
<223> OTHER INFORMATION: Part of Fab'

<400> SEQUENCE: 139

Cys Asp Lys Thr His Thr Cys Pro Pro Cys Pro Ala Pro Glu Leu Leu
1               5                   10                  15

Gly Gly

<210> SEQ ID NO 140
<211> LENGTH: 17
<212> TYPE: PRT
<213> ORGANISM: Artificial
<220> FEATURE:
<223> OTHER INFORMATION: Part of Fab'

<400> SEQUENCE: 140

Cys Asp Lys Thr His Thr Cys Pro Pro Cys Pro Ala Pro Glu Leu Leu
1               5                   10                  15

Gly
```